(12) United States Patent
Snyder et al.

(10) Patent No.: US 9,185,909 B2
(45) Date of Patent: Nov. 17, 2015

(54) SYNTHESIS OF RESVERATROL-BASED NATURAL PRODUCTS

(75) Inventors: Scott Alan Snyder, Dobbs Ferry, NY (US); Steven P. Breazzano, La Jolla, CA (US); Audrey G. Ross, New York, NY (US); Yunqing Lin, New York, NY (US); Alexandros L. Zografos, Thessaloniki (GR)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 519 days.

(21) Appl. No.: 12/733,750

(22) PCT Filed: Sep. 17, 2008

(86) PCT No.: PCT/US2008/010834
§ 371 (c)(1),
(2), (4) Date: May 7, 2010

(87) PCT Pub. No.: WO2009/038731
PCT Pub. Date: Mar. 26, 2009

(65) Prior Publication Data
US 2010/0247462 A1    Sep. 30, 2010

Related U.S. Application Data

(60) Provisional application No. 61/005,840, filed on Dec. 7, 2007, provisional application No. 60/994,243, filed on Sep. 17, 2007.

(51) Int. Cl.
| | |
|---|---|
| *A61K 31/09* | (2006.01) |
| *A61K 31/05* | (2006.01) |
| *A01N 31/16* | (2006.01) |
| *C07C 37/00* | (2006.01) |
| *C07C 37/055* | (2006.01) |
| *C07C 41/18* | (2006.01) |
| *C07C 41/22* | (2006.01) |
| *C07C 41/24* | (2006.01) |
| *C07C 41/26* | (2006.01) |
| *C07C 41/30* | (2006.01) |
| *C07C 49/755* | (2006.01) |
| *C07C 67/04* | (2006.01) |
| *C07C 67/11* | (2006.01) |
| *C07C 319/14* | (2006.01) |

(52) U.S. Cl.
CPC ............. *A01N 31/16* (2013.01); *C07C 37/00* (2013.01); *C07C 37/055* (2013.01); *C07C 41/18* (2013.01); *C07C 41/22* (2013.01); *C07C 41/24* (2013.01); *C07C 41/26* (2013.01); *C07C 41/30* (2013.01); *C07C 49/755* (2013.01); *C07C 67/04* (2013.01); *C07C 67/11* (2013.01); *C07C 319/14* (2013.01); *C07C 2102/08* (2013.01); *C07C 2103/32* (2013.01); *C07C 2103/40* (2013.01); *C07C 2103/86* (2013.01); *C07C 2103/90* (2013.01)

(58) Field of Classification Search
CPC   C07C 39/17;  C07C 2103/78;  C07C 2103/90; A61K 31/09; A61K 31/05
See application file for complete search history.

(56) References Cited

U.S. PATENT DOCUMENTS

| | | | |
|---|---|---|---|
| 3,669,969 | A | 6/1972 | Lunn |
| 5,646,283 | A | 7/1997 | Suzuki et al. |
| 6,593,374 | B2 | 7/2003 | Pinney et al. |
| 2003/0118617 | A1 | 6/2003 | Soby et al. |
| 2005/0240062 | A1 | 10/2005 | Pettit et al. |
| 2009/0247490 | A1 | 10/2009 | Declercq et al. |
| 2010/0247462 | A1 | 9/2010 | Snyder et al. |
| 2013/0338390 | A1 | 12/2013 | Snyder et al. |

FOREIGN PATENT DOCUMENTS

| | | |
|---|---|---|
| JP | 7309795 | 11/1995 |
| WO | WO 2009/038731 | 3/2009 |
| WO | WO 2009/091324 | 7/2009 |
| WO | WO 2010/074764 | 7/2010 |
| WO | WO 2011/103442 | 8/2011 |
| WO | WO 2012/012609 | 1/2012 |
| WO | WO 2012/037069 | 3/2012 |
| WO | WO 2013/049364 A1 | 4/2013 |

OTHER PUBLICATIONS

Baba et al, Chemical and Pharmaceutical Bulletin, Chemical Studies on Heartwood of Cassia garrettiana CRAIB, III. Structure of Two New Polyphenolic Compounds, 1988, 36(8), pp. 2977-2983.*
Greene, Protective Groups in Organic Chemistry, 1981, John Wiley & Sons, Inc., pp. 14-16.*
Cristol et al, Journal of Organic Chemistry, Bridged Polycyclic Compounds. LXI. Synthesis and Some Properties of Tribenzobicyclo[3.2.2]-nonatriene (Homotriptycene) and Derivatives, 1970, 35(7), pp. 2357-2361.*
International Search Report in connection with PCT International Application No. PCT/US2008/010834, issued Feb. 17, 2009.
Written Opinion of the International Search Authority in connection with PCT International Application No. PCT/US2009/006713 issued Apr. 23, 2010.
International Preliminary Report on Patentability in connection with PCT International Application No. PCT/US2009/006713 issued Jun. 29, 2011.
Notification of Transmittal of International Preliminary Report on Patentability in connection with PCT International Application No. PCT/US2009/006713 issued Jul. 7, 2011.
International Search Report in connection with PCT International Application No. PCT/US2009/006713 issued Apr. 23, 2010.
Written Opinion of the International Search Authority in connection with PCT International Application No. PCT/US2011/025454, issued Aug. 29, 2011.
International Preliminary Report on Patentability in connection with PCT International Application No. PCT/US2011/025454, issued Aug. 21, 2012.

(Continued)

*Primary Examiner* — Paul A Zucker
(74) *Attorney, Agent, or Firm* — John P. White; Cooper & Dunham LLP

(57) ABSTRACT

Processes for synthesizing resveratrol-based oligomers are provided. In addition, resveratrol-based oligomer compounds free of plant extract are provided.

8 Claims, 37 Drawing Sheets

(56) References Cited

OTHER PUBLICATIONS

Notification of Transmittal of International Preliminary Report on Patentability in connection with PCT International Application No. PCT/US2011/025454, issued Aug. 30, 2012.

International Search Report in connection with PCT International Application No. PCT/US2011/025454, issued Aug. 29, 2011.

Notification of Transmittal of the International Search Report and the Written Opinion of the International Searching Authority in connection with PCT International Application No. PCT/US2011/51311, issued Apr. 11, 2012.

Notification of Transmittal of the International Search Report and the Written Opinion of the International Searching Authority in connection with PCT International Application No. PCT/US2011/44806, issued Dec. 16, 2011.

Lee, Hyun Jung, et al. (2004) "Syntheses and radical scavenging activities of resveratrol derivates" Bioorganic & Medicinal Chemistry Letters 14.2: 463-466).

Fan, Y. (2011) "A Concise Approach to the Dalesconol Skeleton" Organic Letters, vol. 13, p. 4494-4497.

Snyder et al. (2010) "Total Synthesis of Dalesconol A and B" Angew. Chem., vol. 122, p. 5272-5276.

Snyder et al. (2007) "Total Synthesis of Resveratrol-Based Natural Products: A Chemoselective Solution" Angew. Chem. Int. Ed., vol. 46, p. 8186-8191.

Zhang et al. (2008) "Unprecedented Immunosuppressive Polyketides from Daldinia eschscholzii, a Mantis-Asscociated Fungus" Angew. Chem., vol. 120, p. 5907-5910.

Tezuka et al. (2000) Helicterins A-F, Six New Dimeric (7.5', 8.2')-Neolignans From the Indonesian Medicinal Plant Helicteres Isora. Helvitica Chimica Acta, vol. 83, p. 2908-2919.

O'Malley et al. (2005) Total Synthesis of (+)-Lithospermic Acid by Asymmetric Intramolecular Alkylation via Catalytic C—H Bond Activation. Journal of American Chemical Society, vol. 66, 68-77 127, pp. 13496-13497.

Ward, Robert S. (1995) Lignans, neolignans, and related Compounds. Natural Product Reports, vol. 12, pp. 43-74.

Snyder and Treitler (2009) "Et2SBr•SbCl5Br: An Effective Reagent for Direct Bromonium-Induced Polyene Cyclizations" Angew. Chem. Int. Ed., vol. 48, pp. 7899-7903.

International Search Report issued by the International Searching Authority (ISA/US) in connection with International Application No. PCT/US2008/010834.

Notification concerning transmittal of international preliminary report on patentability in connection with PCT International Application No. PCT/US2008/010834, issued Apr. 1, 2010.

International preliminary report on patentability in connection with PCT International Application No. PCT/US2008/010834, issued Mar. 24, 2010.

Snyder, S. A., et al. "Total Synthesis of Diverse Carbogenic Complexity within the Resveratrol Class from a Common Building Block" J. Am. Chem. Soc. (2009), vol. 131, pp. 1753-1765.

Snyder, S.A.; Kontes, F. "Explorations into Neolignan Biosynthesis: Concise Total Syntheses of Helicterin B, Helisorin, Helisticulin A from a Common Intermediate" J. Am. Chem. Soc. (2009), vol. 131, pp. 1745-1752.

International Search Report issued Dec. 10, 2012 in connection with PCT International Application No. PCT/US2012/057587.

International Preliminary Report on Patentability Chapter I in connection with PCT International Application No. PCT/US2011/44806, issued Feb. 11, 2014.

Office Action issued Feb. 19, 2014 in connection with U.S. Appl. No. 13/810,093.

International Preliminary Report on Patentability Chapter I in connection with PCT International Application No. PCT/US2011/51311, issued Feb. 11, 2014.

International Search Report in connection with PCT International Application No. PCT/US2012/57587, issued Dec. 12, 2012.

Office Action issued Jun. 30, 2014 in connection with U.S. Appl. No. 13/810,093.

Written Opinion of the International Search Authority in connection with PCT International Application No. PCT/US2012/057587, issued Dec. 10, 2012.

International Preliminary Report on Patentability Chapter I in connection with PCT International Application No. PCT/US2012/057587, issued Apr. 1, 2014.

Kuznetsov et al. (1974) Chemical Abstracts Vo. 81, No. 37460.

* cited by examiner

SYNTHESIS OF RESVERATROL-BASED NATURAL PRODUCTS

This application is a §371 national stage of PCT International Application No. PCT/US2008/010834, filed Sep. 17, 2008, and claims the benefit of U.S. Provisional Application Nos. 61/005,840, filed Dec. 7, 2007, and 60/994,243, filed Sep. 17, 2007, the contents of all of which are hereby incorporated by reference into this application.

Throughout this application, various publications are referenced by citation in parentheses. The disclosures of these publications in their entireties are hereby incorporated by reference into this application in order to more fully describe the state of the art as known to those skilled therein as of the date of the invention described and claimed herein.

BACKGROUND

The past decade has witnessed tremendous interest in the relatively small natural product resveratrol (1, FIG. 1) based primarily on its possession of a promising and selective array of in vitro and in vivo activity against a collection of disease states, including inflammation, heart disease, aging, and cancer [1]. In fact, its truly unique biochemical profile, coupled with its relatively high concentration in red wine (~100 mM) and near absence in white varietals and grape juice, has led to the popularly held notion that resveratrol is the main protagonist for the so-called "French paradox" [2]. Amazingly, however, virtually no effort has been devoted to the large family of resveratrol-based oligomers (such as 2-8) [3] produced combinatorially by plants throughout the world in response to environmental stress, compounds which initial screening suggest should have unique, if not superior, activity profiles to resveratrol itself [4].

SUMMARY OF THE INVENTION

In one embodiment, this invention provides a process for making a compound having the structure:

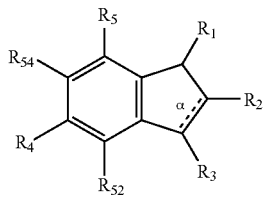

wherein $R_1$, $R_2$, $R_4$, $R_5$, $R_{52}$ and $R_{54}$ are, independently, H, OH, OMe or

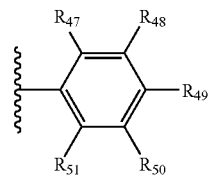

wherein each of $R_{47}$, $R_{48}$, $R_{49}$, $R_{50}$, and $R_{51}$ are, independently, H, OH, alkyl, alkenyl, alkynyl, —$OR_{61}$, —$SR_{62}$, —$N(R_{63})_2$, —$S(O)(O)R_{64}$, —$C(O)OR_{65}$, —$R_{66}OR_{67}$, cycloalkyl, cycloalkenyl, a substituted or unsubstituted aryl, a substituted or unsubstituted heteroaryl, a substituted or unsubstituted heterocyclyl, or X, where X is a halogen, where $R_{61}$, $R_{62}$, $R_{64}$, $R_{65}$, $R_{67}$, and each occurrence of $R_{63}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{66}$ is alkylene, alkenylene or alkynylene, wherein each occurrence of alkyl, alkenyl, alkynyl, alkylene, alkenylene, and alkynylene is substituted or unsubstituted, $R_3$ is H, =O, —OH, X, —$OR_{68}$, —$SR_{69}$, —$N(R_{70})_2$,

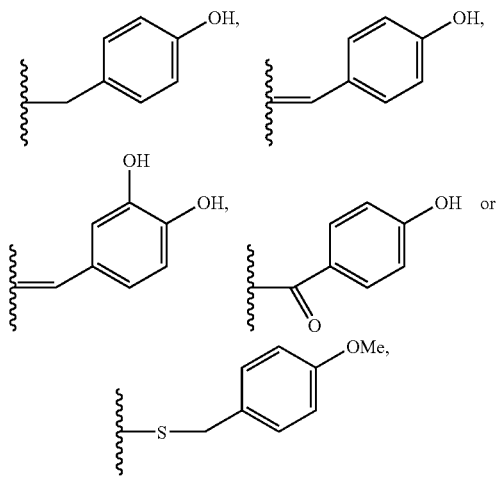

where X is a halogen, and where $R_{68}$, $R_{69}$ and each occurrence of $R_{70}$ are, independently, alkyl, alkenyl, or alkynyl, wherein each occurrence of alkyl, alkenyl, or alkynyl, is substituted or unsubstituted, and where bond α is present or absent, the process comprising:

a) contacting a compound having the structure:

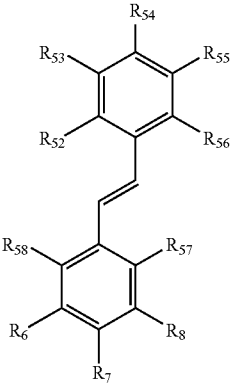

wherein $R_{52}$ and $R_{54}$ are defined as above, $R_6$, $R_7$, $R_8$, $R_{53}$, $R_{55}$, $R_{56}$, $R_{57}$, and $R_{58}$, are, independently, H, OH, alkyl, alkenyl, alkynyl, —$OR_{71}$, —$SR_{72}$, —$N(R_{73})_2$, —$S(O)(O)R_{74}$, —$C(O)OR_{75}$, —$R_{76}OR_{77}$, —$R_{76}R_{77}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{71}$, $R_{72}$, $R_{74}$, $R_{75}$, $R_{77}$ and each occurrence of $R_{73}$ are, independently, H, alkyl, alkenyl, alkynyl cycloalkyl, cycloalkenyl, a substituted or unsubstituted aryl, a substituted or unsubstituted heteroaryl, a substituted or unsubstituted heterocyclyl, and where $R_{76}$ is alkylene, alkenylene or alkynylene, wherein each occurrence of alkyl, alkenyl, alkynyl, alkylene, alkenylene, and alkynylene is substituted or unsubstituted, with an organolithium reagent;

b) contacting the product of step a) with a substituted benzaldehyde so as to form a compound having the structure:

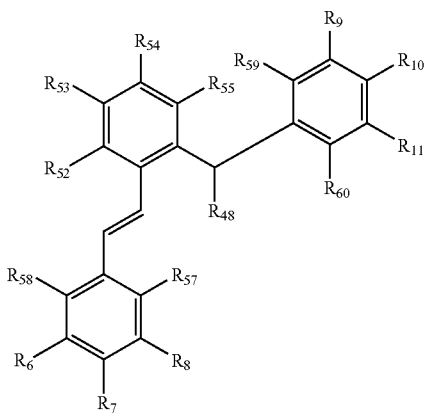

wherein $R_6$, $R_7$, $R_8$, $R_{52}$, $R_{53}$, $R_{54}$, $R_{55}$, $R_{57}$, and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, wherein each occurrence of alkyl, alkenyl, alkynyl, alkylene, alkenylene, and alkynylene is substituted or unsubstituted; and c) contacting the product of step b) with an organic acid so as to produce the compound.

In one embodiment this invention provides a process for making a compound having the structure:

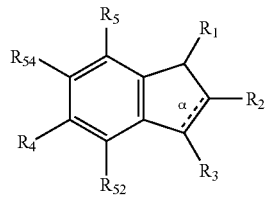

wherein $R_1$, $R_2$, $R_4$, $R_5$, $R_{52}$ and $R_{54}$ are, independently, H, OH, OMe or

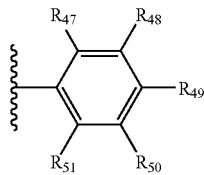

wherein each of $R_{47}$, $R_{48}$, $R_{49}$, $R_{50}$, and $R_{51}$ are, independently, H, OH, alkyl, alkenyl, alkynyl, —$OR_{61}$, —$SR_{62}$, —$N(R_{63})_2$, —$S(O)(O)R_{64}$, —$C(O)OR_{65}$, —$R_{66}OR_{67}$, —$R_{66}R_{67}$, cycloalkyl, cycloalkenyl, a substituted or unsubstituted aryl, a substituted or unsubstituted heteroaryl, a substituted or unsubstituted heterocyclyl, or X, where X is a halogen, where $R_{61}$, $R_{62}$, $R_{64}$, $R_{65}$, $R_{67}$, and each occurrence of $R_{63}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{66}$ is alkylene, alkenylene or alkynylene, wherein each occurrence of alkyl, alkenyl, alkynyl, alkylene, alkenylene, and alkynylene is substituted or unsubstituted, $R_3$ is =O, —OH, X, —$OR_{68}$, —$SR_{69}$, —$N(R_{70})_2$,

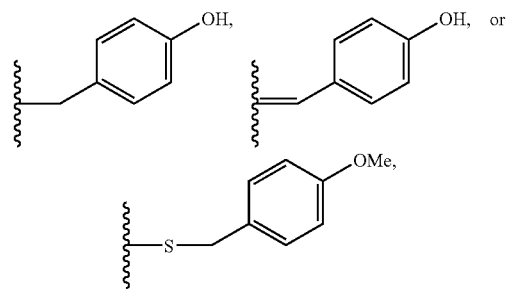

where is a halogen, and where $R_{68}$, $R_{69}$ and each occurrence of $R_{70}$ are, independently, alkyl, alkenyl, or alkynyl, wherein each occurrence of alkyl, alkenyl, or alkynyl, is substituted or unsubstituted, and where bond α is present or absent, the process comprising:

a) contacting a compound having the structure:

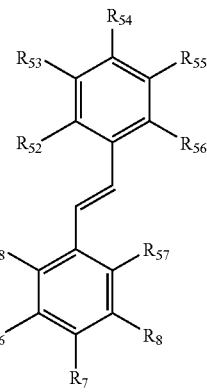

wherein $R_{52}$ and $R_{54}$ are defined as above, $R_6$, $R_7$, $R_8$, $R_{53}$, $R_{55}$, $R_{56}$, $R_{57}$, and $R_{58}$, are, independently, H, OH, alkyl, alkenyl, alkynyl, —OR$_{71}$, —SR$_{72}$, —N(R$_{73}$)$_2$, —S(O)(O)R$_{74}$, —C(O)OR$_{75}$, —R$_{76}$R$_{77}$, —R$_{76}$R$_{77}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{71}$, R$_{72}$, R$_{74}$, R$_{75}$, R$_{77}$ and each occurrence of R$_{73}$ are, independently, H, alkyl, alkenyl, alkynyl cycloalkyl, cycloalkenyl, a substituted or unsubstituted aryl, a substituted or unsubstituted heteroaryl, a substituted or unsubstituted heterocyclyl, and where R$_{76}$ is alkylene, alkenylene or alkynylene, wherein each occurrence of alkyl, alkenyl, alkynyl, alkylene, alkenylene, and alkynylene is substituted or unsubstituted, with an organolithium reagent;

b) contacting the product of step a) with a substituted benzaldehyde so as to form a compound having the structure:

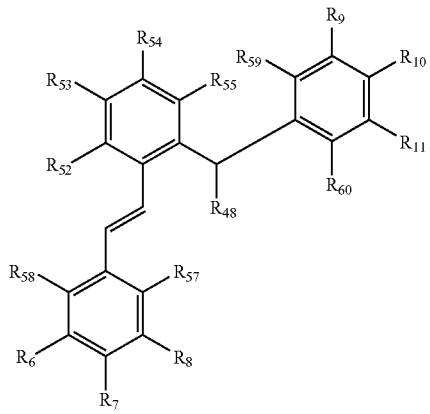

wherein R$_6$, R$_7$, R$_8$, R$_{52}$, R$_{53}$, R$_{54}$, R$_{55}$, R$_{57}$, and R$_{58}$ are defined as above, R$_{48}$ is OH, R$_9$, R$_{10}$, R$_{11}$, R$_{59}$, and R$_{60}$, are, independently, H, OH, alkyl, alkenyl, alkynyl, —OR$_{78}$, —SR$_{79}$, —N(R$_{80}$)$_2$, —S(O)(O) R$_{81}$, —C(O)OR$_{82}$, —R$_{83}$OR$_{84}$, —R$_{83}$R$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{78}$, R$_{79}$, R$_{81}$, R$_{82}$, R$_{84}$ and each occurrence of R$_{80}$ are, independently, H, alkyl, alkenyl, or alkynyl, and where R$_{83}$ is is alkylene, alkenylene or alkynylene, wherein each occurrence of alkyl, alkenyl, alkynyl, alkylene, alkenylene, and alkynylene is substituted or unsubstituted; and d) contacting the product of step b) with an organic acid so as to produce the compound.

In an embodiment, R$_1$ is

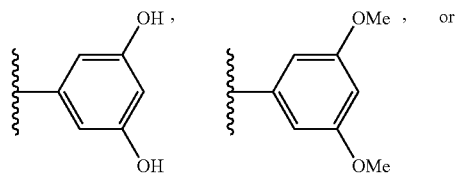

R$_2$ is

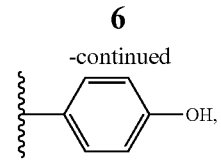

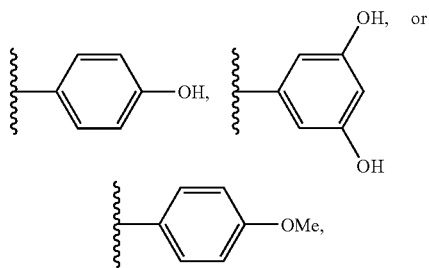

R$_3$ is
=O, —OH

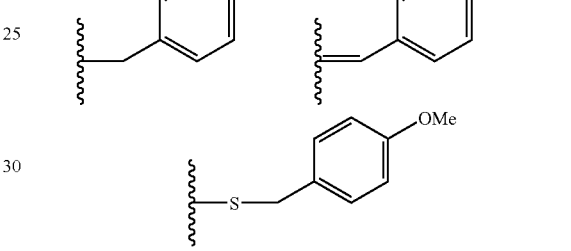

R$_4$ is —OH or —OMe,
R$_5$ is —OH or —OMe,
R$_{52}$ and R$_{54}$ are H,
where bond α is present only when R$_3$ is

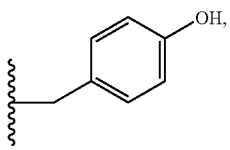

wherein the compound of step a) has the structure:

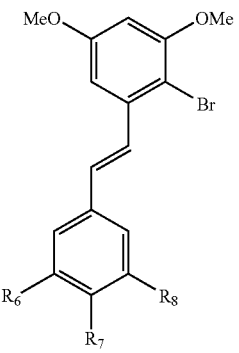

wherein either R$_7$ is —OMe and R$_6$ and R$_8$ are —H, or R$_7$ is —H and R$_6$ and R$_8$ are —OMe, and
wherein in step b) the product of step a) is contacted with 3,5-dimethoxybenzaldehyde or 4-methoxybenzaldehyde so as to form a compound having the structure:

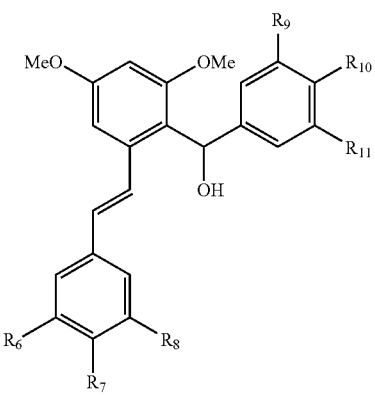

wherein either $R_7$, $R_9$ and $R_{11}$ are —OMe and $R_6$, $R_8$ and $R_{10}$ are H, or wherein $R_7$, $R_9$ and $R_{11}$ are H and $R_6$, $R_8$ and $R_{10}$ are —OMe.

In an embodiment, this invention provides a process for making a compound having the structure:

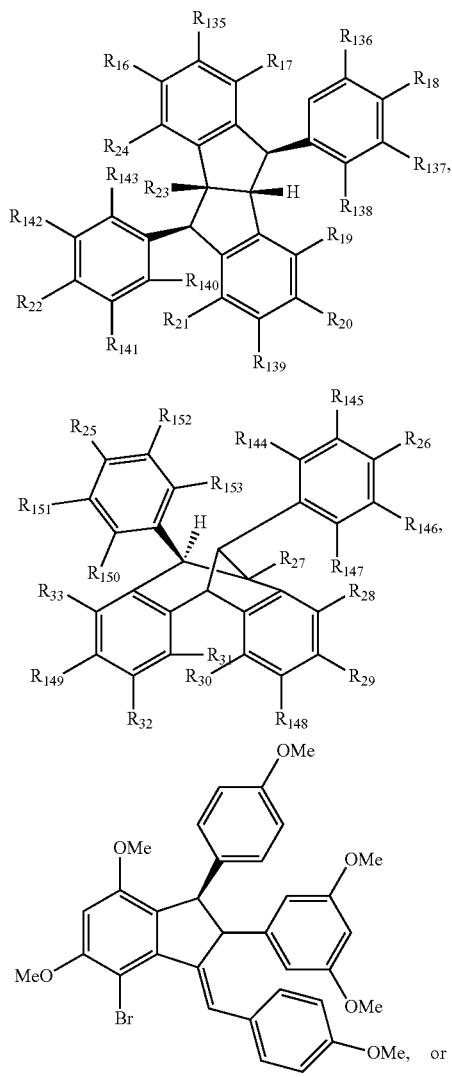

wherein $R_{23}$ and $R_{27}$ are, independently, H or X, wherein $R_{16}$, $R_{17}$, $R_{18}$, $R_{19}$, $R_{20}$, $R_{21}$, $R_{22}$, $R_{24}$, $R_{25}$, $R_{26}$, $R_{28}$, $R_{29}$, $R_{30}$, $R_{31}$, $R_{32}$, $R_{33}$, $R_{135}$, $R_{136}$, $R_{137}$, $R_{138}$, $R_{139}$, $R_{140}$, $R_{141}$, $R_{142}$, $R_{143}$, $R_{144}$, $R_{145}$, $R_{146}$, $R_{147}$, $R_{148}$, $R_{149}$, $R_{150}$, $R_{151}$, $R_{152}$, $R_{153}$ are, independently, H, OH, alkyl, alkenyl, alkynyl, —$OR_{154}$, —$SR_{155}$, —$N(R_{156})_2$, —$S(O)(O)R_{157}$, —$C(O)OR_{158}$, —$R_{159}OR_{160}$, —$R_{159}R_{160}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{154}$, $R_{155}$, $R_{157}$, $R_{158}$, $R_{160}$ and each occurrence of $R_{156}$ are, independently, H, alkyl, alkenyl, or alkynyl, and where $R_{159}$ is is alkylene, alkenylene or alkynylene, wherein each occurrence of alkyl, alkenyl, alkynyl, alkylene, alkenylene, and alkynylene is substituted or unsubstituted, comprising contacting a compound having the structure:

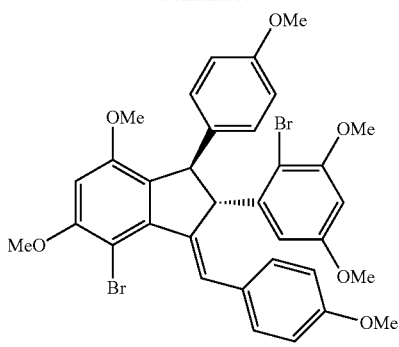

wherein $R_{12}$ and $R_{13}$ are, independently,

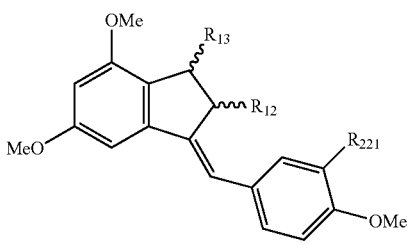

and $R_{221}$ is H or —OMe, with bromine in a first suitable solvent so as to produce the compound.

This invention provides a process for making a compound having the structure:

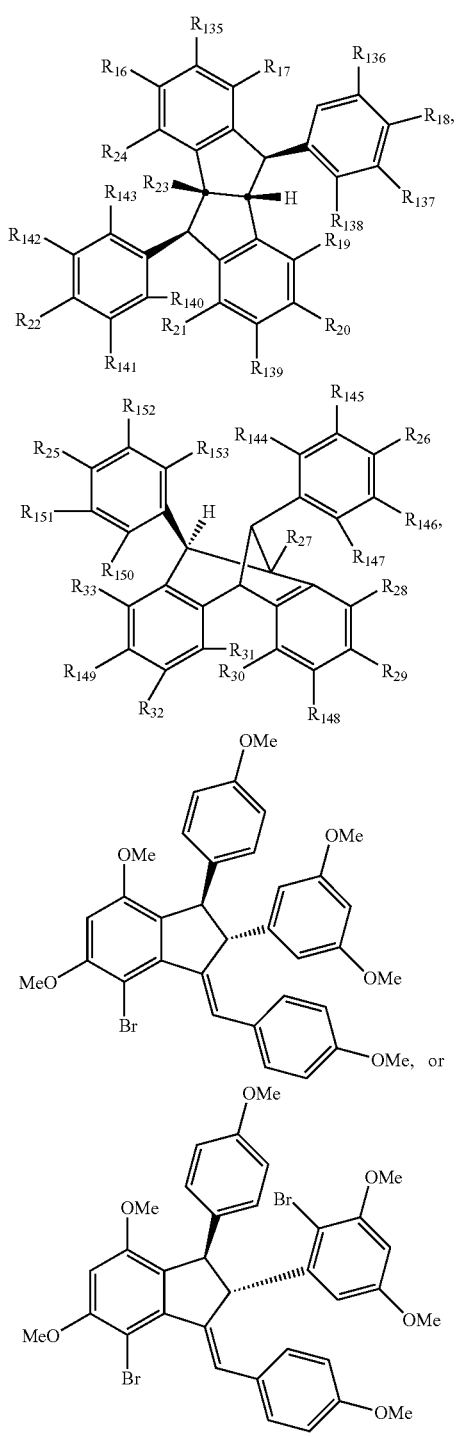

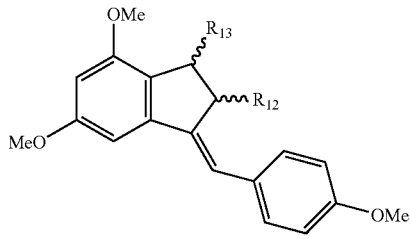

wherein $R_{23}$ and $R_{27}$ are, independently, H or X,
wherein $R_{16}$, $R_{17}$, $R_{18}$, $R_{19}$, $R_{20}$, $R_{21}$, $R_{22}$, $R_{24}$, $R_{25}$, $R_{26}$, $R_{28}$, $R_{29}$, $R_{30}$, $R_{31}$, $R_{32}$, $R_{33}$, $R_{135}$, $R_{136}$, $R_{137}$, $R_{138}$, $R_{139}$, $R_{140}$, $R_{141}$, $R_{142}$, $R_{143}$, $R_{144}$, $R_{145}$, $R_{146}$, $R_{147}$, $R_{148}$, $R_{149}$, $R_{150}$, $R_{151}$, $R_{152}$, $R_{153}$ are, independently, H, OH, alkyl, alkenyl, alkynyl, —$OR_{154}$, —$SR_{155}$, —$N(R_{156})_2$, —$S(O)(O)R_{157}$, —$C(O)OR_{158}$, —$R_{159}OR_{160}$, —$R_{159}R_{160}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{154}$, $R_{155}$, $R_{157}$, $R_{158}$, $R_{160}$ and each occurrence of $R_{156}$ are, independently, H, alkyl, alkenyl, or alkynyl, and where $R_{159}$ is is alkylene, alkenylene or alkynylene, wherein each occurrence of alkyl, alkenyl, alkynyl, alkylene, alkenylene, and alkynylene is substituted or unsubstituted, comprising contacting a compound having the structure:

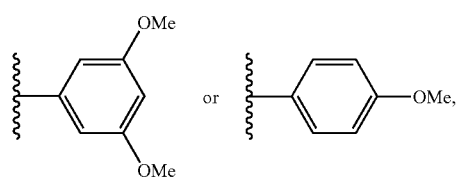

wherein $R_{12}$ and $R_{13}$ are, independently, OMe or

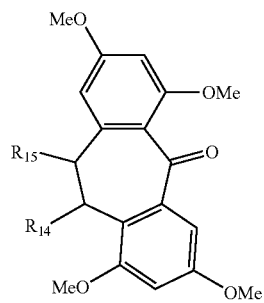

with bromine in a first suitable solvent so as to produce the compound.

This invention provides a process for making a compound having the structure:

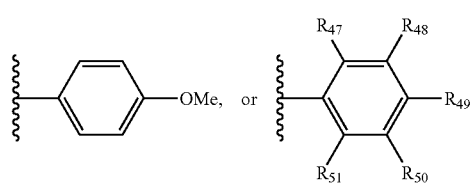

wherein $R_{14}$ and $R_{15}$ are, independently, =O, a halogen, —OH, —OAc, wherein each of $R_{47}$, $R_{48}$, $R_{49}$, $R_{50}$, and $R_{51}$ are, independently, H, OH, alkyl, alkenyl, alkynyl, —$OR_{61}$, —$SR_{62}$, —$N(R_{63})_2$, —$S(O)(O)R_{64}$, —$C(O)OR_{65}$, —$R_{66}OR_{67}$, —$R_{66}R_{67}$, cycloalkyl, cycloalkenyl, a substituted or unsubstituted aryl, a substituted or unsubstituted heteroaryl, a substituted or unsubstituted heterocyclyl, or X, where X is a halogen, where $R_{61}$, $R_{62}$, $R_{64}$, $R_{65}$, $R_{67}$, and each occurrence of $R_{63}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{66}$ is alkylene, alkenylene or alkynylene, wherein each occurrence of alkyl, alkenyl, alkynyl, alkylene, alkenylene, and alkynylene is substituted or unsubstituted, the process comprising contacting a compound having the structure:

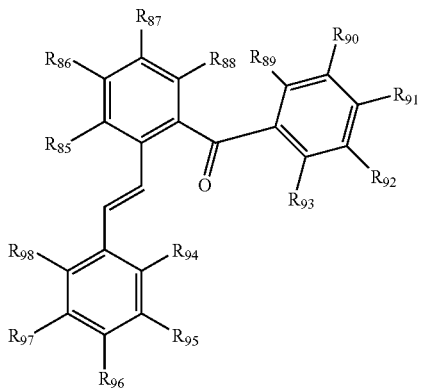

wherein $R_{85}$, $R_{86}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ are, independently, H, OH, alkyl, alkenyl, alkynyl, —$OR_{99}$, —$SR_{100}$, —$N(R_{101})_2$, —$S(O)(O)R_{102}$, —$C(O)OR_{103}$, —$R_{104}OR_{105}$, —$R_{104}R_{105}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{99}$, $R_{100}$, $R_{102}$, $R_{103}$, and $R_{105}$ and each occurrence of $R_{101}$ are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and wherein $R_{104}$ is is alkylene, alkenylene or alkynylene, wherein each occurrence of alkyl, alkenyl, alkynyl, alkylene, alkenylene, and alkynylene is substituted or unsubstituted, with bromine in a first suitable solvent so as to produce the compound.

This invention provides a composition, free of plant extract, comprising a compound having the structure:

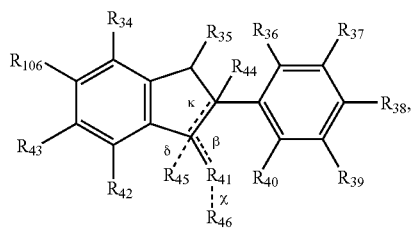

wherein
$R_{34}$, $R_{35}$, $R_{42}$, $R_{43}$, and $R_{106}$ are, independently, H, OH, OMe or

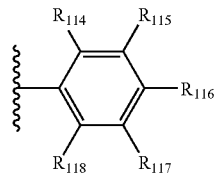

wherein each of $R_{114}$, $R_{115}$, $R_{116}$, $R_{117}$, and $R_{118}$ are, independently, H, OH, alkyl, alkenyl, alkynyl, —$OR_{107}$, —$SR_{108}$, —$N(R_{109})_2$, —$S(O)(O)R_{110}$, —$C(O)OR_{111}$, —$R_{112}OR_{113}$, —$R_{112}R_{113}$, cycloalkyl, cycloalkenyl, a substituted or unsubstituted aryl, a substituted or unsubstituted heteroaryl, a substituted or unsubstituted heterocyclyl, or X, where X is a halogen, where $R_{107}$, $R_{108}$, $R_{109}$, $R_{110}$, $R_{111}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene, wherein each occurrence of alkyl, alkenyl, alkynyl, alkylene, alkenylene, and alkynylene is substituted or unsubstituted, wherein $R_{36}$, $R_{37}$, $R_{38}$, $R_{39}$ and $R_{40}$ are, independently, H, OH, alkyl, alkenyl, alkynyl, —$OR_{114}$, —$SR_{115}$, —$N(R_{116})_2$, —$S(O)(O)R_{117}$, —$C(O)OR_{118}$, —$R_{119}OR_{120}$, —$R_{119}R_{100}$, cycloalkyl, cycloalkenyl, a substituted or unsubstituted aryl, a substituted or unsubstituted heteroaryl, a substituted or unsubstituted heterocyclyl, or X, where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{119}$ is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

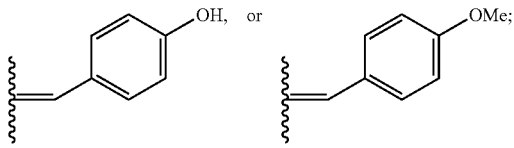

or bond β is absent, bond κ is absent, bond δ is present, $R_{45}$ is present, bond χ and $R_{46}$ are absent, $R_{44}$ is present, and $R_{41}$ is —$OC(O)(CF_3)$, —OH, -alkyl, alkenyl, alkynyl, cycloalkyl, cycloalkenyl, a substituted or unsubstituted aryl, a substituted or unsubstituted heteroaryl, a substituted or unsubstituted heterocyclyl,

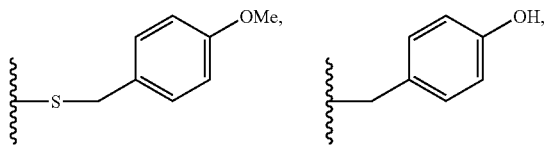

X, $OR_{120}$, $-SR_{121}$, $-N(R_{122})_2$, or $-R'Y$; or
  wherein each occurrence of alkyl, alkenyl, alkynyl, alkylene, alkenylene, and alkynylene is substituted or unsubstituted,
  bond β is absent, bond κ is present, bond δ is absent, $R_{44}$ and $R_{45}$ are absent, bond χ and $R_{46}$ are absent, and $R_{41}$ is H, —OH,

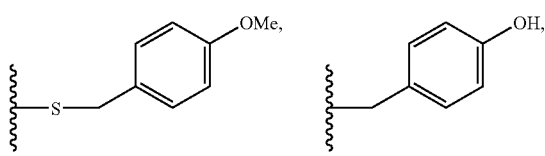

X, $OR_{120}$, $-SR_{121}$, $-N(R_{122})_2$, or $-R'Y$,
  where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or
  wherein each occurrence of alkyl, alkenyl, alkynyl, alkylene, alkenylene, and alkynylene is substituted or unsubstituted,
  bond β is absent, bond κ is absent, each of bond δ, bond χ, $R_{44}$, $R_{45}$ and $R_{46}$ are present, and $R_{41}$ is joined to $R_{40}$ to form a pentacyclic ring,
  $R_{44}$, if present, is H,
  $R_{45}$, if present, is H or Br,
  $R_{46}$, if present, is

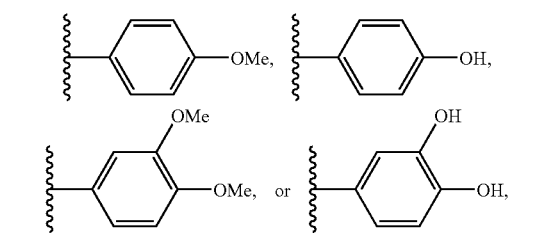

or, cycloalkyl, cycloalkenyl, a substituted or unsubstituted aryl, a substituted or unsubstituted heteroaryl, a substituted or unsubstituted heterocyclyl,
  $R_{106}$ is H,
  wherein when $R_{34}$ and $R_{43}$ are OH, $R_{35}$ is

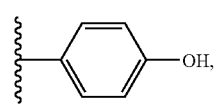

$R_{36}$, $R_{38}$, $R_{40}$, $R_{42}$ and $R_{44}$ are H, $R_{37}$ and $R_{39}$ are OH, and bond β is present, then $R_{41}$ is O or

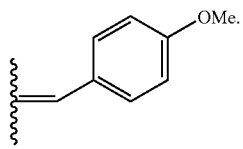

In an embodiment, this invention provides a composition, free of plant extract, comprising a compound having the structure:

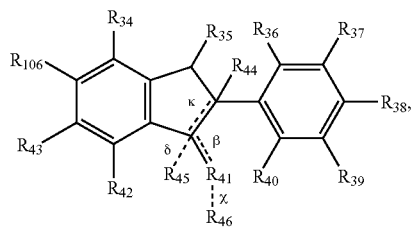

wherein
$R_{34}$, $R_{35}$, $R_{42}$, $R_{43}$, and $R_{106}$ are, independently, H, OH, OMe or

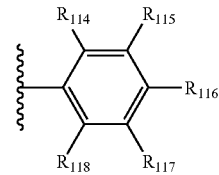

wherein each of $R_{114}$, $R_{115}$, $R_{116}$, $R_{117}$, and $R_{118}$ are, independently, H, OH, alkyl, alkenyl, alkynyl, $-OR_{107}$, $-SR_{108}$, $-N(R_{109})_2$, $-S(O)(O)R_{110}$, $-C(O)OR_{111}$, $-R_{112}OR_{113}$, $-R_{112}R_{113}$, cycloalkyl, cycloalkenyl, a substituted or unsubstituted aryl, a substituted or unsubstituted heteroaryl, a substituted or unsubstituted heterocyclyl, or X,
  where X is a halogen, where $R_{107}$, $R_{108}$, $R_{110}$, $R_{111}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene,
wherein each occurrence of alkyl, alkenyl, alkynyl, alkylene, alkenylene, and alkynylene is substituted or unsubstituted,
wherein $R_{36}$, $R_{37}$, $R_{38}$, $R_{39}$ and $R_{40}$ are, independently, H, OH, alkyl, alkenyl, alkynyl, $-OR_{114}$, $-SR_{115}$, $-N(R_{116})_2$, $-S(O)(O)R_{117}$, $-C(O)OR_{118}$, $-R_{190}OR_{120}$, $-R_{119}R_{120}$, cycloalkyl, cycloalkenyl, a substituted or unsubstituted aryl, a substituted or unsubstituted heteroaryl, a substituted or unsubstituted heterocyclyl, or X,
  where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{119}$ is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

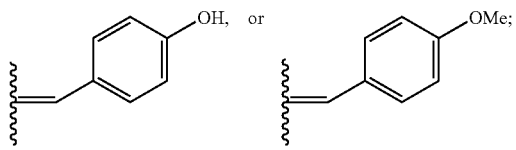

or bond β is absent, bond κ is absent, bond δ is present, $R_{45}$ is present, bond χ and $R_{46}$ are absent, $R_{44}$ is present, and $R_{41}$ is —OC(O)(CF$_3$), —OH, -alkyl, alkenyl, alkynyl, cycloalkyl, cycloalkenyl, a substituted or unsubstituted aryl, a substituted or unsubstituted heteroaryl, a substituted or unsubstituted heterocyclyl,

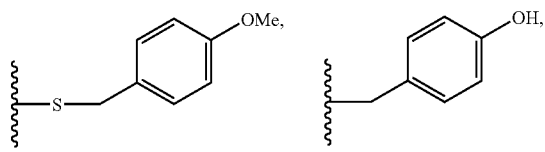

X, OR$_{120}$, —SR$_{121}$, —(R$_{122}$)$_2$, or —R'Y; or wherein each occurrence of alkyl, alkenyl, alkynyl, alkylene, alkenylene, and alkynylene is substituted or unsubstituted, bond β is absent, bond κ is present, bond δ is absent, $R_{44}$ and $R_{45}$ are absent, bond χ and $R_{46}$ are absent, and $R_{41}$ is —OH,

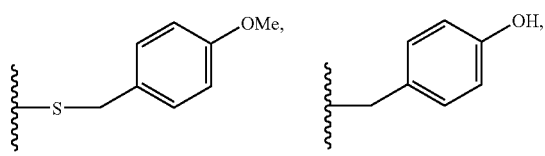

X, OR$_{120}$, —SR$_{121}$, —N(R$_{122}$)$_2$, or —R'Y.

where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or wherein each occurrence of alkyl, alkenyl, alkynyl, alkylene, alkenylene, and alkynylene is substituted or unsubstituted, bond β is absent, bond κ is absent, each of bond δ, bond χ, $R_{44}$, $R_{45}$ and $R_{46}$ are present, and $R_{41}$ is joined to $R_{40}$ to form a pentacyclic ring, $R_{44}$, if present, is H, $R_{45}$, if present, is H or Br, $R_{46}$, if present, is

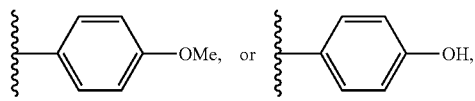

cycloalkyl, cycloalkenyl, a substituted or unsubstituted aryl, a substituted or unsubstituted heteroaryl, a substituted or unsubstituted heterocyclyl, $R_{106}$ is H, wherein when $R_{34}$ and $R_{43}$ are OH, $R_{35}$ is

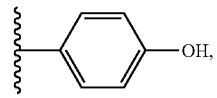

$R_{36}$, $R_{39}$, $R_{40}$, $R_{42}$ and $R_{44}$ are H, $R_{37}$ and $R_{38}$ are OH, and bond β is present, then $R_{41}$ is O or

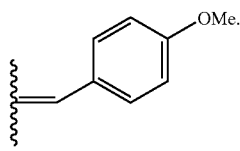

In an embodiment the composition comprises a compound having the structure:

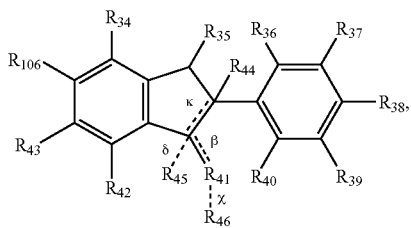

wherein $R_{34}$ and $R_{43}$ are, independently, OH or OMe, $R_{35}$ is

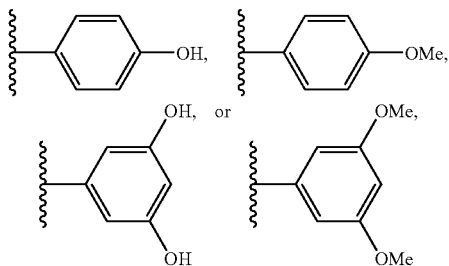

$R_{36}$ is Br, or H, $R_{37}$ is H, OH, or OMe, $R_{38}$ is H, OH, or OMe, $R_{39}$ is H, OH, or OMe, $R_{40}$ is H, or is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

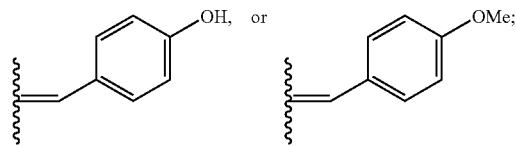

or
bond β is absent, bond κ is absent, bond δ is present, $R_{45}$ is present, bond χ and $R_{46}$ are absent, $R_{44}$ is present, and $R_{41}$ is —OC(O)(CF$_3$), —OH,

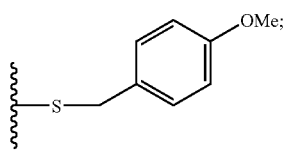 [SMILES: *SCc1ccc(OC)cc1]

or
bond β is absent, bond κ is present, bond δ is absent, $R_{44}$ and $R_{45}$ are absent, bond χ and $R_{46}$ are absent, and $R_{41}$ is

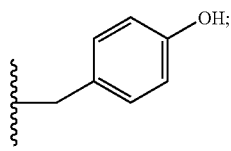 [SMILES: *Cc1ccc(O)cc1]

or
bond β is absent, bond κ is absent, each of bond δ, bond χ, $R_{44}$, $R_{45}$ and $R_{46}$ are present, and $R_{41}$ is joined to $R_{40}$ to form a pentacyclic ring,
$R_{42}$ is H, or Br,
$R_{43}$ is H, OMe, or OH
$R_{44}$, if present, is H,
$R_{45}$, if present, is H or Br,
$R_{46}$, if present, is

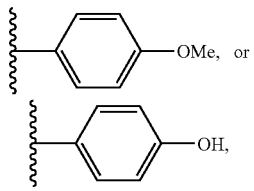

and
$R_{106}$ is H,
wherein when $R_{34}$ and $R_{43}$ are OH, $R_{35}$ is

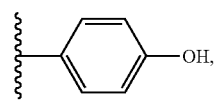

$R_{36}$, $R_{38}$, $R_{40}$, $R_{42}$ and $R_{44}$ are H, $R_{37}$ and $R_{39}$ are OH, and bond β is present, then $R_{41}$ is O or

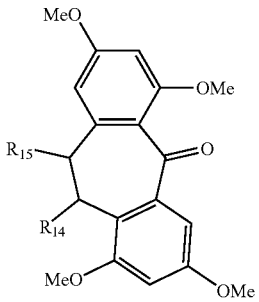

and when $R_{40}$ is joined to $R_{41}$ to form a pentacyclic ring, and $R_{34}$ and $R_{43}$ are OH, $R_{35}$ and $R_{46}$ are

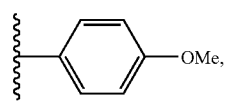

$R_{36}$, $R_{38}$, $R_{42}$ and $R_{44}$ are H, $R_{37}$ and $R_{39}$ are OH, then $R_{45}$ is Br.

This invention provides a compound having the structure:

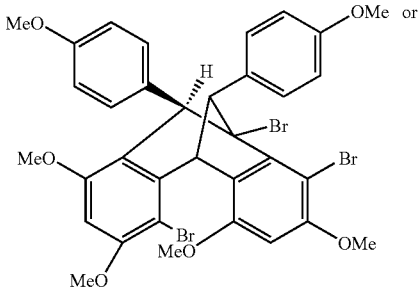

wherein $R_{14}$ is =O, OH, OAc or

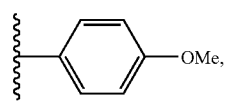

and $R_{15}$ is

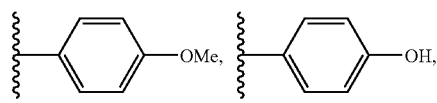

or Br.

This invention provides a compound having the structure:

-continued

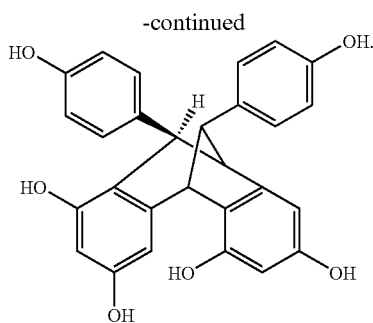

This invention provides a compound having the structure:

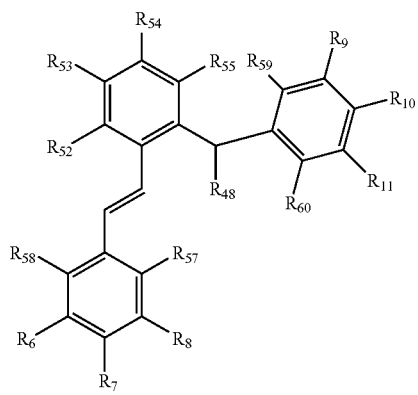

wherein $R_6$, $R_7$, $R_8$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}R_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, and wherein each occurrence of alkyl, alkenyl, alkynyl, alkylene, alkenylene, and alkynylene is substituted or unsubstituted.

This inventions provides a process for making a compound having the structure:

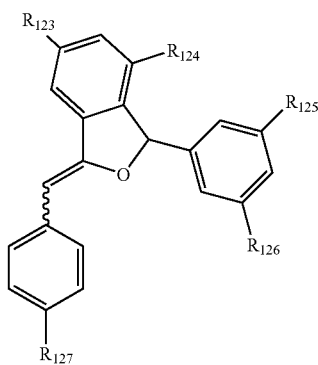

wherein $R_{123}$, $R_{124}$, $R_{125}$, $R_{126}$, and $R_{127}$, are, independently, H, OH, —OMe, alkyl, alkenyl, alkynyl, —$OR_{128}$, —$SR_{129}$, —$N(R_{130})_2$, —$S(O)(O)R_{131}$, —$C(O)OR_{132}$, —$R_{133}OR_{134}$, $R_{133}R_{134}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{128}$, $R_{129}$, $R_{131}$, $R_{132}$, $R_{134}$ and each occurrence of $R_{130}$ are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{133}$ is is alkylene, alkenylene or alkynylene, wherein each occurrence of alkyl, alkenyl, alkynyl, alkylene, alkenylene, and alkynylene is substituted or unsubstituted, the process comprising contacting a compound having the structure:

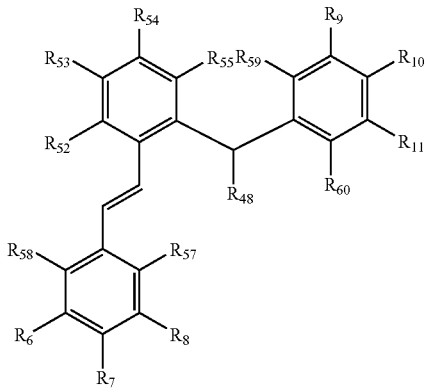

wherein $R_6$, $R_7$, $R_8$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, wherein each occurrence of alkyl, alkenyl, alkynyl, alkylene, alkenylene, and alkynylene is substituted or unsubstituted, with a metal catalyst so as to make the compound.

In an embodiment, this invention provides a process for making a compound having the structure:

21

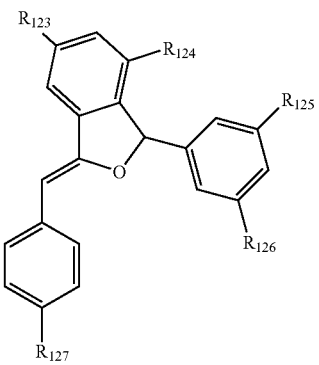

wherein $R_{123}$, $R_{124}$, $R_{125}$, $R_{126}$, and $R_{127}$, are, independently, H, OH, —OMe, alkyl, alkenyl, alkynyl, —$OR_{128}$, —$SR_{129}$, —$N(R_{130})_2$, —$S(O)(O)R_{131}$, —$C(O)OR_{132}$, —$R_{133}OR_{134}$, —$R_{133}R_{134}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{128}$, $R_{129}$, $R_{131}$, $R_{132}$, $R_{134}$ and each occurrence of $R_{130}$ are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{133}$ is is alkylene, alkenylene or alkynylene, wherein each occurrence of alkyl, alkenyl, alkynyl, alkylene, alkenylene, and alkynylene is substituted or unsubstituted, the process comprising contacting a compound having the structure:

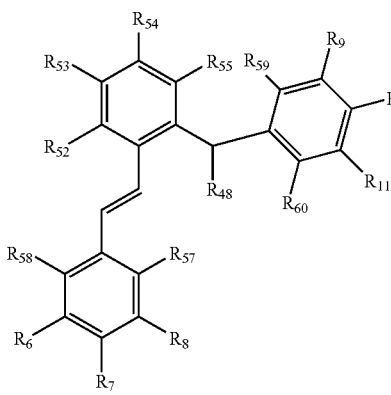

wherein $R_6$, $R_7$, $R_8$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, wherein each occurrence of alkyl, alkenyl, alkynyl, alkylene, alkenylene, and alkynylene is substituted or unsubstituted, with a metal catalyst so as to make the compound.

22

A process is provided for making a compound having the structure:

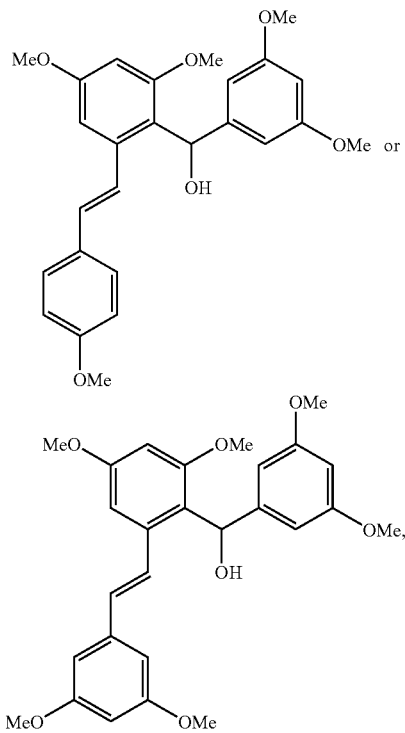

comprising reacting a compound having the structure:

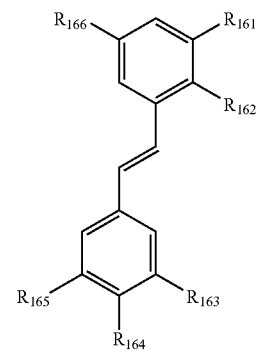

wherein $R_{161}$ and $R_{166}$ are OMe, $R_{162}$ is Br and $R_{165}$ and $R_{163}$ are OMe and $R_{164}$ is H or $R_{165}$ and $R_{163}$ are H and $R_{164}$ is OMe, with n-BuLi and a compound having the structure:

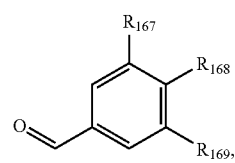

wherein $R_{167}$ is H or OMe, Rise is H or OMe, and $R_{169}$ is H or OMe, so as to produce the compound.

A process is provided for making a compound having the structure:

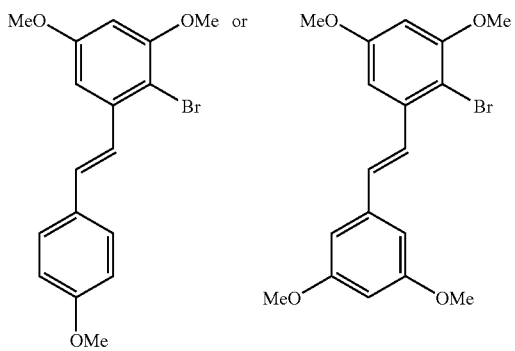 [SMILES: COc1ccc(/C=C/c2cc(OC)cc(OC)c2Br)cc1 ; COc1cc(/C=C/c2cc(OC)cc(OC)c2Br)cc(OC)c1]

comprising:
a) reacting:

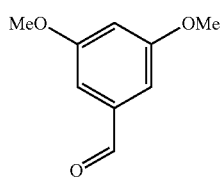

with NaBH$_4$ and PBR$_3$ to produce a compound having the structure:

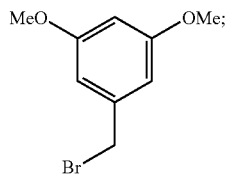 [SMILES: COc1cc(CBr)cc(OC)c1]

b) reacting the product of step a) with NBS in a suitable solvent;
c) reacting the product of step b) with KHMDS and HP(O)(OEt)$_2$ so as to produce a compound having the structure:

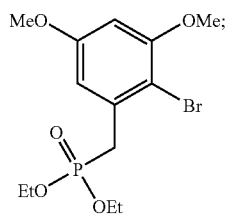 [SMILES: CCOP(=O)(Cc1cc(OC)cc(OC)c1Br)OCC]

d) reacting the product of step c) with KOt-Bu and p-methoxybenzaldehyde or 3,5-dimethoxybenzaldehyde so as to make the compound.

A compound is provided having the structure:

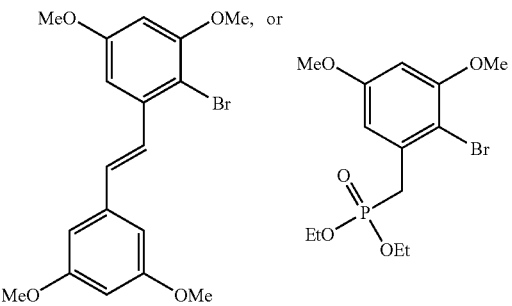

A compound having the structure:

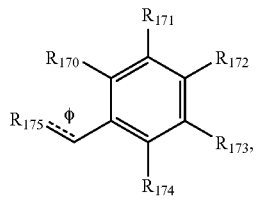

wherein
bond Φ is absent, R$_{170}$ and R$_{172}$ are —OMe, R$_{171}$ and R$_{174}$ are, and R$_{175}$ is —P(O)(OEt)(OEt), R$_{173}$ is Br, or bond Φ is present, R$_{170}$, R$_{171}$, R$_{172}$, R$_{173}$ and R$_{174}$ are, independently, H or OMe.

A compound is provided having the structure:

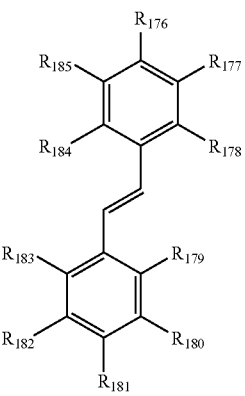

wherein R$_{176}$, R$_{177}$, R$_{178}$, R$_{179}$, R$_{180}$, R$_{181}$, R$_{182}$, R$_{183}$, R$_{184}$, R$_{185}$ are, independently, H, Br, or OMe.

A composition, free of plant extract, is provided comprising a compound having the structure:

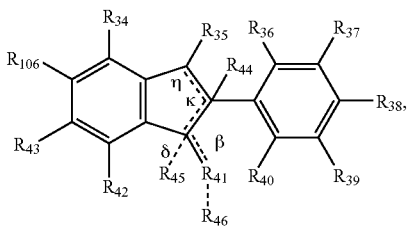

wherein $R_{34}$, $R_{35}$, $R_{42}$, $R_{43}$, and $R_{106}$ are, independently, H, OH, OMe, $OC(O)_{R186}$, or

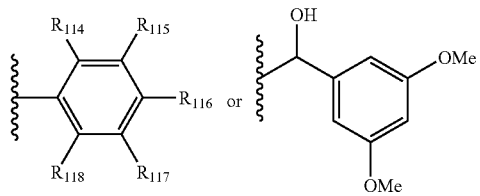

wherein each of $R_{114}$, $R_{115}$, $R_{116}$, $R_{117}$, and $R_{118}$ are, independently, H, OH, —OC(O)alkyl, alkyl, alkenyl, alkynyl, —$OR_{107}$, —$SR_{108}$, —$N(R_{109})_2$, —$S(O)(O)R_{110}$, —$C(O)OR_{111}$, —$R_{112}OR_{113}$, —$R_{112}R_{113}$, cycloalkyl, cycloalkenyl, a substituted or unsubstituted aryl, a substituted or unsubstituted heteroaryl, a substituted or unsubstituted heterocyclyl, or X, where X is a halogen, where $R_{107}$, $R_{108}$, $R_{110}$, $R_{111}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene, wherein each occurrence of alkyl, alkenyl, alkynyl, alkylene, alkenylene, and alkynylene is substituted or unsubstituted, wherein $R_{186}$ is alkyl or alkenyl wherein $R_{36}$, $R_{37}$, $R_{38}$, $R_{39}$ and $R_{40}$ are, independently, H, OH, —OC(O)alkyl, alkyl, alkenyl, alkynyl, —$OR_{114}$, —$SR_{115}$, —$N(R_{116})_2$, —$S(O)(O)$ $R_{117}$, —$C(O)OR_{118}$, —$R_{119}OR_{120}$, —$R_{119}R_{120}$, cycloalkyl, cycloalkenyl, a substituted or unsubstituted aryl, a substituted or unsubstituted heteroaryl, a substituted or unsubstituted heterocyclyl, or X, where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{119}$ is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

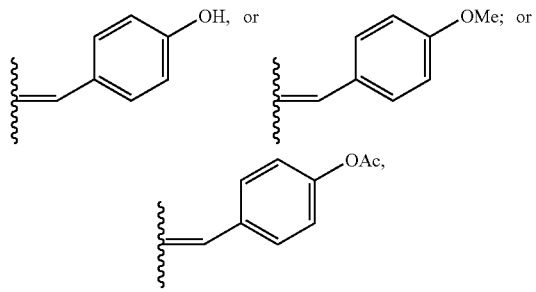

or bond β is absent, bond κ is absent, bond δ is present, $R_{45}$ is present, bond χ and $R_{46}$ are absent, $R_{44}$ is present, and $R_{41}$ is —OC(O)(CF$_3$), —OH, -alkyl, alkenyl, alkynyl, cycloalkyl, cycloalkenyl, a substituted or unsubstituted aryl, a substituted or unsubstituted heteroaryl, a substituted or unsubstituted heterocyclyl,

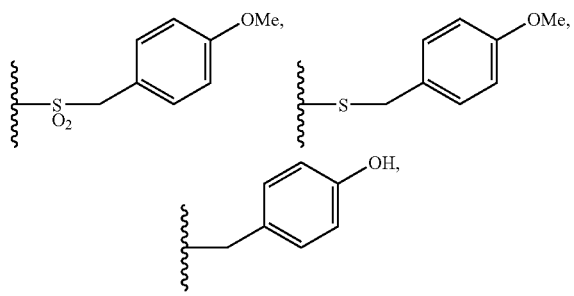

X, $OR_{120}$, —$SR_{121}$, —$N(R_{122})_2$, or —R'Y; or wherein each occurrence of alkyl, alkenyl, alkynyl, alkylene, alkenylene, and alkynylene is substituted or unsubstituted, bond β is absent, bond κ0 is present, bond δ is absent, $R_{44}$ and $R_{45}$ are absent, bond χ and $R_{46}$ are absent, and $R_{41}$ is a halogen, —OH,

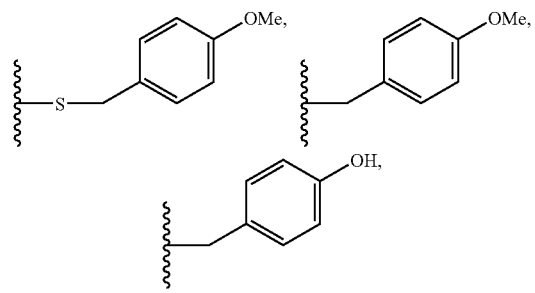

X, $OR_{120}$, —$SR_{121}$, —$N(R_{122})_2$, or —R'Y, where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or wherein each occurrence of alkyl, alkenyl, alkynyl, alkylene, alkenylene, and alkynylene is substituted or unsubstituted, bond β is absent, bond κ is absent, each of bond δ, bond χ, $R_{44}$, $R_{45}$ and $R_{46}$ are present, and $R_{41}$ is joined to $R_{40}$ to form a pentacyclic ring, $R_{44}$, if present, is H, $R_{45}$, if present, is H or Br, $R_{46}$, if present, is

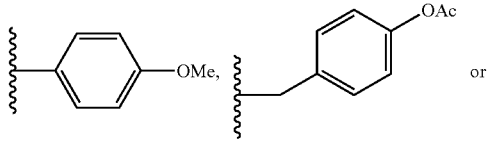

-continued

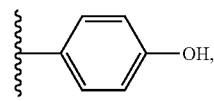

cycloalkyl, cycloalkenyl, a substituted or unsubstituted aryl, a substituted or unsubstituted heteroaryl, a substituted or unsubstituted heterocyclyl, wherein $R_{46}$ is only present if $R_{41}$ is joined to $R_{40}$ to form a pentacyclic ring, $R_{106}$ is H, wherein when $R_{34}$ and $R_{43}$ are OH, $R_{35}$ is

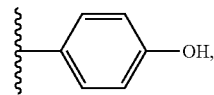

$R_{36}$, $R_{38}$, $R_{40}$, $R_{42}$ and $R_{44}$ are H, $R_{37}$ and $R_{39}$ are OH, and bond β is present, then $R_{41}$ t is O or

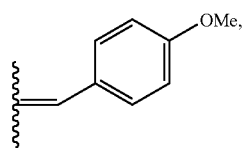

and when $R_{40}$ is joined to $R_{41}$ to form a pentacyclic ring, and $R_{34}$ and $R_{43}$ are OH, $R_{35}$ and $R_{46}$ are

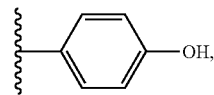

$SR_{36}$, $R_{38}$, $R_{42}$ and $R_{44}$ are H, $R_{37}$ and $R_{39}$ are OH, then $R_{45}$ is Br.

wherein bond η is present or absent, but when present bond κ is absent.

A compound is provided having the structure:

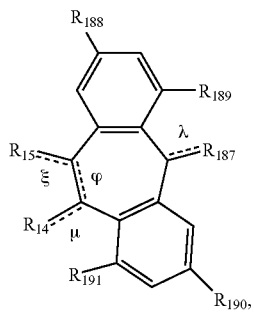

wherein $R_{14}$, $R_{15}$, $R_{188}$, $R_{187}$, $R_{187}$, $R_{189}$, $R_{190}$, $R_{191}$, are, independently, =O, H, OH, —OC(O)alkyl, alkyl, alkenyl, alkynyl, —$OR_{212}$, —$SR_{213}$, —$N(R_{214})_2$, —$S(O)(O)R_{215}$, —$C(O)OR_{216}$, —$R_{217}OR_{218}$, —$R_{217}R_{218}$, —$SO_2$—$R_{219}$, cycloalkyl, cycloalkenyl, a substituted or unsubstituted aryl, a substituted or unsubstituted heteroaryl, a substituted or unsubstituted heterocyclyl, or X, where X is a halogen, where $R_{212}$, $R_{213}$, $R_{215}$, $R_{216}$, $R_{128}$, $R_{219}$, and each occurrence of $R_{214}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{217}$ is alkylene, alkenylene or alkynylene, wherein each occurrence of alkyl, alkenyl, alkynyl, alkylene, alkenylene, and alkynylene is substituted or unsubstituted, wherein bonds φ, ε, λ, and μ are present or absent, but wherein when bond φ is present bonds ε and p are absent, and wherein when bond μ is present bond φ is absent, and wherein when bond ε is present bond φ is absent.

This inventions provides a composition, free of plant extract, comprising one or more of the above compounds.

This invention provides a compound having the structure:

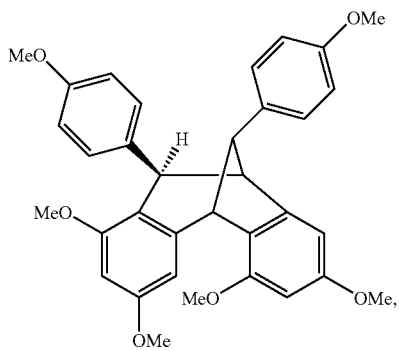

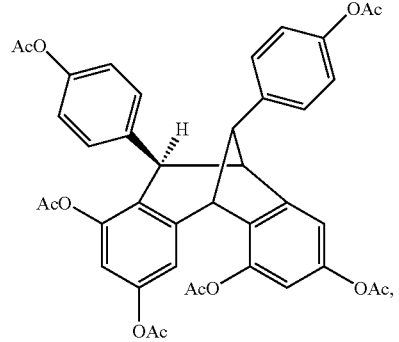

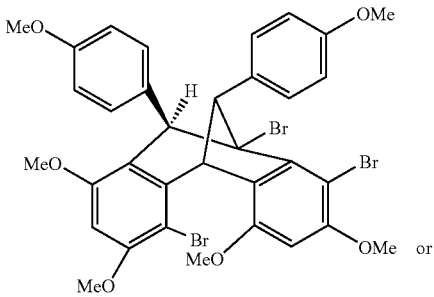

or

-continued

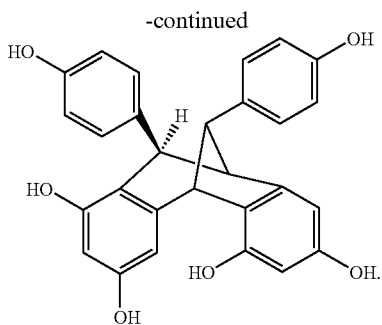

This invention provides a compound having the structure:

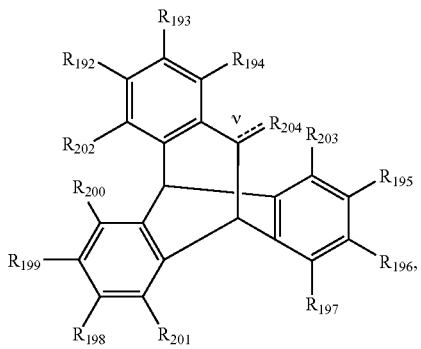

wherein $R_{192}$, $R_{192}$, $R_{193}$, $R_{194}$, $R_{195}$, $R_{196}$, $R_{197}$, $R_{198}$, $R_{199}$, $R_{200}$, $R_{201}$, $R_{202}$, and $R_{203}$ are, independently, H, OH, =O, —OC(O)alkyl, alkyl, alkenyl, alkynyl, —OR$_{205}$, —SR$_{206}$, —N(R$_{207}$)$_2$, —S(O)(O)R$_{208}$, —C(O)OR$_{209}$, —R$_{210}$OR$_{211}$, —R$_{210}$R$_{211}$, cycloalkyl, cycloalkenyl, a substituted or unsubstituted aryl, a substituted or unsubstituted heteroaryl, a substituted or unsubstituted heterocyclyl, or X, where X is a halogen, where $R_{205}$, $R_{206}$, $R_{208}$, $R_{209}$, $R_{211}$, and each occurrence of $R_{207}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{210}$ is alkylene, alkenylene or alkynylene, wherein each occurrence of alkyl, alkenyl, alkynyl, alkylene, alkenylene, and alkynylene is substituted or unsubstituted and wherein bond v is present or absent.

A compound is provided having the structure:

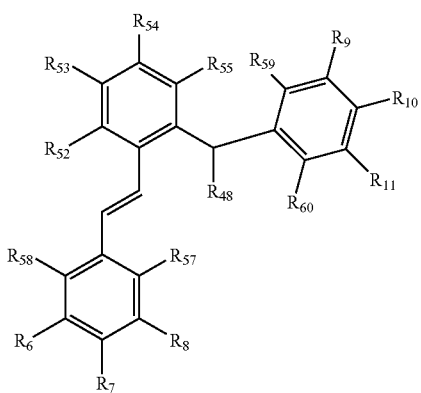

wherein $R_6$, $R_7$, $R_8$, $R_9$, $R_{10}$, $R_{11}$, $R_{52}$, $R_{53}$, $R_{54}$, $R_{55}$, $R_{57}$, $R_{58}$, $R_{59}$, $R_{60}$ are, independently, H, OH, —OMe, —OAc, alkyl, alkenyl, alkynyl, —OR$_{78}$, —SR$_{79}$, —N(R$_{80}$)$_2$, —S(O)(O)R$_{81}$, —C(O)OR$_{82}$, —R$_{83}$OR$_{84}$, —R$_{83}$R$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, and wherein each occurrence of alkyl, alkenyl, alkynyl, alkylene, alkenylene, and alkynylene is substituted or unsubstituted $R_{48}$ is H, =O, OH, —OAc, —OMe,

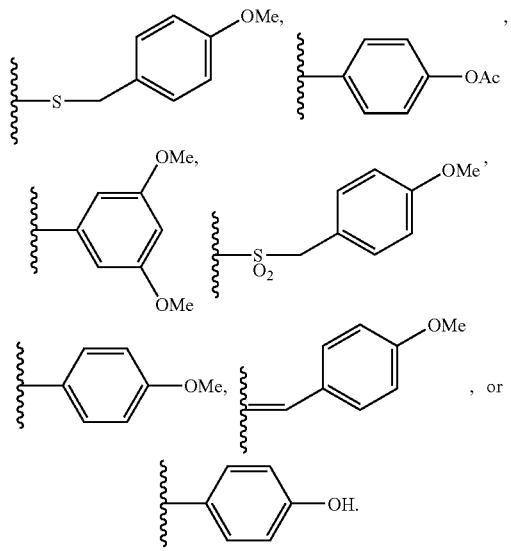

, or

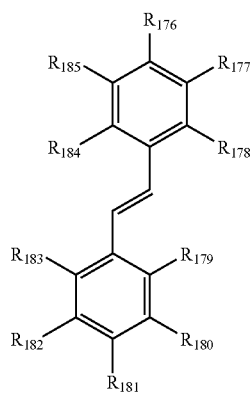

A compound is provided having the structure:

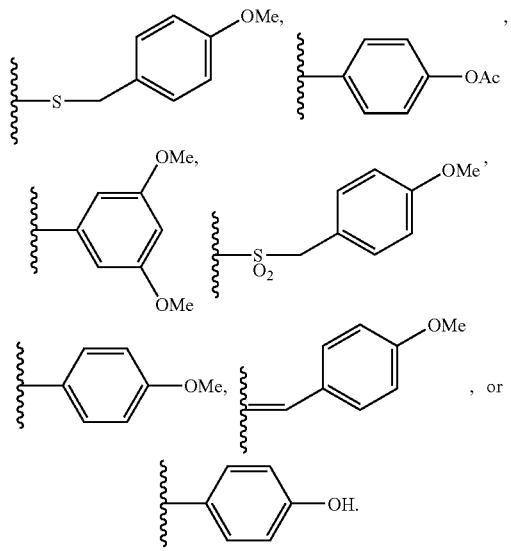

wherein $R_{176}$, $R_{177}$, $R_{178}$, $R_{179}$, $R_{180}$, $R_{181}$, $R_{182}$, $R_{183}$, $R_{184}$, $R_{185}$ are, independently, H, Br, OH, OAc, or OMe, wherein when $R_{185}$ and $R_{177}$ are OMe, $R_{176}$, $R_{178}$, $R_{179}$, $R_{180}$, $R_{182}$, $R_{183}$, $R_{184}$, are H and $R_{178}$ is Br, then $R_{181}$ is Br, OH, H or OMe.

A process is provided for making a compound having the structure:

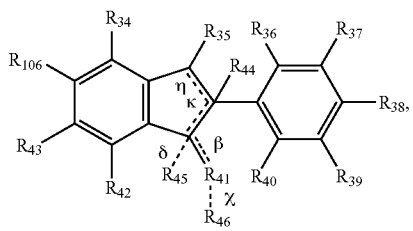

wherein $R_{34}$, $R_{35}$, $R_{42}$, $R_{43}$, and $R_{106}$ are, independently, H, OH, Ome, $OC(O)_{R186}$, or

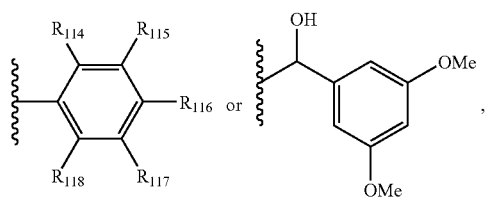

wherein each of $R_{114}$, $R_{115}$, $R_{116}$, $R_{117}$, and $R_{118}$ are, independently, H, OH, —OC(O)alkyl, alkyl, alkenyl, alkynyl, —$OR_{107}$, —$SR_{108}$, —$N(R_{109})_2$, —$S(O)(O)R_{110}$, —$C(O)OR_{111}$, —$R_{112}R_{113}$, —$R_{112}R_{113}$, cycloalkyl, cycloalkenyl, a substituted or unsubstituted aryl, a substituted or unsubstituted heteroaryl, a substituted or unsubstituted heterocyclyl, or X, where X is a halogen, where $R_{107}$, $R_{108}$, $R_{110}$, $R_{111}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene, wherein each occurrence of alkyl, alkenyl, alkynyl, alkylene, alkenylene, and alkynylene is substituted or unsubstituted, wherein $R_{186}$ is alkyl or alkenyl wherein $R_{36}$, $R_{37}$, $R_{38}$, $R_{39}$ and $R_{40}$ are, independently, H, OH, —OC(O)alkyl, alkyl, alkenyl, alkynyl, —$OR_{114}$, —$SR_{115}$, —$N(R_{116})_2$, —$S(O)(O)R_{117}$, —$C(O)OR_{115}$, —$R_{119}OR_{120}$, —$R_{119}R_{120}$, cycloalkyl, cycloalkenyl, a substituted or unsubstituted aryl, a substituted or unsubstituted heteroaryl, a substituted or unsubstituted heterocyclyl, or X, where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{119}$ is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

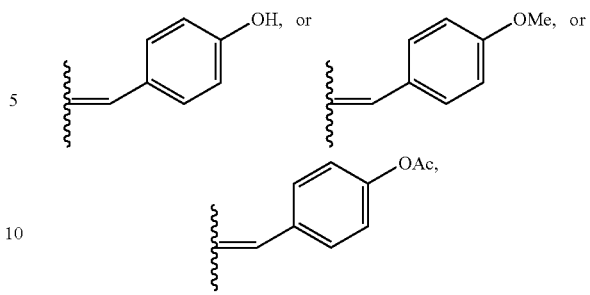

or bond β is absent, bond κ is absent, bond δ is present, $R_{45}$ is present, bond χ and $R_{46}$ are absent, $R_{44}$ is present, and $R_{41}$ is —OC(O)(CF$_3$), —OH, -alkyl, alkenyl, alkynyl, cycloalkyl, cycloalkenyl, a substituted or unsubstituted aryl, a substituted or unsubstituted heteroaryl, a substituted or unsubstituted heterocyclyl,

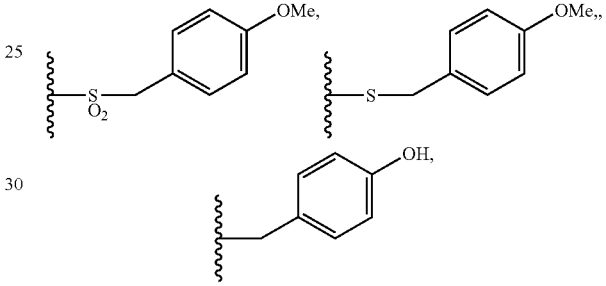

X, $OR_{120}$, —$SR_{121}$, —$N(R_{122})_2$, or —R'Y; or wherein each occurrence of alkyl, alkenyl, alkynyl, alkylene, alkenylene, and alkynylene is substituted or unsubstituted, bond β is absent, bond κ is present, bond δ is absent, $R_{44}$ and $R_{45}$ are absent, bond χ and $R_{46}$ are absent, and $R_{41}$ is a halogen, —OH,

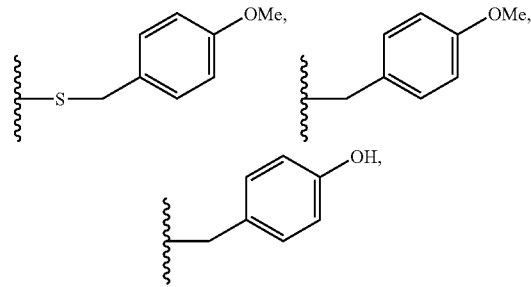

X, $OR_{120}$, —$SR_{121}$, —$N(R_{122})_2$, or —R'Y.

where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or wherein each occurrence of alkyl, alkenyl, alkynyl, alkylene, alkenylene, and alkynylene is substituted or unsubstituted, bond β is absent, bond κ is absent, each of bond δ, bond χ, R$_{44}$, R$_{45}$ and R$_{46}$ are present, and R$_{41}$ is joined to R$_{40}$ to form a pentacyclic ring, R$_{44}$, if present, is H, R$_{45}$, if present, is H or Br, R$_{46}$, if present, is

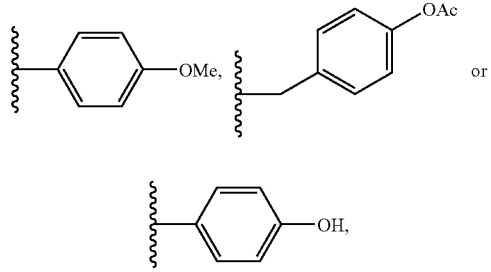

cycloalkyl, cycloalkenyl, a substituted or unsubstituted aryl, a substituted or unsubstituted heteroaryl, a substituted or unsubstituted heterocyclyl, wherein R$_{46}$ is only present if R$_{41}$ is joined to R$_{40}$ to form a pentacyclic ring, R$_{106}$ is H, wherein bond η is present or absent, but when present bond κ is absent, comprising the step of reacting a compound having the structure:

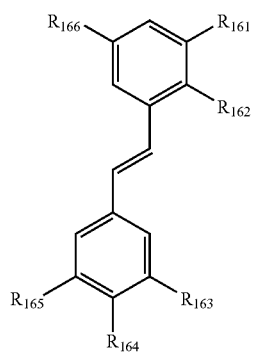

wherein R$_{161}$ and R$_{166}$ are OMe or OAc, R$_{162}$ is Br and R$_{165}$ and R$_{163}$ are OMe or OAc and R$_{164}$ is H or R$_{165}$ and R$_{163}$ are H and R$_{164}$ is OMe or OAc, with n-BuLi and a compound having the structure:

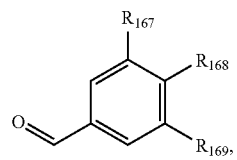

wherein R$_{161}$ is H or OMe, R$_{165}$ is H or OMe, and R$_{119}$ is H or OMe, so as to produce the compound.

This invention provides a process for making a compound having the structure:

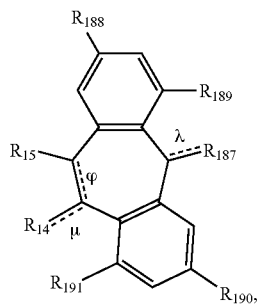

wherein R$_{14}$, R$_{15}$, R$_{188}$, R$_{187}$, R$_{188}$, R$_{189}$, R$_{190}$, R$_{191}$, are, independently, =O, H, OH, —OC(O)alkyl, alkyl, alkenyl, alkynyl, —OR$_{212}$, —SR$_{213}$, —N(R$_{214}$)$_2$, —S(O)(O)R$_{215}$, —C(O)OR$_{216}$, —R$_{217}$OR$_{218}$, —R$_{217}$R$_{218}$, —SO$_2$—R$_{219}$, cycloalkyl, cycloalkenyl, a substituted or unsubstituted aryl, a substituted or unsubstituted heteroaryl, a substituted or unsubstituted heterocyclyl, or X, where X is a halogen, where R$_{212}$, R$_{213}$, R$_{215}$, R$_{216}$, R$_{218}$, R$_{219}$, and each occurrence of R$_{214}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where R$_{217}$ is alkylene, alkenylene or alkynylene, wherein each occurrence of alkyl, alkenyl, alkynyl, alkylene, alkenylene, and alkynylene is substituted or unsubstituted, and wherein bonds φ, λ and μ are present or absent, but wherein when bond φ is present bond μ is absent, and wherein when bond μ is present bond φ is absent, comprising:

a) reacting a compound having the structure:

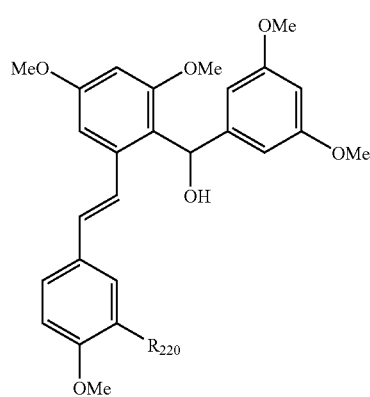

with an oxidizing agent so as to obtain a compound having the structure:

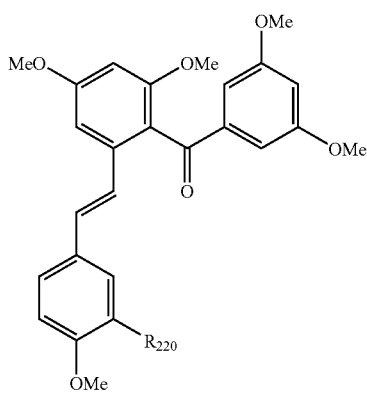

wherein $R_{220}$ is H or —OMe,
and b) contacting the product of step a) with a dioxirane, an acid, or $Br_2$ so as to obtain the compound.

In an embodiment, a process is provided for making a compound having the structure:

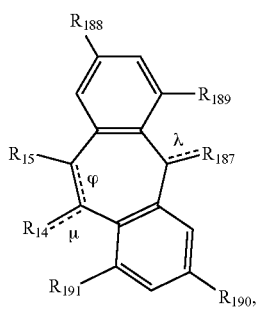

wherein $R_{14}$, $R_{15}$, $R_{188}$, $R_{187}$, $R_{188}$, $R_{189}$, $R_{190}$, $R_{191}$, are, independently, =O, H, OH, —OC(O)alkyl, alkyl, alkenyl, alkynyl, —$OR_{212}$, —$SR_{213}$, —$N(R_{214})_2$, —S(O)(O)$R_{215}$, —C(O)O$R_{216}$, —$R_{217}R_{218}$, —$R_{217}R_{218}$, —$SO_2$—$R_{219}$, cycloalkyl, cycloalkenyl, a substituted or unsubstituted aryl, a substituted or unsubstituted heteroaryl, a substituted or unsubstituted heterocyclyl, or X, where X is a halogen, where $R_{212}$, $R_{213}$, $R_{215}$, $R_{216}$, $R_{218}$, $R_{219}$, and each occurrence of $R_{214}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{217}$ is alkylene, alkenylene or alkynylene, wherein each occurrence of alkyl, alkenyl, alkynyl, alkylene, alkenylene, and alkynylene is substituted or unsubstituted, and wherein bonds φ, λ, and μ are present or absent, but wherein when bond φ is present bond μ is absent, and wherein when bond μ is present bond φ is absent, comprising:
a) reacting a compound having the structure:

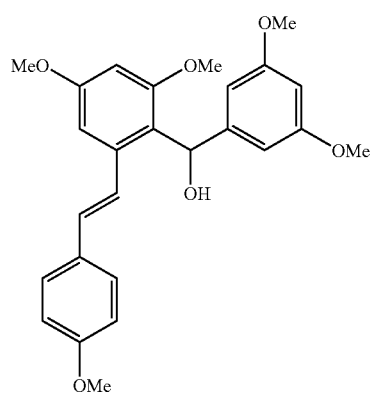

with an oxidizing agent so as to obtain a compound having the structure:

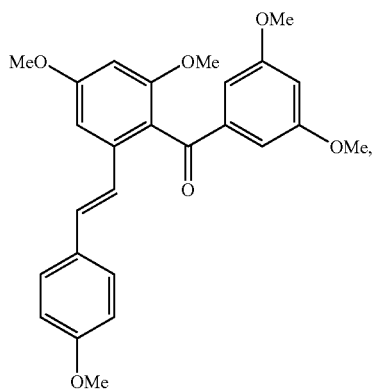

b) contacting the product of step a) with $Br_2$ so as to obtain the compound.

A process is provided for making a compound having the structure:

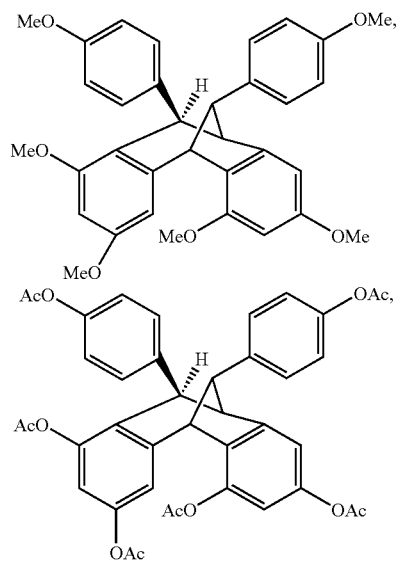

-continued

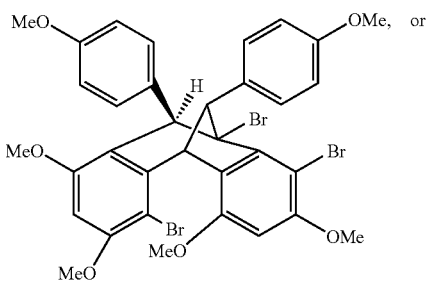

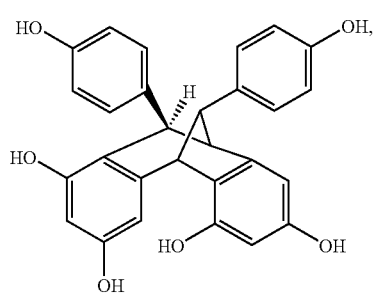

comprising the step of reacting a compound having the structure:

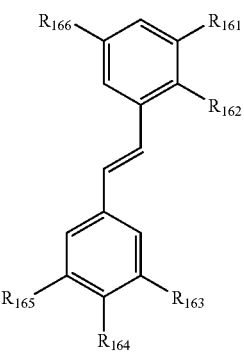

wherein $R_{161}$ and $R_{166}$ are OMe, $R_{162}$ is Br and $R_{165}$ and $R_{163}$ are H and $R_{164}$ is OMe, with n-BuLi and a compound having the structure:

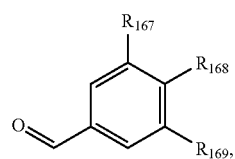

wherein $R_{167}$ is OMe, $R_{168}$ is H, and $R_{169}$ is OMe, so as to produce the compound.

A process is provided for making a compound having the structure:

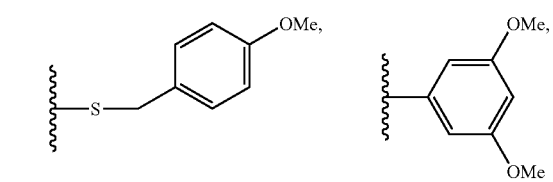

wherein $R_{192}$, $R_{192}$, $R_{193}$, $R_{194}$, $R_{195}$, $R_{196}$, $R_{197}$, $R_{198}$, $R_{199}$, $R_{200}$, $R_{201}$, $R_{202}$, and $R_{203}$ are, independently, H, OH, Br, —OMe, —OAc,

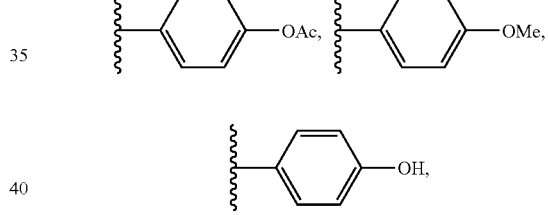

and wherein $R_{204}$ is H, OH, =O, Br, —OAc, —OMe, and wherein bond v is present when $R_{204}$ is =O, comprising the step of reacting a compound having the structure:

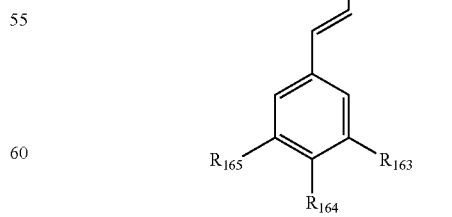

wherein $R_{161}$ and $R_{166}$ are OMe or OAc, $R_{162}$ is Br and $R_{164}$ and $R_{163}$ are OMe or OAc and $R_{165}$ is H or $R_{165}$ and $R_{163}$ are H and $R_{164}$ is OMe or OAc, with n-BuLi and a compound having the structure:

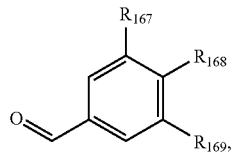

wherein $R_{167}$ is H or OMe or OAc, Rise is H or OMe or OAc, and $R_{169}$ is H or OMe or OAc, so as to produce the compound.

A process is provided for making a compound having the structure:

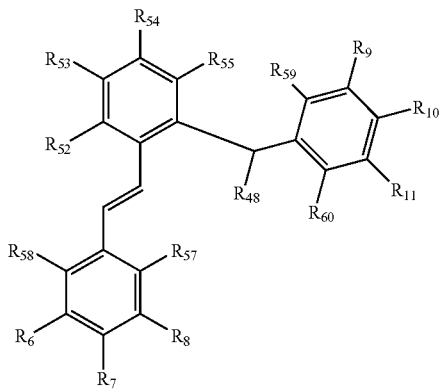

wherein $R_6$, $R_7$, $R_8$, $R_9$, $R_{10}$, $R_{11}$, $R_{52}$, $R_{53}$, $R_{54}$, $R_{55}$, $R_{57}$, $R_{58}$, $R_{59}$, $R_{60}$ are, independently, H, OH, —OMe, —OAc, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, and wherein each occurrence of alkyl, alkenyl, alkynyl, alkylene, alkenylene, and alkynylene is substituted or unsubstituted $R_{48}$ is H, =O, OH, —OAc, —OMe,

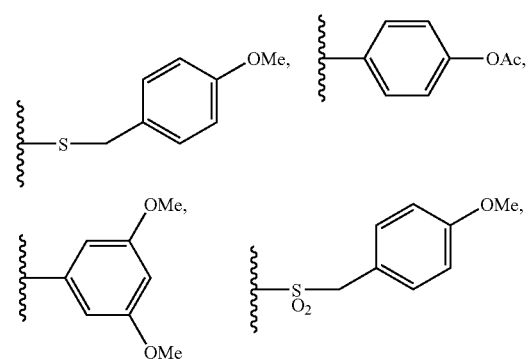

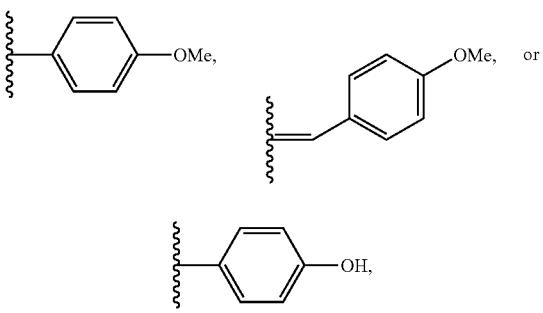

comprising reacting a compound having the structure:

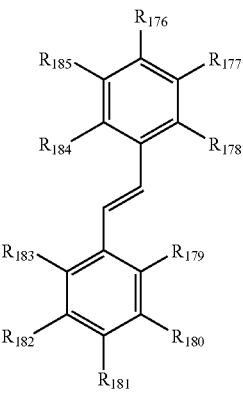

wherein $R_{176}$, $R_{177}$, $R_{178}$, $R_{179}$, $R_{180}$, $R_{181}$, $R_{182}$, $R_{183}$, $R_{184}$, $R_{185}$ are, independently, H, Br, or OMe, with with n-BuLi and a compound having the structure:

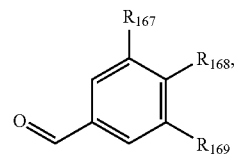

wherein $R_{167}$ is H, OAc or OMe, $Rx_{16}$ is H, OAc or OMe, and $R_{169}$ is H, OAc or OMe, so as to produce the compound.

A process is provided for making a compound having the structure:

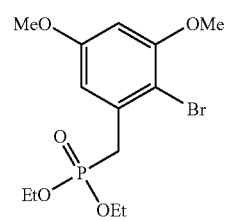 [SMILES: CCOP(=O)(Cc1cc(OC)cc(OC)c1Br)OCC]

comprising
a) reacting a compound having the structure:

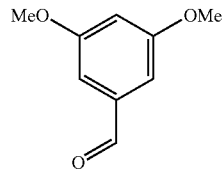 [SMILES: COc1cc(C=O)cc(OC)c1]

with NaBH$_4$ and PBR$_3$ to produce a compound having the structure:

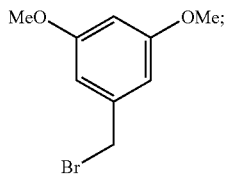

b) reacting the product of step a) with NBS in a suitable solvent;
c) reacting the product of step b) with KHMDS and HP(O)(OEt)$_2$ so as to produce the compound.

A process is provided for making a compound having the structure:

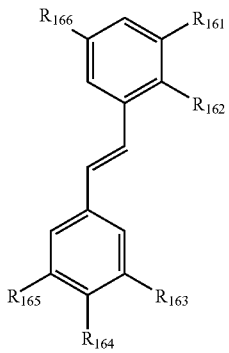

wherein R$_{161}$ and R$_{166}$ are OMe or OAc, R$_{162}$ is Br and R$_{164}$ and R$_{163}$, are OMe or OAc and R$_{165}$ is H comprising:

a) contacting a compound having the structure:

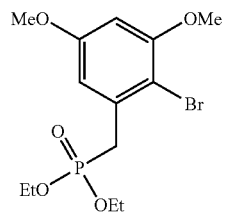 [SMILES: CCOP(=O)(Cc1cc(OC)cc(OC)c1Br)OCC]

with KOt-Bu; and
b) reacting the product of step a) with 3,4-dimethoxybenzaldehyde so as to obtain the compound.

A composition free of plant-extract is provided comprising any of the compounds described herein.

This invention provides a compound having the structure:

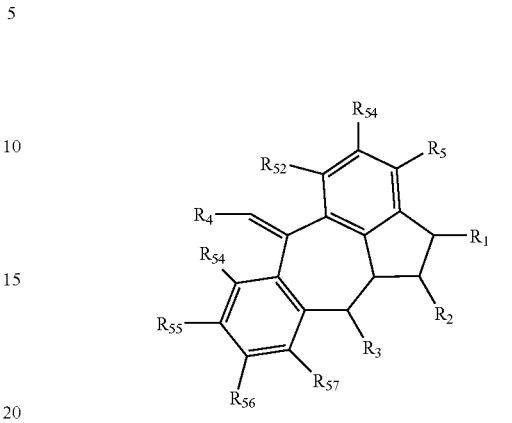

wherein R$_1$, R$_2$, R$_3$, R$_4$, R$_5$, R$_{52}$, R$_{54}$, R$_{55}$, R$_{56}$, R$_{57}$ are defined as above.

This invention provides a compound having the structure:

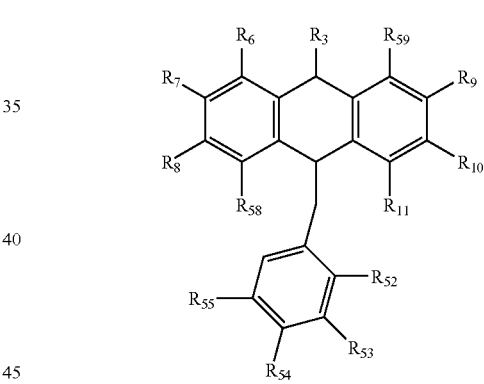

wherein R$_3$, R$_6$, R$_7$, R$_8$, R$_{52}$, R$_{53}$, R$_{54}$, R$_{55}$, and R$_{58}$ are defined as above, R$_9$, R$_{10}$, R$_{11}$, and R$_{59}$, are, independently, H, OH, alkyl, alkenyl, alkynyl, —OR$_{78}$, —SR$_{79}$, —N(R$_{80}$)$_2$, —S(O)(O)R$_{81}$, —C(O)OR$_{82}$, —R$_{83}$OR$_{84}$, —R$_{83}$R$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{78}$, R$_{79}$, R$_{81}$, R$_{82}$, R$_{84}$ and each occurrence of R$_{80}$ are, independently, H, alkyl, alkenyl, or alkynyl, and where R$_{83}$ is is alkylene, alkenylene or alkynylene, wherein each occurrence of alkyl, alkenyl, alkynyl, alkylene, alkenylene, and alkynylene is substituted or unsubstituted.

This invention provides a composition, free of extract, comprising:

a compound having the structure:

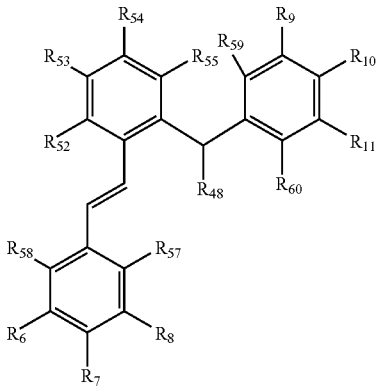

wherein R$_6$, R$_7$, R$_8$, R$_9$, R$_{10}$, R$_{11}$, R$_{52}$, R$_{53}$, R$_{54}$, R$_{55}$, R$_{57}$, R$_{58}$, R$_{59}$, R$_{60}$ are, independently, H, OH, —OMe, —OAc, alkyl, alkenyl, alkynyl, —OR$_{78}$, —SR$_{79}$, —N(R$_{80}$)$_2$, —S(O)(O)R$_{81}$, —C(O)OR$_{82}$, —R$_{83}$OR$_{84}$, —R$_{83}$R$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{78}$, R$_{79}$, R$_{81}$, R$_{82}$, R$_{84}$ and each occurrence of R$_{80}$ are, independently, H, alkyl, alkenyl, or alkynyl, and where R$_{83}$ is is alkylene, alkenylene or alkynylene, and wherein each occurrence of alkyl, alkenyl, alkynyl, alkylene, alkenylene, and alkynylene is substituted or unsubstituted R$_{48}$ is H, =O, OH, —OAc, —OMe,

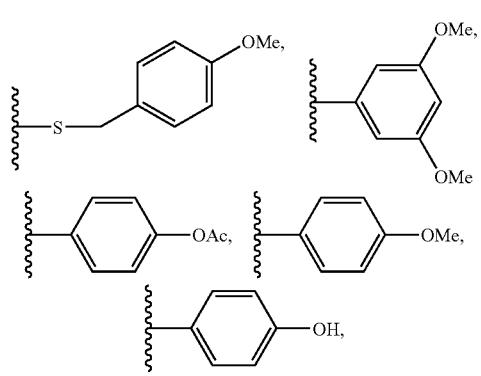

or a compound having the structure:

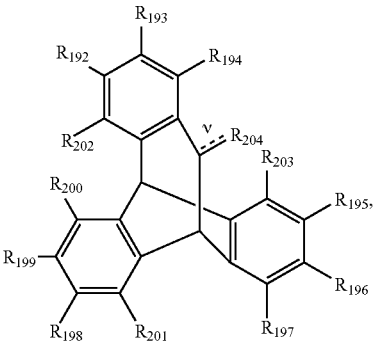

wherein R$_{192}$, R$_{192}$, R$_{193}$, R$_{194}$, R$_{195}$, R$_{196}$, R$_{197}$, R$_{198}$, R$_{199}$, R$_{200}$, R$_{201}$, R$_{202}$, and R$_{203}$ are, independently, H, OH, Br, —OMe, —OAc,

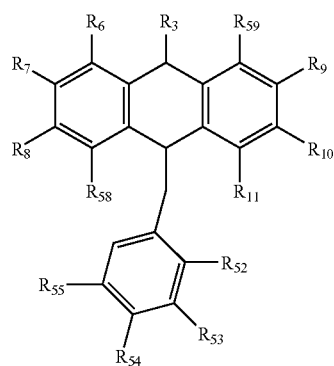

and wherein R$_{204}$ is H, OH, =O, Br, —OAc, —OMe, and wherein bond v is present when R$_{204}$ is =O; or a compound having the structure:

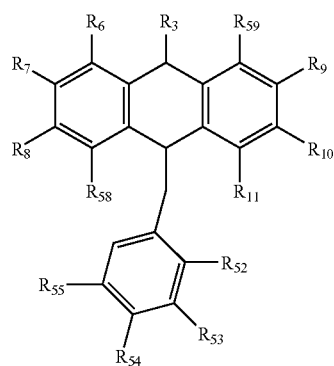

wherein R$_3$, R$_6$, R$_7$, R$_8$, R$_{52}$, R$_{53}$, R$_{54}$, R$_{55}$, and R$_{58}$ are defined as above, R$_9$, R$_{10}$, R$_{11}$, and R$_{59}$, are, independently, H, OH, alkyl, alkenyl, alkynyl, —OR$_{78}$, —SR$_{79}$, —N(R$_{80}$)$_2$, —S(O)(O)R$_{82}$, —C(O)OR$_{82}$, —R$_{83}$OR$_{84}$, —R$_{83}$R$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{78}$, R$_{79}$, R$_{81}$, R$_{82}$, R$_{84}$ and each occurrence of R$_{80}$ are, independently, H, alkyl, alkenyl, or alkynyl, and where R$_{83}$ is is alkylene, alkenylene or alkynylene, wherein each occurrence of alkyl, alkenyl, alkynyl, alkylene, alkenylene, and alkynylene is substituted or unsubstituted.

DETAILED DESCRIPTION

Figure 1:
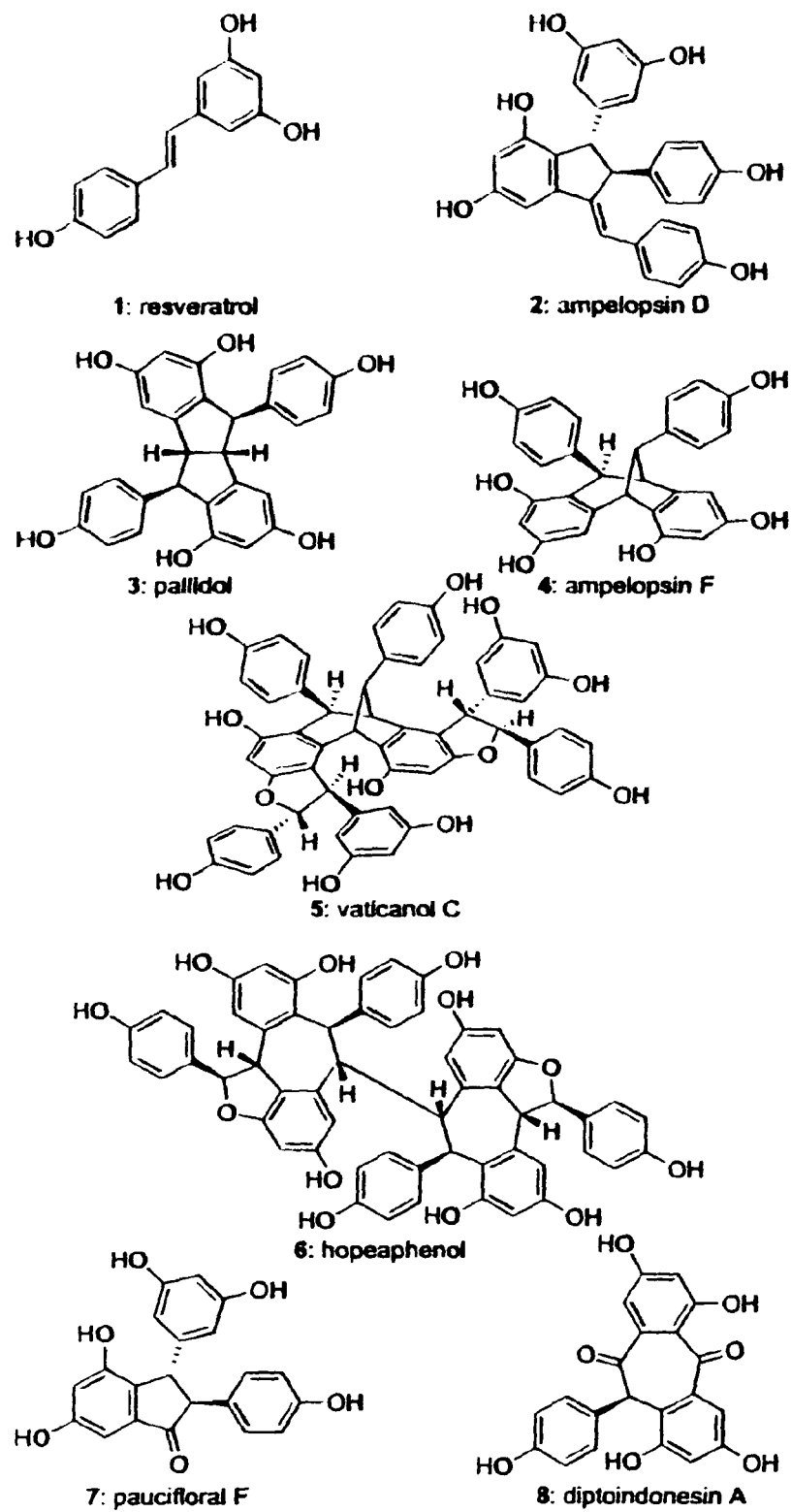
FIG. 1: Selected examples of polyphenolic natural products presumed to arise from the union of resveratrol monomers.

This invention provides for a process for making a compound having the structure:

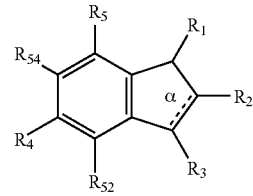

wherein R$_1$, R$_2$, R$_4$, R$_5$, R$_{52}$ and R$_{54}$ are, independently, H, OH, OMe or

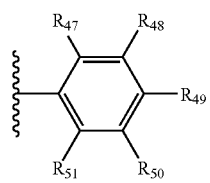

wherein each of R$_{47}$, R$_{48}$, R$_{49}$, R$_{50}$, and R$_{51}$ are, independently, H, OH, alkyl, alkenyl, alkynyl, —OR$_{61}$, —SR$_{62}$, —N(R$_{63}$)$_2$, —S(O)(O)R$_{64}$, —C(O)OR$_{65}$, —R$_{66}$OR$_{67}$, cycloalkyl, cycloalkenyl, a substituted or unsubstituted aryl, a substituted or unsubstituted heteroaryl, a substituted or unsubstituted heterocyclyl, or X,
  where X is a halogen, where R$_{61}$, R$_{62}$, R$_{64}$, R$_{65}$, R$_{67}$, and each occurrence of R$_{63}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where R$_{66}$ is alkylene, alkenylene or alkynylene, wherein each occurrence of alkyl, alkenyl, alkynyl, alkylene, alkenylene, and alkynylene is substituted or unsubstituted, R$_3$ is H, =O, —OH, X, —OR$_{68}$, —SR$_{69}$, —N(R$_{70}$)$_2$,

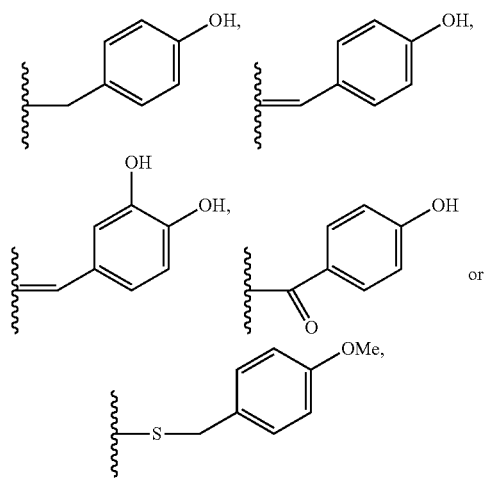

where X is a halogen, and where R$_{68}$, R$_{69}$ and each occurrence of R$_{70}$ are, independently, alkyl, alkenyl, or alkynyl, wherein each occurrence of alkyl, alkenyl, or alkynyl, is substituted or unsubstituted, and where bond α is present or absent, the process comprising:

a) contacting a compound having the structure:

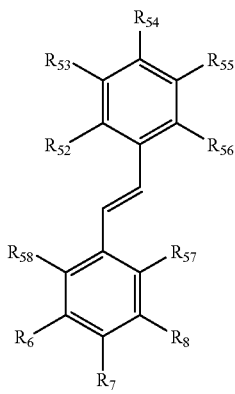

wherein $R_{52}$ and $R_{54}$ are defined as above, $R_6$, $R_7$, $R_8$, $R_{53}$, $R_{55}$, $R_{56}$, $R_{57}$, and $R_{58}$, are, independently, H, OH, alkyl, alkenyl, alkynyl, $-OR_{71}$, $-SR_{72}$, $-N(R_{73})_2$, $-S(O)(O)R_{74}$, $-C(O)OR_{75}$, $-R_{76}OR_{77}$, $-R_{76}R_{77}$, cycloalkyl, cycloalkenyl, a substituted or unsubstituted aryl, a substituted or unsubstituted heteroaryl, a substituted or unsubstituted heterocyclyl, or $-X$, where X is a halogen, and where $R_{71}$, $R_{72}$, $R_{74}$, $R_{75}$, $R_{77}$ and each occurrence of $R_{73}$ are, independently, H, alkyl, alkenyl, alkynyl cycloalkyl, cycloalkenyl, a substituted or unsubstituted aryl, a substituted or unsubstituted heteroaryl, a substituted or unsubstituted heterocyclyl, and where $R_{76}$ is alkylene, alkenylene or alkynylene, wherein each occurrence of alkyl, alkenyl, alkynyl, alkylene, alkenylene, and alkynylene is substituted or unsubstituted, with an organolithium reagent;

b) contacting the product of step a) with a substituted benzaldehyde so as to form a compound having the structure:

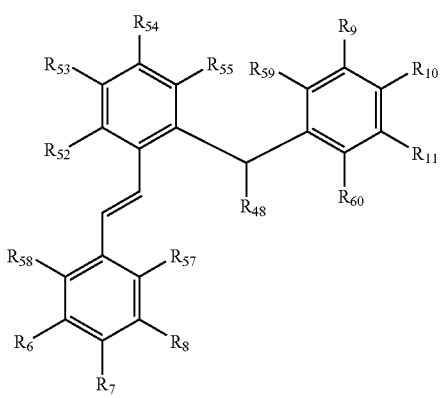

wherein $R_6$, $R_7$, $R_8$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, $-OR_{78}$, $-SR_{79}$, $-N(R_{80})_2$, $-S(O)(O)R_{81}$, $-C(O)OR_{82}$, $-R_{83}OR_{84}$, $-R_{83}R_{84}$, cycloalkyl, cycloalkenyl, a substituted or unsubstituted aryl, a substituted or unsubstituted heteroaryl, a substituted or unsubstituted heterocyclyl, or $-X$, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, wherein each occurrence of alkyl, alkenyl, alkynyl, alkylene, alkenylene, and alkynylene is substituted or unsubstituted; and contacting the product of step b) with an organic acid so as to produce the compound.

In an embodiment, the process for making a compound having the structure:

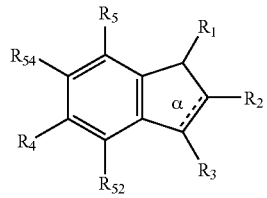

wherein $R_1$, $R_2$, $R_4$, $R_5$, $R_{52}$ and $R_{54}$ are, independently, H, OH, OMe or

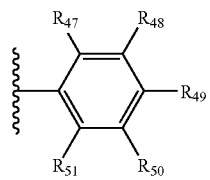

wherein each of $R_{47}$, $R_{48}$, $R_{49}$, $R_{50}$, and $R_{51}$ are, independently, H, OH, alkyl, alkenyl, alkynyl, $-OR_{61}$, $-SR_{62}$, $-N(R_{63})_2$, $-S(O)(O)R_{64}$, $-C(O)OR_{65}$, $-R_{66}OR_{67}$, $-R_{66}R_{67}$, cycloalkyl, cycloalkenyl, a substituted or unsubstituted aryl, a substituted or unsubstituted heteroaryl, a substituted or unsubstituted heterocyclyl, or X, where X is a halogen, where $R_{61}$, $R_{62}$, $R_{64}$, $R_{65}$, $R_{67}$, and each occurrence of $R_{63}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{66}$ is alkylene, alkenylene or alkynylene, wherein each occurrence of alkyl, alkenyl, alkynyl, alkylene, alkenylene, and alkynylene is substituted or unsubstituted, $R_3$ is $=O$, $-OH$, X, $-OR_{68}$, $-SR_{69}$, $-N(R_{70})_2$,

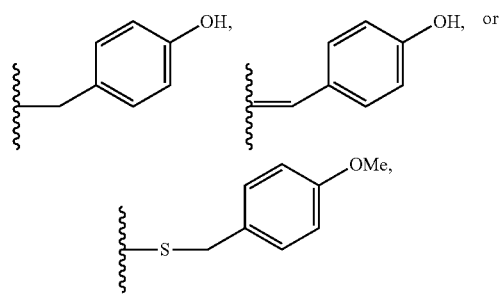

where X is a halogen, and where $R_{68}$, $R_{69}$ and each occurrence of $R_{70}$ are, independently, alkyl, alkenyl, or alkynyl, wherein each occurrence of alkyl, alkenyl, or alkynyl, is substituted or unsubstituted, and
where bond α is present or absent,
the process comprising:
a) contacting a compound having the structure:

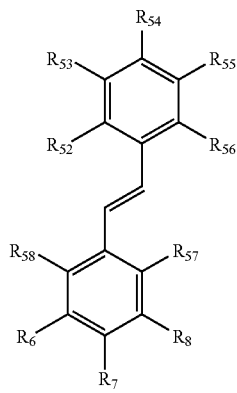

wherein $R_{52}$ and $R_{54}$ are defined as above, $R_6$, $R_7$, $R_8$, $R_{53}$, $R_{55}$, $R_{56}$, $R_{57}$, and $R_{58}$, are, independently, H, OH, alkyl, alkenyl, alkynyl, —$OR_{71}$, —$SR_{72}$, —$N(R_{73})_2$, —$S(O)(O)R_{74}$, —$C(O)OR_{75}$, —$R_{76}OR_{77}$, —$R_{76}R_{77}$, cycloalkyl, cycloalkenyl, a substituted or unsubstituted aryl, a substituted or unsubstituted heteroaryl, a substituted or unsubstituted heterocyclyl, or —X,
  where X is a halogen, and where $R_{71}$, $R_{72}$, $R_{74}$, $R_{75}$, $R_{77}$ and each occurrence of $R_{73}$ are, independently, H, alkyl, alkenyl, alkynyl cycloalkyl, cycloalkenyl, a substituted or unsubstituted aryl, a substituted or unsubstituted heteroaryl, a substituted or unsubstituted heterocyclyl, and where $R_{76}$ is alkylene, alkenylene or alkynylene, wherein each occurrence of alkyl, alkenyl, alkynyl, alkylene, alkenylene, and alkynylene is substituted or unsubstituted, with an organolithium reagent;
b) contacting the product of step a) with a substituted benzaldehyde so as to form a compound having the structure:

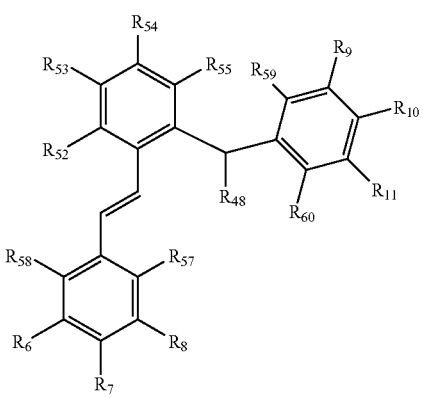

wherein $R_6$, $R_7$, $R_8$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —$OR_{78}$, —$SR_{79}$, —$N(R_{80})$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene,
  wherein each occurrence of alkyl, alkenyl, alkynyl, alkylene, alkenylene, and alkynylene is substituted or unsubstituted; and
e) contacting the product of step b) with an organic acid so as to produce the compound.

In an embodiment, $R_1$ is

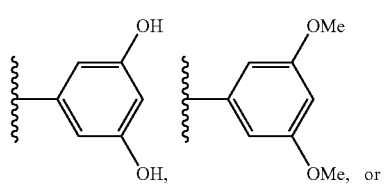

$R_2$ is

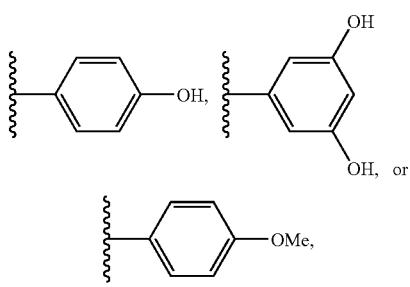

$R_3$ is
=O, —OH,

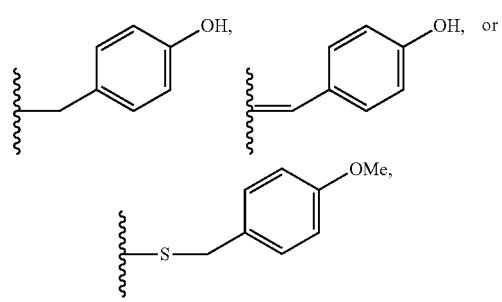

$R_4$ is —OH or —OMe,
$R_5$ is —OH or —OMe,
$R_{52}$ and $R_{54}$ are H, where bond α is present only when $R_3$ is

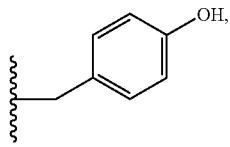

wherein the compound of step a) has the structure:

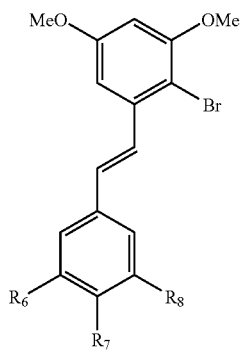

wherein either $R_7$ is —OMe and $R_6$ and $R_8$ are —H, or
$R_7$ is —H and $R_6$ and $R_8$ are —OMe, and
wherein in step b) the product of step a) is contacted with 3,5-dimethoxybenzaldehyde or 4-methoxybenzaldehyde so as to form a compound having the structure:

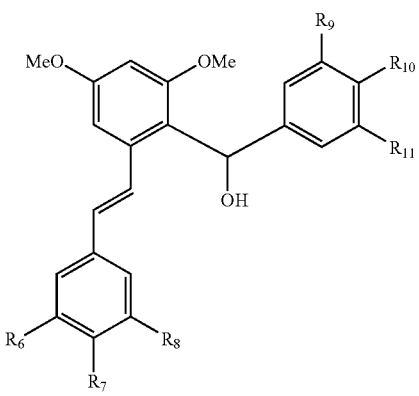

wherein either $R_7$, $R_9$ and $R_{11}$ are —OMe and $R_6$, $R_8$ and $R_{10}$ are H, or wherein $R_7$, $R_9$ and $R_{11}$ are H and $R_6$, $R_8$ and $R_{10}$ are —OMe.

In an embodiment of the instant process, the organolithium reagent is n-butyllithium. In an embodiment of the instant process the organic acid is trifluoroacetic acid or p-toluenesulfonic acid.

In an embodiment, the process wherein the organic acid is p-toluenesulfonic acid and further comprising:
i. contacting the product of step c) with the compound having the structure

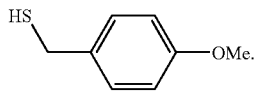

This invention provides the instant process further comprising:
i) contacting the product of step c) with m-chloroperoxybenzoic acid and a base in a first suitable solvent;
ii) contacting the product of step i) with t-butyl base in a second suitable solvent and an alkaline base; and
iii) contacting the product of step ii) with a suitable halide in a third suitable solvent so as to produce the compound.

In an embodiment of the instant process, the t-butyl base is t-BuOH and the second suitable solvent is $CCl_4$, or wherein the t-butyl base is KOt-Bu, N-chlorosuccinimide, and the second suitable solvent is tetrahydrofuran. In an embodiment of the instant process, the suitable halide is $BBr_3$, 9-I-BBN, $BCl_3$ or HI.

This invention further provides the instant process wherein the product of step iii) is contacted with an acid in a fourth suitable solvent so as to produce the compound. In an embodiment the acid is HCl, $MeSO_3H$, $H_2SO_4$, p-TsOH or $H_3PO_4$.

This invention further provides the instant process comprising quenching the product of step c) of with a suitable base in a alcohol solvent. In an embodiment the suitable base is $K_2CO_3$, $NaHCO_3$, KOH, $Ca(OH)_2$, NaOH, $CsCO_3$, or $Ba(OH)_2$.

In an embodiment, the process of further comprises exposing the quenched product to dehydrative conditions so as to form a compound having the structure:

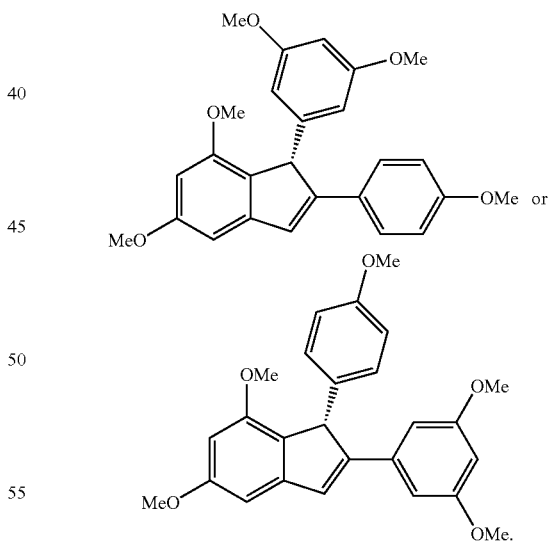

In an embodiment, the process further comprises:
ii. contacting the quenched product with Dess-Martin periodinane; and
iii. contacting the product of step i) with KHMDS.

This invention further provides the instant process further comprising:
i) contacting the quenched product with Dess-Martin periodinane and a second suitable base in a suitable fifth solvent; and ii) contacting the product of step i) with boron tribromide in a sixth suitable solvent so as to produce the compound.

This invention further provides the instant process, further comprising:

i) contacting the product of step c) with Dess-Martin periodinane and a base in a third suitable seventh solvent; and ii) contacting the product of step i) with 9-iodo-9-borabicyclo[3.3.1]nonane in a eighth suitable solvent so as to produce the compound.

In embodiments the instant processes produce a compound having the structure:

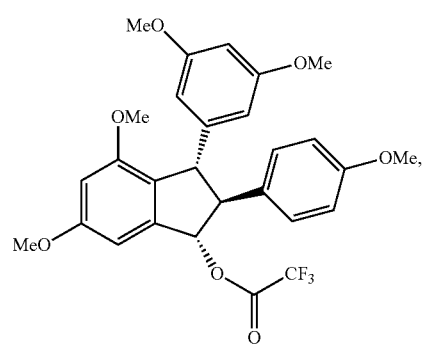

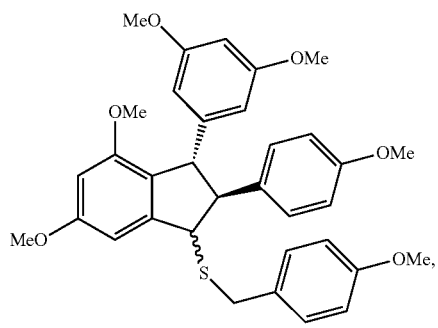

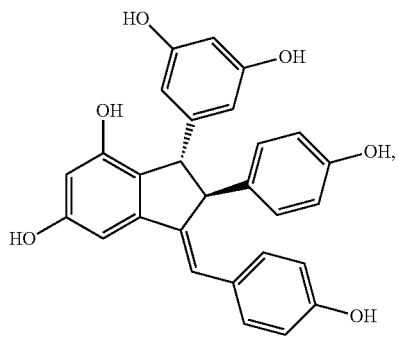

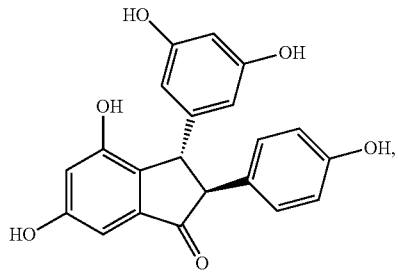

-continued

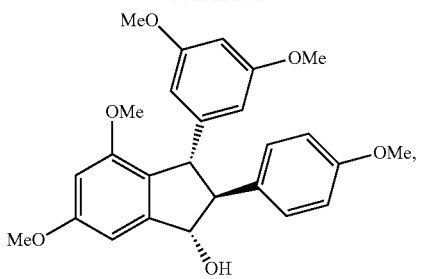

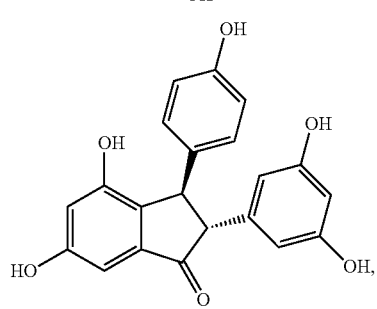

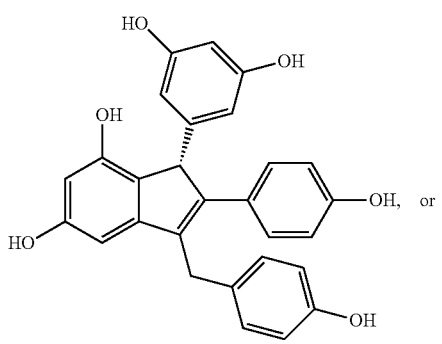

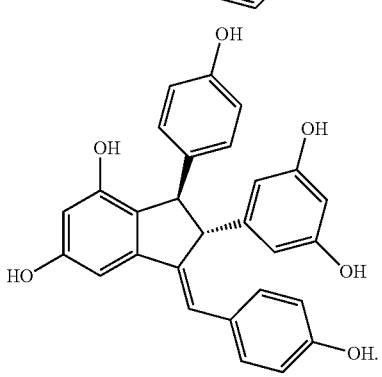

In embodiments the instant processes produce a compound having the structure:

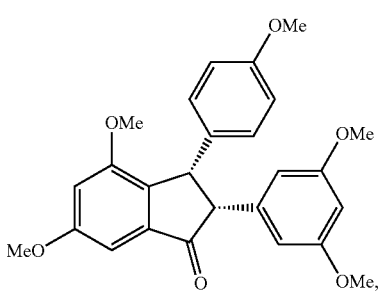

-continued

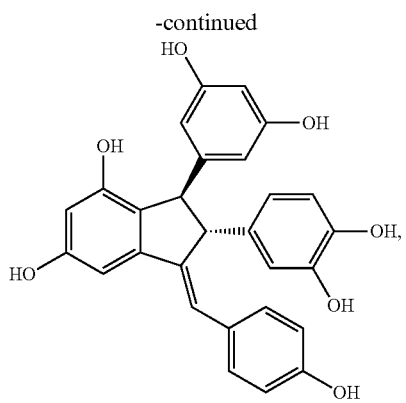

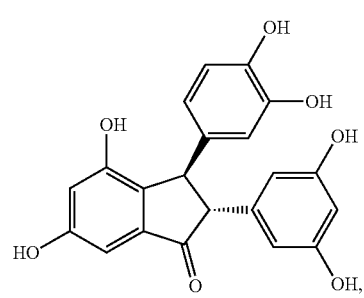

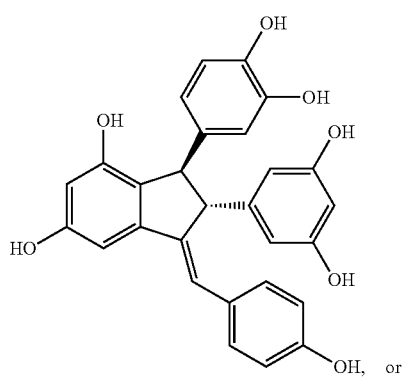

, or

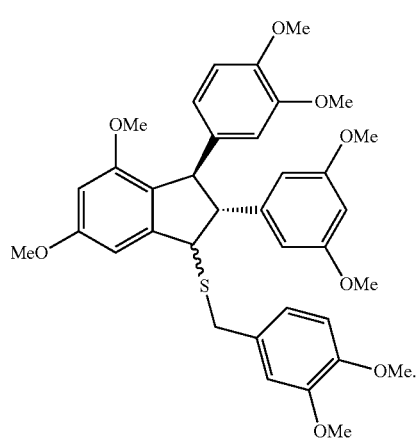

In embodiments the instant processes produce a compound having the structure:

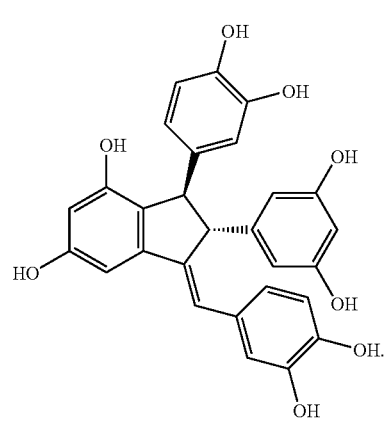 [SMILES: Oc1cc(O)cc([C@@H]2/C(=C\c3ccc(O)c(O)c3)c3cc(O)cc(O)c3[C@H]2c2ccc(O)c(O)c2)c1]

In an embodiment, the process further comprises:
iv. contacting the product with a hydride source;
v. contacting the product of step i) with In(OTf)$_3$ in the presence of

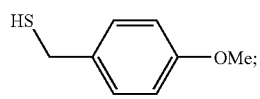

vi. contacting the product of step ii) with Dess-Martin periodinane;
vii. contacting the product of step iii) with m-chloroperoxybenzoic acid;
viii. contacting the product of step iv) with a borane source followed by a hydroxide source;
ix. contacting the product of step v) with Dess-Martin periodinane;
x. exposing the product of step vi) to boron tribromide so as to form the compound having the structure:

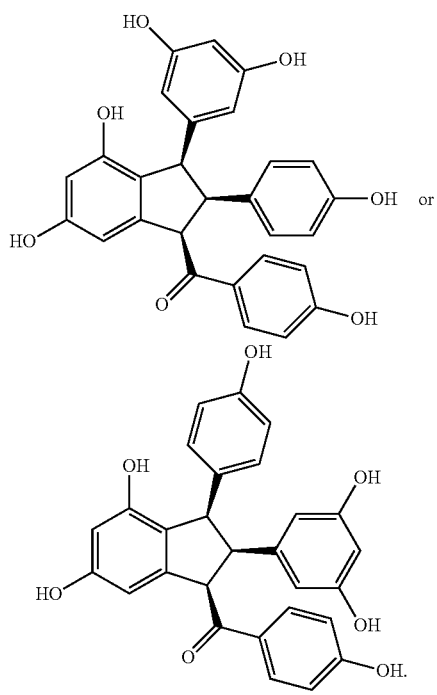

This invention provides a process for making a compound having the structure:

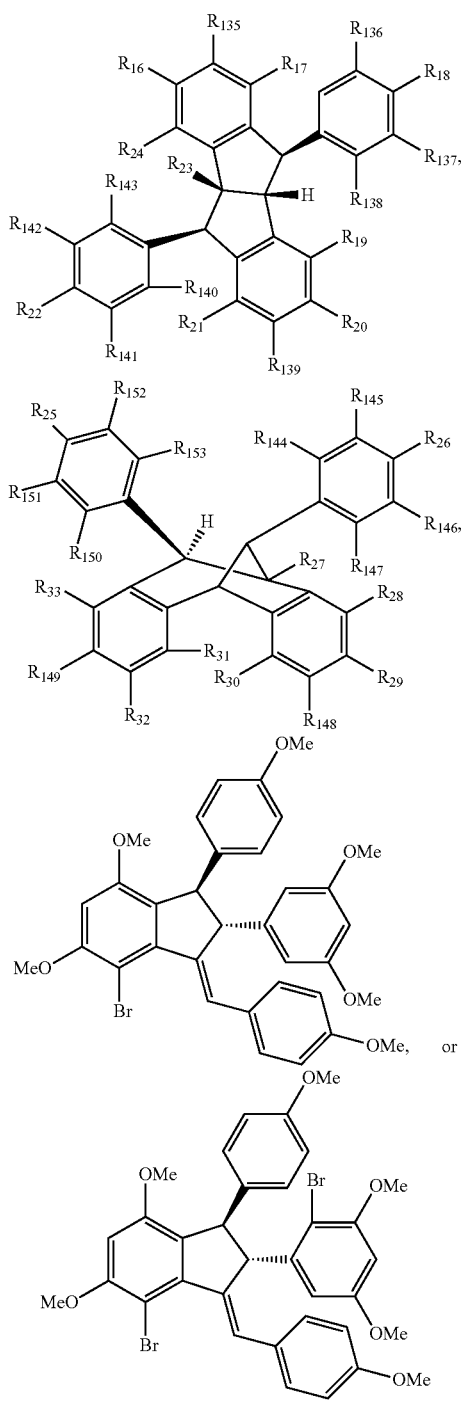

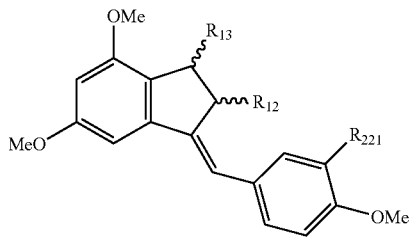

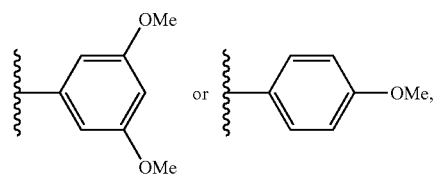

wherein $R_{23}$ and $R_{27}$ are, independently, H or X, wherein $R_{16}$, $R_{17}$, $R_{18}$, $R_{19}$, $R_{20}$, $R_{21}$, $R_{22}$, $R_{24}$, $R_{25}$, $R_{26}$, $R_{28}$, $R_{29}$, $R_{30}$, $R_{31}$, $R_{32}$, $R_{33}$, $R_{135}$, $R_{136}$, $R_{137}$, $R_{138}$, $R_{139}$, $R_{140}$, $R_{141}$, $R_{142}$, $R_{143}$, $R_{144}$, $R_{145}$, $R_{146}$, $R_{147}$, $R_{148}$, $R_{149}$, $R_{150}$, $R_{151}$, $R_{152}$, $R_{153}$ are, independently, H, OH, alkyl, alkenyl, alkynyl, —$OR_{154}$, —$SR_{155}$, —$N(R_{156})_2$, —$S(O)(O)R_{157}$, —$C(O)OR_{158}$, —$R_{159}OR_{160}$, —$R_{159}R_{160}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{154}$, $R_{155}$, $R_{157}$, $R_{158}$, $R_{160}$ and each occurrence of $R_{156}$ are, independently, H, alkyl, alkenyl, or alkynyl, and where $R_{159}$ is is alkylene, alkenylene or alkynylene, wherein each occurrence of alkyl, alkenyl, alkynyl, alkylene, alkenylene, and alkynylene is substituted or unsubstituted, comprising contacting a compound having the structure:

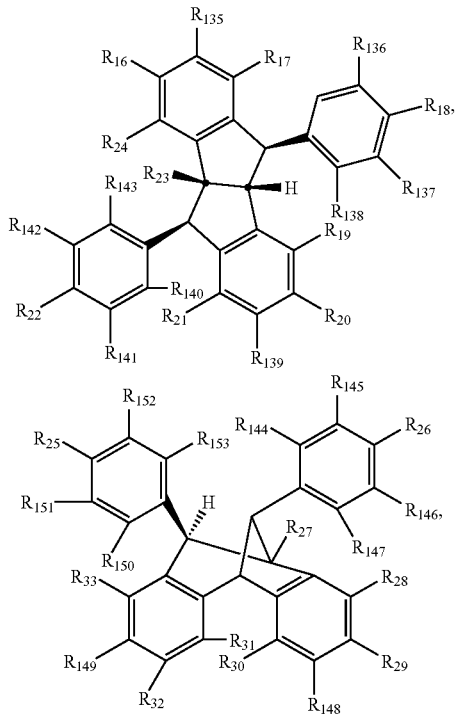

wherein $R_{12}$ and $R_{13}$ are, independently, and $R_{221}$ is H or —OMe, with bromine in a first suitable solvent so as to produce the compound.

In an embodiment, the instant process produces a compound having the structure:

-continued

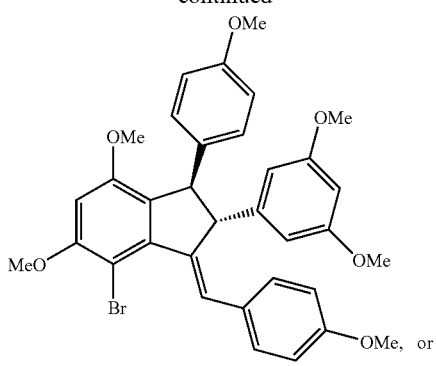

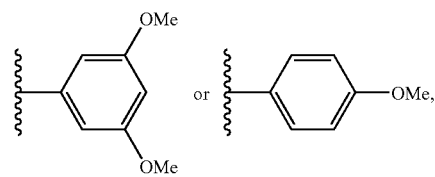

with bromine in a first suitable solvent so as to produce the compound.

In an embodiment the compound made has the structure:

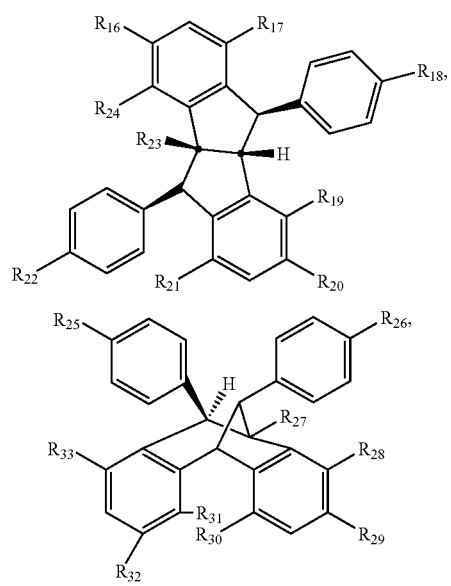

wherein $R_{23}$ and $R_{27}$ are, independently, H or X, wherein $R_{16}$, $R_{17}$, $R_{18}$, $R_{19}$, $R_{20}$, $R_{21}$, $R_{22}$, $R_{24}$, $R_{25}$, $R_{26}$, $R_{28}$, $R_{29}$, $R_{30}$, $R_{31}$, $R_{32}$, $R_{33}$, $R_{135}$, $R_{136}$, $R_{137}$, $R_{138}$, $R_{139}$, $R_{140}$, $R_{141}$, $R_{142}$, $R_{143}$, $R_{144}$, $R_{145}$, $R_{146}$, $R_{147}$, $R_{148}$, $R_{149}$, $R_{150}$, $R_{151}$, $R_{152}$, $R_{153}$ are, independently, H, OH, alkyl, alkenyl, alkynyl, $-OR_{154}$, $-SR_{155}$, $-N(R_{156})_2$, $-S(O)(O)R_{157}$, $-C(O)OR_{158}$, $-R_{159}OR_{160}$, $-R_{159}R_{160}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{154}$, $R_{155}$, $R_{157}$, $R_{158}$, $R_{160}$ and each occurrence of $R_{156}$ are, independently, H, alkyl, alkenyl, or alkynyl, and where $R_{159}$ is is alkylene, alkenylene or alkynylene, wherein each occurrence of alkyl, alkenyl, alkynyl, alkylene, alkenylene, and alkynylene is substituted or unsubstituted, comprising contacting a compound having the structure:

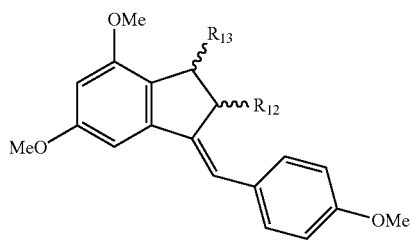

wherein $R_{12}$ and $R_{13}$ are, independently,

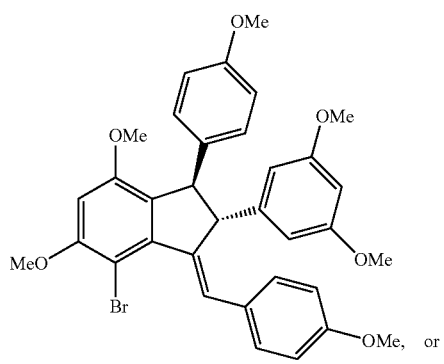

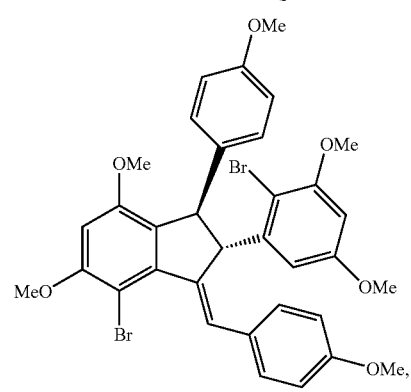

wherein $R_{16}$, $R_{17}$, $R_{18}$, $R_{20}$, $R_{21}$, $R_{22}$, $R_{25}$, $R_{26}$, $R_{29}$, $R_{30}$, $R_{32}$, and $R_{33}$ are, independently, —OH or —OMe, and $R_{19}$, $R_{23}$, $R_{24}$, $R_{27}$, $R_{28}$, and $R_{31}$ are, independently, —Br or —H.

In an embodiment the instant process further comprises, after contacting with bromine in a first suitable solvent:

a) hydrogenatively replacing bromide groups present in the product; and b) cleaving methyl ethers present in the product of step a) with a suitable halide in a second suitable solvent so as to produce the compound.

In an embodiment the suitable halide is $BBr_3$, 9-I-BBN, $BCl_3$ or HI. In an embodiment, in step a), the bromide groups are hydrogenatively replaced by contacting the product with activated palladium/carbon catalyst in the presence of $H_2$. In an embodiment, in step a), the bromide groups are hydrogenatively replaced by contacting the product with (trimethylsilyl)$_3$SiH and 2,2'-azobisisobutyronitrile in third suitable solvent.

This invention further provides the instant process wherein the compound produced has the structure:

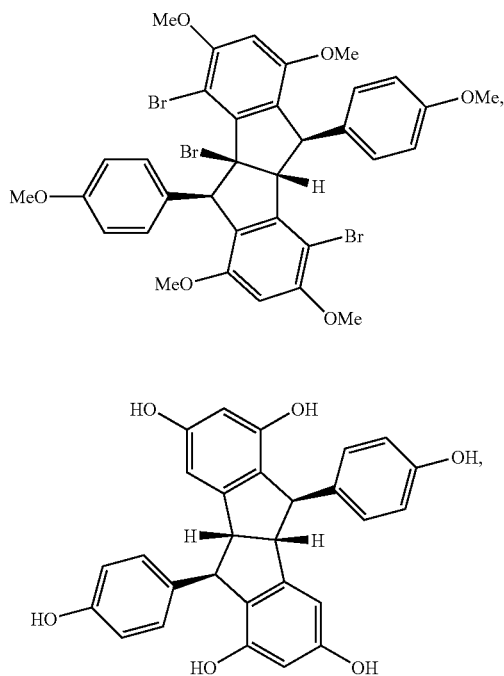

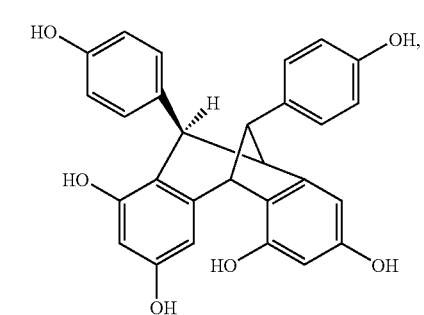

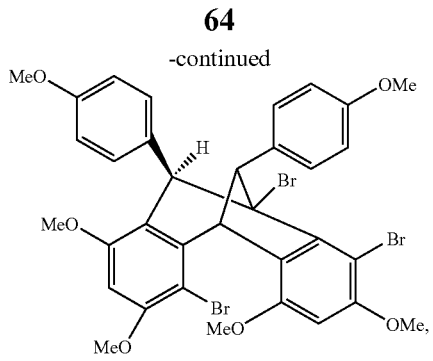

In an embodiment, the process produces a compound having the structure:

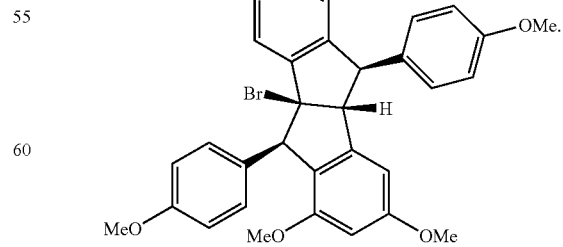

In an embodiment, the process produces a compound having the structure:

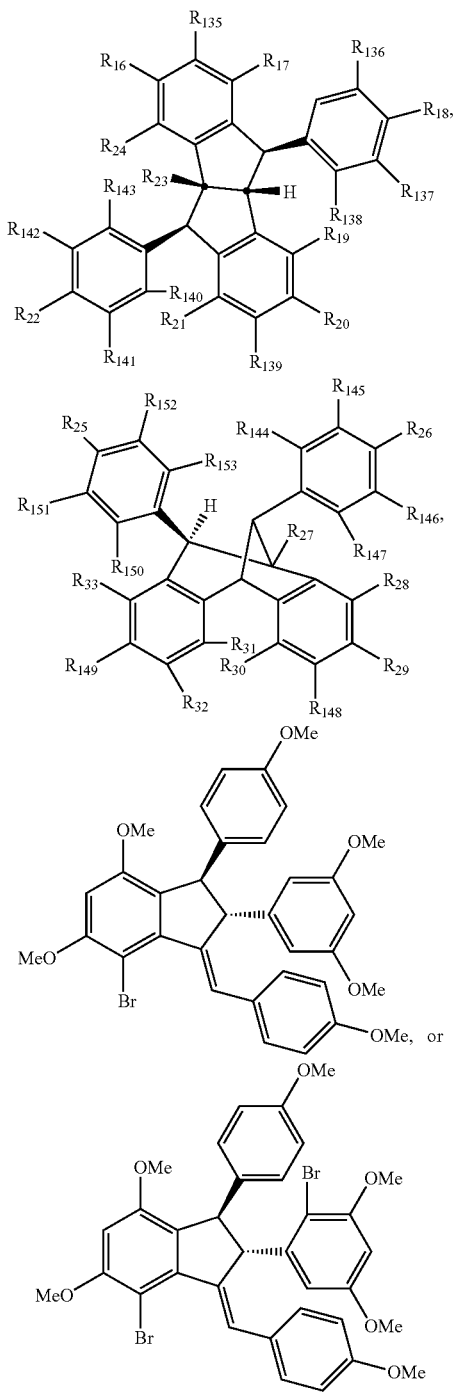

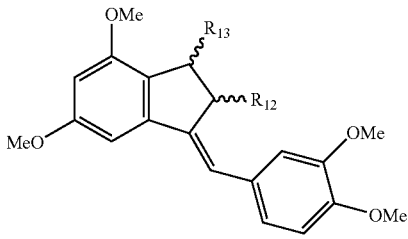

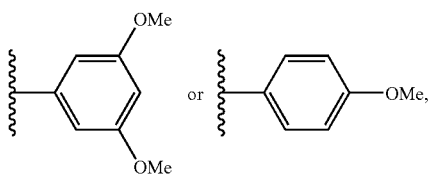

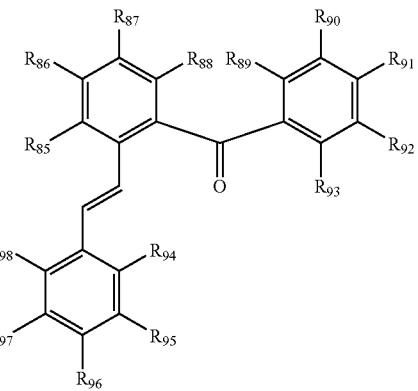

wherein R$_{23}$ and R$_{27}$ are, independently, H or X, wherein R$_{16}$, R$_{17}$, R$_{18}$, R$_{19}$, R$_{20}$, R$_{21}$, R$_{22}$, R$_{24}$, R$_{25}$, R$_{26}$, R$_{28}$, R$_{29}$, R$_{30}$, R$_{31}$, R$_{32}$, R$_{33}$, R$_{135}$, R$_{136}$, R$_{137}$, R$_{138}$, R$_{139}$, R$_{140}$, R$_{141}$, R$_{142}$, R$_{143}$, R$_{144}$, R$_{145}$, R$_{146}$, R$_{147}$, R$_{148}$, R$_{149}$, R$_{150}$, R$_{151}$, R$_{152}$, R$_{153}$ are, independently, H, OH, alkyl, alkenyl, alkynyl, —OR$_{154}$, —SR$_{155}$, —N(R$_{156}$)$_2$, —S(O)(O)R$_{157}$, —C(O)OR$_{158}$, —R$_{159}$OR$_{160}$, —R$_{159}$R$_{160}$, cycloalkyl, cycloalkenyl, a substituted or unsubstituted aryl, a substituted or unsubstituted heteroaryl, a substituted or unsubstituted heterocyclyl, or —X where X is a halogen, and where R$_{154}$, R$_{155}$, R$_{157}$, R$_{158}$, R$_{160}$ and each occurrence of R$_{156}$ are, independently, H, alkyl, alkenyl, or alkynyl, and where R$_{159}$ is is alkylene, alkenylene or alkynylene, wherein each occurrence of alkyl, alkenyl, alkynyl, alkylene, alkenylene, and alkynylene is substituted or unsubstituted, comprises contacting a compound having the structure:

wherein R$_{12}$ and R$_{13}$ are, independently, OMe or with bromine in a first suitable solvent so as to produce the compound.

In an embodiment, the process further comprises, after contacting with bromine in a first suitable solvent:
a) hydrogenatively replacing bromide groups present in the product; and
b) cleaving methyl ethers present in the product of step a) with a suitable halide in a second suitable solvent so as to produce the compound.
wherein each occurrence of alkyl, alkenyl, alkynyl, alkylene, alkenylene, and alkynylene is substituted or unsubstituted, the process comprising contacting a compound having the structure:

wherein R$_{85}$, R$_{86}$, R$_{87}$, R$_{88}$, R$_{89}$, R$_{90}$, R$_{91}$, R$_{92}$, R$_{93}$, R$_{94}$, R$_{95}$, R$_{96}$, R$_{97}$ and R$_{98}$ are, independently, H, OH, alkyl, alkenyl, alkynyl, —OR$_{99}$, —SR$_{100}$, —N(R$_{101}$)$_2$, —S(O)(O)R$_{102}$, —C(O)OR$_{103}$, —R$_{104}$OR$_{105}$, —R$_{104}$R$_{105}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{99}$, $R_{100}$, $R_{102}$, $R_{103}$, and $R_{105}$ and each occurrence of $R_{101}$ are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and wherein $R_{104}$ is is alkylene, alkenylene or alkynylene, wherein each occurrence of alkyl, alkenyl, alkynyl, alkylene, alkenylene, and alkynylene is substituted or unsubstituted, with bromine in a first suitable solvent so as to produce the compound.

In an embodiment, $R_{14}$ is =O, —OAc or

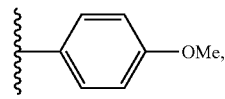

and $R_{15}$

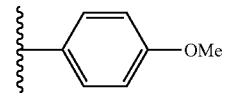

is or —Br, and the compound contacted with bromine has the structure:

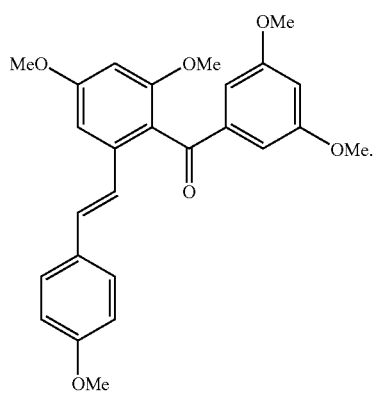 [SMILES: COc1ccc(/C=C/c2cc(OC)cc(OC)c2C(=O)c2cc(OC)cc(OC)c2)cc1]

This invention provides the instant process further comprising, after contacting with bromine in a first suitable solvent, contacting the product with AgOAc in a second suitable solvent.

This invention provides the instant process further comprising, after contacting with AgOAc in a second suitable solvent:

a) contacting the product with a carbonate in a third suitable solvent;

b) contacting the product of step a) with Dess-Martin periodinane

In an embodiment of the instant processes the compound produced has the structure:

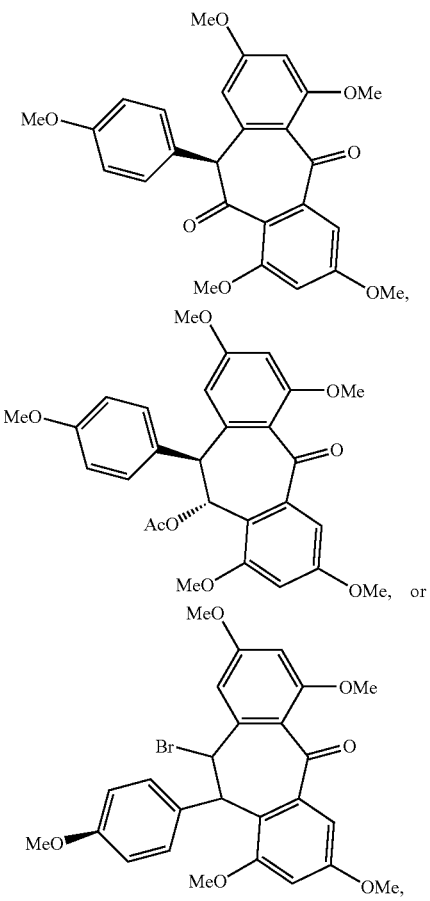

This invention provides a composition, free of plant extract, comprising a compound having the structure:

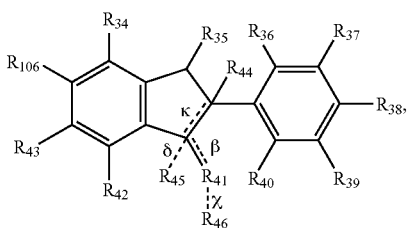

wherein $R_{34}$, $R_{35}$, $R_{42}$, $R_{43}$, and $R_{106}$ are, independently, H, OH, OMe or

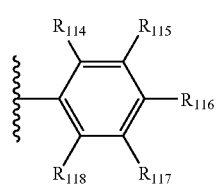

wherein each of $R_{114}$, $R_{115}$, $R_{116}$, $R_{117}$, and $R_{118}$ are, independently, H, OH, alkyl, alkenyl, alkynyl, —$OR_{107}$, —$SR_{108}$, —$N(R_{109})_2$, —$S(O)(O)R_{110}$, —$C(O)OR_{111}$, —$R_{120}OR_{113}$, —$R_{112}R_{113}$, cycloalkyl, cycloalkenyl, a substituted or unsubstituted aryl, a substituted or unsubstituted heteroaryl, a substituted or unsubstituted heterocyclyl, or X, where X is a halogen, where $R_{107}$, $R_{108}$, $R_{110}$, $R_{111}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene, wherein each occurrence of alkyl, alkenyl, alkynyl, alkylene, alkenylene, and alkynylene is substituted or unsubstituted, wherein $R_{36}$, $R_{37}$, $R_{38}$, $R_{39}$ and $R_{40}$ are, independently, H, OH, alkyl, alkenyl, alkynyl, $—OR_{114}$, $—SR_{115}$, $—N(R_{116})_2$, $—S(O)(O)R_{117}$, $—C(O)OR_{118}$, $—R_{119}R_{120}$, $—R_{119}R_{120}$, cycloalkyl, cycloalkenyl, a substituted or unsubstituted aryl, a substituted or unsubstituted heteroaryl, a substituted or unsubstituted heterocyclyl, or X, where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{119}$ is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

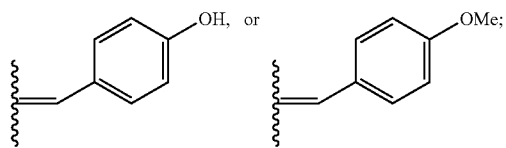

bond β is absent, bond κ is absent, bond δ is present, $R_{45}$ is present, bond χ and $R_{46}$ are absent, $R_{44}$ is present, and $R_{41}$ is $—OC(O)(CF_3)$, $—OH$, -alkyl, alkenyl, alkynyl, cycloalkyl, cycloalkenyl, a substituted or unsubstituted aryl, a substituted or unsubstituted heteroaryl, a substituted or unsubstituted heterocyclyl,

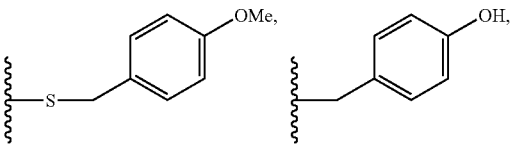

X, $OR_{120}$, $—SR_{121}$, $—N(R_{122})_2$, or $—R'Y$; or wherein each occurrence of alkyl, alkenyl, alkynyl, alkylene, alkenylene, and alkynylene is substituted or unsubstituted, bond β is absent, bond κ is present, bond δ is absent, $R_{44}$ and $R_{45}$ are absent, bond χ and $R_{46}$ are absent, and $R_{41}$ is H, $—OH$,

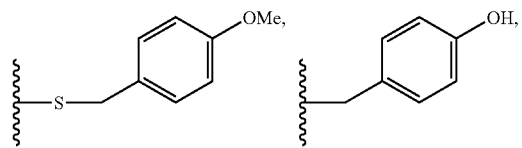

X, $OR_{120}$, $—SR_{121}$, $—N(R_{122})_2$, or $—R'Y$, where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or wherein each occurrence of alkyl, alkenyl, alkynyl, alkylene, alkenylene, and alkynylene is substituted or unsubstituted, bond β is absent, bond κ is absent, each of bond δ, bond χ, $R_{44}$, $R_{45}$ and $R_{46}$ are present, and $R_{41}$ is joined to $R_{40}$ to form a pentacyclic ring, $R_{44}$, if present, is H, $R_{45}$, if present, is H or Br, $R_{46}$, if present, is

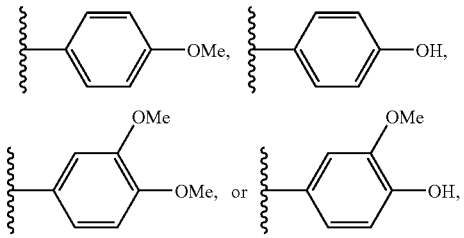

cycloalkyl, cycloalkenyl, a substituted or unsubstituted aryl, a substituted or unsubstituted heteroaryl, a substituted or unsubstituted heterocyclyl, $R_{106}$ is H, wherein when $R_{34}$ and $R_{43}$ are OH, $R_{35}$ is

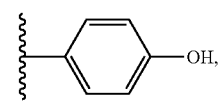

$R_{36}$, $R_{38}$, $R_{40}$, $R_{42}$ and $R_{44}$ are H, $R_{37}$ and $R_{39}$ are OH, and bond β is present, then $R_{41}$ is O or

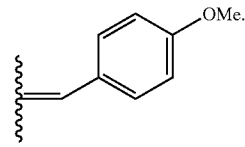

In an embodiment, the composition, free of plant extract, comprises a compound having the structure:

71

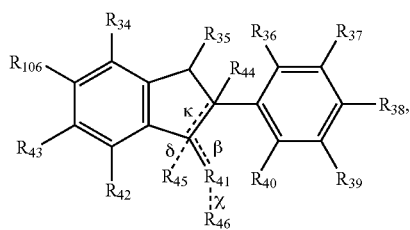

wherein $R_{34}$, $R_{35}$, $R_{42}$, $R_{43}$, and $R_{106}$ are, independently, H, OH, OMe or

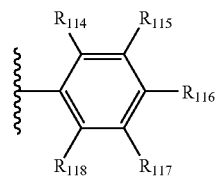

wherein each of $R_{114}$, $R_{115}$, $R_{116}$, $R_{117}$, and $R_{118}$ are, independently, H, OH, alkyl, alkenyl, alkynyl, —$OR_{107}$, —$SR_{108}$, —$N(R_{109})_2$, —$S(O)(O)R_{110}$, —$C(O)OR_{111}$, —$R_{112}OR_{113}$, —$R_{112}R_{113}$, cycloalkyl, cycloalkenyl, a substituted or unsubstituted aryl, a substituted or unsubstituted heteroaryl, a substituted or unsubstituted heterocyclyl, or X, where X is a halogen, where $R_{107}$, $R_{108}$, $R_{110}$, $R_{111}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene, wherein each occurrence of alkyl, alkenyl, alkynyl, alkylene, alkenylene, and alkynylene is substituted or unsubstituted, wherein $R_{36}$, $R_{37}$, $R_{38}$, $R_{39}$ and $R_{40}$ are, independently, H, OH, alkyl, alkenyl, alkynyl, —$OR_{114}$, —$SR_{115}$, —$N(R_{116})_2$, —$S(O)(O)R_{117}$, —$C(O)OR_{118}$, —$R_{119}OR_{120}$, —$R_{119}R_{120}$, cycloalkyl, cycloalkenyl, a substituted or unsubstituted aryl, a substituted or unsubstituted heteroaryl, a substituted or unsubstituted heterocyclyl, or X, where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{119}$ is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

72

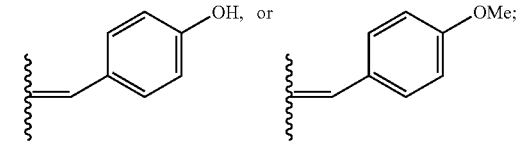

or bond β is absent, bond κ is absent, bond δ is present, $R_{45}$ is present, bond χ and $R_{46}$ are absent, $R_{44}$ is present, and $R_{41}$ is —OC(O)(CF$_3$), —OH, -alkyl, alkenyl, alkynyl, cycloalkyl, cycloalkenyl, a substituted or unsubstituted aryl, a substituted or unsubstituted heteroaryl, a substituted or unsubstituted heterocyclyl,

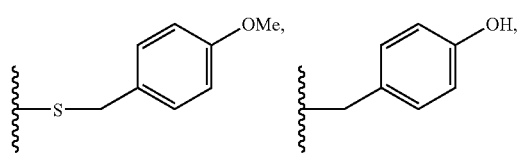

X, $OR_{120}$, —$SR_{121}$, —$N(R_{122})_2$, or —R'Y; or wherein each occurrence of alkyl, alkenyl, alkynyl, alkylene, alkenylene, and alkynylene is substituted or unsubstituted, bond β is absent, bond κ is present, bond δ is absent, $R_{44}$ and $R_{45}$ are absent, bond χ and $R_{46}$ are absent, and $R_{41}$ is —OH,

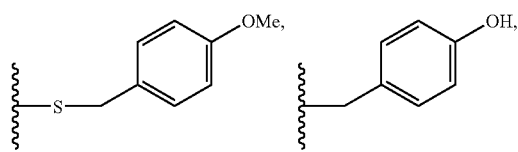

X $OR_{120}$, —$SR_{121}$, —$N(R_{122})_2$, or —R'Y, where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or wherein each occurrence of alkyl, alkenyl, alkynyl, alkylene, alkenylene, and alkynylene is substituted or unsubstituted, bond β is absent, bond κ is absent, each of bond δ, bond χ, $R_{44}$, $R_{45}$ and $R_{46}$ are present, and $R_{41}$ is joined to $R_{40}$ to form a pentacyclic ring, $R_{44}$, if present, is H, $R_{45}$, if present, is H or Br, $R_{46}$, if present, is

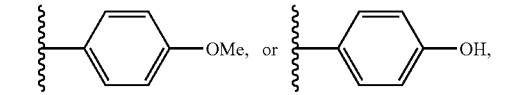

cycloalkyl, cycloalkenyl, a substituted or unsubstituted aryl, a substituted or unsubstituted heteroaryl, a substituted or unsubstituted heterocyclyl, $R_{106}$ is H, wherein when $R_{34}$ and $R_{43}$ are OH, $R_{35}$ is

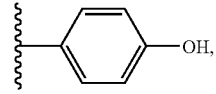

$R_{36}$, $R_{38}$, $R_{40}$, $R_{42}$ and $R_{44}$ are H, $R_{37}$ and $R_{39}$ are OH, and bond β is present, then $R_{41}$ is O or

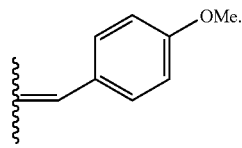

In an embodiment, the composition comprises a compound having the structure:

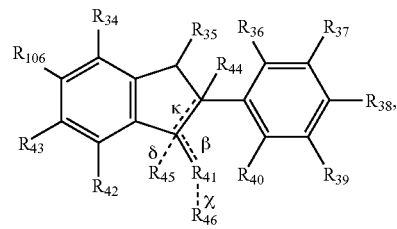

wherein
$R_{34}$ and $R_{43}$ are, independently, OH or OMe,
$R_{35}$ is

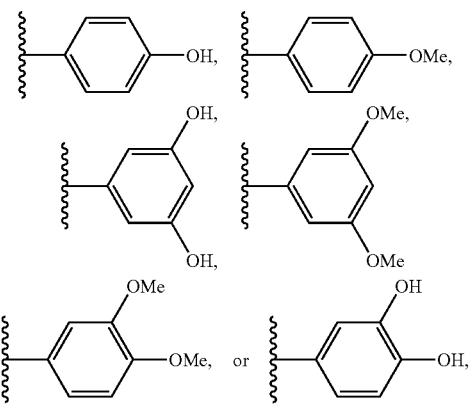

$R_{36}$ is Br, or H,
$R_{37}$ is H, OH, or OMe,
$R_{38}$ is H, OH, or OMe,
$R_{39}$ is H, OH, or OMe,
$R_{40}$ is H, or is joined to $R_{41}$ to form a pentacyclic ring,
bond β is present, each of bond χ, bond δ, bond κ, $R_{45}$ and $R_{46}$ are absent, $R_{44}$ is present, and $R_{41}$ is O,

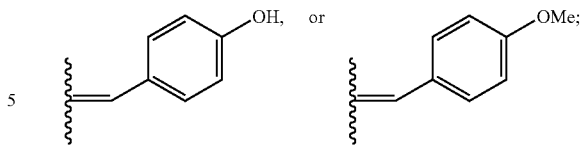

or
bond β is absent, bond κ is absent, bond δ is present, $R_{45}$ is present, bond χ and $R_{46}$ are absent, $R_{44}$ is present, and $R_{41}$ is —OC(O)(CF$_3$), —OH,

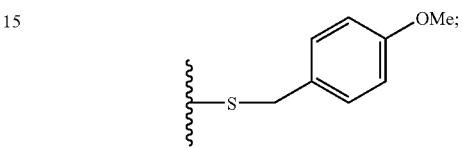

or
bond β is absent, bond κ is present, bond δ is absent, $R_{44}$ and $R_{45}$ are absent, bond χ and $R_{46}$ are absent, and $R_{41}$ is H or

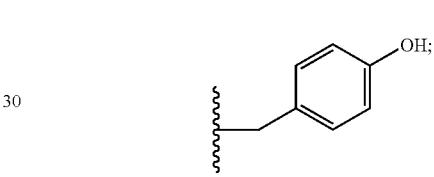

or
bond β is absent, bond κ is absent, each of bond δ, bond χ, $R_{44}$, $R_{45}$ and $R_{46}$ are present, and $R_{41}$ is joined to $R_{40}$ to form a pentacyclic ring,
$R_{42}$ is H, or Br,
$R_{43}$ is H, OMe, or OH
$R_{44}$, if present, is H,
$R_{45}$, if present, is H or Br,
$R_{46}$, if present, is

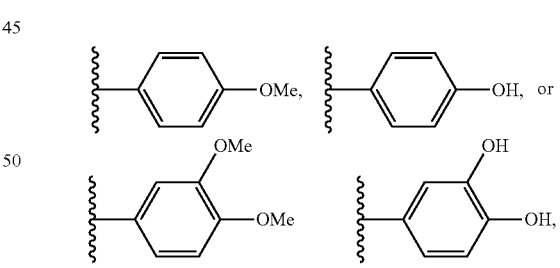

and
$R_{106}$ is H,
wherein when $R_{34}$ and $R_{43}$ are OH, $R_{35}$ is

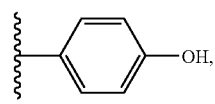

$R_{36}$, $R_{38}$, $R_{40}$, $R_{42}$ and $R_{44}$ are H, $R_{37}$ and $R_{39}$ are OH, and bond β is present, then $R_{41}$ is O or

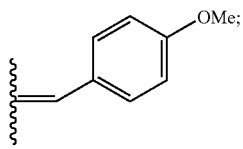
and when R$_{40}$ is joined to R$_{41}$ to form a pentacyclic ring, and R$_{34}$ and R$_{43}$ are OH, R$_{35}$ and R$_{46}$ are
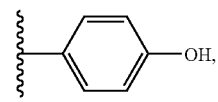
R$_{36}$, R$_{38}$, R$_{42}$ and R$_{44}$ are H, R$_{37}$ and R$_{39}$ are OH, then R$_{45}$ is Br.
In embodiments, the composition comprises the compound having the structure:
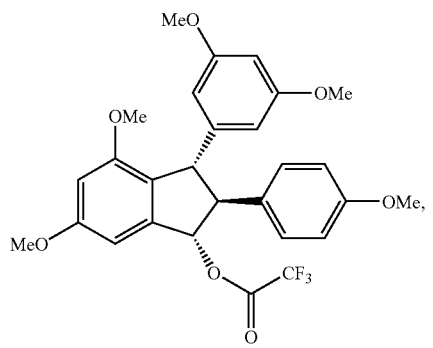
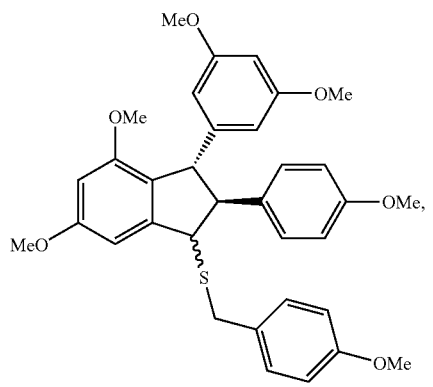
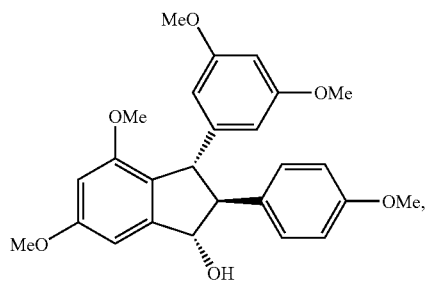
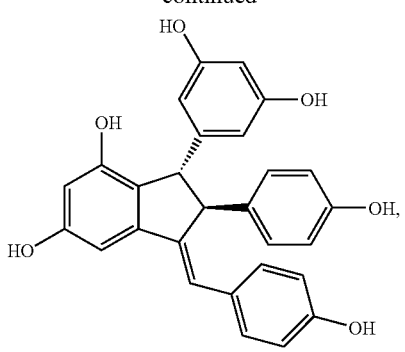
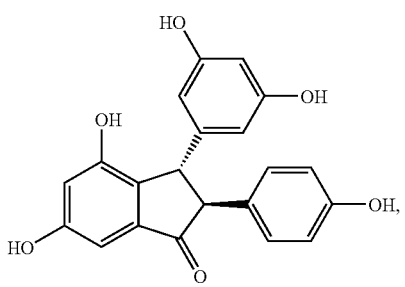
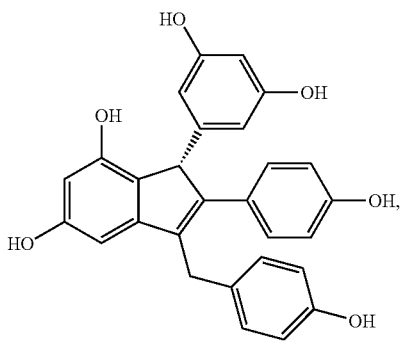
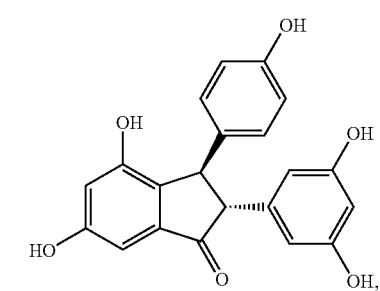
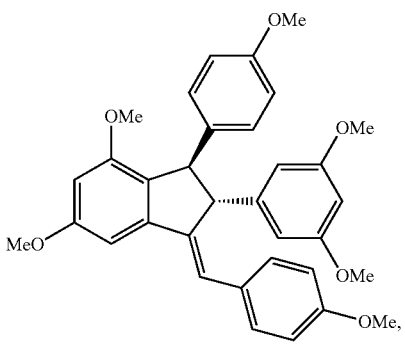

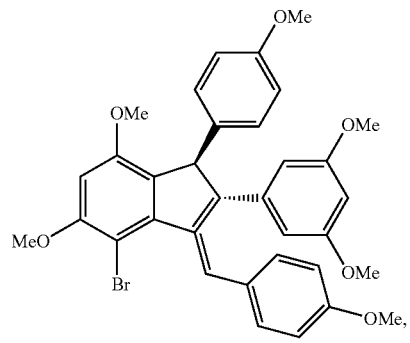
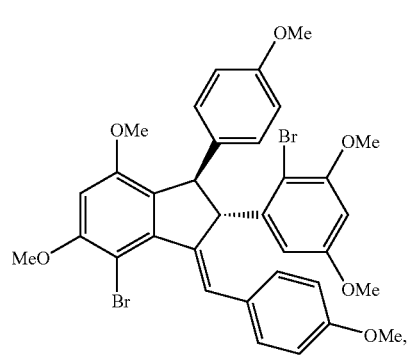
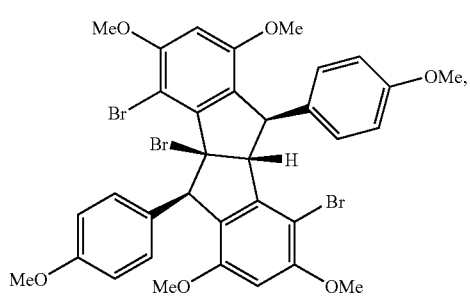
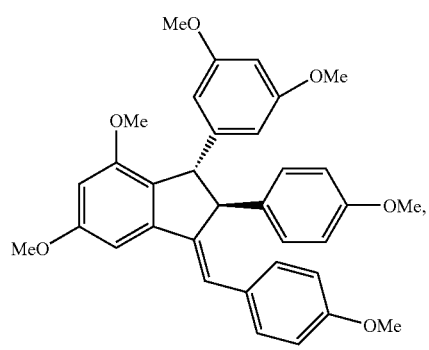
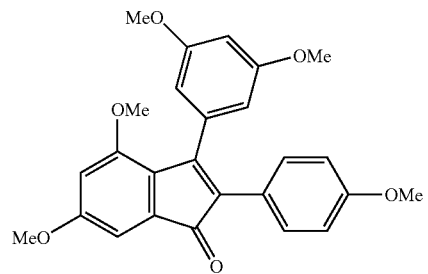
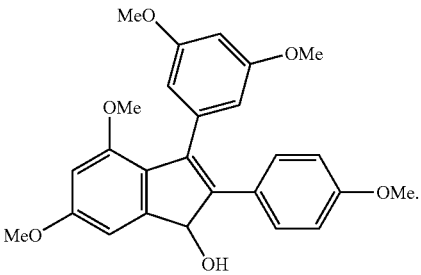
In embodiments, the composition comprises the compound having the structure:
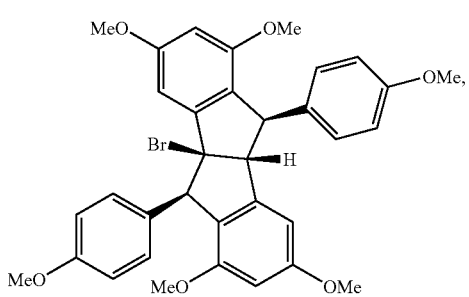
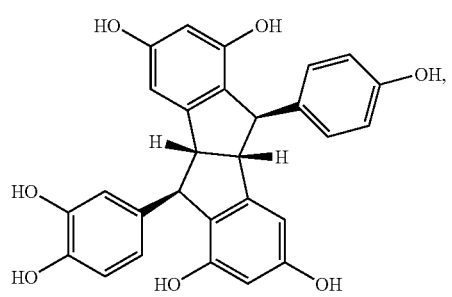
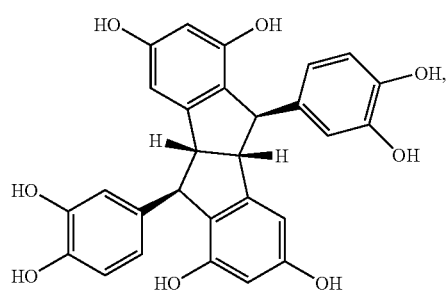
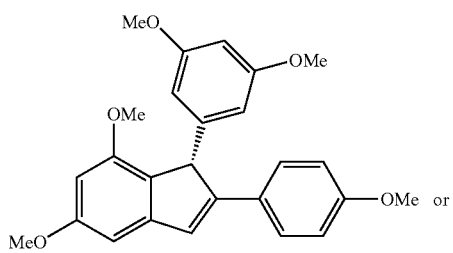

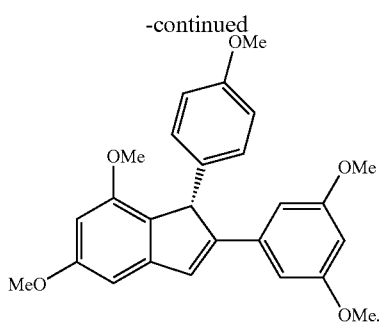

In embodiments, the composition comprises the compound having the structure:

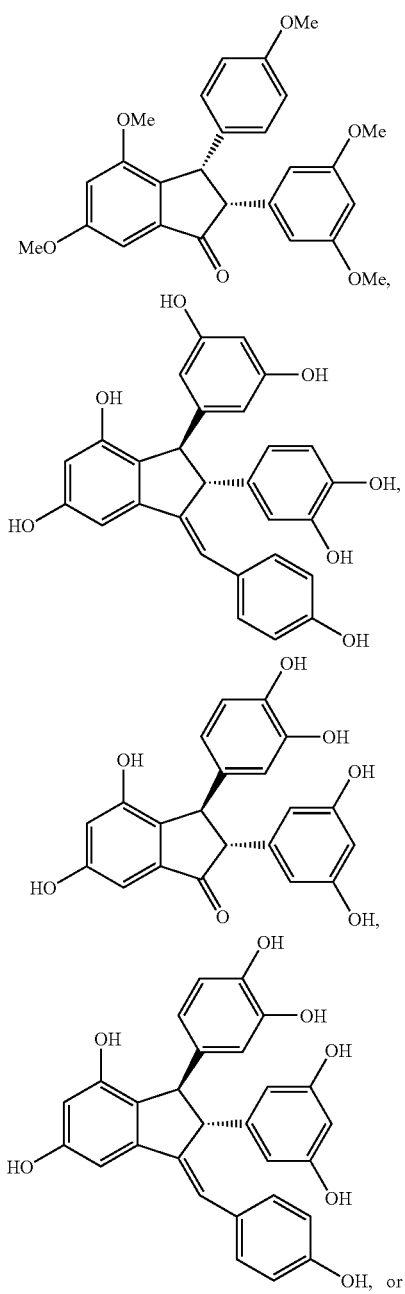

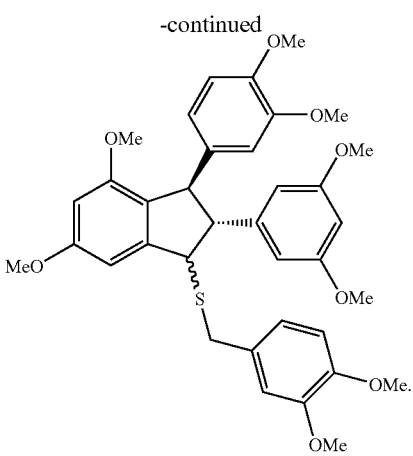

This invention provides a compound having the structure:

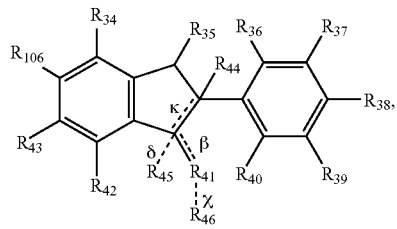

wherein
$R_{34}$ and $R_{43}$ are, independently, OH or OMe,
$R_{35}$ is

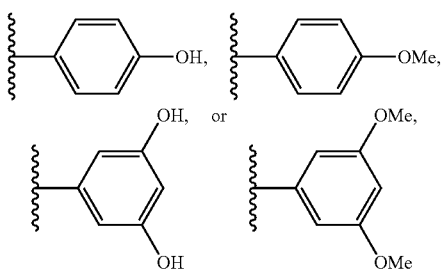

$R_{36}$ is Br, or H,
$R_{37}$ is H, OH, or OMe,
$R_{38}$ is H, OH, or OMe,
$R_{39}$ is H, OH, or OMe,
$R_{40}$ is H, or is joined to $R_{41}$ to form a pentacyclic ring,
bond β is present, each of bond χ, bond δ, bond κ, $R_{45}$ and $R_{46}$ are absent, $R_{44}$ is present, and $R_{41}$ is O,

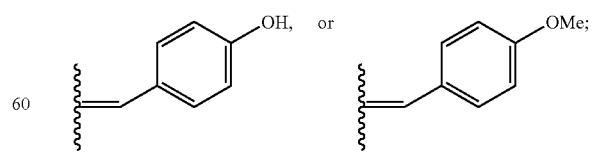

or
bond β is absent, bond κ is absent, bond δ is present, $R_{45}$ is present, bond χ and $R_{46}$ are absent, $R_{44}$ is present, and $R_{41}$ is —OC(O)(CP$_3$), —OH,

81

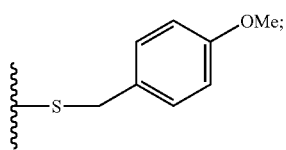 [SMILES: *SCc1ccc(OC)cc1]

or
bond β is absent, bond κ is present, bond δ is absent, $R_{44}$ and $R_{45}$ are absent, bond χ and $R_{46}$ are absent, and $R_{41}$ is

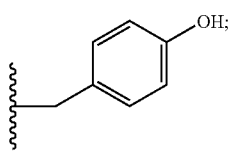

or
bond β is absent, bond κ is absent, each of bond δ, bond χ, $R_{44}$, $R_{45}$ and $R_{46}$ are present, and $R_{41}$ is joined to $R_{40}$ to form a pentacyclic ring,
$R_{42}$ is H, or Br,
$R_{43}$ is H, OMe, or OH
$R_{44}$, if present, is H,
$R_{45}$, if present, is H or Br,
$R_{46}$, if present, is

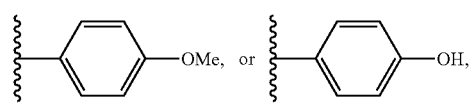

and
$R_{106}$ is H,
wherein when $R_{34}$ and $R_{43}$ are OH, $R_{35}$ is

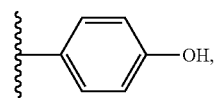

$R_{36}$, $R_{38}$, $R_{40}$, $R_{42}$ and $R_{44}$ are H, $R_{37}$ and $R_{39}$ are OH, and bond β is present, then $R_{41}$ is O or

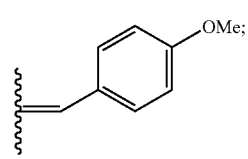

and when $R_{40}$ is joined to $R_{41}$ to form a pentacyclic ring, and $R_{34}$ and $R_{43}$ are OH, $R_{35}$ and $R_{46}$ are

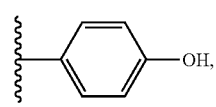

82

$R_{36}$, $R_{38}$, $R_{42}$ and $R_{44}$ are H, $R_{37}$ and $R_{39}$ are OH, then $R_{45}$ is Br.

In an embodiment of the instant processes the compound has the structure:

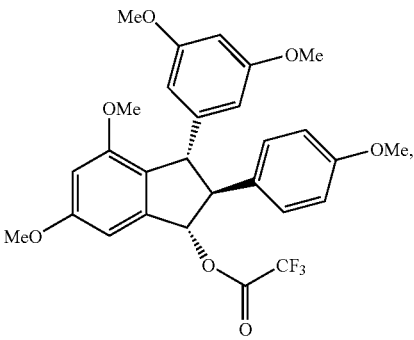

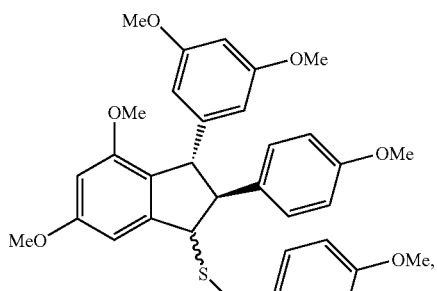

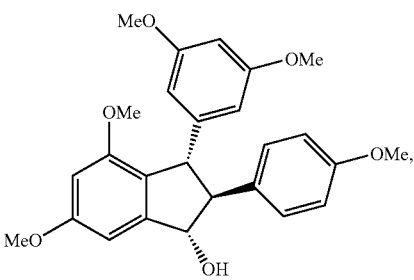

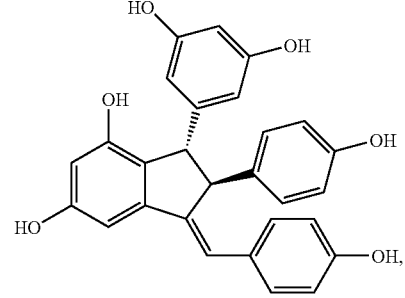

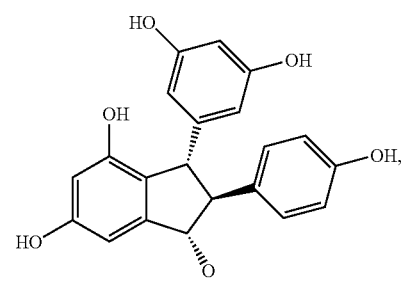

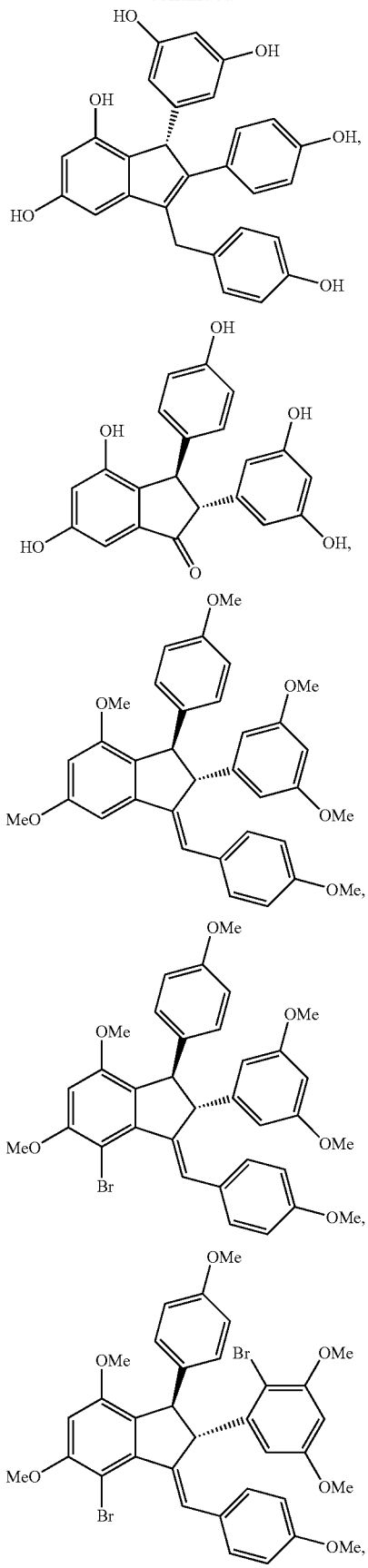
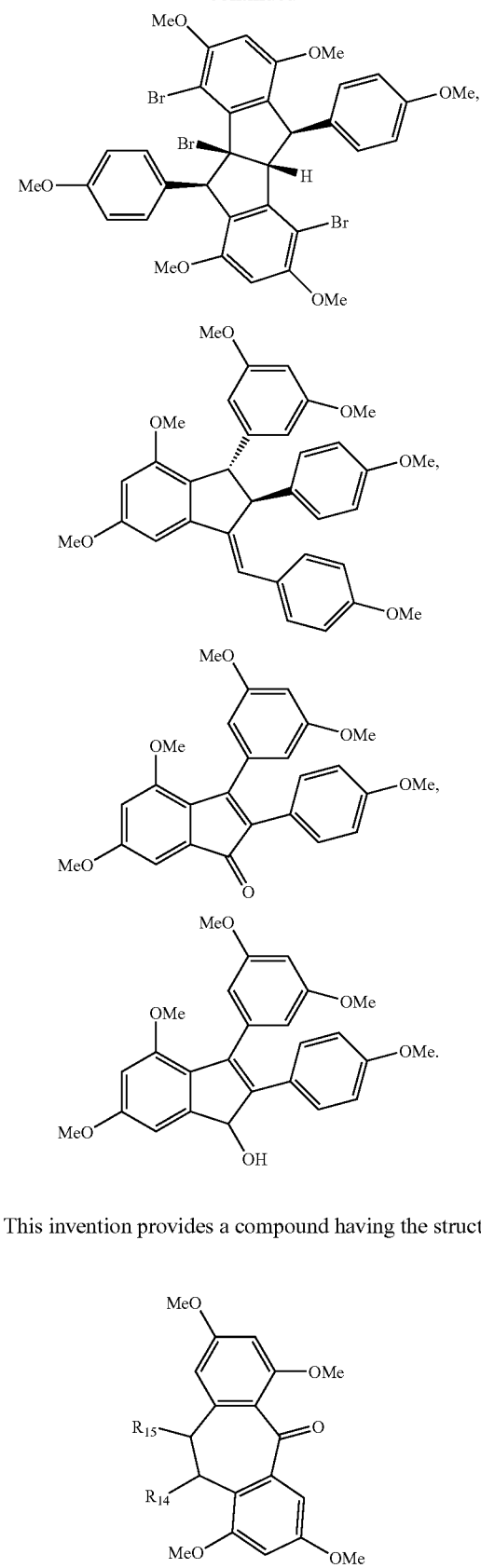
This invention provides a compound having the structure:
wherein $R_{14}$ is =O, OH, OAc or

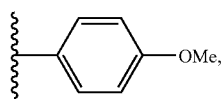

and R$_{15}$ is

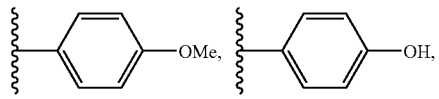

or Br.

In an embodiment the compound has the structure:

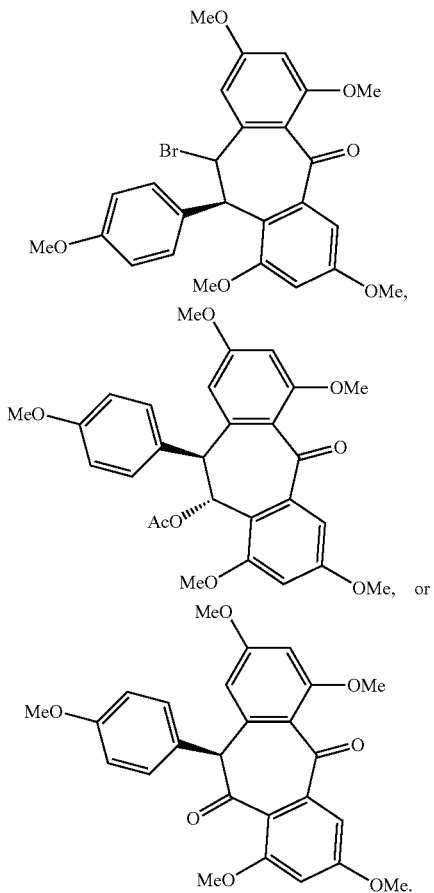

This invention provides a compound having the structure:

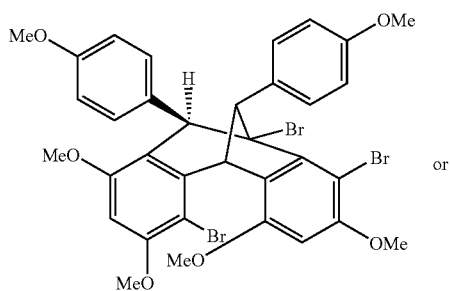

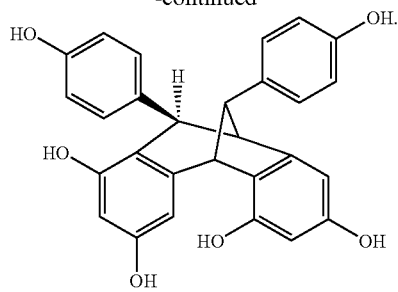

This invention provides a compound having the structure:

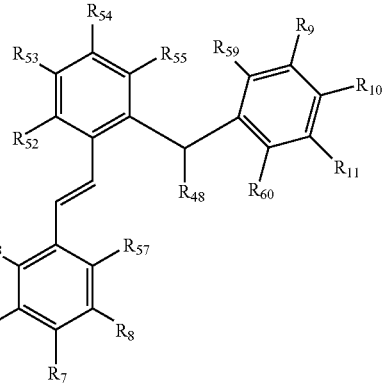

wherein R$_6$, R$_7$, R$_8$, R$_{52}$, R$_{53}$, R$_{54}$, R$_{55}$, R$_{57}$ and R$_{58}$ are defined as above, R$_{48}$ is OH, R$_9$, R$_{10}$, R$_{11}$, R$_{59}$, and R$_{60}$, are, independently, H, OH, alkyl, alkenyl, alkynyl, —OR$_{78}$, —SR$_{79}$, —N(R$_{80}$)$_2$, —S(O)(O)R$_{81}$, —C(O)OR$_{82}$, —R$_{83}$OR$_{84}$, —R$_{83}$R$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{78}$, R$_{79}$, R$_{81}$, R$_{82}$, R$_{84}$ and each occurrence of R$_{80}$ are, independently, H, alkyl, alkenyl, or alkynyl, and where R$_{83}$ is is alkylene, alkenylene or alkynylene, and wherein each occurrence of alkyl, alkenyl, alkynyl, alkylene, alkenylene, and alkynylene is substituted or unsubstituted.

In an embodiment the compound has the structure:

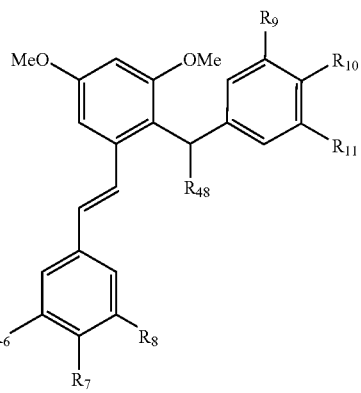

wherein R$_{48}$ is =O or OH, and
wherein either R$_7$, R$_9$ and R$_{11}$ are OMe and R$_6$, R$_8$ and R$_{10}$ are H, or wherein R$_7$, R$_9$ and R$_{11}$ are H and R$_6$, R$_8$ and R$_{10}$ are OMe.

This invention provides a compound having the structure:

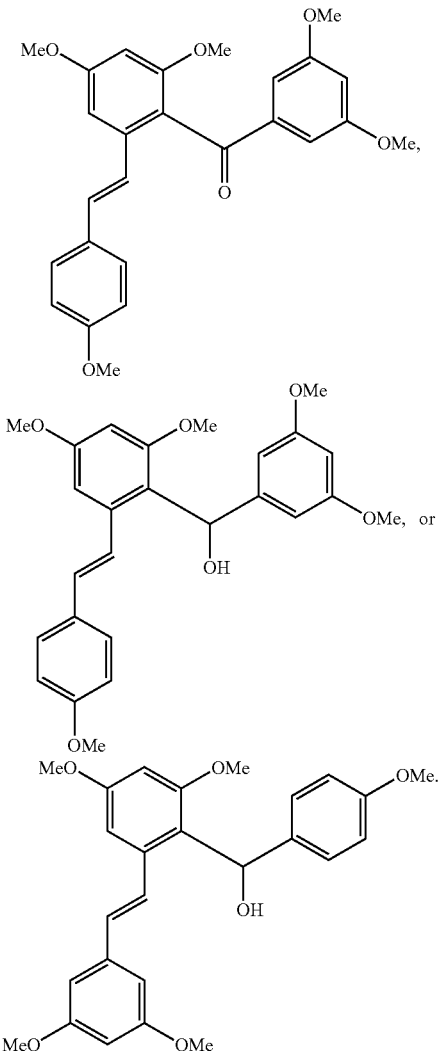

This invention provides a composition comprising one or more of the instant compounds. In an embodiment the composition is free from plant extract. In an embodiment the compound comprises a pharmaceutical carrier.

This invention provides a process for making a compound having the structure:

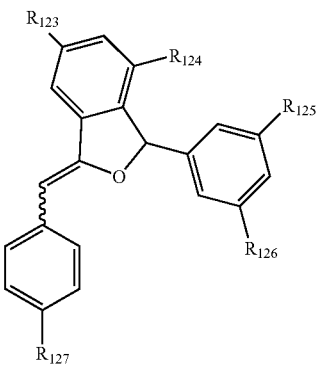

wherein $R_{123}$, $R_{124}$, $R_{125}$, $R_{126}$, and $R_{127}$, are, independently, H, OH, —Ome, alkyl, alkenyl, alkynyl, —OR$_{128}$, —SR$_{129}$, —N(R$_{130}$)$_2$, —S(O)(O)R$_{131}$, —C(O)OR$_{132}$, —R$_{133}$OR$_{134}$, R$_{133}$R$_{134}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{128}$, R$_{129}$, R$_{131}$, R$_{132}$, R$_{134}$ and each occurrence of R$_{130}$ are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where R$_{133}$ is is alkylene, alkenylene or alkynylene, wherein each occurrence of alkyl, alkenyl, alkynyl, alkylene, alkenylene, and alkynylene is substituted or unsubstituted, the process comprising contacting a compound having the structure:

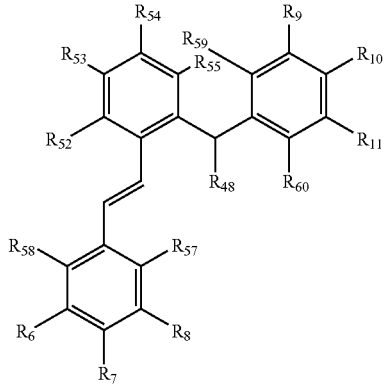

wherein $R_6$, $R_7$, $R_8$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —OR$_{78}$, —SR$_{59}$, —N(R$_{80}$)$_2$, —S(O)(O)R$_{81}$, —C(O)OR$_{82}$, —R$_{83}$OR$_{84}$, —R$_{83}$R$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{78}$, R$_{79}$, R$_{81}$, R$_{82}$, R$_{84}$ and each occurrence of R$_{80}$ are, independently, H, alkyl, alkenyl, or alkynyl, and where R$_{83}$ is is alkylene, alkenylene or alkynylene, wherein each occurrence of alkyl, alkenyl, alkynyl, alkylene, alkenylene, and alkynylene is substituted or unsubstituted, with a metal catalyst so as to make the compound.

In an embodiment, the process produces a compound having the structure:

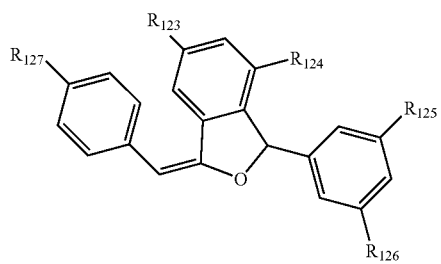

89 wherein $R_{123}$, $R_{124}$, $R_{125}$, $R_{126}$, and $R_{127}$, are, independently, H, OH, —OMe, alkyl, alkenyl, alkynyl, —$OR_{128}$, —$SR_{129}$, —$N(R_{130})_2$, —$S(O)(O)R_{131}$, —$C(O)OR_{132}$, —$R_{133}OR_{134}$, $R_{133}R_{134}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{128}$, $R_{129}$, $R_{131}$, $R_{132}$, $R_{134}$ and each occurrence of $R_{130}$ are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{133}$ is is alkylene, alkenylene or alkynylene, wherein each occurrence of alkyl, alkenyl, alkynyl, alkylene, alkenylene, and alkynylene is substituted or unsubstituted, the process comprises contacting a compound having the structure:

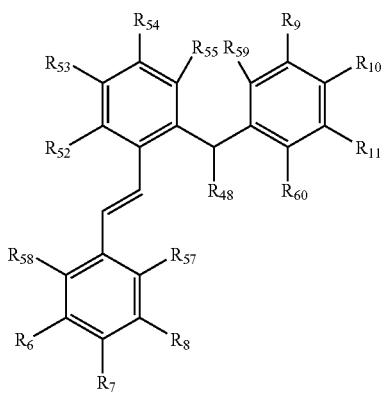

wherein $R_6$, $R_7$, $R_7$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, wherein each occurrence of alkyl, alkenyl, alkynyl, alkylene, alkenylene, and alkynylene is substituted or unsubstituted, with a metal catalyst so as to make the compound.

This invention provides a process for making a compound having the structure:

90

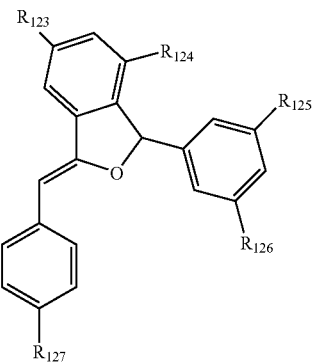

wherein $R_{123}$, $R_{124}$, $R_{125}$, $R_{126}$, and $R_{127}$, are, independently, H, OH, —OMe, alkyl, alkenyl, alkynyl, —$OR_{129}$, —$SR_{129}$, —$N(R_{130})_2$, —$S(O)(O)R_{31}$, —$C(O)OR_{132}$, —$R_{131}OR_{134}$, $R_{133}R_{134}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{128}$, $R_{129}$, $R_{131}$, $R_{132}$, $R_{134}$ and each occurrence of $R_{130}$ are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{133}$ is is alkylene, alkenylene or alkynylene, wherein each occurrence of alkyl, alkenyl, alkynyl, alkylene, alkenylene, and alkynylene is substituted or unsubstituted, the process comprising contacting a compound having the structure:

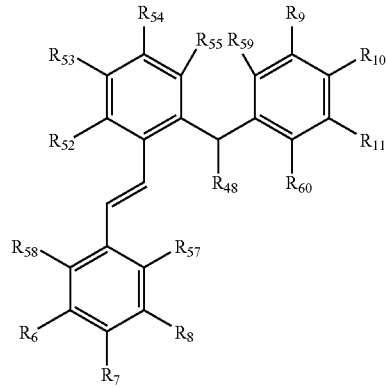

wherein $R_6$, $R_7$, $R_8$, $R_{52}$, $R_{53}$, $R_{54}$, $R_{55}$, $R_{57}$ and $R_{58}$ are defined as above, $R_{48}$ is OH, $R_9$, $R_{10}$, $R_{11}$, $R_{59}$, and $R_{60}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}R_{84}$, —$R_{83}OR_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, wherein each occurrence of alkyl, alkenyl, alkynyl, alkylene, alkenylene, and alkynylene is substituted or unsubstituted, with a metal catalyst so as to make the compound.

In an embodiment of the instant process the compound contacted with the metal catalyst has the structure:

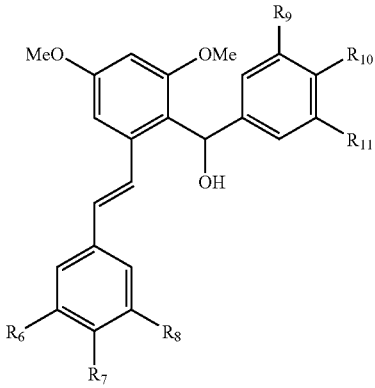

wherein either $R_7$, $R_9$ and $R_{11}$ are —OMe and $R_6$, $R_8$ and $R_{10}$ are H, or wherein $R_7$, $R_9$ and $R_{11}$ are H and $R_6$, $R_8$ and $R_{10}$ are —OMe.

In an embodiment, the metal catalyst is $Pd(OTFA)_2$. In another embodiment, the metal catalyst is $Pd(OAc)_2$ or $PdCl_2$ (benzonitrile)$_2$.

In an embodiment, the compound made has the structure:

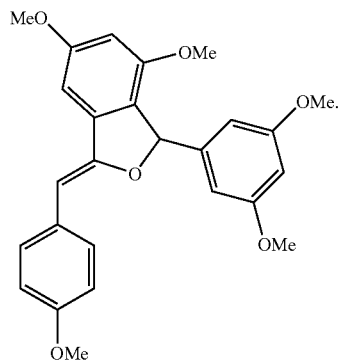 [SMILES: COc1ccc(/C=C2\OC(c3cc(OC)cc(OC)c3)c3c(OC)cc(OC)cc32)cc1]

In an embodiment, the method further comprises contacting the product with an acid in a suitable solvent so as to form a compound having the structure:

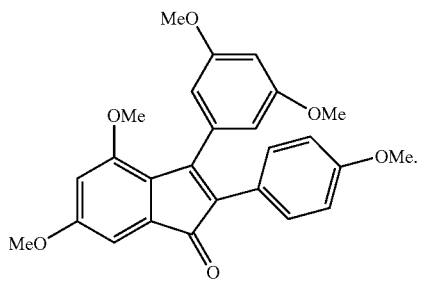 [SMILES: COc1ccc(C2=C(c3cc(OC)cc(OC)c3)c3c(OC)cc(OC)cc3C2=O)cc1]

In an embodiment, the process further comprises contacting the the product with boron tribromide to form a compound having the structure:

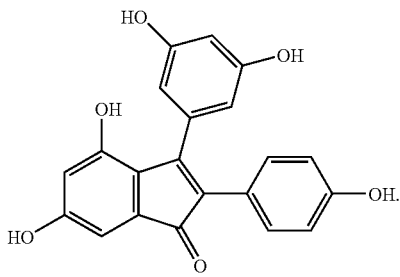 [SMILES: O=C1C(c2ccc(O)cc2)=C(c2cc(O)cc(O)c2)c2c(O)cc(O)cc21]

In an embodiment, the acid is HCl and the solvent is MeOH.

In embodiments, the processes produce a compound having the structure:

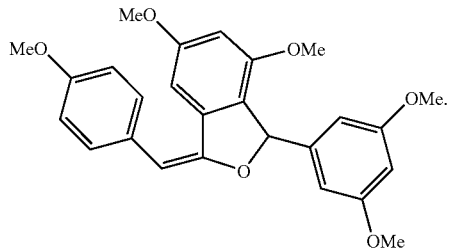 [SMILES: COc1ccc(/C=C2/OC(c3cc(OC)cc(OC)c3)c3c(OC)cc(OC)cc32)cc1]

In embodiments, each of $R_1$, $R_2$, $R_4$, $R_5$ through $R_{40}$, $R_{42}$, $R_{43}$, $R_{47}$ through $R_{60}$, $R_{85}$ through $R_{98}$, $R_{106}$, and $R_{114}$ through $R_{118}$ can independently be any of the following:

R1 =

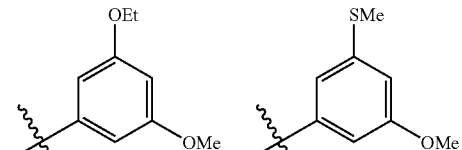

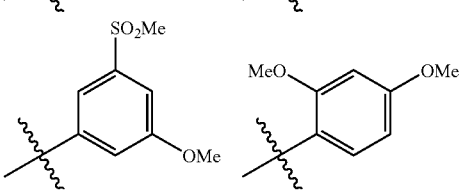

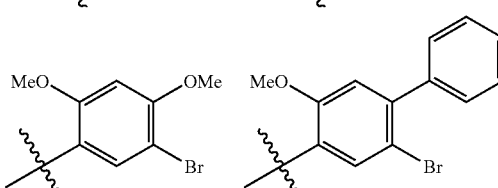

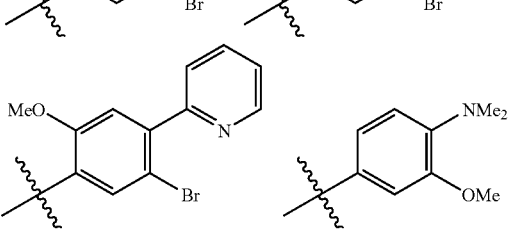

In embodiments, a compound of the invention has one of the following structures:

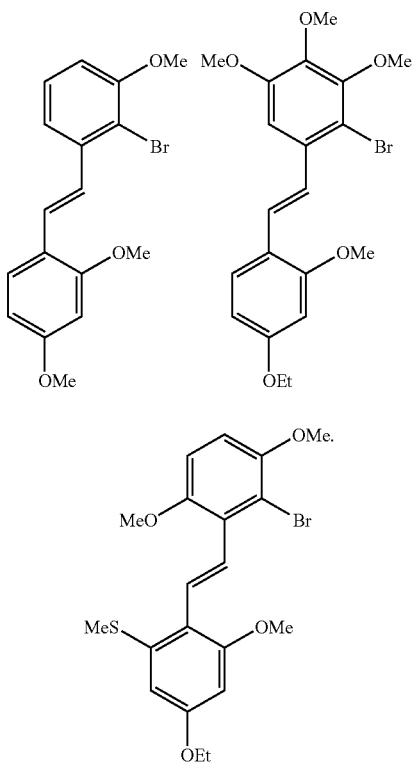

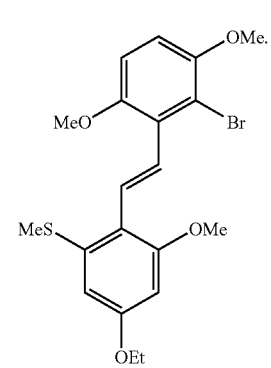

A process is provided for making a compound having the structure:

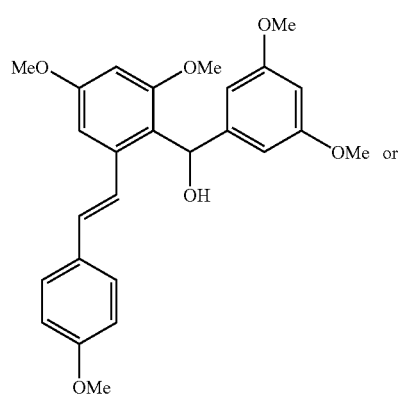

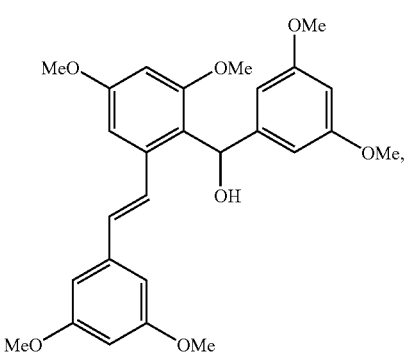

comprising reacting a compound having the structure:

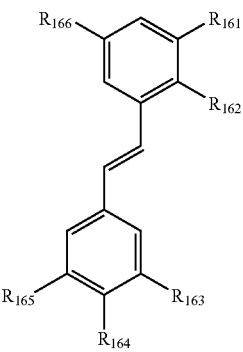

wherein $R_{161}$ and $R_{166}$ are OMe, $R_{162}$ is Br and
$R_{165}$ and $R_{163}$ are OMe and $R_{164}$ is H or $R_{165}$ and $R_{163}$ are H and $R_{164}$ is OMe,
with n-BuLi and a compound having the structure:

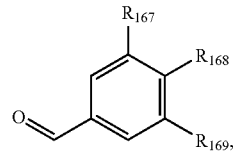

wherein $R_{167}$ is H or OMe, $R_{168}$ is H or OMe, and $R_{169}$ is H or OMe, so as to produce the compound.

In an embodiment, $R_{165}$ and $R_{163}$ are OMe, $R_{164}$ is H, $R_{167}$ is H, $R_{168}$ is OMe, and $R_{169}$ is H, and the compound produced is:

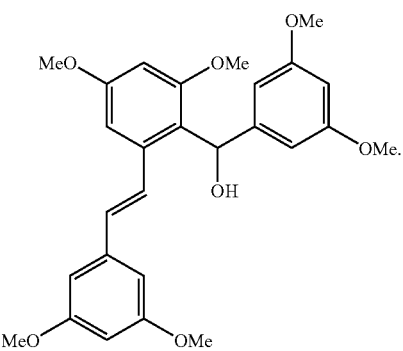 [SMILES: COc1cc(/C=C/c2cc(OC)cc(OC)c2C(O)c2cc(OC)cc(OC)c2)cc(OC)c1]

In an embodiment, $R_{165}$ and $R_{163}$ are H and $R_{164}$ is OMe, $R_{167}$ is OMe, $R_{168}$ is H, and $R_{169}$ is OMe and the compound produced is:

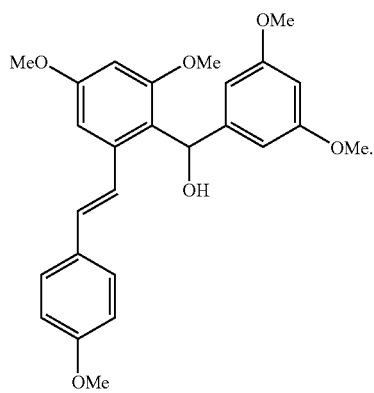

In an embodiment the process further comprises exposing

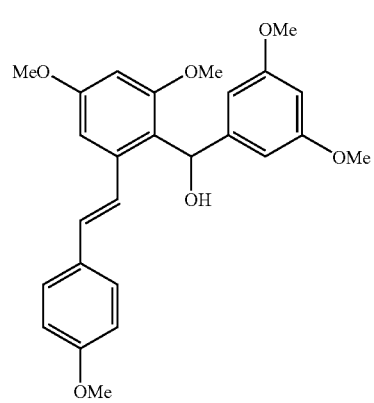 [SMILES: COc1ccc(/C=C/c2cc(OC)cc(OC)c2C(O)c2cc(OC)cc(OC)c2)cc1]

to an oxidizing agent so as to obtain a compound having the structure:

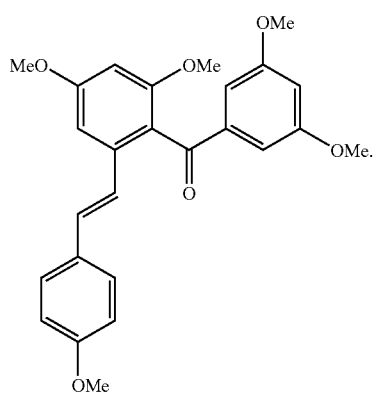

A process is provided for making a compound having the structure:

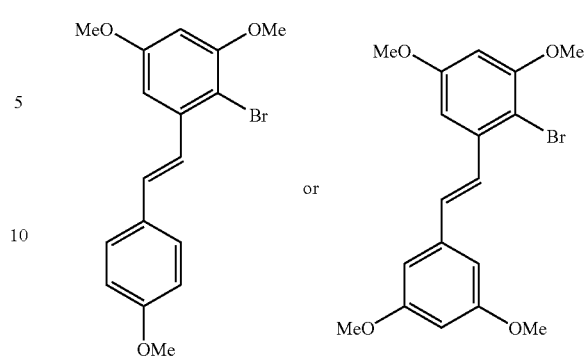

comprising:

e) reacting:

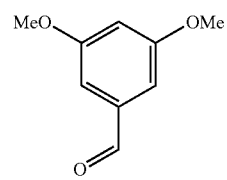

with NaBH₄ and PBR₃ to produce a compound having the structure:

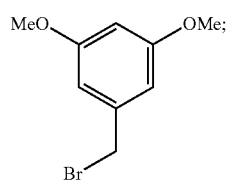 [SMILES: COc1cc(CBr)cc(OC)c1]

f) reacting the product of step a) with NBS in a suitable solvent;

g) reacting the product of step b) with KHMDS and HP(O)(OEt)₂ so as to produce a compound having the structure:

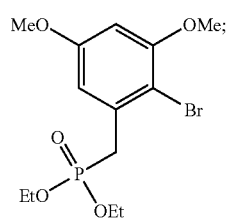 [SMILES: CCOP(=O)(Cc1cc(OC)cc(OC)c1Br)OCC]

h) reacting the product of step c) with KOt-Bu and p-methoxybenzaldehyde or 3,5-dimethoxybenzaldehyde so as to make the compound.

In an embodiment in step d) the product of step c) is reacted with KOt-Bu and p-methoxybenzaldehyde so as to produce the compound:

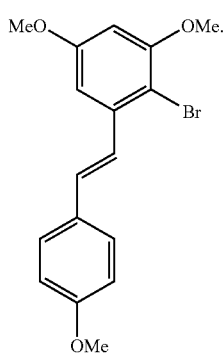 [SMILES: COc1ccc(/C=C/c2cc(OC)cc(OC)c2Br)cc1]

In an embodiment in step d) the product of step c) is reacted with KOt-Bu and 3,5-dimethoxybenzaldehyde so as to produce the compound:

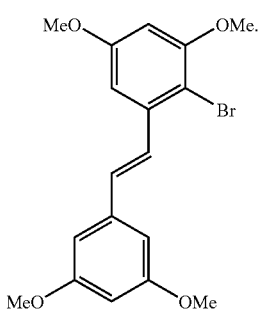 [SMILES: COc1cc(/C=C/c2cc(OC)cc(OC)c2Br)cc(OC)c1]

A compound is provided having the structure:

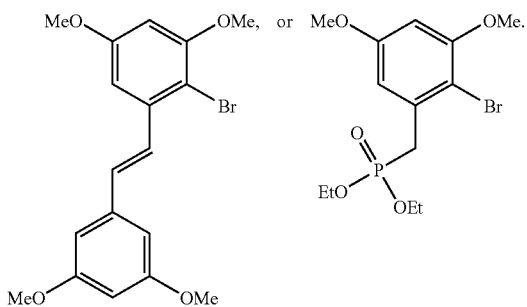

A compound having the structure:

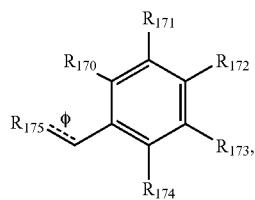

wherein
bond Φ is absent, $R_{170}$ and $R_{172}$ are —OMe, $R_{171}$ and $R_{174}$ are, and $R_{175}$ is —P(O)(OEt)(OEt), $R_{173}$ is Br, or
bond Φ is present, $R_{170}$, $R_{171}$, $R_{172}$, $R_{173}$ and $R_{174}$ are, independently, H or OMe.
In an embodiment, bond Φ is absent, $R_{170}$ and $R_{172}$ are H, $R_{171}$ and $R_{173}$ are —OMe, $R_{174}$ is Br, and $R_{175}$ is —P(O)(OEt)(OEt). In an embodiment, bond Φ is present, $R_{171}$ and $R_{173}$ are —OMe, $R_{170}$, $R_{172}$, $R_{174}$ are H. In an embodiment, bond Φ is present, $R_{172}$ is —OMe, $R_{170}$, $R_{171}$, $R_{173}$, and $R_{174}$ are H.

A compound is provided having the structure:

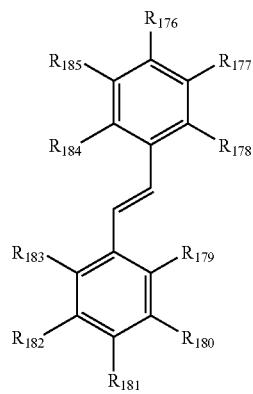

wherein $R_{176}$, $R_{177}$, $R_{178}$, $R_{179}$, $R_{180}$, $R_{181}$, $R_{182}$, $R_{183}$, $R_{184}$, $R_{185}$ are, independently, H, Br, or OMe.

In an embodiment, $R_{176}$ is H, $R_{177}$ is —OMe, $R_{178}$ is Br, $R_{179}$ is H, $R_{180}$ is —OMe or H, $R_{181}$ is —OMe or H, $R_{182}$ is —OMe or H, $R_{183}$ is H, $R_{184}$ is H and $R_{185}$ is —OMe.

A composition, free of plant extract, is provided comprising a compound having the structure:

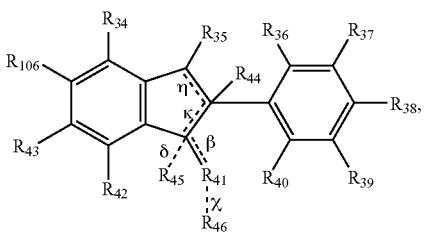

wherein
$R_{34}$, $R_{35}$, $R_{42}$, $R_{43}$, and $R_{106}$ are, independently, H, OH, OMe, $OC(O)_{R186}$, or

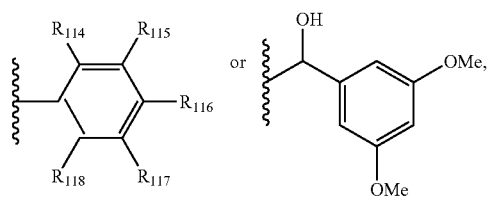

wherein each of $R_{114}$, $R_{115}$, $R_{116}$, $R_{117}$, and $R_{118}$ are, independently, H, OH, —OC(O)alkyl, alkyl, alkenyl, alkynyl, —$OR_{107}$, —$SR_{108}$, —$N(R_{109})_2$, —$S(O)(O)R_{110}$, —$C(O)OR_{111}$, —$R_{112}OR_{113}$, —$R_{112}R_{113}$, cycloalkyl, cycloalkenyl, a substituted or unsubstituted aryl, a substituted or unsubstituted heteroaryl, a substituted or unsubstituted heterocyclyl, or X,
where X is a halogen, where $R_{107}$, $R_{108}$, $R_{110}$, $R_{11}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene, wherein each occurrence of alkyl, alkenyl, alkynyl, alkylene, alkenylene, and alkynylene is substituted or unsubstituted, wherein $R_{186}$ is alkyl or alkenyl wherein $R_{36}$, $R_{37}$, $R_{38}$, $R_{39}$ and $R_{40}$ are, independently, H, OH, —OC(O)alkyl, alkyl, alkenyl, alkynyl, —OR$_{114}$, —SR$_{115}$, —N(R$_{116}$)$_2$, —S(O)(O)R$_{117}$, —C(O)OR$_{118}$, —R$_{119}$OR$_{120}$, —R$_{119}$R$_{120}$, cycloalkyl, cycloalkenyl, a substituted or unsubstituted aryl, a substituted or unsubstituted heteroaryl, a substituted or unsubstituted heterocyclyl, or X, where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{119}$ is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

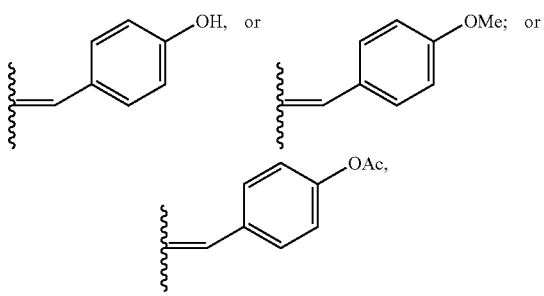

or bond β is absent, bond κ is absent, bond δ is present, $R_{45}$ is present, bond χ and $R_{46}$ are absent, $R_{44}$ is present, and $R_{41}$ is —OC(O)(CF$_3$), —OH, -alkyl, alkenyl, alkynyl, cycloalkyl, cycloalkenyl, a substituted or unsubstituted aryl, a substituted or unsubstituted heteroaryl, a substituted or unsubstituted heterocyclyl,

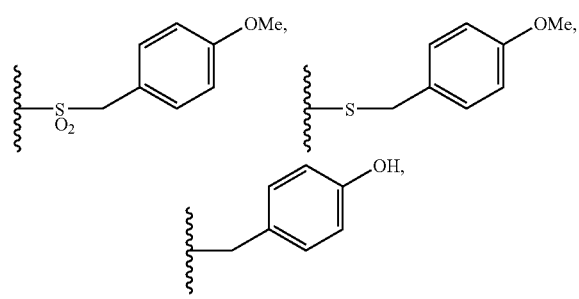

X, OR$_{120}$, —SR$_{121}$, —N(R$_{122}$)$_2$, or —R'Y; or wherein each occurrence of alkyl, alkenyl, alkynyl, alkylene, alkenylene, and alkynylene is substituted or unsubstituted, bond β is absent, bond κ is present, bond δ is absent, $R_{44}$ and $R_{45}$ are absent, bond χ and $R_{46}$ are absent, and $R_{41}$ is a halogen, —OH,

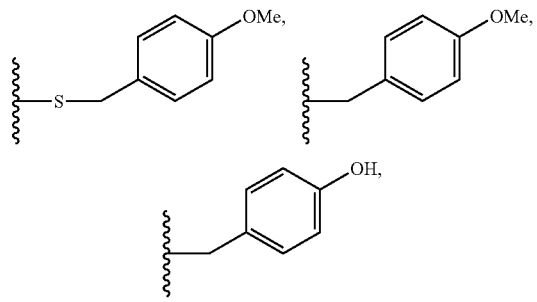

X, OR$_{120}$, —SR$_{121}$, —N(R$_{122}$)$_2$, or —R'Y, where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or wherein each occurrence of alkyl, alkenyl, alkynyl, alkylene, alkenylene, and alkynylene is substituted or unsubstituted, bond β is absent, bond κ is absent, each of bond δ, bond χ, $R_{44}$, $R_{45}$ and $R_{46}$ are present, and $R_{41}$ is joined to $R_{40}$ to form a pentacyclic ring, $R_{44}$, if present, is H, $R_{45}$, if present, is H or Br, $R_{46}$, if present, is

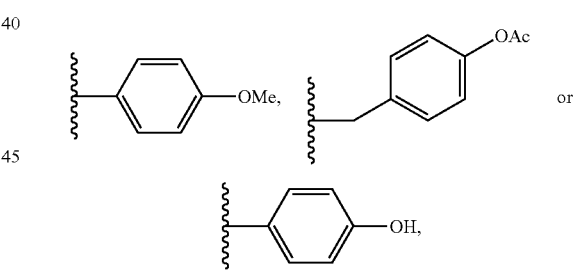

cycloalkyl, cycloalkenyl, a substituted or unsubstituted aryl, a substituted or unsubstituted heteroaryl, a substituted or unsubstituted heterocyclyl, wherein $R_{46}$ is only present if $R_{41}$ is joined to $R_{40}$ to form a pentacyclic ring, $R_{106}$ is H, wherein when $R_{34}$ and $R_{43}$ are OH, $R_{35}$ is

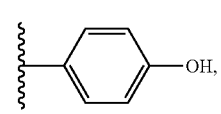

$R_{36}$, $R_{38}$, $R_{40}$, $R_{42}$ and $R_{44}$ are H, $R_{37}$ and $R_{39}$ are OH, and bond β is present, then $R_{41}$, is O or

101

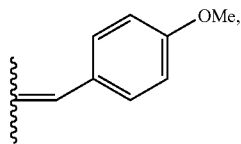

and when $R_{40}$ is joined to $R_{41}$ to form a pentacyclic ring, and $R_{34}$ and $R_{43}$ are OH, $R_{35}$ and $R_{46}$ are

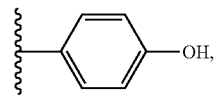

$R_{36}$, $R_{38}$, $R_{42}$ and $R_{44}$ are H, $R_{37}$ and $R_{39}$ are OH, then $R_{45}$ is Br.

wherein bond η is present or absent, but when present bond κ is absent.

In an embodiment, $R_{186}$ is alkyl and is $CH_3$.

In an embodiment, the compound has the structure:

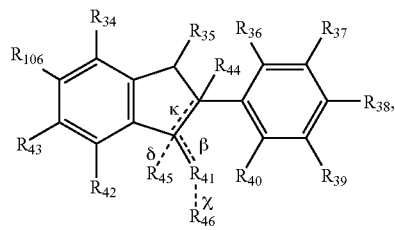

wherein $R_{34}$ and $R_{43}$ are, independently, OH or OMe, $R_{35}$ is

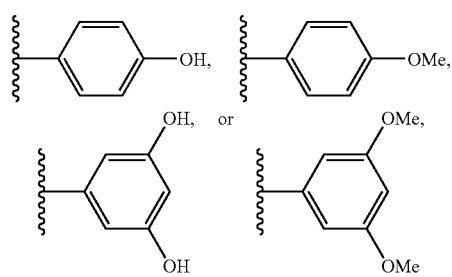

$R_{36}$ is Br, or H, $R_{37}$ is H, OH, or OMe, $R_{38}$ is H, OH, or OMe, $R_{39}$ is H, OH, or OMe, $R_{40}$ is H, or is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

102

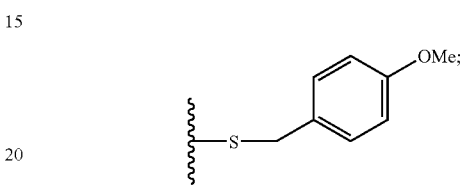

or bond β is absent, bond κ is absent, bond δ is present, $R_{45}$ is present, bond χ and $R_{46}$ are absent, $R_{44}$ is present, and $R_{41}$ is —OC(O)(CF$_3$), —OH,

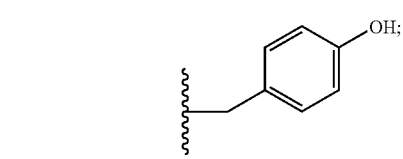

or bond β is absent, bond κ is present, bond δ is absent, $R_{44}$ and $R_{45}$ are absent, bond χ and $R_{46}$ are absent, and $R_{41}$ is

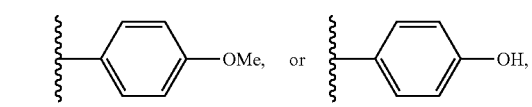

or bond β is absent, bond κ is absent, each of bond δ, bond χ, $R_{44}$, $R_{45}$ and $R_{46}$ are present, and $R_{41}$ is joined to $R_{40}$ to form a pentacyclic ring, $R_{42}$ is H, or Br, $R_{43}$ is H, OMe, or OH $R_{44}$, if present, is H, $R_{45}$, if present, is H or Br, $R_{46}$, if present, is

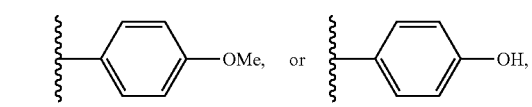

and $R_{106}$ is H, wherein when $R_{34}$ and $R_{43}$ are OH, $R_{35}$ is

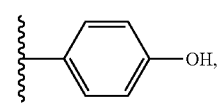

$R_{36}$, $R_{38}$, $R_{40}$, $R_{42}$ and $R_{44}$ are H, $R_{37}$ and $R_{39}$ are OH, and bond β is present, then $R_{41}$ is O or

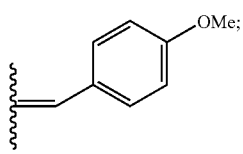
and when $R_{40}$ is joined to $R_{41}$ to form a pentacyclic ring, and $R_{34}$ and $R_{43}$ are OH, $R_{35}$ and $R_{46}$ are
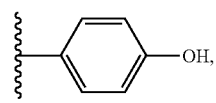
$R_{36}$, $R_{38}$, $R_{42}$ and $R_{44}$ are H, $R_{37}$ and $R_{39}$ are OH, then $R_{45}$ is Br.
In an embodiment, the compound has the structure:
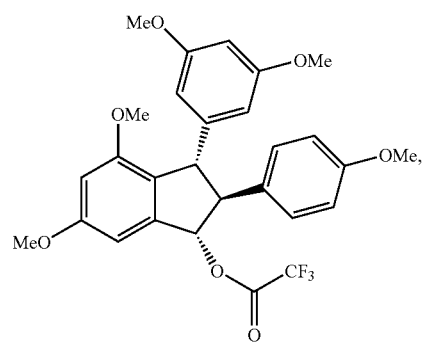
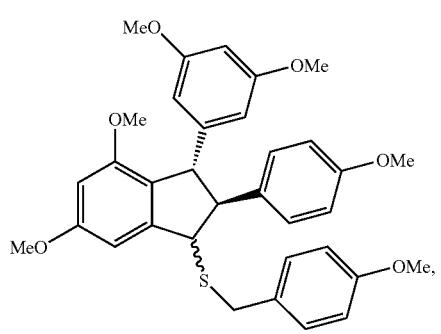
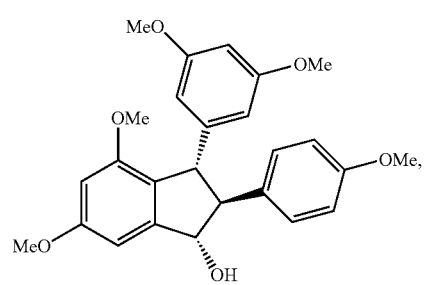
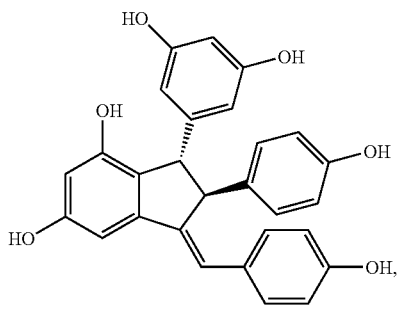
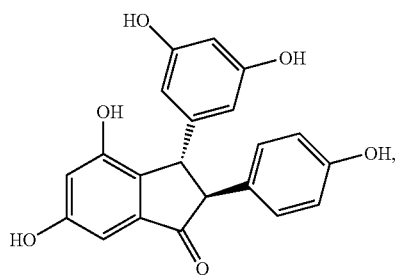
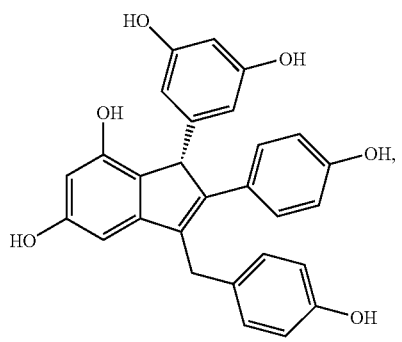
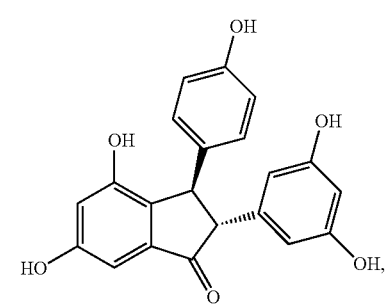
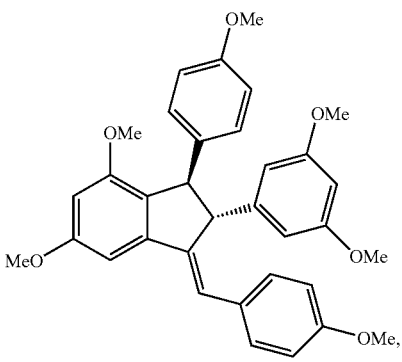

105
-continued
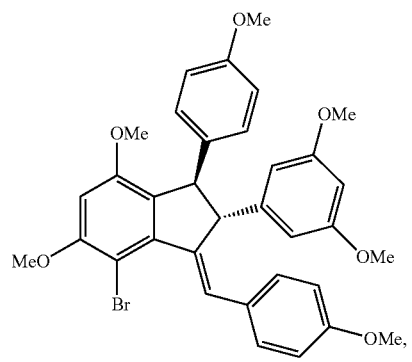
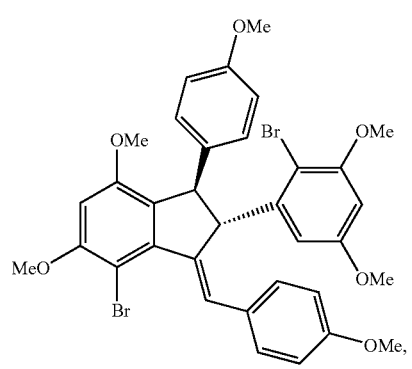
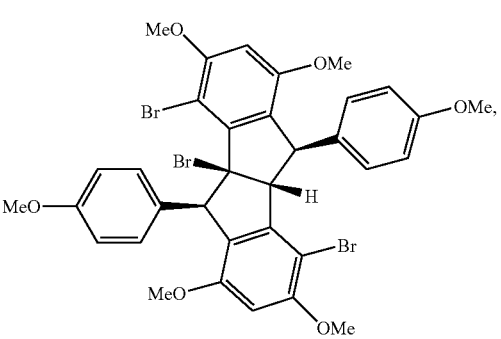
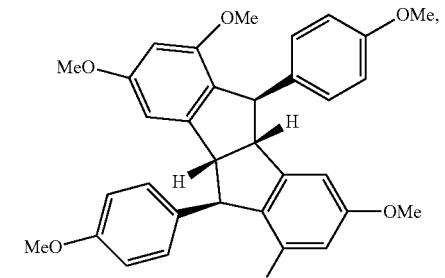
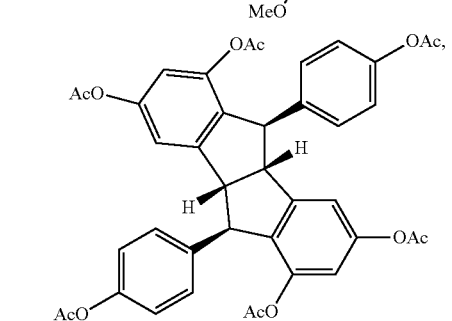
106
-continued
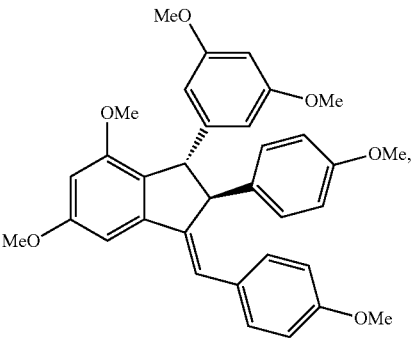
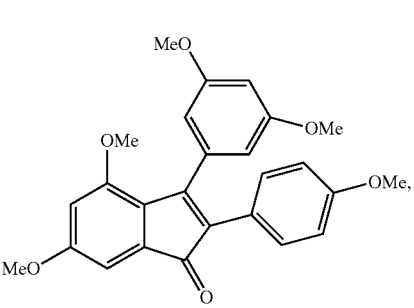
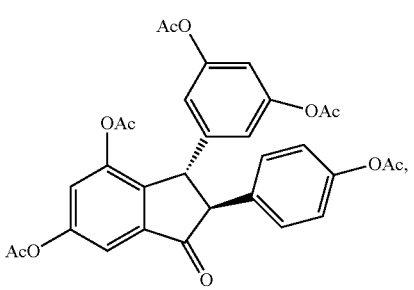
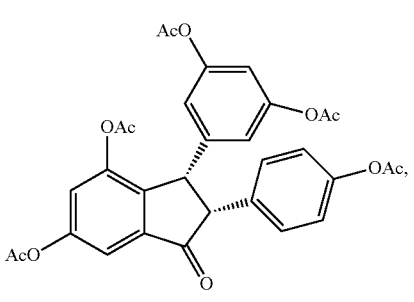
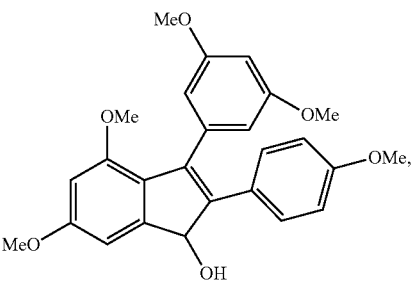

107
-continued
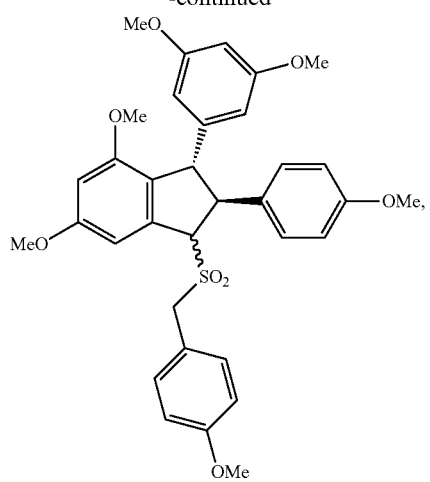
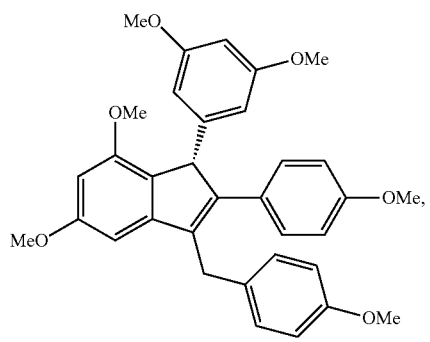
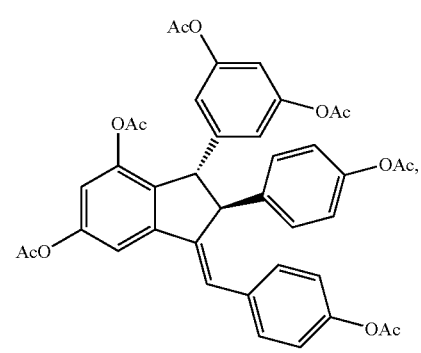
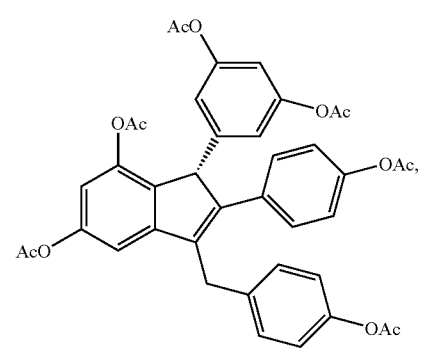
108
-continued
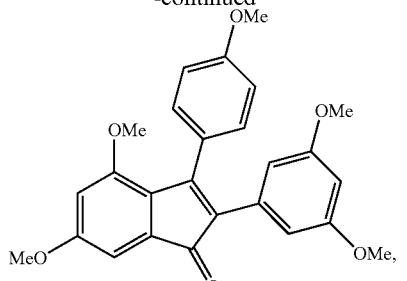
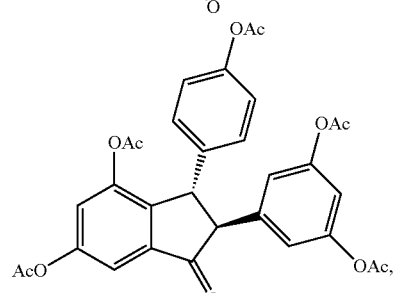
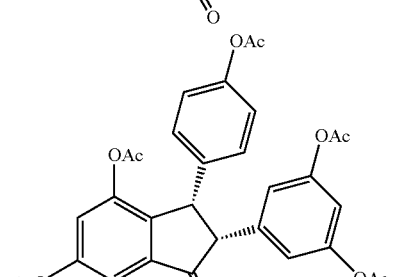
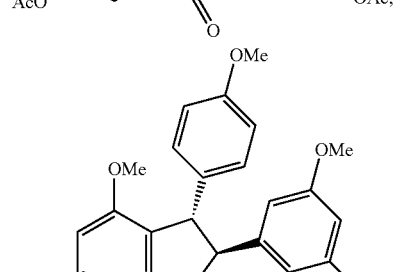
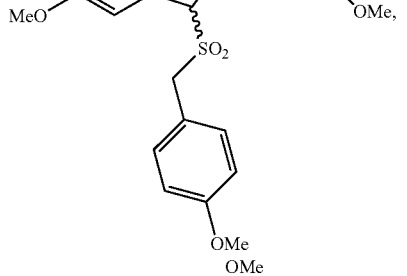
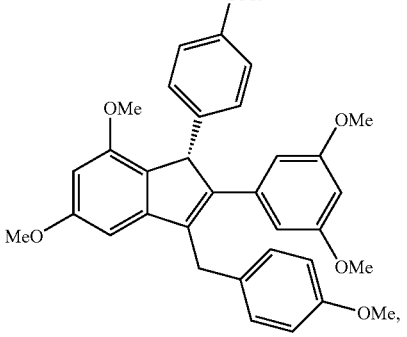

109
-continued
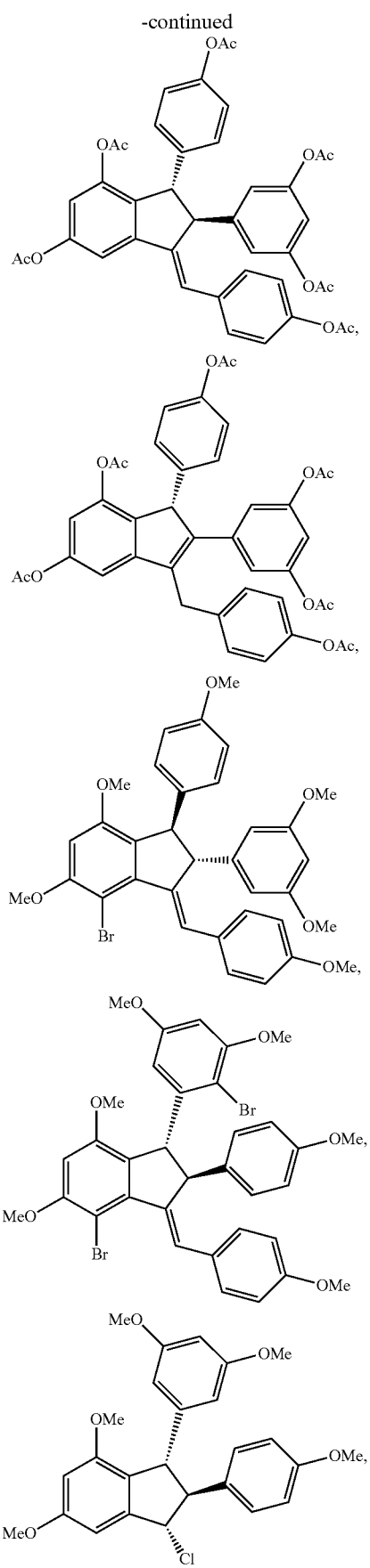
110
-continued
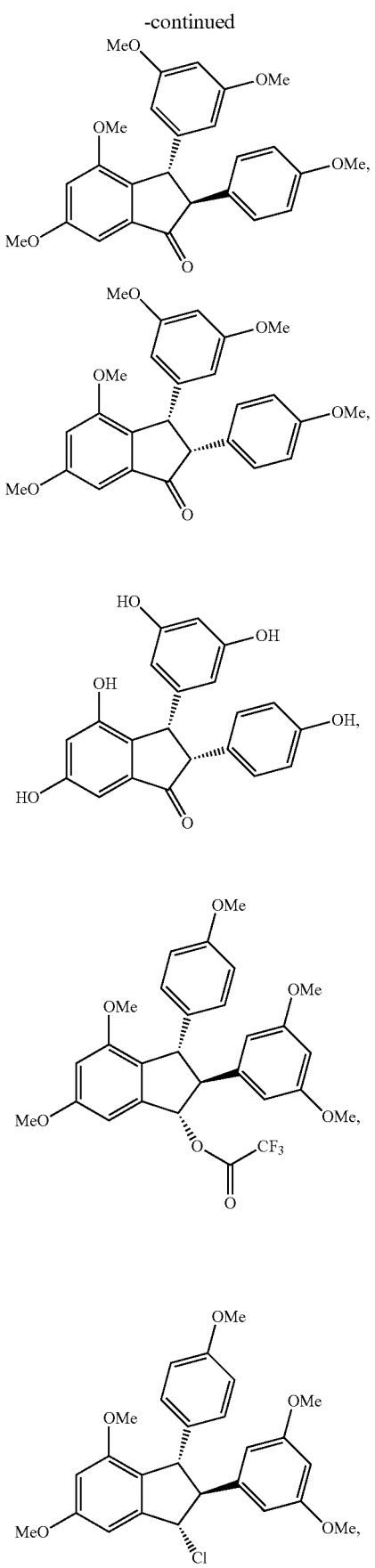

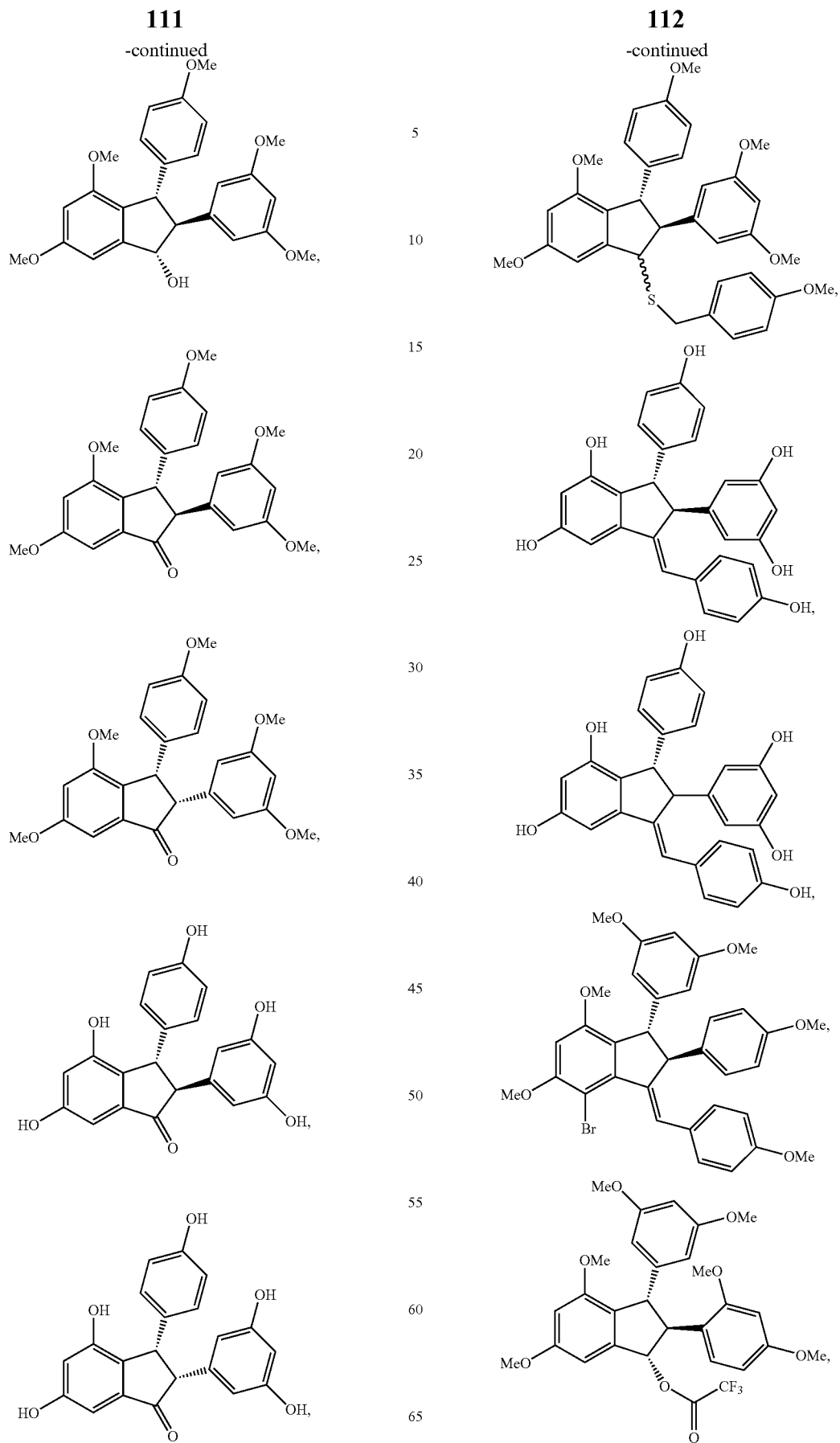

-continued
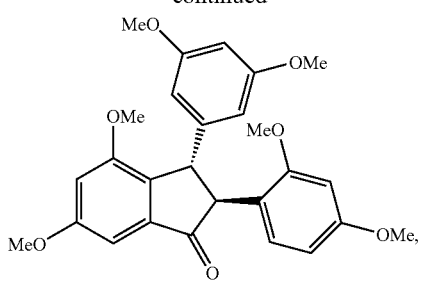
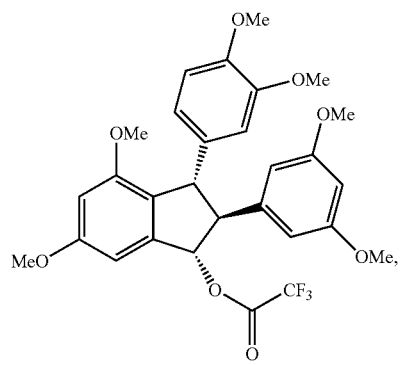
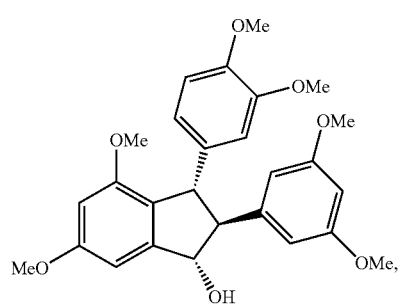
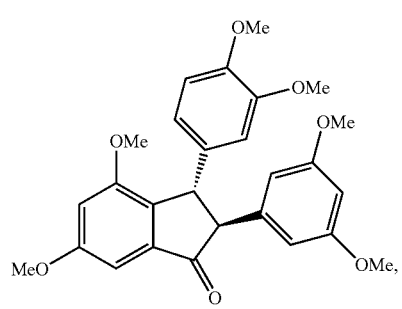
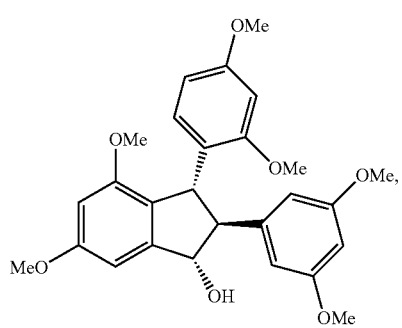
-continued
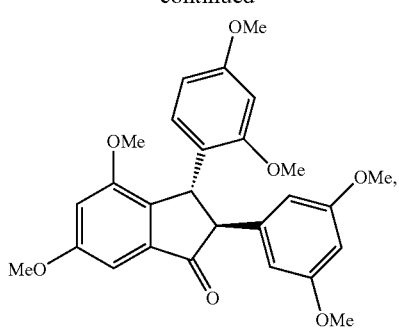
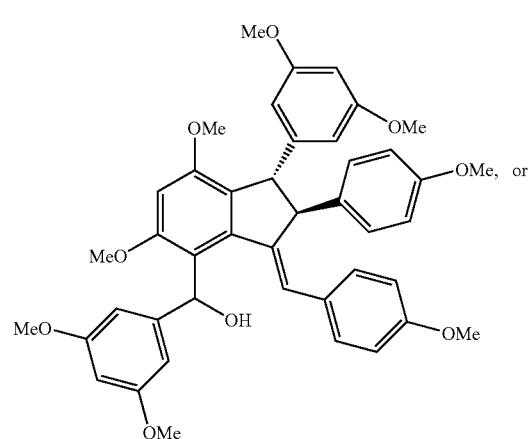
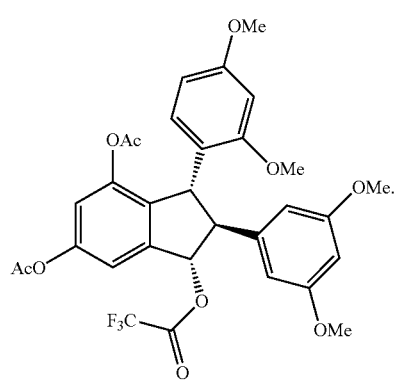
In an embodiment, the composition comprises the compound having the structure:
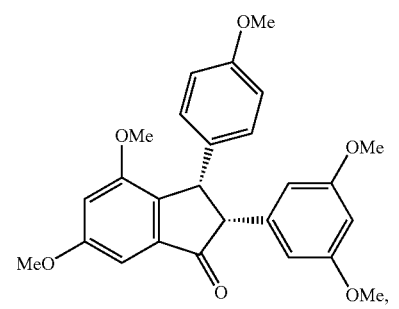

-continued

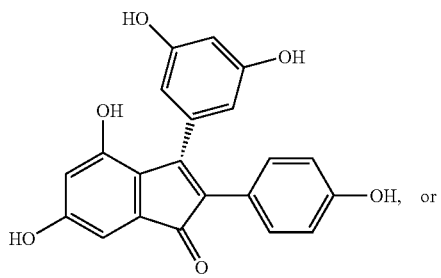

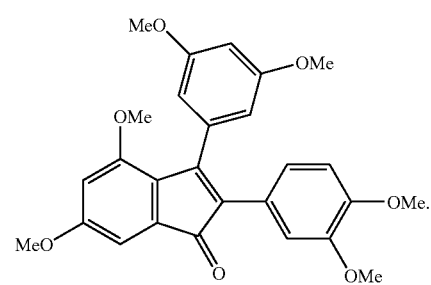

A compound is provided having the structure:

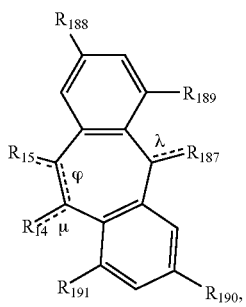

wherein $R_{14}$, $R_{15}$, $R_{188}$, $R_{187}$, $R_{188}$, $R_{189}$, $R_{190}$, $R_{191}$, are, independently, =O, H, OH, —OC(O)alkyl, alkyl, alkenyl, alkynyl, —OR$_{212}$, —SR$_{213}$, —N(R$_{214}$)$_2$, —S(O)(O)R$_{21}$, —C(O)OR$_{216}$, —R$_{217}$OR$_{218}$, —R$_{217}$R$_{218}$, —SO$_2$—R$_{219}$, cycloalkyl, cycloalkenyl, a substituted or unsubstituted aryl, a substituted or unsubstituted heteroaryl, a substituted or unsubstituted heterocyclyl, or X, where X is a halogen, where $R_{212}$, $R_{213}$, $R_{215}$, $R_{216}$, $R_{218}$, $R_{219}$, and each occurrence of $R_{214}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{217}$ is alkylene, alkenylene or alkynylene, wherein each occurrence of alkyl, alkenyl, alkynyl, alkylene, alkenylene, and alkynylene is substituted or unsubstituted, wherein bonds φ, ξ, λ, and μ are present or absent, but wherein when bond φ is present bonds ξ and μ are absent, and wherein when bond μ is present bond φ is absent, and wherein when bond ξ is present bond φ is absent.

In an embodiment $R_{190}$ is

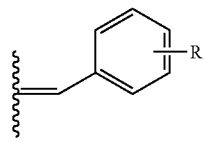

and R is OH, —O-alkyl, alkyl, alkenyl, alkynyl, cycloalkyl, cycloalkenyl, a substituted or unsubstituted aryl, a substituted or unsubstituted heteroaryl, a substituted or unsubstituted heterocyclyl, or OAc.

In an embodiment the compound has the structure:

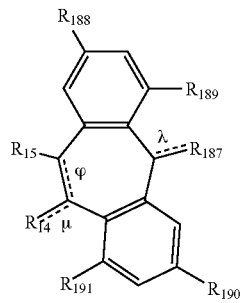

wherein $R_{14}$ is Br, H, =O, OH, OAc,

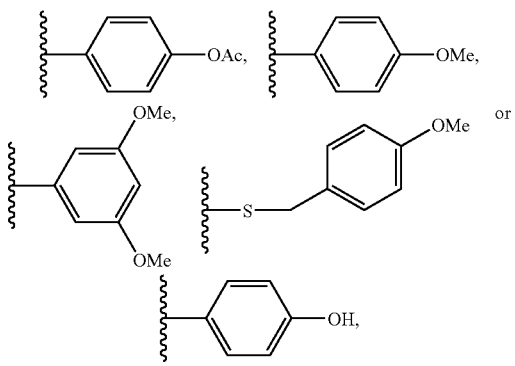

$R_{15}$ is =O, Br, H, OH, OAc,

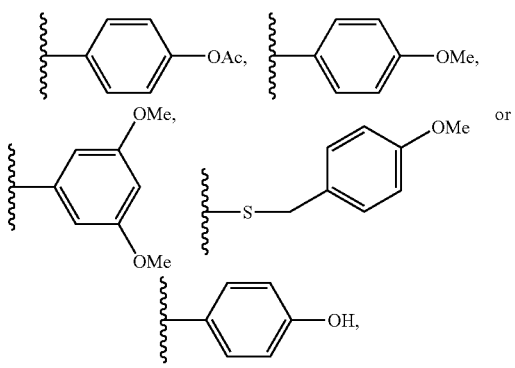

wherein $R_{187}$ is H, OH, —OAc, —OMe, or =O,

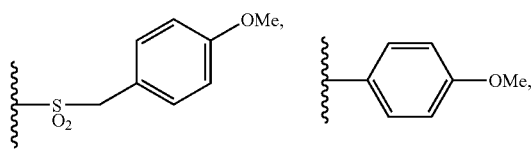

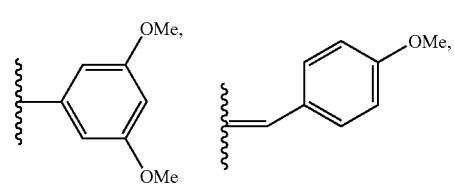

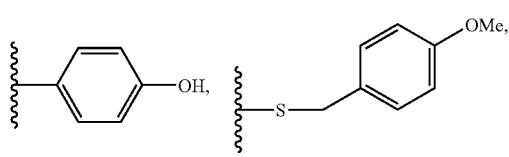

$R_{188}$, $R_{189}$, $R_{190}$ and $R_{191}$ are, independently,

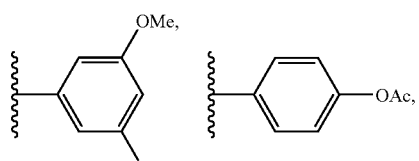

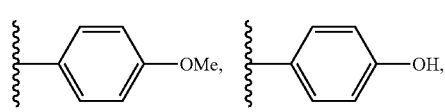

OAc, H or OH, wherein bond φ is present or absent, wherein bond λ is present when $R_{187}$ is =O or

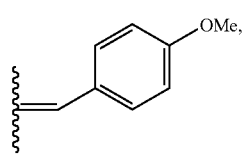

wherein bond μ is present when $R_{14}$ is =O and bond φ is absent, and wherein at least one of $R_{188}$, $R_{189}$, $R_{190}$ and $R_{191}$ is, —OMe, —OAc, or H when $R_{14}$ is

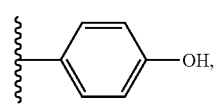

and $R_{15}$ and $R_{187}$ are =O.

In an embodiment the compound has the structure:

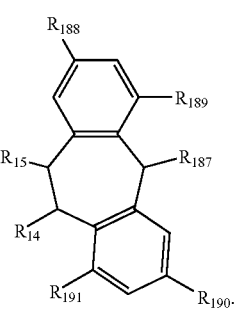

In an embodiment the compound has the structure:

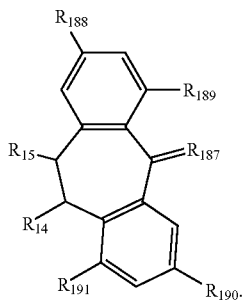

In an embodiment the compound has the structure:

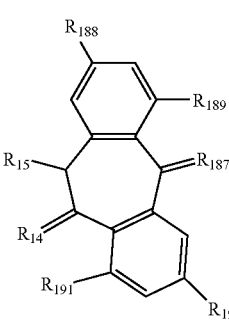 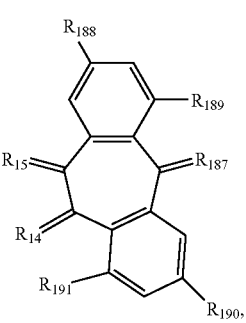

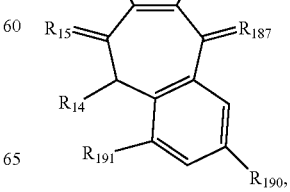 or 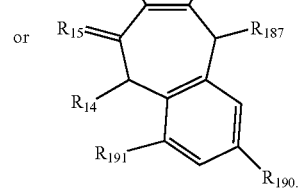

In an embodiment the compound has the
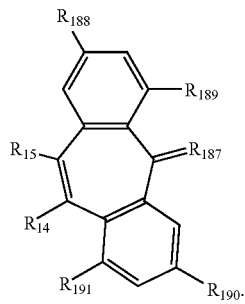
In an embodiment the compound has the structure:
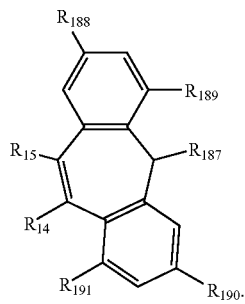
In an embodiment the compound has the structure:
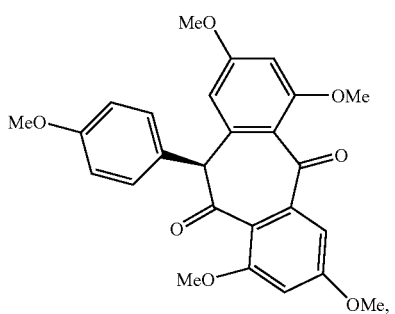
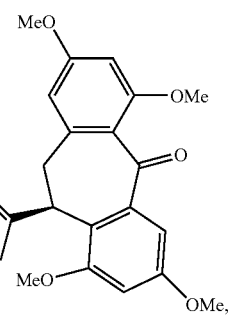
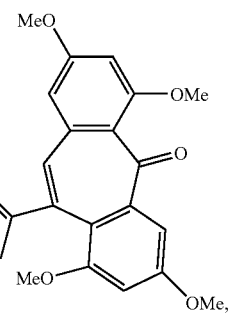
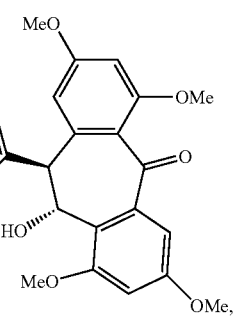
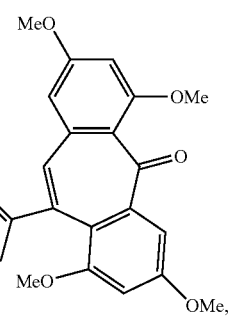

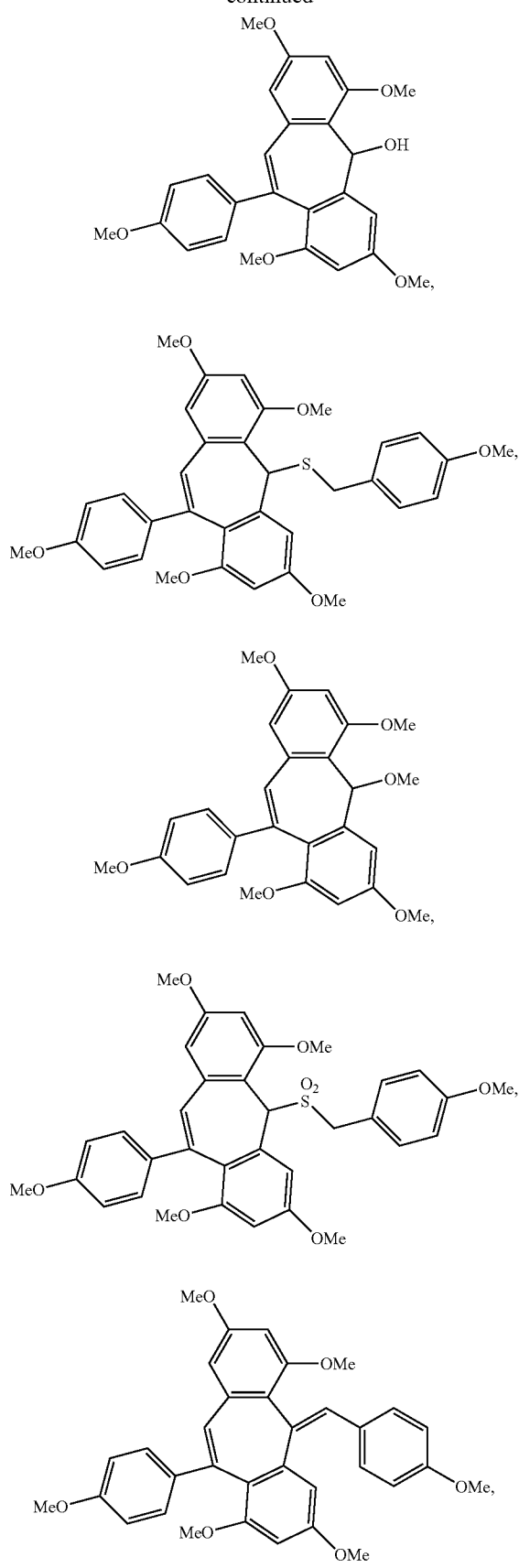
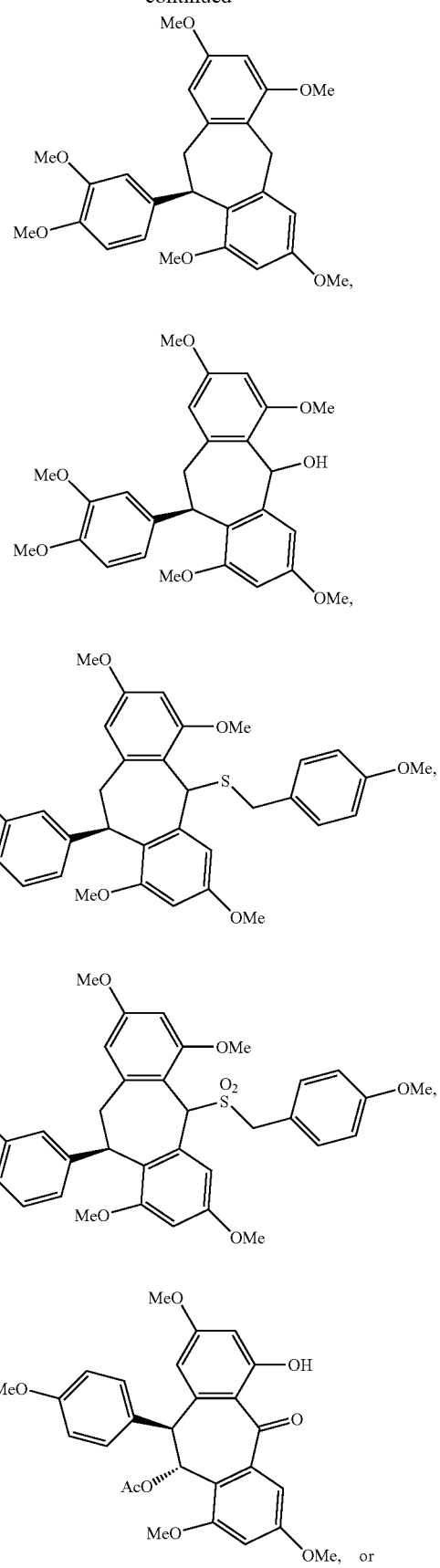

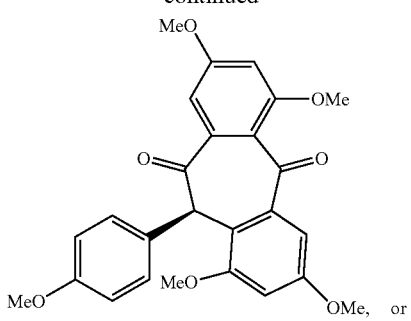
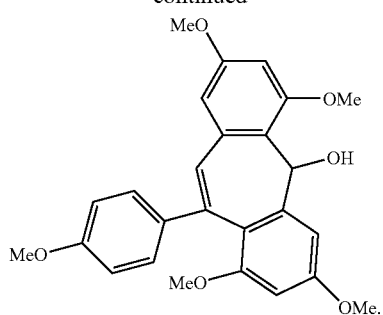
In an embodiment, the compound has the structure:
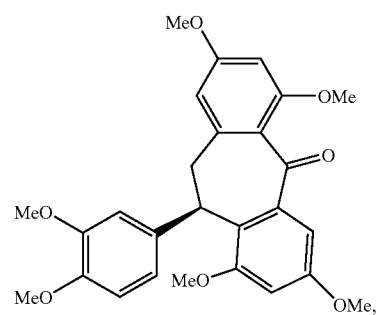
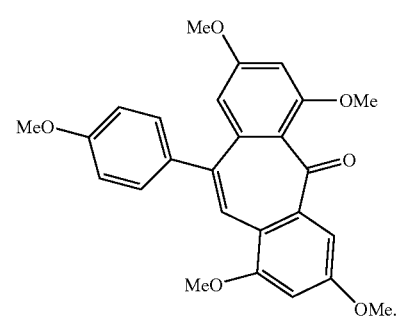 [SMILES: COc1ccc(-c2cc3c(OC)cc(OC)cc3c(=O)c3c(OC)cc(OC)cc23)cc1]
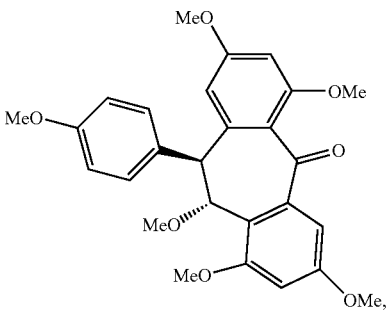
This invention provides a composition, free of plant extract, comprising one or more of the above compounds.
This invention provides a compound having the structure:
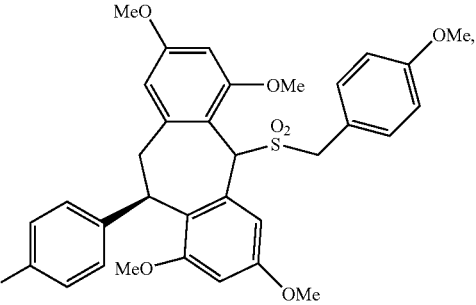
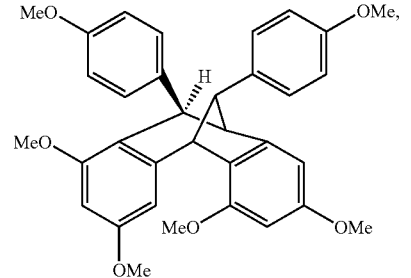
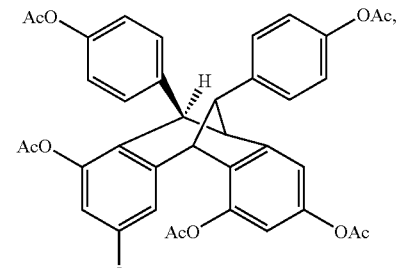
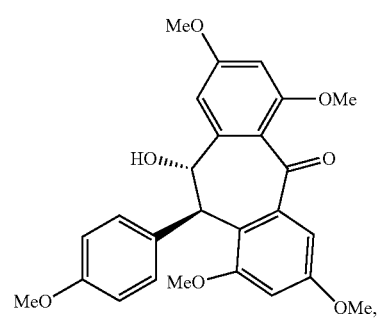
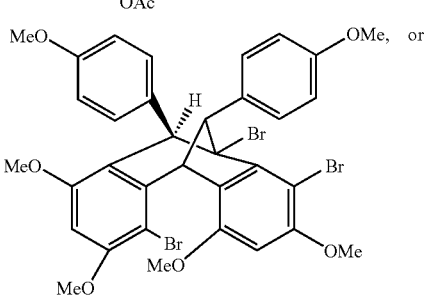

-continued

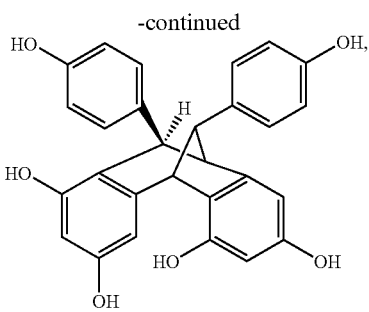

This invention provides a compound having the structure:

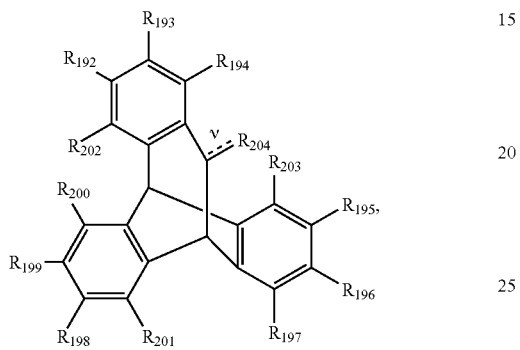

wherein $R_{192}$, $R_{192}$, $R_{193}$, $R_{194}$, $R_{195}$, $R_{196}$, $R_{197}$, $R_{198}$, $R_{199}$, $R_{200}$, $R_{201}$, $R_{202}$, and $R_{203}$ are, independently, H, OH, =O, —OC(O)alkyl, alkyl, alkenyl, alkynyl, —OR$_{205}$, —SR$_{206}$, —N(R$_{207}$)$_2$, —S(O)(O)R$_{208}$, —C(O)OR$_{209}$, —R$_{210}$OR$_{211}$, —R$_{210}$R$_{211}$, cycloalkyl, cycloalkenyl, a substituted or unsubstituted aryl, a substituted or unsubstituted heteroaryl, a substituted or unsubstituted heterocyclyl, or X, where X is a halogen, where $R_{205}$, $R_{206}$, $R_{208}$, $R_{209}$, $R_{211}$, and each occurrence of $R_{207}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where R$_{210}$ is alkylene, alkenylene or alkynylene, wherein each occurrence of alkyl, alkenyl, alkynyl, alkylene, alkenylene, and alkynylene is substituted or unsubstituted and wherein bond v is present or absent.

In an embodiment the compound has the structure:

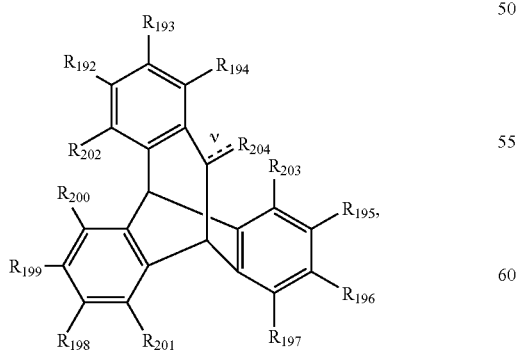

wherein $R_{192}$, $R_{192}$, $R_{193}$, $R_{194}$, $R_{195}$, $R_{196}$, $R_{196}$, $R_{197}$, $R_{198}$, $R_{199}$, $R_{200}$, $R_{201}$, $R_{202}$, and $R_{203}$ are, independently, H, OH, Br, —OMe, —OAc,

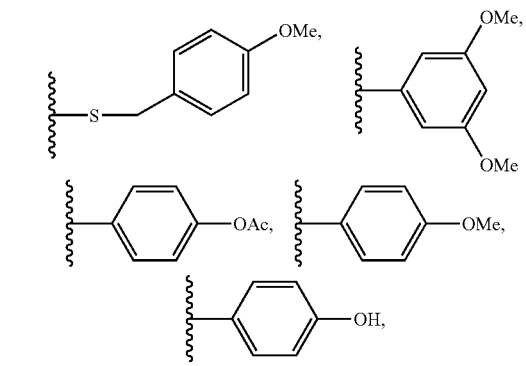

and wherein $R_{204}$ is H, OH, =O, Br, —OAc, —OMe, and wherein bond v is present when $R_{204}$ is =O.

In an embodiment the compound has the structure:

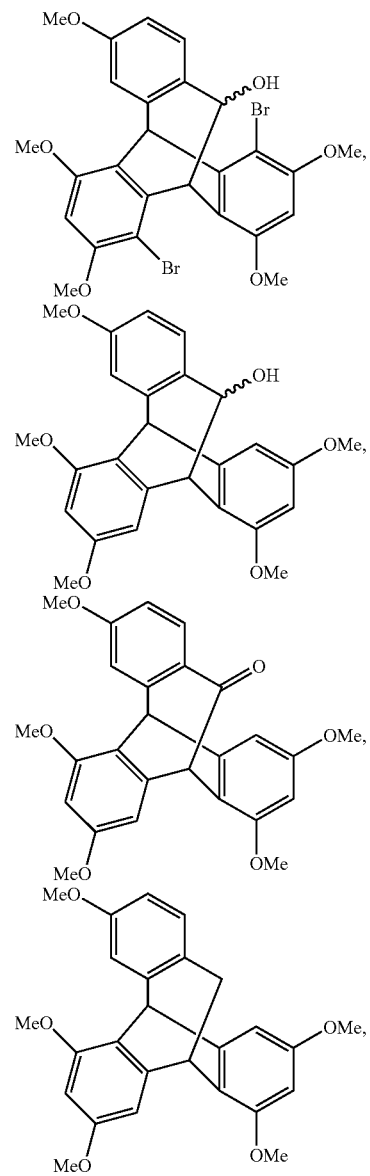

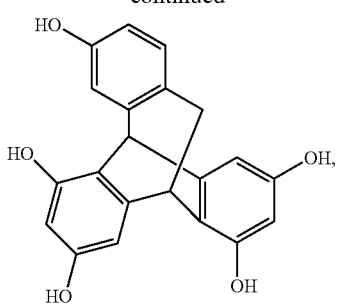
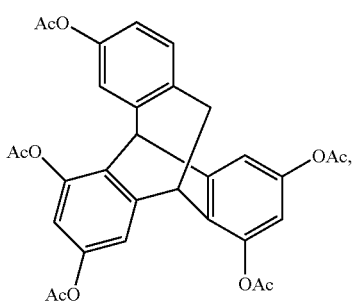
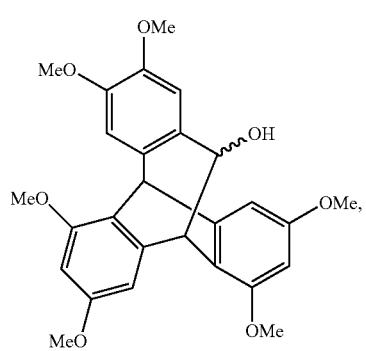
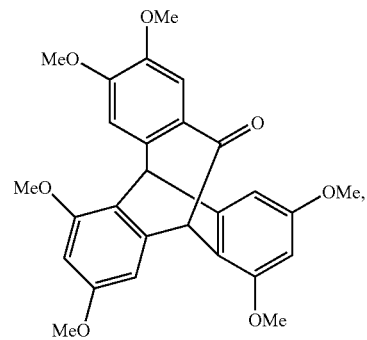
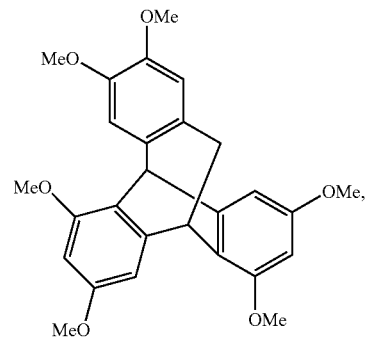
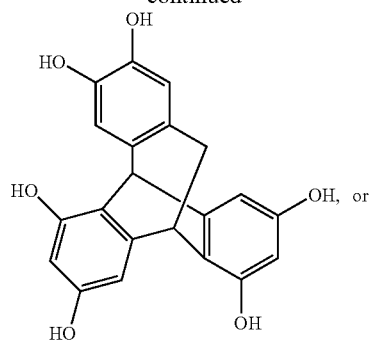
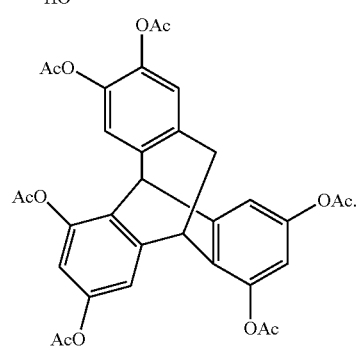
In an embodiment, the compound has the structure:
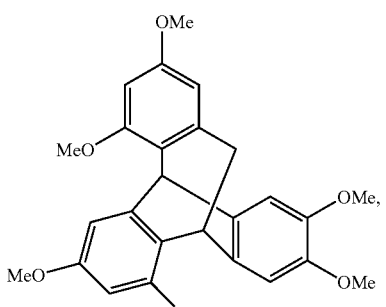
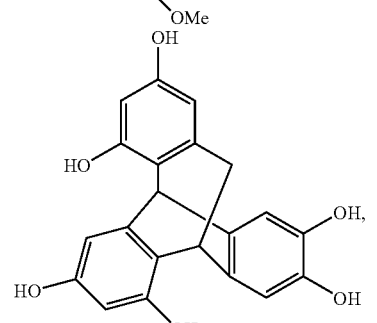
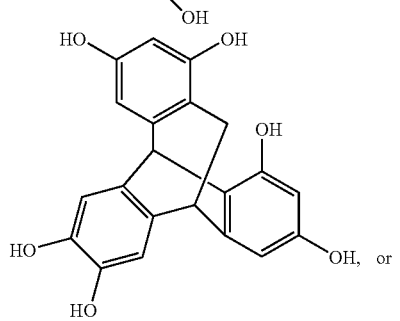

-continued

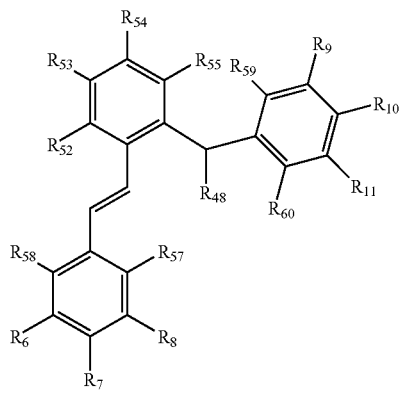

A compound is provided having the structure:

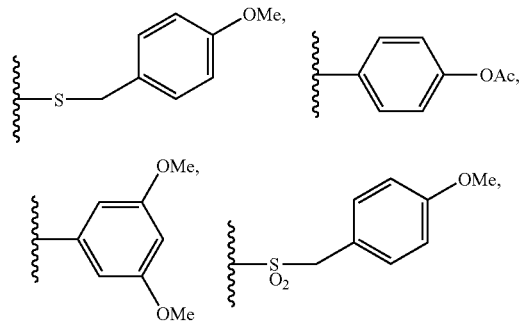

wherein $R_6$, $R_7$, $R_8$, $R_9$, $R_{10}$, $R_{11}$, $R_{52}$, $R_{53}$, $R_{54}$, $R_{55}$, $R_{57}$, $R_{58}$, $R_{59}$, $R_{60}$ are, independently, H, OH, —OMe, —OAc, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, and wherein each occurrence of alkyl, alkenyl, alkynyl, alkylene, alkenylene, and alkynylene is substituted or unsubstituted $R_{48}$ is H, =O, OH, —OAc, —OMe,

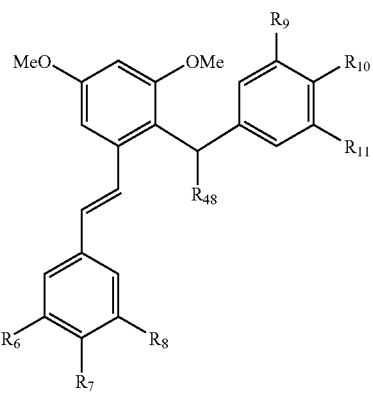

In an embodiment, the compound has the structure:

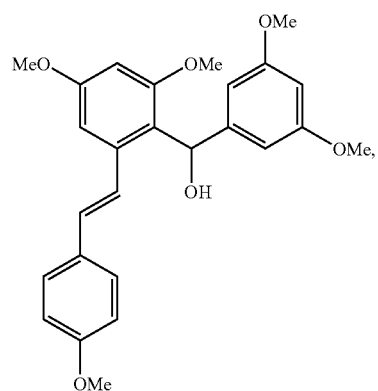

wherein $R_{48}$ is =O or OH, and wherein either $R_7$, $R_9$ and $R_{11}$ are OMe and $R_6$, $R_8$ and $R_{10}$ are H, or wherein $R_7$, $R_9$ and $R_{11}$ are H and $R_6$, $R_8$ and $R_{10}$ are OMe.

In an embodiment, the compound has the structure:

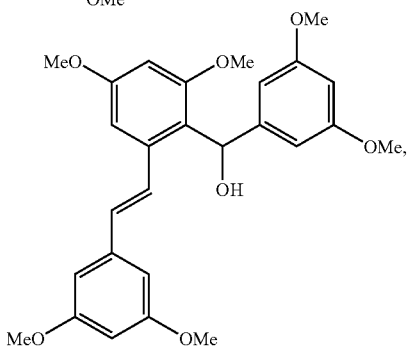

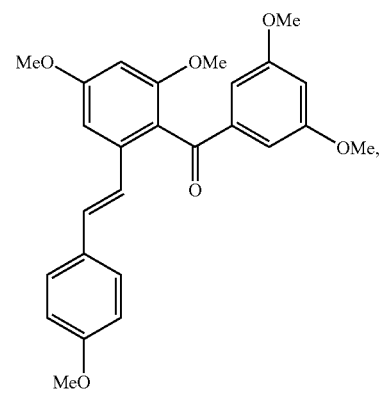
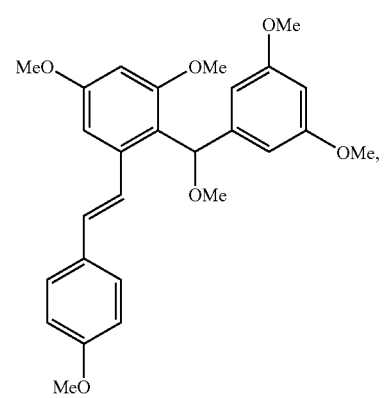
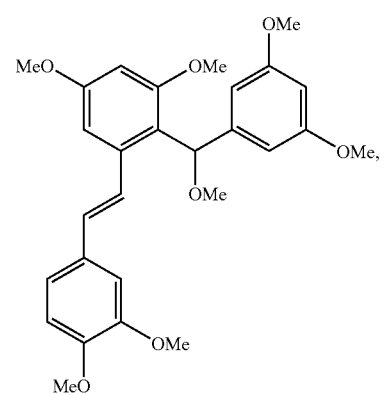
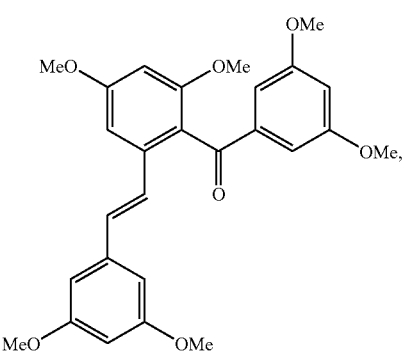
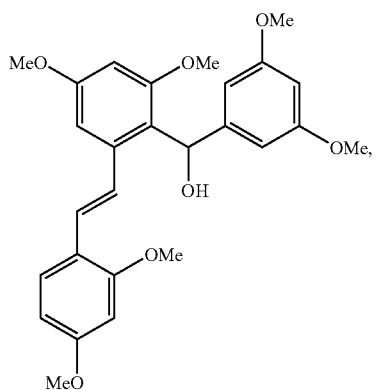
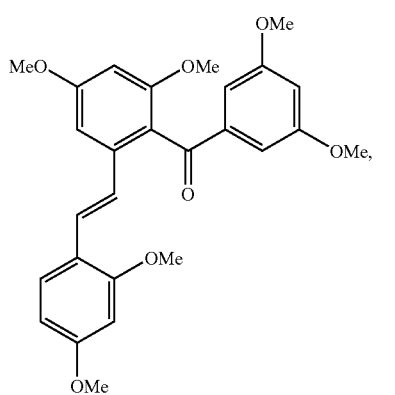
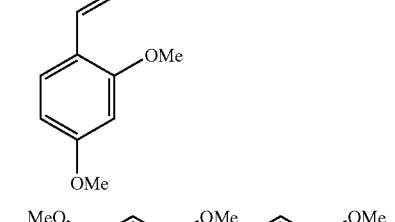
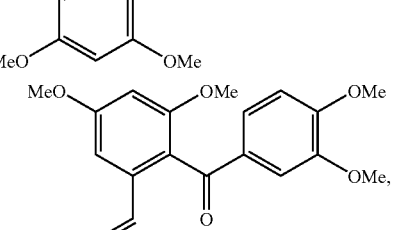
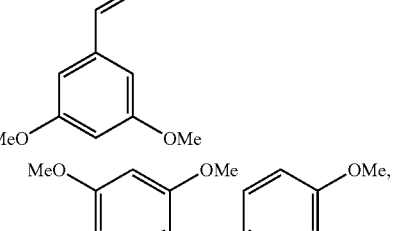
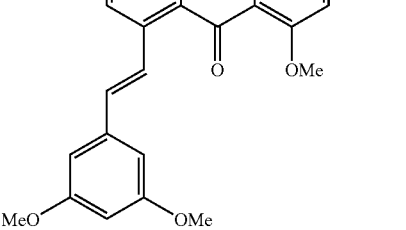

133
-continued
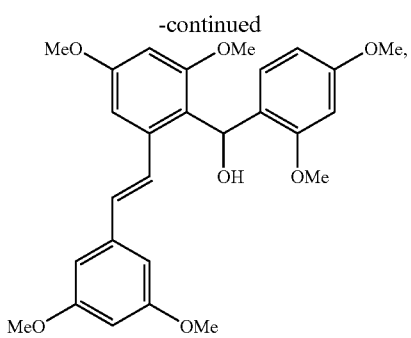
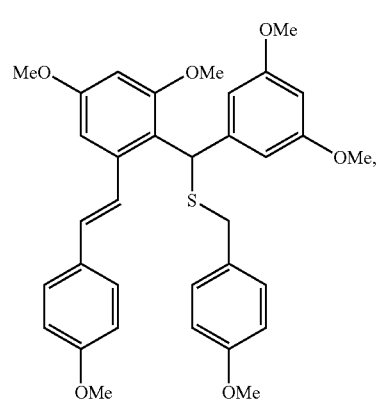
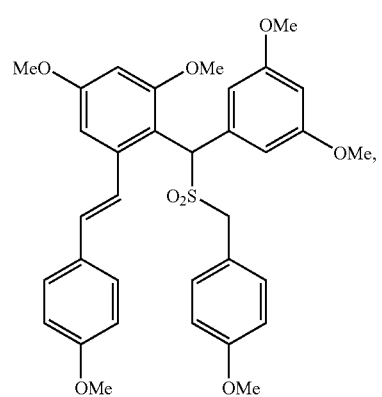
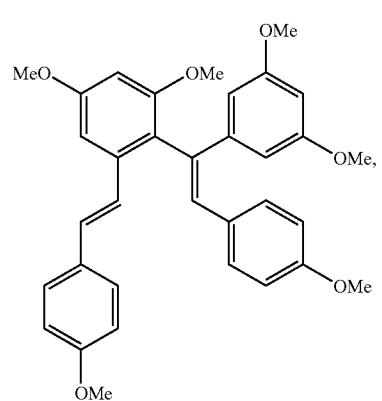
134
-continued
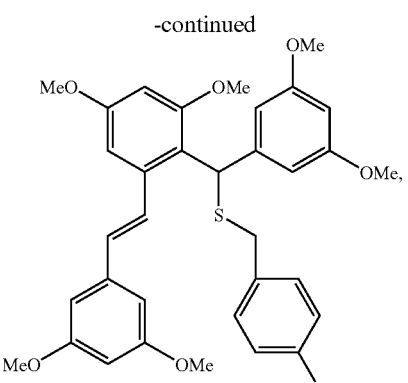
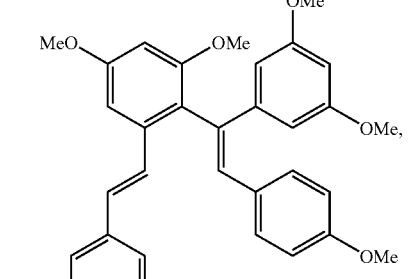
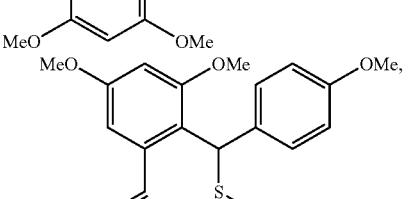
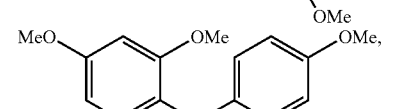
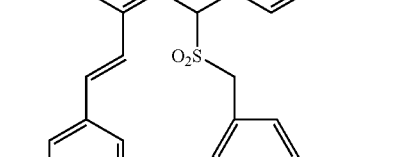

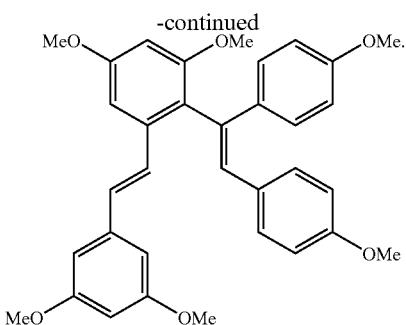

In an embodiment, the compound of has the structure:

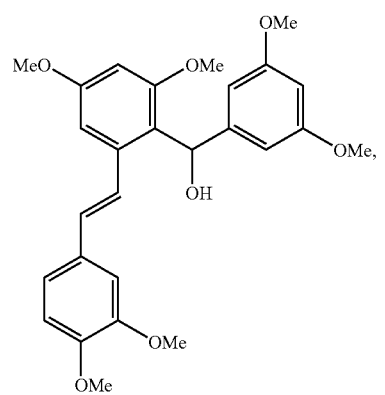

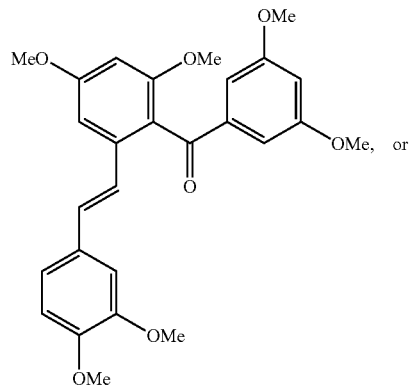

or

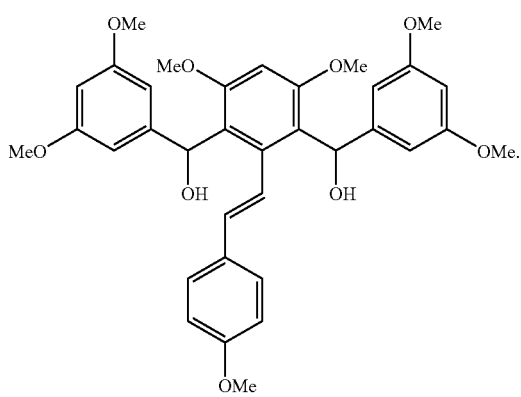

A compound is provided having the structure:

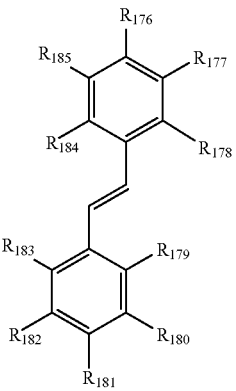

wherein $R_{176}$, $R_{177}$, $R_{178}$, $R_{179}$, $R_{180}$, $R_{181}$, $R_{182}$, $R_{183}$, $R_{184}$, $R_{185}$ are, independently, H, Br, OH, OAc, or OMe, wherein when $R_{185}$ and $R_{177}$ are OMe, $R_{176}$, $R_{178}$, $R_{179}$, $R_{180}$, $R_{182}$, $R_{183}$, $R_{184}$, are H and $R_{178}$ is Br, then $R_{181}$ is Br, OH, H or OMe.

In an embodiment, the compound has the structure:

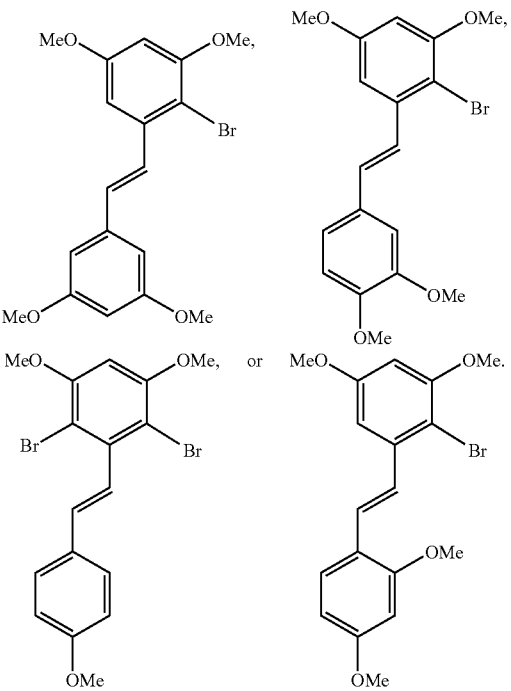

A process is provided for making a compound having the structure:

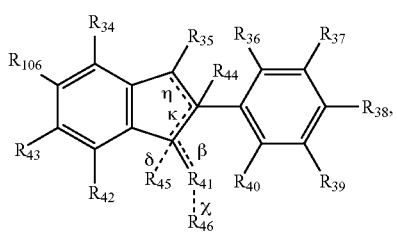

wherein $R_{34}$, $R_{35}$, $R_{42}$, $R_{43}$, and $R_{106}$ are, independently, H, OH, Ome, $OC(O)_{R186}$, or

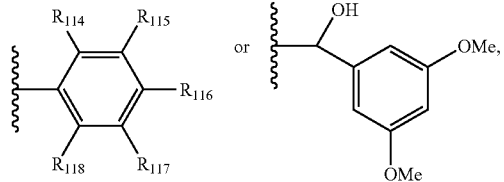

wherein each of $R_{114}$, $R_{115}$, $R_{116}$, $R_{117}$, and $R_{118}$ are, independently, H, OH, —OC(O)alkyl, alkyl, alkenyl, alkynyl, —$OR_{107}$, —$SR_{108}$, —$N(R_{109})_2$, —$S(O)(O)R_{110}$, —$C(O)OR_{111}$, —$R_{120}OR_{113}$, —$R_{112}R_{113}$, cycloalkyl, cycloalkenyl, a substituted or unsubstituted aryl, a substituted or unsubstituted heteroaryl, a substituted or unsubstituted heterocyclyl, or X, where X is a halogen, where $R_{107}$, $R_{108}$, $R_{110}$, $R_{111}$, $R_{113}$, and each occurrence of $R_{109}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{112}$ is alkylene, alkenylene or alkynylene, wherein each occurrence of alkyl, alkenyl, alkynyl, alkylene, alkenylene, and alkynylene is substituted or unsubstituted, wherein $R_{186}$ is alkyl or alkenyl wherein $R_{36}$, $R_{37}$, $R_{38}$, $R_{39}$ and $R_{40}$ are, independently, H, OH, —OC(O)alkyl, alkyl, alkenyl, alkynyl, —$OR_{114}$, —$SR_{115}$, —$N(R_{116})_2$, —$S(O)(O)R_{117}$, —$C(O)OR_{118}$, —$R_{119}OR_{120}$, —$R_{119}R_{120}$, cycloalkyl, cycloalkenyl, a substituted or unsubstituted aryl, a substituted or unsubstituted heteroaryl, a substituted or unsubstituted heterocyclyl, or X, where X is a halogen, where $R_{114}$, $R_{115}$, $R_{117}$, $R_{118}$, $R_{120}$, and each occurrence of $R_{116}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where Rue is alkylene, alkenylene or alkynylene, wherein each occurrence of alkyl, alkenyl, alkynyl, alkylene, alkenylene, and alkynylene is substituted or unsubstituted, or $R_{40}$ is joined to $R_{41}$ to form a pentacyclic ring, bond β is present, each of bond χ, bond δ, bond κ, $R_{45}$ and $R_{46}$ are absent, $R_{44}$ is present, and $R_{41}$ is O,

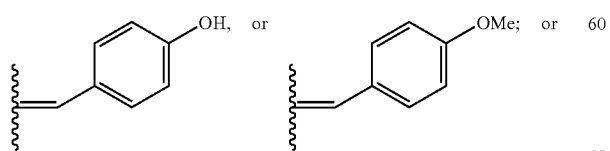

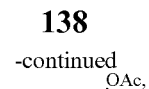

or bond β is absent, bond κ is absent, bond δ is present, $R_{45}$ is present, bond χ and $R_{46}$ are absent, $R_{44}$ is present, and $R_{41}$ is —OC(O) ($CF_3$), —OH, -alkyl, alkenyl, alkynyl, cycloalkyl, cycloalkenyl, a substituted or unsubstituted aryl, a substituted or unsubstituted heteroaryl, a substituted or unsubstituted heterocyclyl,

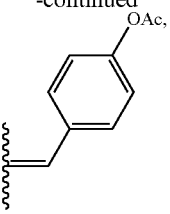

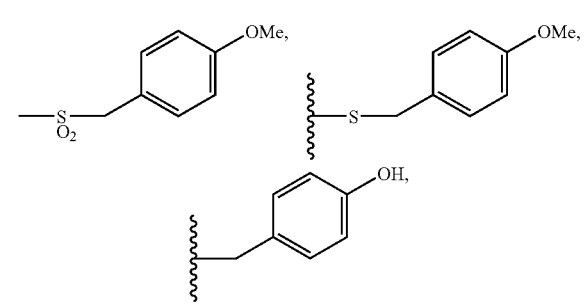

$OR_{120}$, —$SR_{121}$, —$N(R_{122})_2$, or —R'Y; or wherein each occurrence of alkyl, alkenyl, alkynyl, alkylene, alkenylene, and alkynylene is substituted or unsubstituted, bond β is absent, bond κ is present, bond δ is absent, $R_{44}$ and $R_{45}$ are absent, bond χ and $R_{46}$ are absent, and $R_{41}$ is a halogen, —OH,

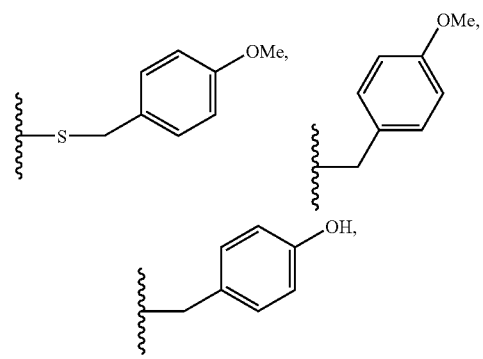

X, $OR_{120}$, —$SR_{121}$, —$N(R_{122})_2$, or —R'Y, where $R_{120}$, $R_{121}$ and each occurrence of $R_{122}$ are alkyl, alkenyl or alkynyl, and where R' is alkylene, alkenylene or alkynylene and Y is cycloalkyl, cycloalkenyl, a substituted or unsubstituted aryl, a substituted or unsubstituted heteroaryl, a substituted or unsubstituted heterocyclyl; or wherein each occurrence of alkyl, alkenyl, alkynyl, alkylene, alkenylene, and alkynylene is substituted or unsubstituted, bond β is absent, bond κ is absent, each of bond δ, bond χ, $R_{44}$, $R_{45}$ and $R_{46}$ are present, and $R_{41}$ is joined to $R_{40}$ to form a pentacyclic ring, $R_{44}$, if present, is H, $R_{45}$, if present, is H or Br, $R_{46}$, if present, is

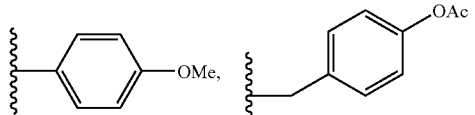

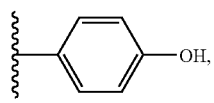

cycloalkyl, cycloalkenyl, a substituted or unsubstituted aryl, a substituted or unsubstituted heteroaryl, a substituted or unsubstituted heterocyclyl, wherein $R_{46}$ is only present if $R_{41}$ is joined to $R_{40}$ to form a pentacyclic ring, $R_{106}$ is H, wherein bond η is present or absent, but when present bond κ is absent, comprising the step of reacting a compound having the structure:

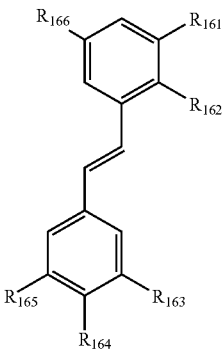

wherein $R_{161}$ and $R_{166}$ are OMe or OAc, $R_{162}$ is Br and $R_{165}$ and $R_{163}$ are OMe or OAc and $R_{164}$ is H or $R_{165}$ and $R_{163}$ are H and $R_{164}$ is OMe or OAc, with n-BuLi and a compound having the structure:

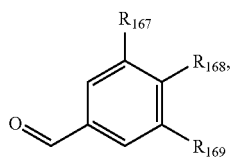

wherein $R_{167}$ is H or OMe, $R_{168}$ is H or OMe, and $R_{169}$ is H or OMe, so as to produce the compound.

In an embodiment, $R_{165}$ and $R_{163}$ are OMe, $R_{164}$ is H, $R_{167}$ is H, $R_{168}$ is OMe, and $R_{169}$ is H. In an embodiment, $R_{165}$ and $R_{163}$ are H and $R_{164}$ is OMe, $R_{167}$ is OMe, $R_{168}$ is H, and $R_{169}$ is OMe. In an embodiment, the compound made has the structure:

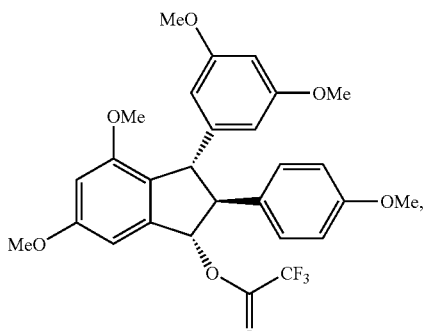

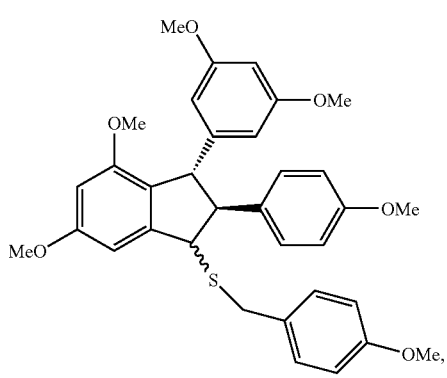

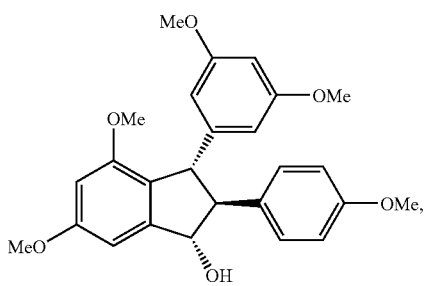

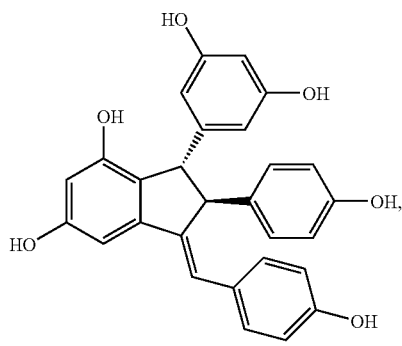

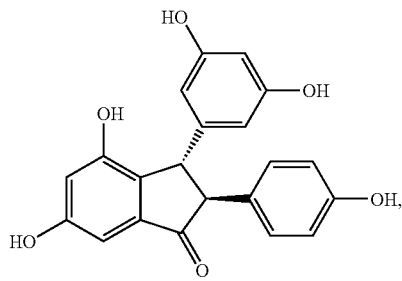

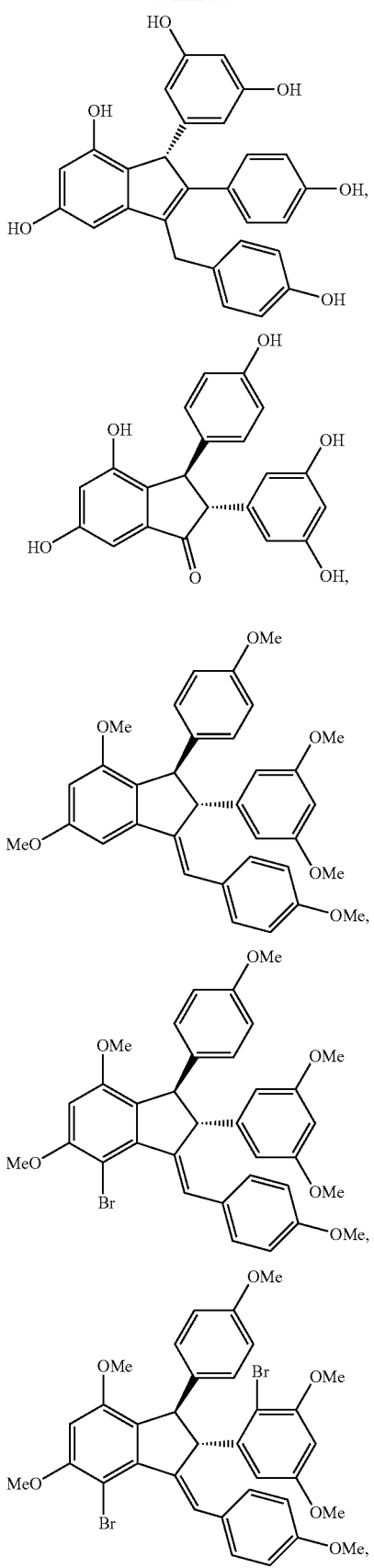
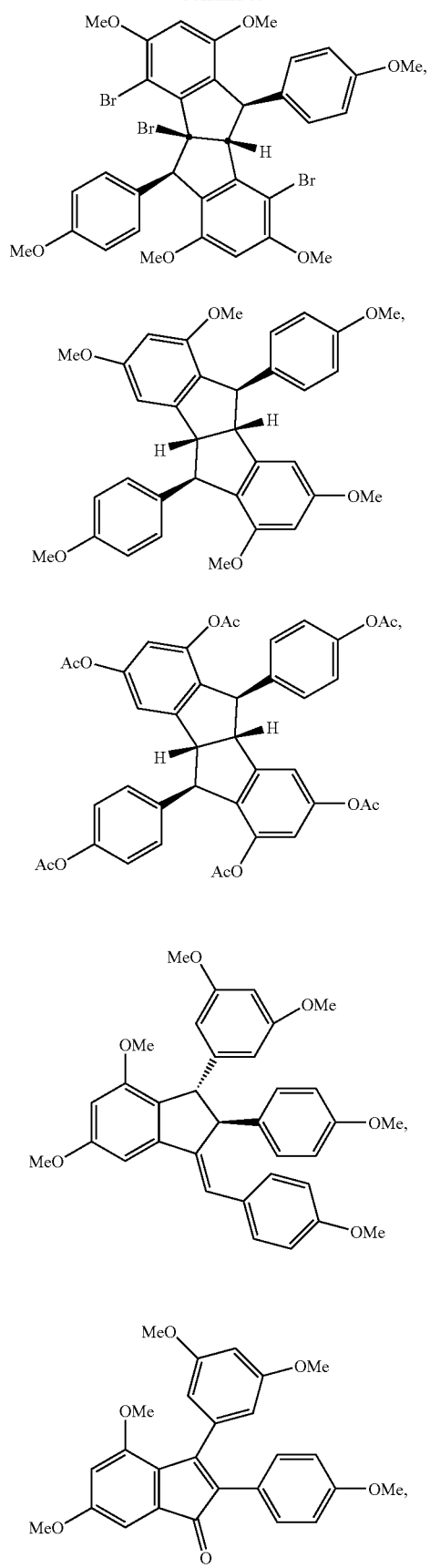

143
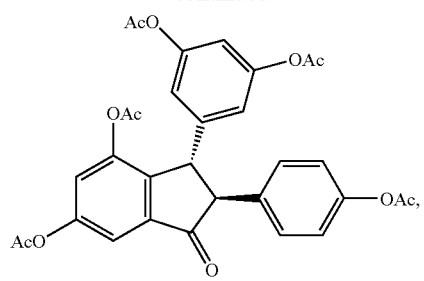
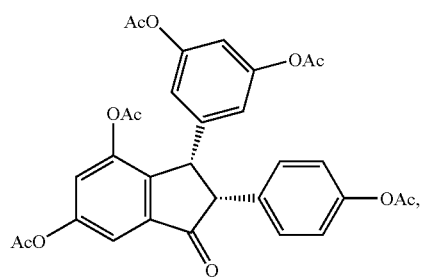
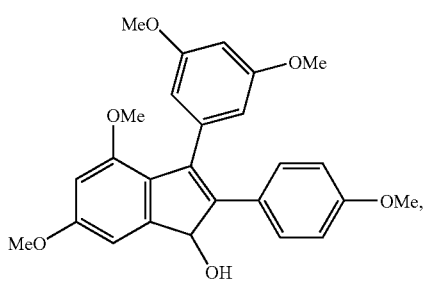
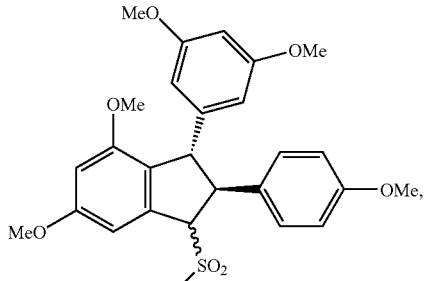
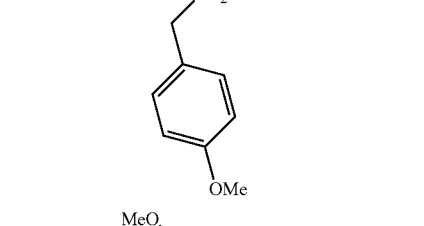
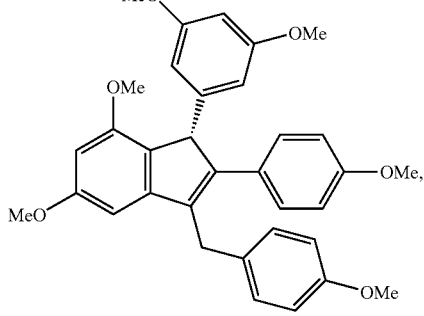
144
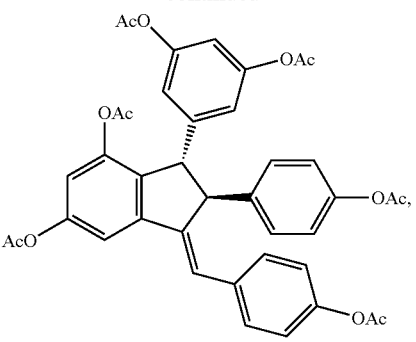
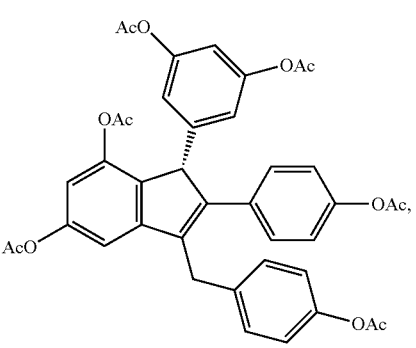
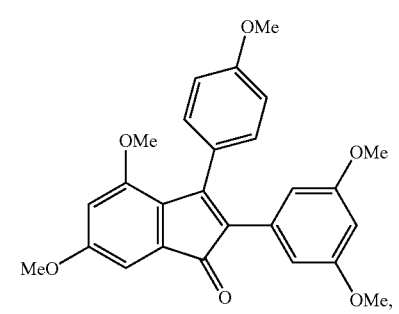
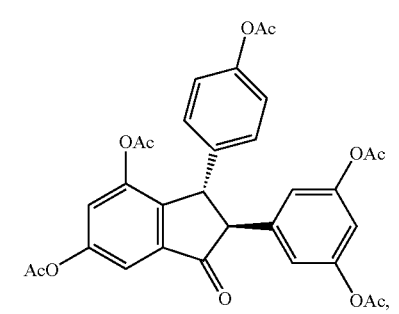
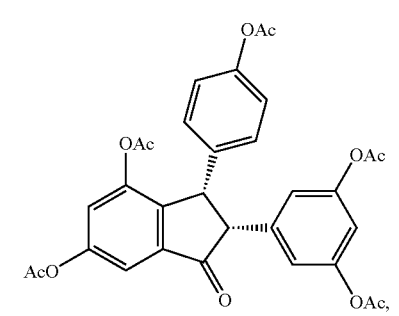

-continued

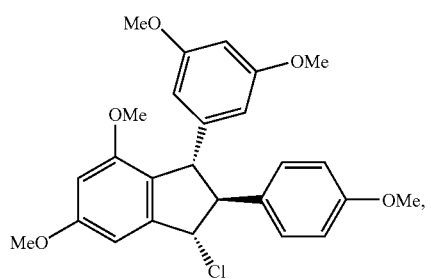
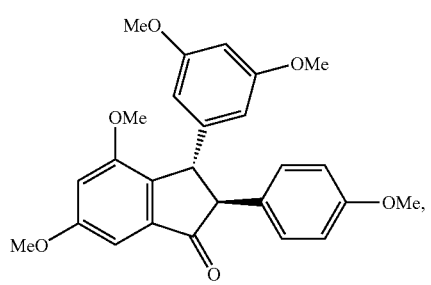
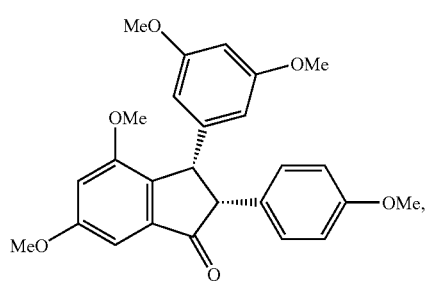
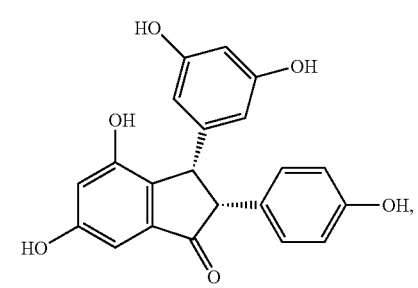
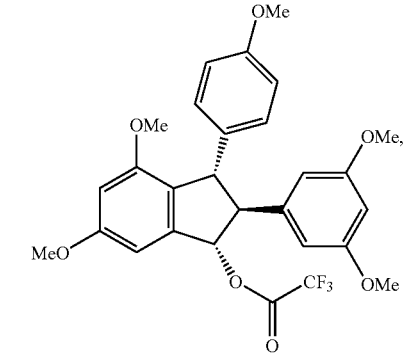
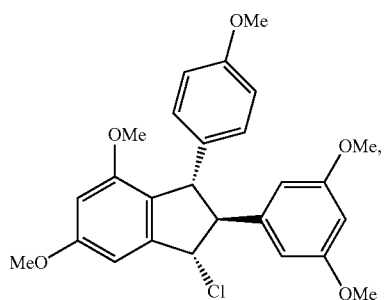
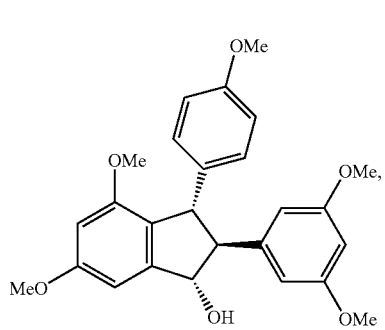
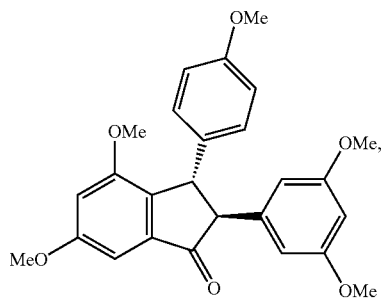
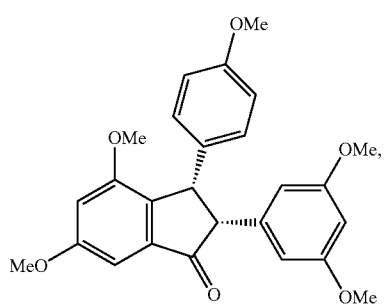
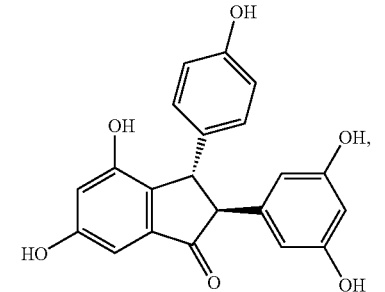

149
-continued
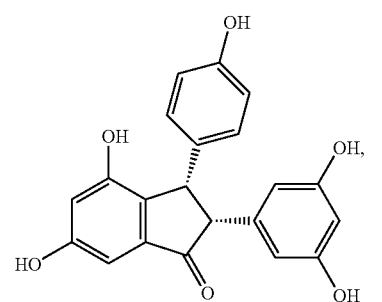
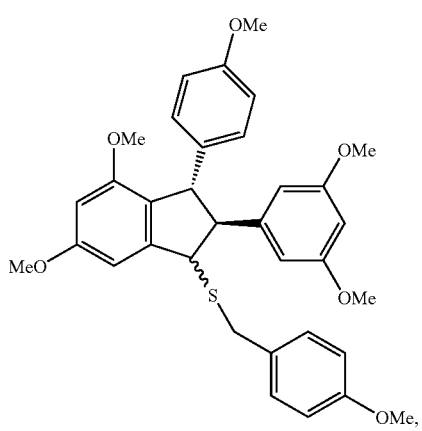
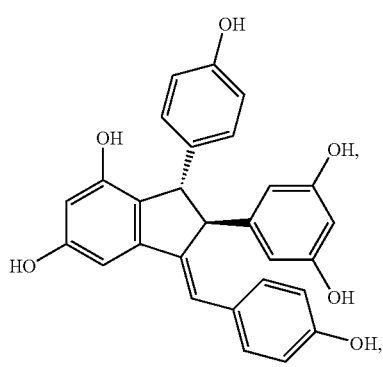
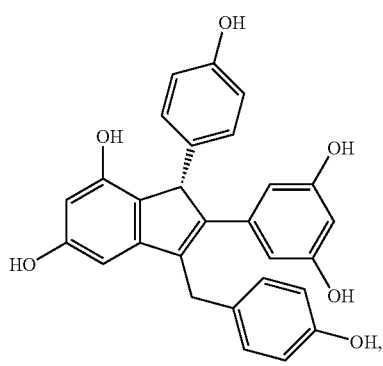
150
-continued
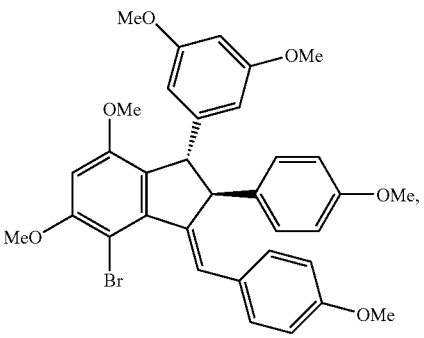
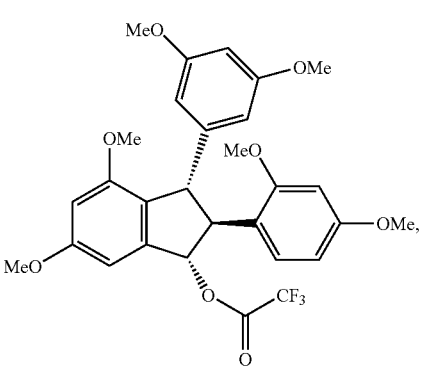
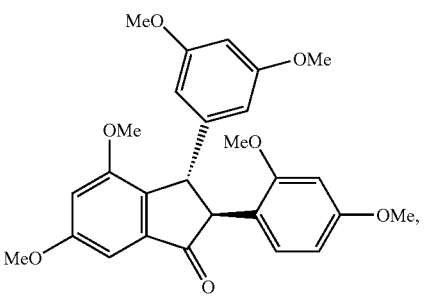
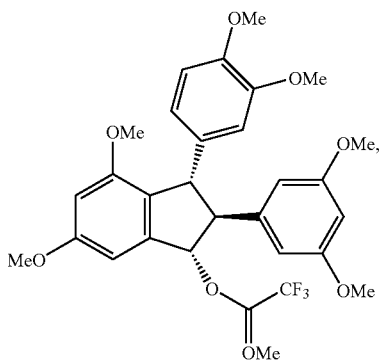
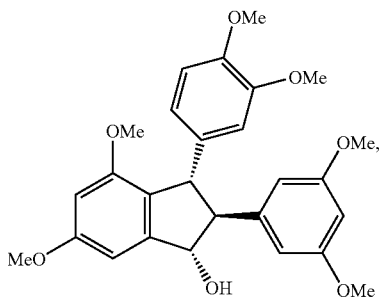

151
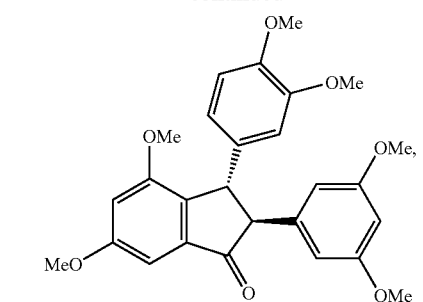
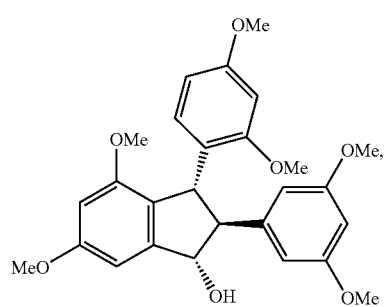
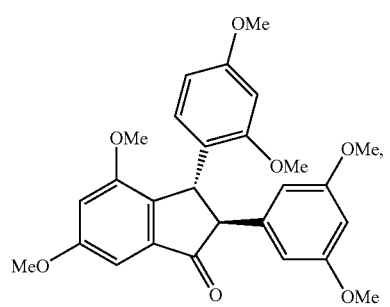
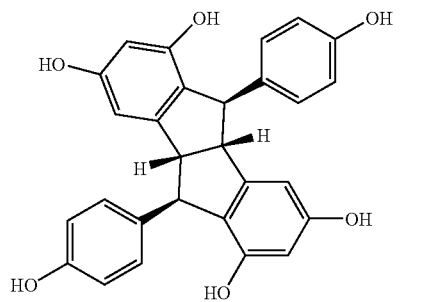
or
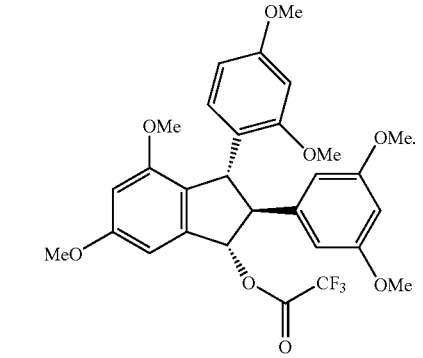
In an embodiment, the process produces the compound having structure:
152
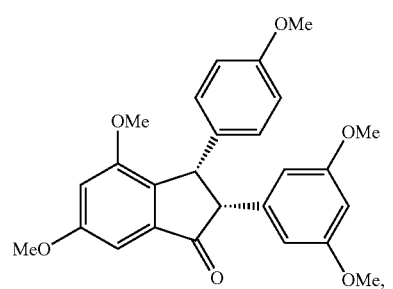
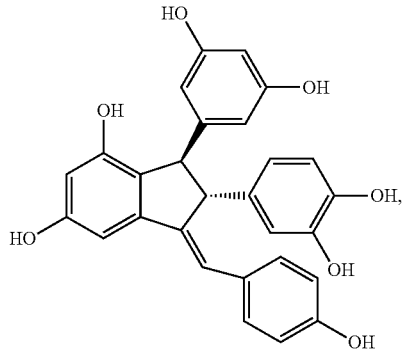
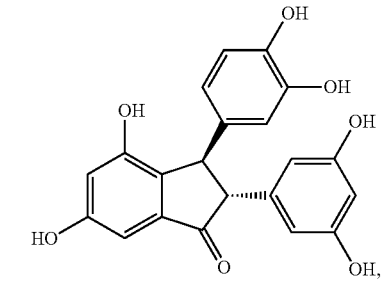
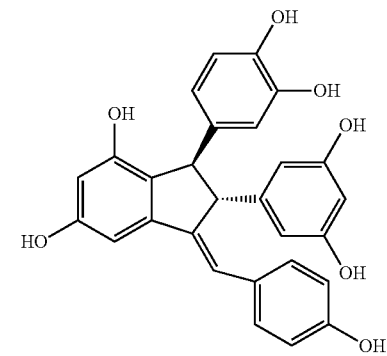
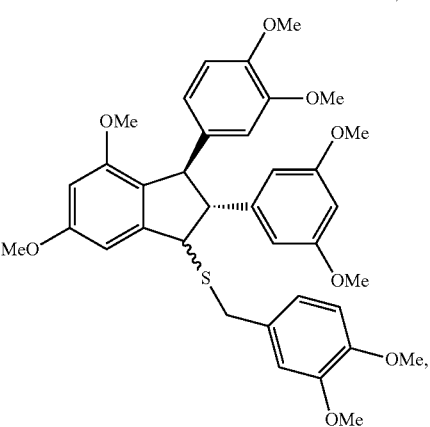

153

-continued

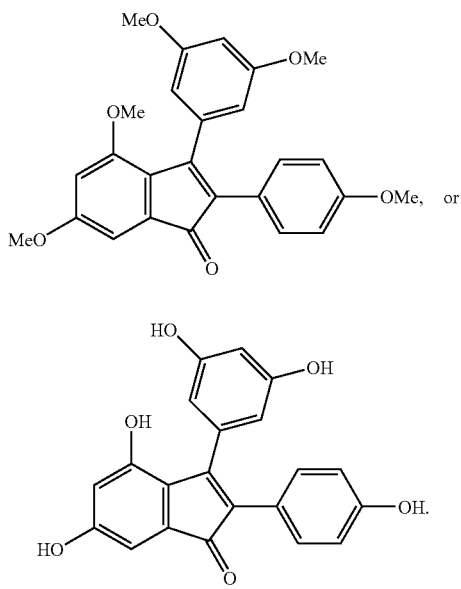

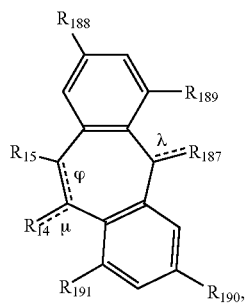

This invention provides a process for making a compound having the structure:

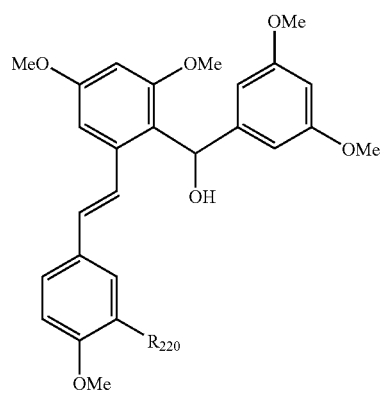

wherein $R_{14}$, $R_{15}$, $R_{186}$, $R_{187}$, $R_{188}$, $R_{189}$, $R_{190}$, $R_{191}$, are, independently, =O, H, OH, —OC(O)alkyl, alkyl, alkenyl, alkynyl, —OR$_{212}$, —SR$_{213}$, —N(R$_{214}$)$_2$, —S(O)(O)R$_{215}$, —C(O)OR$_{216}$, —R$_{217}$OR$_{218}$, —R$_{217}$R$_{218}$, —SO$_2$—R$_{219}$, cycloalkyl, cycloalkenyl, a substituted or unsubstituted aryl, a substituted or unsubstituted heteroaryl, a substituted or unsubstituted heterocyclyl, or X, where X is a halogen, where R$_{212}$, R$_{213}$, R$_{215}$, R$_{216}$, R$_{218}$, R$_{219}$, and each occurrence of R$_{214}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where R$_{217}$ is alkylene, alkenylene or alkynylene, wherein each occurrence of alkyl, alkenyl, alkynyl, alkylene, alkenylene, and alkynylene is substituted or unsubstituted, and wherein bonds φ, λ, and μ are present or absent, but wherein when bond φ is present bond μ is absent, and wherein when bond μ is present bond φ is absent,

154 comprising:
a) reacting a compound having the structure:

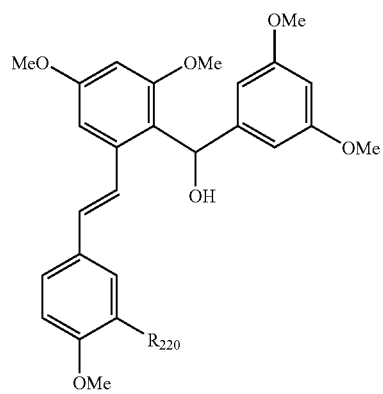

with an oxidizing agent so as to obtain a compound having the structure:

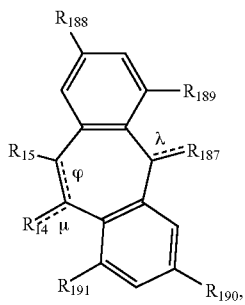

wherein R$_{220}$ is H or —OMe, and
b) contacting the product of step a) with a dioxirane, an acid, or Br$_2$ so as to obtain the compound.

A process is provided for making a compound having the structure:

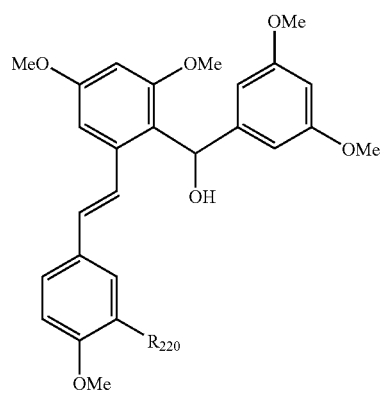

wherein $R_{14}$, $R_{15}$, $R_{186}$, $R_{187}$, $R_{188}$, $R_{189}$, $R_{190}$, $R_{191}$, are, independently, =O, H, OH, —OC(O)alkyl, alkyl, alkenyl, alkynyl, —OR$_{212}$, —SR$_{213}$, —N(R$_{214}$)$_2$, —S(O)(O)R$_{21}$, —C(O)OR$_{216}$, —R$_{217}$OR$_{218}$, —R$_{217}$R$_{218}$, —SO$_2$—R$_{219}$, cycloalkyl, cycloalkenyl, a substituted or unsubstituted aryl, a substituted or unsubstituted heteroaryl, a substituted or unsubstituted heterocyclyl, or X, where X is a halogen, where $R_{212}$, $R_{213}$, $R_{215}$, $R_{216}$, $R_{218}$, $R_{219}$, and each occurrence of $R_{214}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{217}$ is alkylene, alkenylene or alkynylene, wherein each occurrence of alkyl, alkenyl, alkynyl, alkylene, alkenylene, and alkynylene is substituted or unsubstituted, and wherein bonds φ, λ, and μ are present or absent, but wherein when bond φ is present bond μ is absent, and wherein when bond μ is present bond φ is absent, comprising:

a) reacting a compound having the structure:

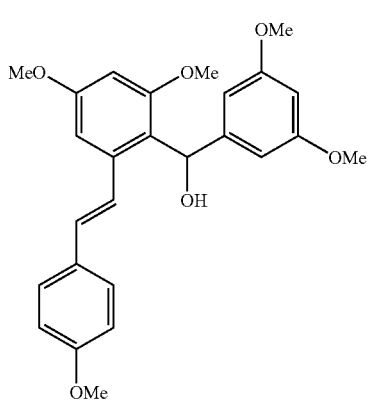 [SMILES: COc1ccc(/C=C/c2cc(OC)cc(OC)c2C(O)c2cc(OC)cc(OC)c2)cc1]

with an oxidizing agent so as to obtain a compound having the structure:

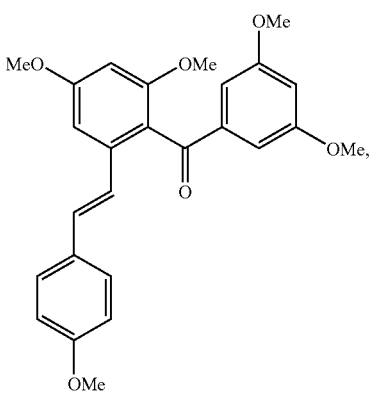

and b) contacting the product of step a) with $Br_2$ so as to obtain the compound.

In an embodiment the compound has the structure:

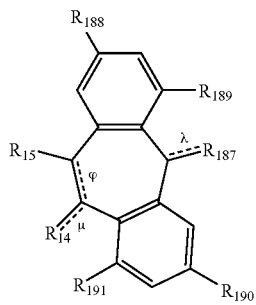

wherein $R_{14}$ is Br, H, =O, OH, OAc,

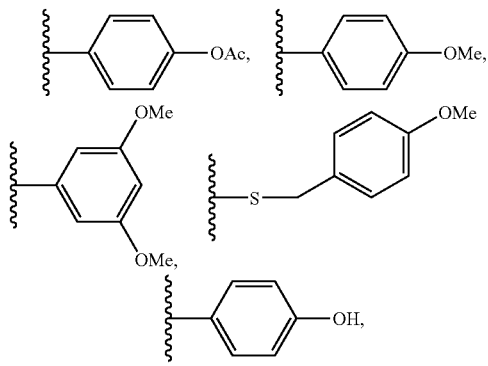

or $R_{15}$ is Br, H, OH, OAc,

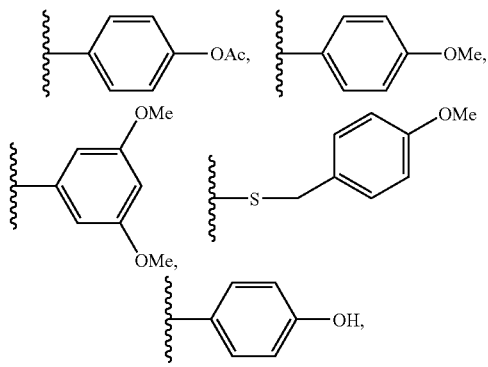

or wherein $R_{187}$ is H, OH, —OAc, —OMe, or =O,

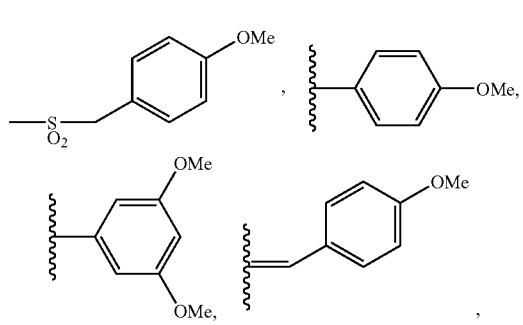

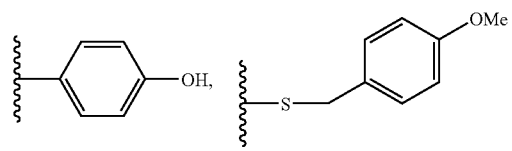
$R_{188}$, $R_{189}$, $R_{190}$ and $R_{191}$ are, independently,
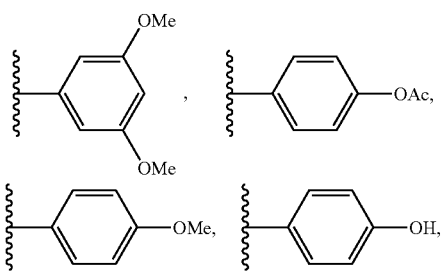
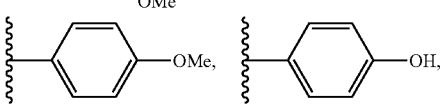
—OMe, —OAc, H or OH,
wherein bond ϕ is present or absent,
wherein bond λ is present when $R_{187}$ is =O or
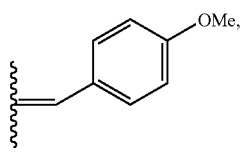
wherein bond μ is present when $R_{14}$ is =O and bond ϕ is absent,
In an embodiment the compound produced has the structure:
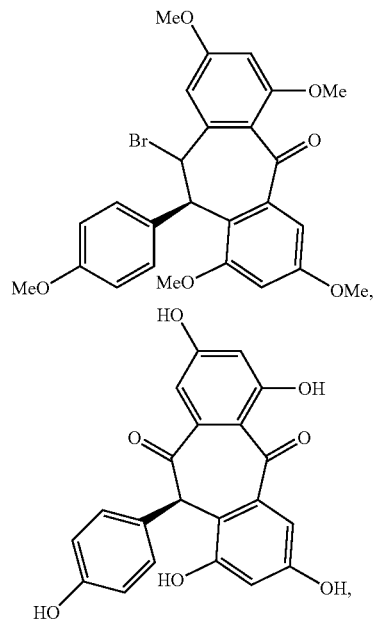
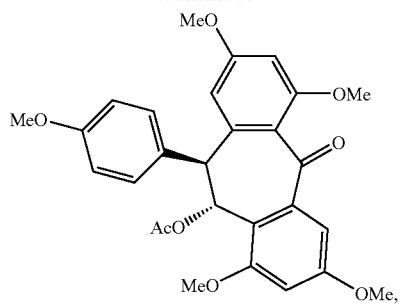
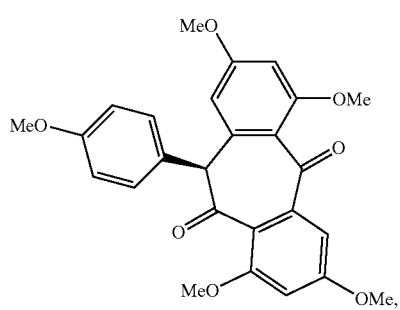
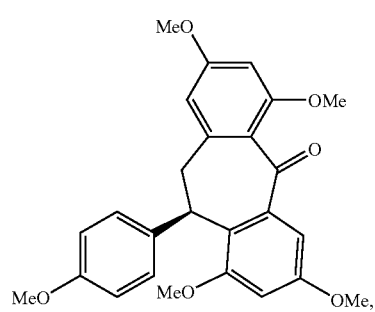
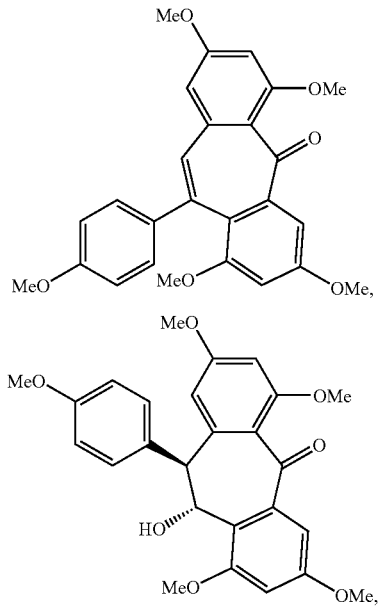

159
-continued
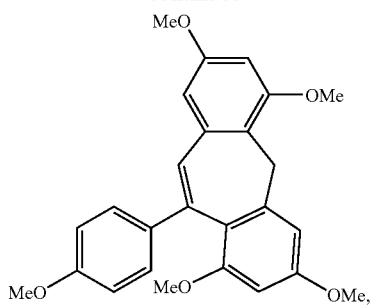
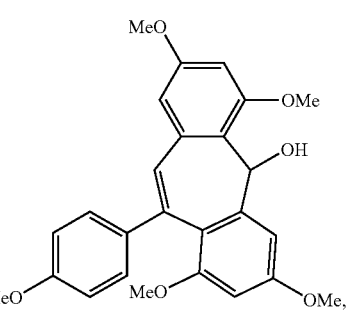
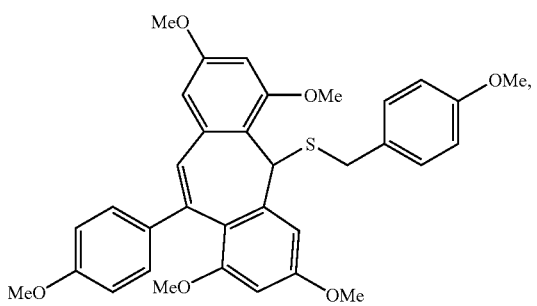
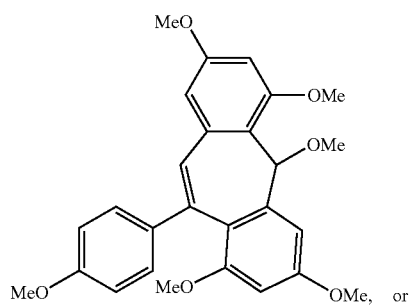, or
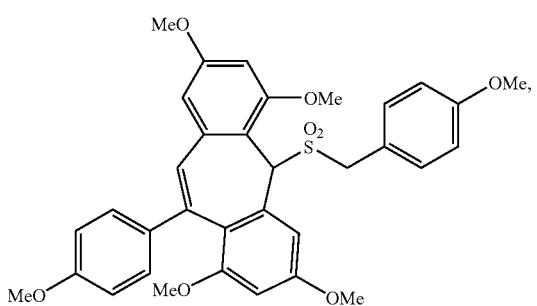
160
-continued
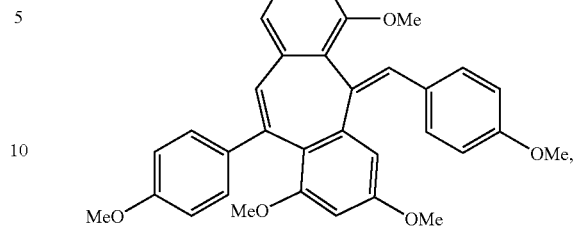
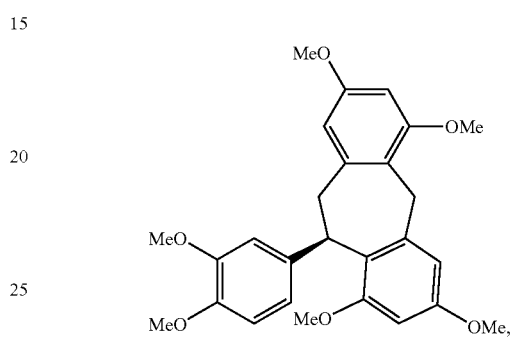
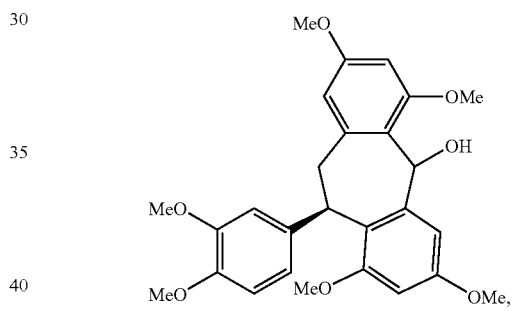
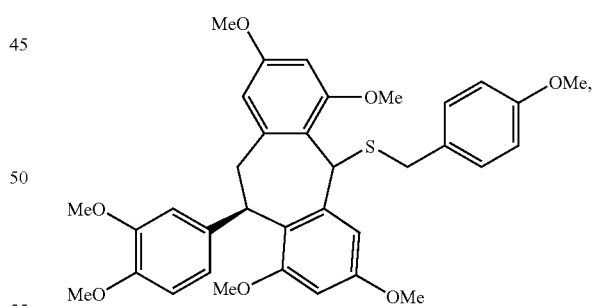
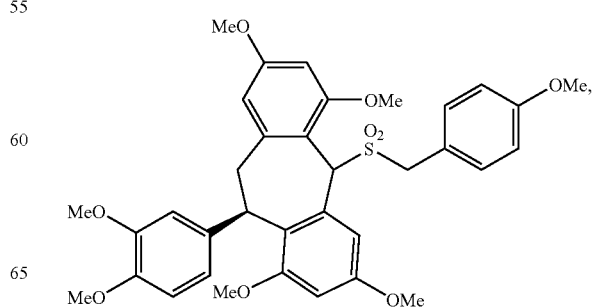

-continued

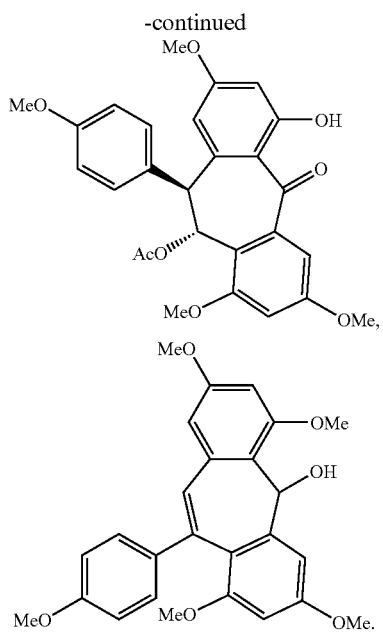

In embodiments, the process produces the compound having the structure:

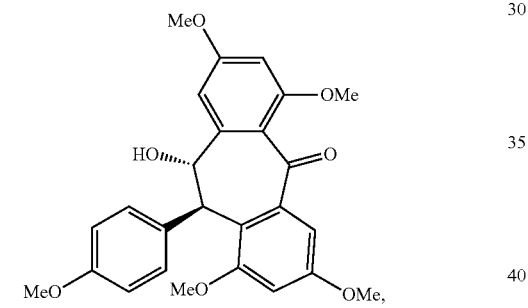

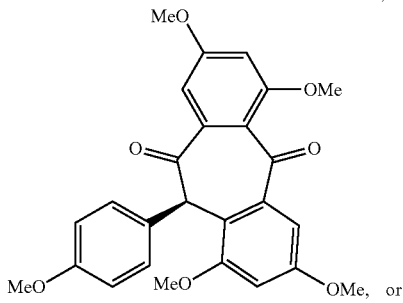

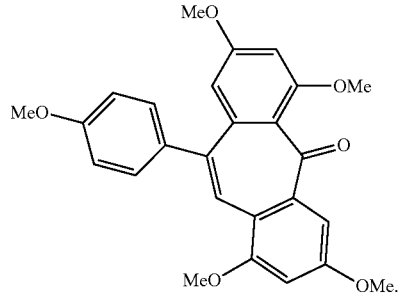

In an embodiment, the process for making a compound having the structure:

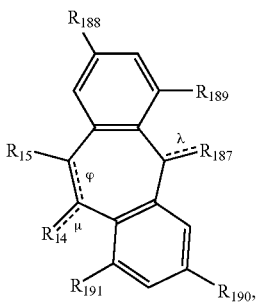

wherein $R_{14}$, $R_{15}$, $R_{188}$, $R_{187}$, $R_{188}$, $R_{189}$, $R_{190}$, $R_{191}$, are, independently, =O, H, OH, —OC(O)alkyl, alkyl, alkenyl, alkynyl, —OR$_{212}$, —SR$_{213}$, —N(R$_{214}$)$_2$, —S(O)(O)R$_{215}$, —C(O)OR$_{216}$, —R$_{217}$OR$_{218}$, —R$_{217}$R$_{218}$, —SO$_2$—R$_{219}$, cycloalkyl, cycloalkenyl, a substituted or unsubstituted aryl, a substituted or unsubstituted heteroaryl, a substituted or unsubstituted heterocyclyl, or X, where X is a halogen, where $R_{212}$, $R_{213}$, $R_{213}$, $R_{216}$, $R_{218}$, $R_{219}$, and each occurrence of $R_{214}$, are, independently, H, alkyl, alkenyl, alkynyl, cycloalkyl, cycloalkenyl, a substituted or unsubstituted aryl, a substituted or unsubstituted heteroaryl, a substituted or unsubstituted heterocyclyl, and where $R_{217}$ is alkylene, alkenylene or alkynylene, wherein each occurrence of alkyl, alkenyl, alkynyl, alkylene, alkenylene, and alkynylene is substituted or unsubstituted, and wherein bonds φ, λ, and μ are present or absent, but wherein when bond φ is present bond μ is absent, and wherein when bond μ is present bond φ is absent, comprises:

a) reacting a compound having the structure:

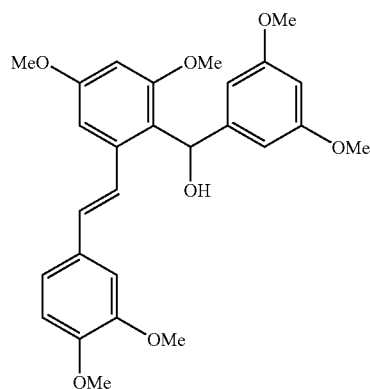 [SMILES: COc1cc(OC)cc(C(O)c2c(/C=C/c3ccc(OC)c(OC)c3)cc(OC)cc2OC)c1]

with an oxidizing agent so as to obtain a compound having the structure:

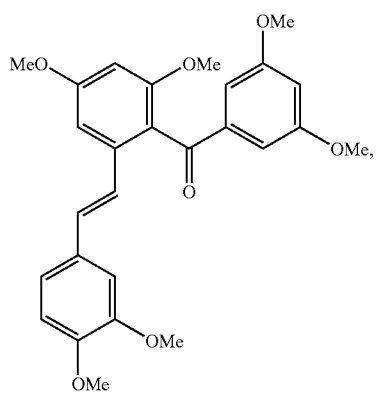
and
b) contacting the product of step a) with $Br_2$ so as to obtain the compound.
In an embodiment, the process produces the compound having the structure:
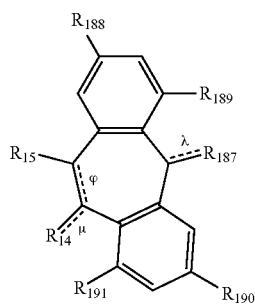
wherein $R_{14}$ is Br, H, =O, OH, OAc,
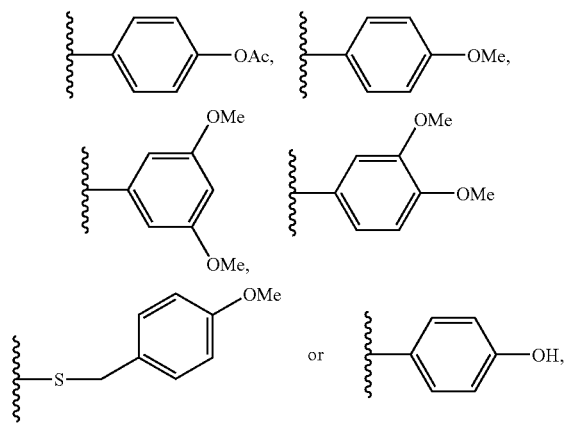
$R_{15}$ is Br, H, OH, OAc,
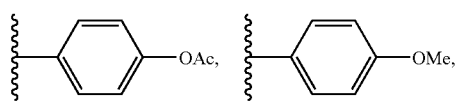
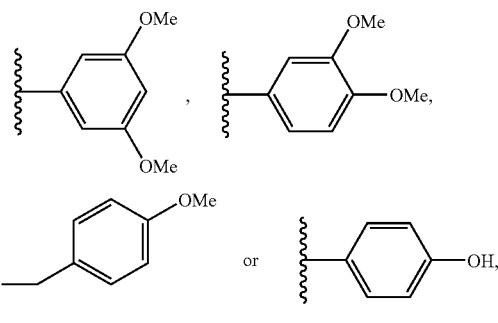
wherein $R_{187}$, is H, OH, —OAc, —OMe, or =O,
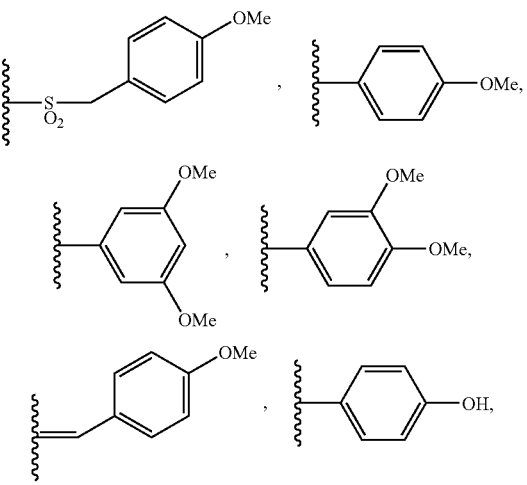
$R_{188}$, $R_{189}$, $R_{190}$ and $R_{191}$ are, independently,
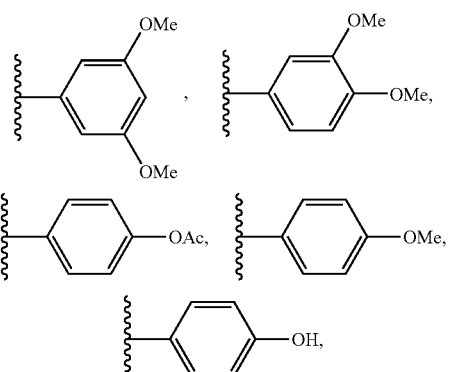
—OMe, —OAc, H or OH, wherein bond φ is present or absent,

165 wherein bond λ is present when $R_{187}$ is =O or

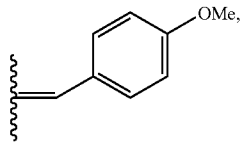

wherein bond μ is present when $R_{14}$ is =O and bond μ is absent.

In embodiments, the instant processes produce the compound having the structure:

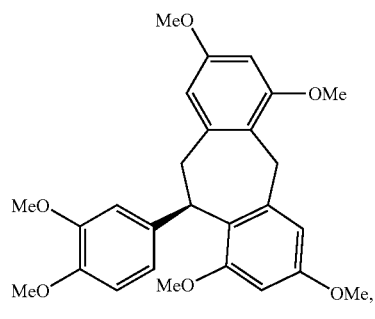

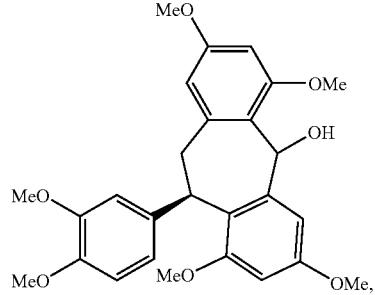

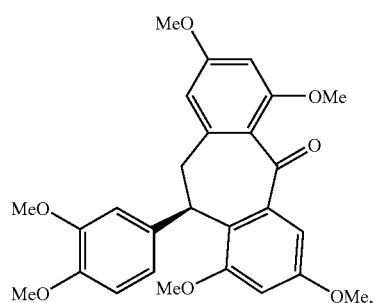

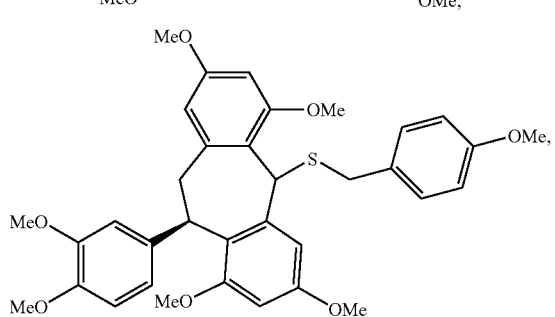

166

-continued

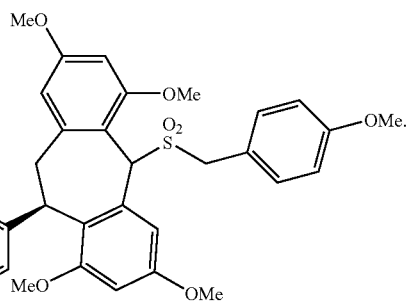

In an embodiment of the instant process, a suitable dioxirane is used.

In an embodiment of the instant process, the dioxirane used is (trifluoromethyl)methyldioxirane.

In an embodiment of the instant process, an acid is used.

In an embodiment of the instant process, the acid used is is HCl, MeSO$_3$H, H$_2$SO$_4$, p-TsOH or H$_3$PO$_4$.

A process is provided for making a compound having the structure:

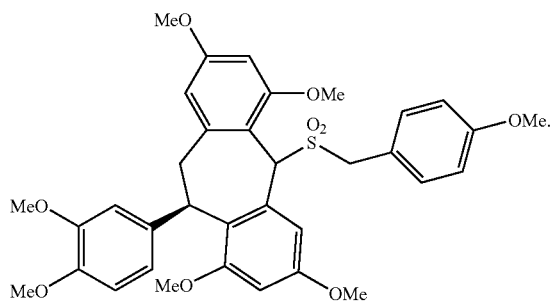

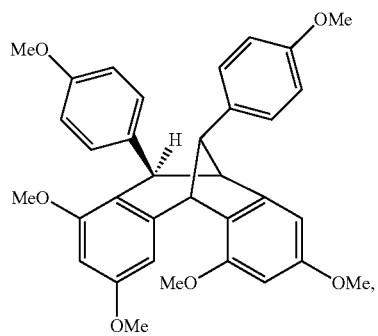

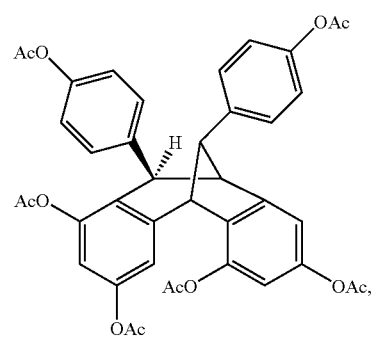

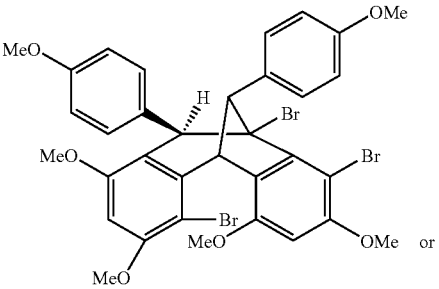

or

-continued

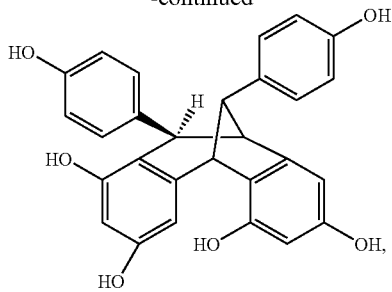

comprising the step of reacting a compound having the structure:

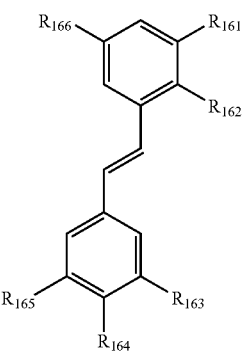

wherein $R_{161}$ and $R_{166}$ are OMe, $R_{162}$ is Br and $R_{165}$ and $R_{163}$ are H and Rise is OMe,
with n-BuLi and a compound having the structure:

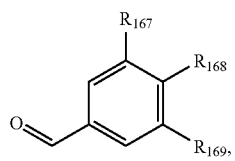

wherein $R_{167}$ is OMe, $R_{168}$ is H, and $R_{169}$ is OMe, so as to produce the compound.

A process is provided for making a compound having the structure:

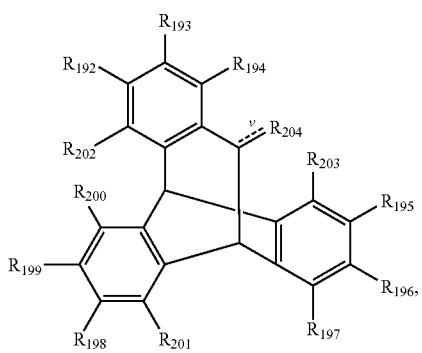

wherein $R_{192}$, $R_{192}$, $R_{193}$, $R_{194}$, $R_{195}$, $R_{196}$, $R_{197}$, $R_{198}$, $R_{199}$, $R_{200}$, $R_{201}$, $R_{202}$, and $R_{203}$ are, independently, H, OH, Br, —OMe, —OAc,

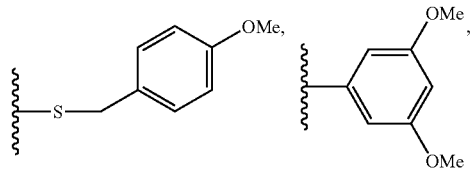

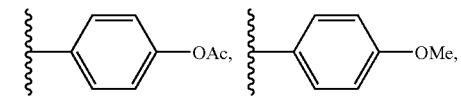

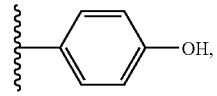

and wherein $R_{204}$ is H, OH, =O, Br, —OAc, —OMe,
and wherein bond v is present when $R_{204}$ is =O,
comprising the step of reacting a compound having the structure:

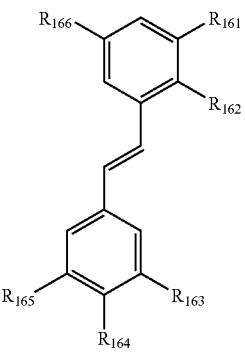

wherein $R_{161}$ and $R_{166}$ are OMe or OAc, $R_{162}$ is Br and $R_{164}$ and $R_{163}$ are OMe or OAc and $R_{165}$ is H or $R_{165}$ and $R_{163}$ are H and $R_{164}$ is OMe or OAc,
with n-BuLi and a compound having the structure:

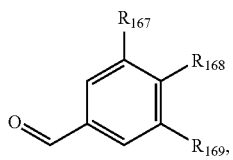

wherein $R_{167}$ is H or OMe or OAc, $R_{168}$ is H or OMe or OAc, and $R_{169}$ is H or OMe or OAc,
so as to produce the compound.

In an embodiment, $R_{164}$ and $R_{163}$ are OMe or OAc and $R_{165}$ is H.

In an embodiment, $R_{165}$ and $R_{163}$ are H and $R_{164}$ is OMe or OAc.

In an embodiment, the compound produced has the structure:

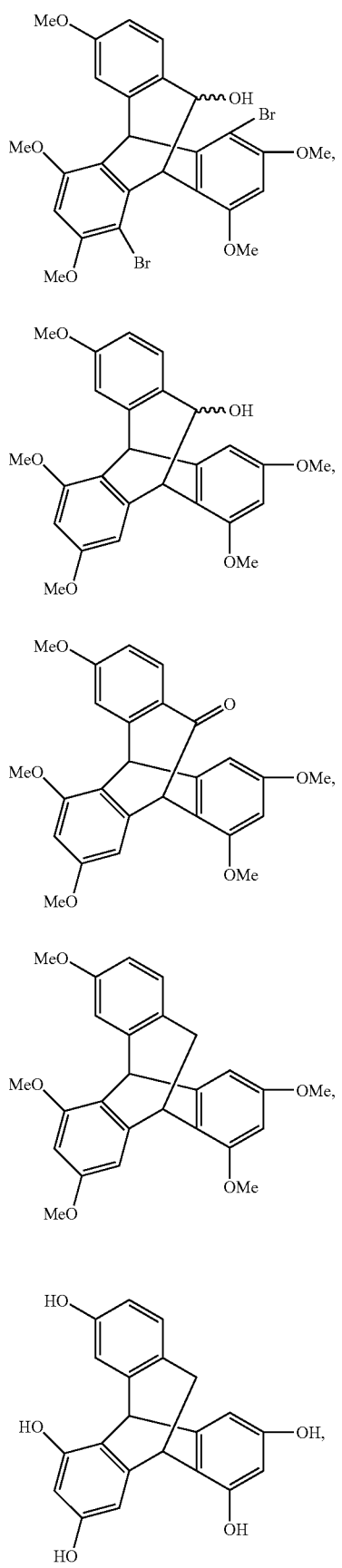
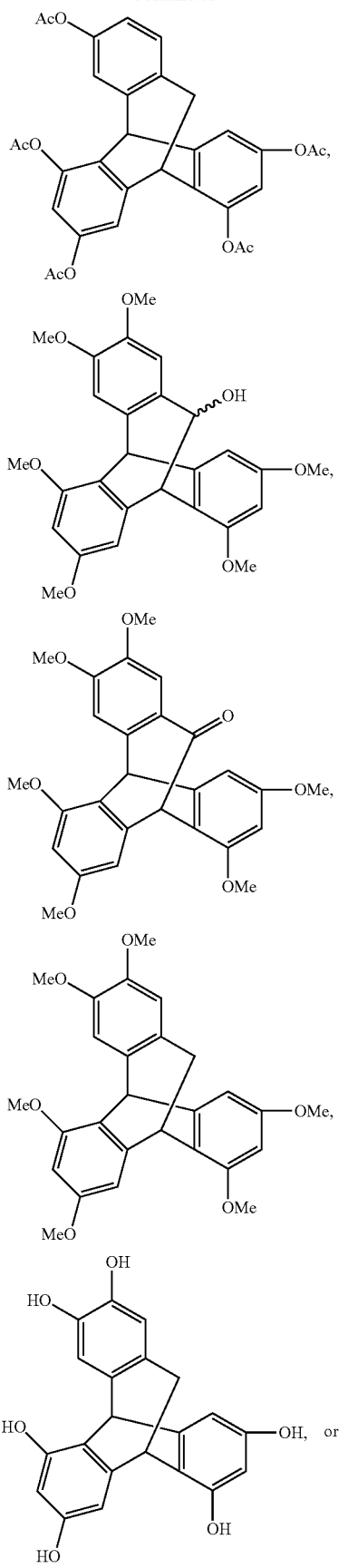

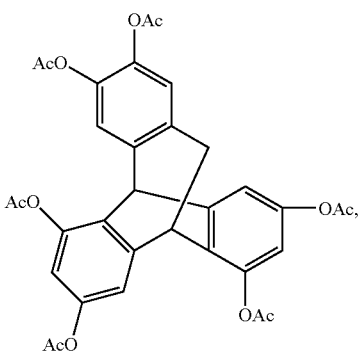

In an embodiment, the process further comprises:
i. contacting the product with a suitable oxidant;
ii. contacting the product of step i) with an acid;
iii. contacting the product of step iii) with a hydride source so as to produce the compound.

In an embodiment, the process wherein the suitable oxidant is Dess-Martin periodinane.

In an embodiment, the process wherein the acid is HCl, MeSO$_3$H, H$_2$SO$_4$, p-TsOH or H$_3$PO$_4$.

In an embodiment, the process wherein the hydride source is lithiumaluminumhydride or sodium cyanoborohydride.

In an embodiment, the process further comprises:
i. exposing the product to methyl iodide in the presence of a suitable first base;
ii. contacting the product of step i) with Br$_2$;
iii. contacting the product of step ii) with a suitable second base in the presence of water;
iv. contacting the product of step iii) with a suitable hydride source so as to produce the compound.

In an embodiment, the process wherein the suitable first base is sodium hydride.

In an embodiment, the process wherein the suitable second base is K$_2$CO$_3$, NaHCO$_3$, KOH, Ca(OH)$_2$, NaOH, CsCO$_3$, or Ba(OH)$_2$.

In an embodiment, the process wherein the suitable hydride source is sodium cyanoborohydride.

In an embodiment, the process further comprises:
i. exposing the product to a suitable bromine source in the presence of a suitable solvent so as to produce the compound.

In an embodiment, the process wherein the suitable bromine source is phosphorus tribromide or HBr.

In an embodiment, the process wherein the suitable solvent is pyridine when phosphorus tribromide is the suitable bromine source.

In an embodiment, the process wherein the suitable solvent is acetic acid when HBr is the suitable bromine source.

In an embodiment, the process further comprises:
i. cleaving methyl ethers present in the final product with a suitable halide so as to produce the compound.

In an embodiment, the process wherein the suitable halide is BBr$_3$, 9-I-BBN, BCl$_3$ or HI.

A process is provided for making a compound having the structure:

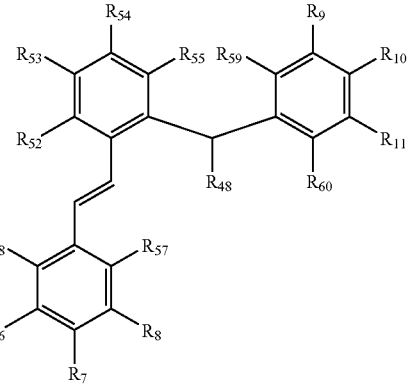

wherein R$_6$, R$_7$, R$_8$, R$_9$, R$_{10}$, R$_{11}$, R$_{52}$, R$_{53}$, R$_{54}$, R$_{55}$, R$_{57}$, R$_{58}$, R$_{59}$, R$_{60}$ are, independently, H, OH, —OMe, —OAc, alkyl, alkenyl, alkynyl, —OR$_{78}$, —SR$_{79}$, —N(R$_{80}$)$_2$, —S(O)(O)R$_{81}$, —C(O)OR$_{82}$, —R$_{83}$OR$_{84}$, cycloalkyl, cycloalkenyl, a substituted or unsubstituted aryl, a substituted or unsubstituted heteroaryl, a substituted or unsubstituted heterocyclyl, or —X, where X is a halogen, and where R$_{78}$, R$_{79}$, R$_{81}$, R$_{82}$, R$_{84}$ and each occurrence of R$_{80}$ are, independently, H, alkyl, alkenyl, or alkynyl, and where R$_{83}$ is alkylene, alkenylene or alkynylene, and wherein each occurrence of alkyl, alkenyl, alkynyl, alkylene, alkenylene, and alkynylene is substituted or unsubstituted R$_{48}$ is H, =O, OH, —OAc, —OMe,

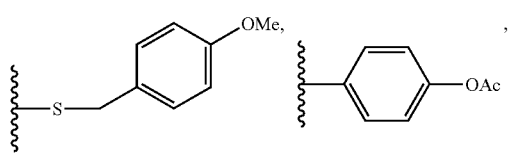

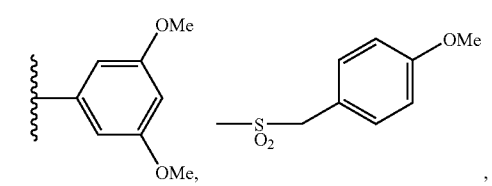

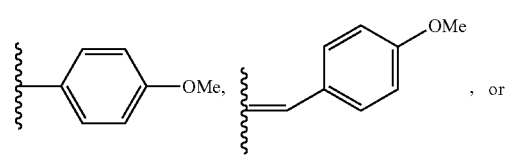

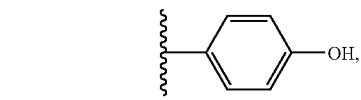

comprising reacting a compound having the structure:
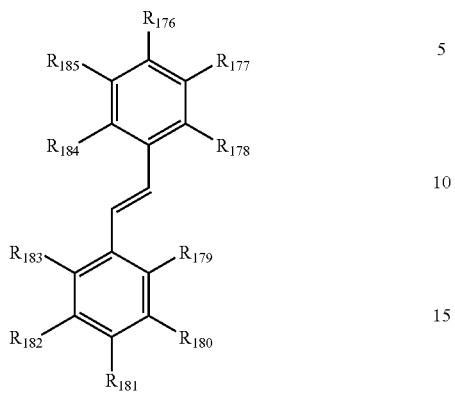
wherein $R_{176}$, $R_{177}$, $R_{178}$, $R_{179}$, $R_{180}$, $R_{181}$, $R_{182}$, $R_{183}$, $R_{184}$, $R_{185}$ are, independently, H, Br, or OMe, with with n-BuLi and a compound having the structure:
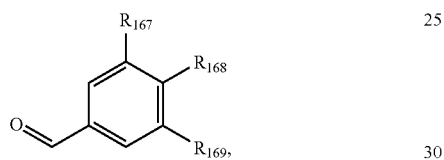
wherein $R_{167}$ is H, OAc or OMe, $R_{168}$ is H, OAc or OMe, and $R_{169}$ is H, OAc or OMe, so as to produce the compound.
In an embodiment the compound produced has the structure:
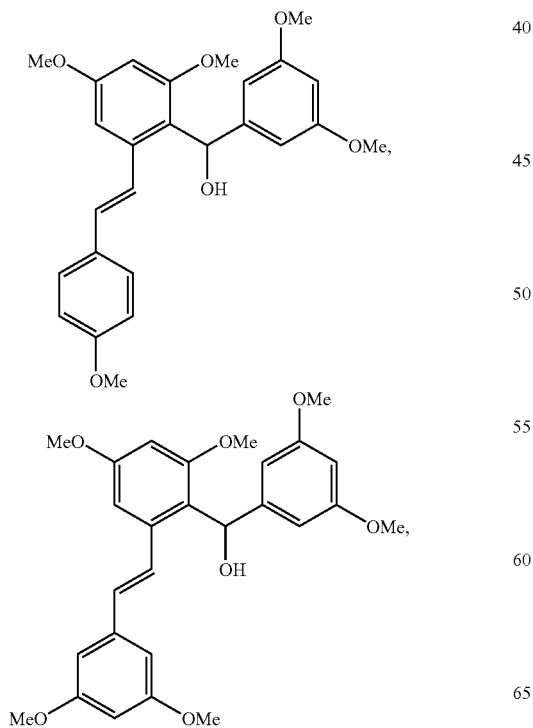
-continued
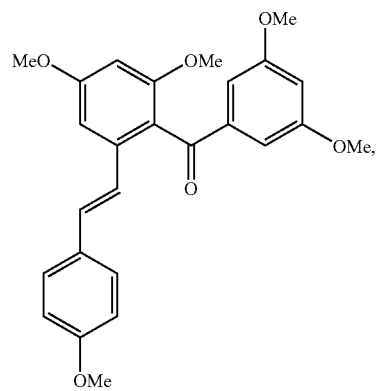
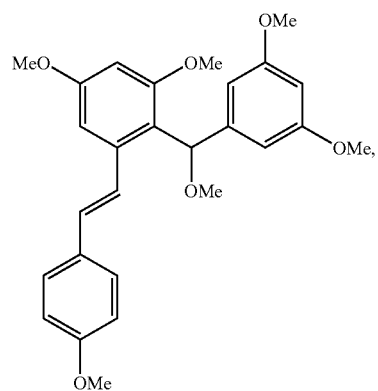
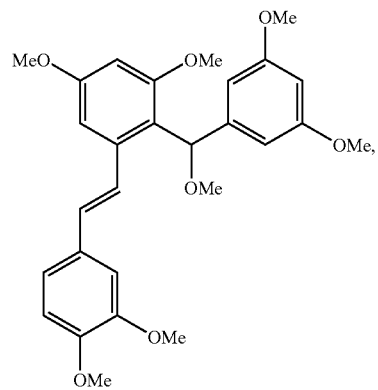
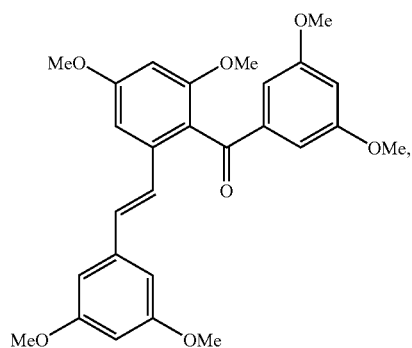

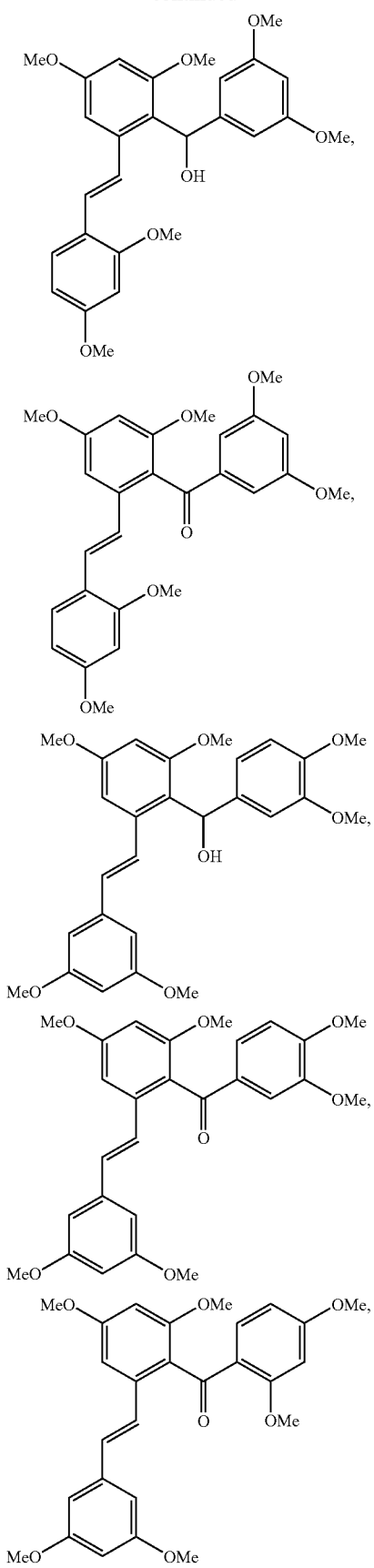
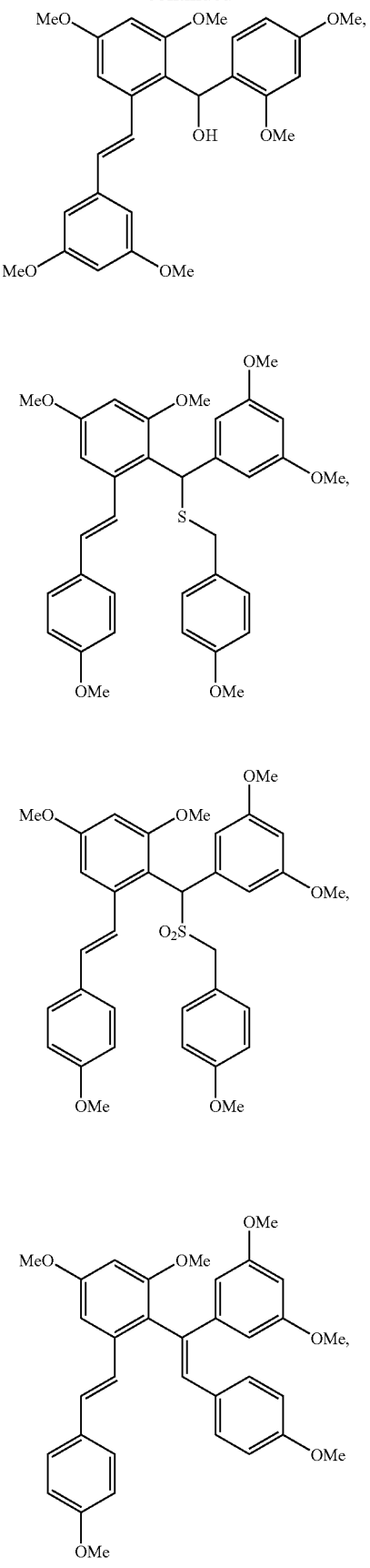

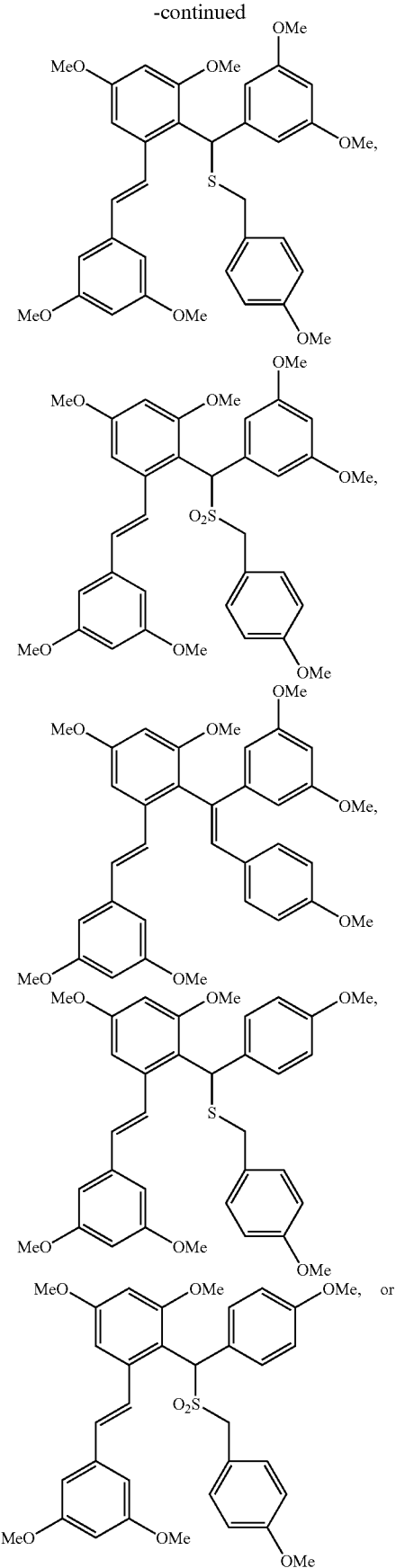
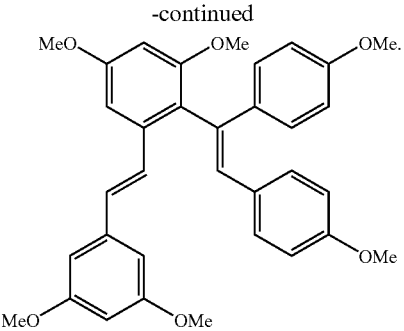
In an embodiment, the process produces the compound having the structure:
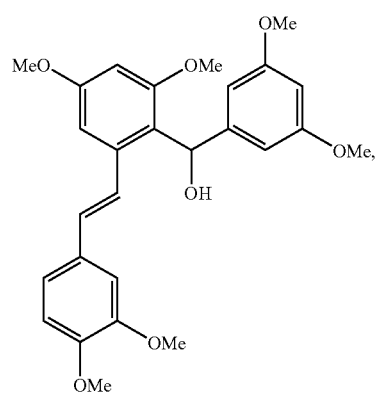
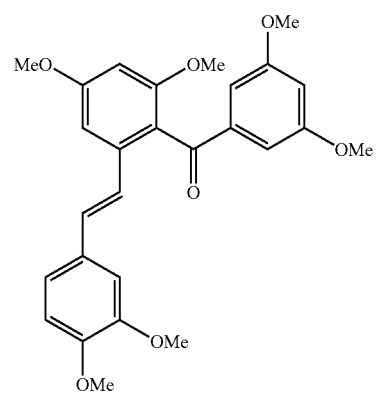
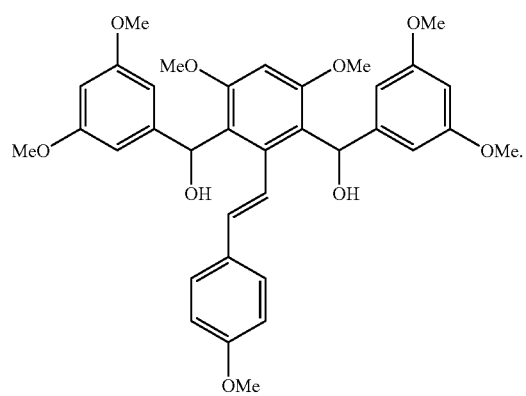
A process is provided for making a compound having the structure:

179

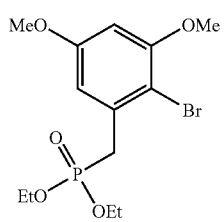

comprising a) reacting a compound having the structure:

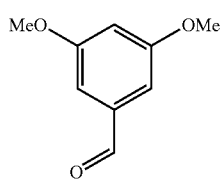

with NaBH$_4$ and PBR$_3$ to produce a compound having the structure:

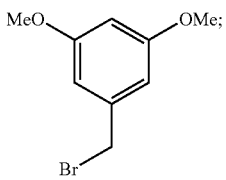 [SMILES: COc1cc(CBr)cc(OC)c1]

b) reacting the product of step a) with NBS in a suitable solvent;
c) reacting the product of step b) with KHMDS and HP(O)(OEt)$_2$ so as to produce the compound.

A process is provided for making a compound having the structure:

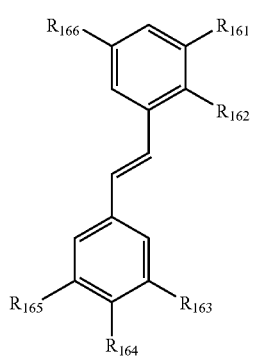

wherein R$_{161}$ and R$_{166}$ are OMe or OAc, R$_{162}$ is Br and R$_{164}$ and R$_{163}$ are OMe or OAc and R$_{165}$ is H comprising:

180 a) contacting a compound having the structure:

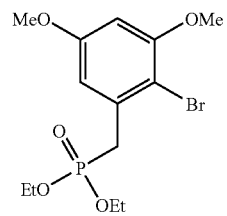 [SMILES: CCOP(=O)(Cc1cc(OC)cc(OC)c1Br)OCC]

with KOt-Bu; and b) reacting the product of step a) with 3,4-dimethoxybenzaldehyde so as to obtain the compound.

A composition, free of plant extract is provided comprising a compound having the structure:

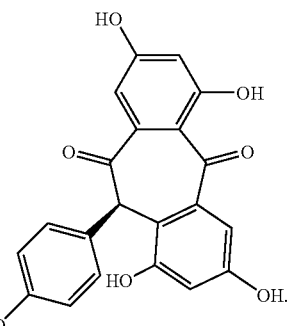

A composition free of plant-extract is provided comprising any of the compounds described herein.

This invention provides a compound having the structure:

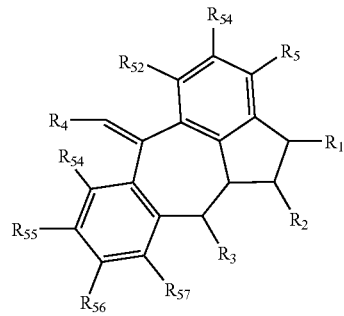

wherein R$_1$, R$_2$, R$_3$, R$_4$, R$_5$, R$_{52}$, R$_{54}$, R$_{55}$, R$_{56}$, R$_{57}$ are defined as above.

In an embodiment, the compound has the structure:

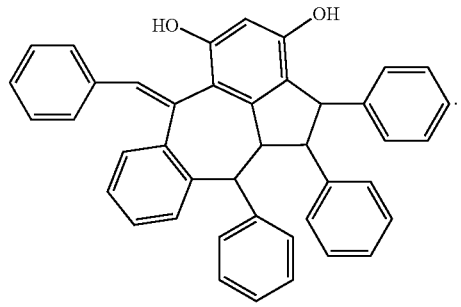 [SMILES: Oc1cc(O)c2c3c1/C(=C/c1ccccc1)c1ccccc1C(c1ccccc1)C3C(c1ccccc1)C2c1ccccc1]

181

In an embodiment, the compound has the structure:

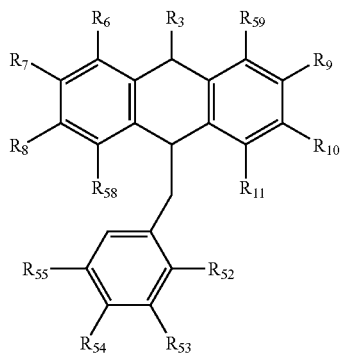

wherein $R_3$, $R_6$, $R_7$, $R_8$, $R_{52}$, $R_{53}$, $R_{54}$, $R_{55}$, and $R_{58}$ are defined as above, $R_9$, $R_{10}$, $R_{11}$, and $R_{59}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, wherein each occurrence of alkyl, alkenyl, alkynyl, alkylene, alkenylene, and alkynylene is substituted or unsubstituted.

In an embodiment, the compound of has the structure:

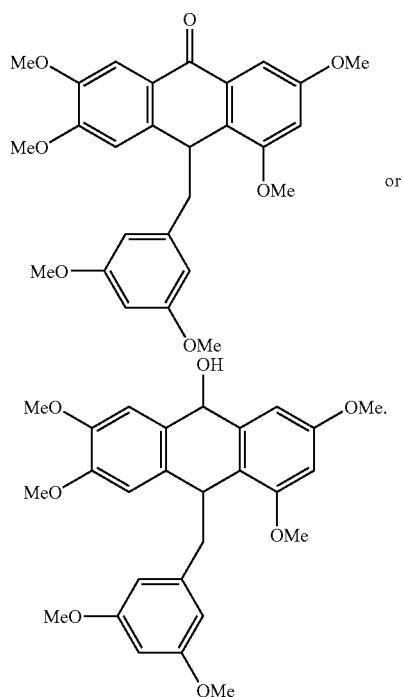

This invention provides a composition, free of extract, comprising:

182 a compound having the structure:

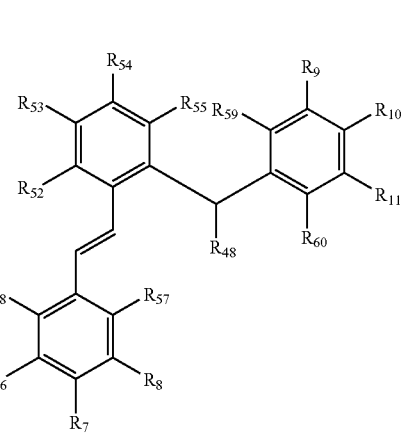

wherein $R_6$, $R_7$, $R_8$, $R_9$, $R_{10}$, $R_{11}$, $R_{52}$, $R_{53}$, $R_{54}$, $R_{55}$, $R_{57}$, $R_{58}$, $R_{59}$, $R_{60}$ are, independently, H, OH, —OMe, —OAc, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X, where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, and wherein each occurrence of alkyl, alkenyl, alkynyl, alkylene, alkenylene, and alkynylene is substituted or unsubstituted $R_{48}$ is H, —O, OH, —OAc, —OMe,

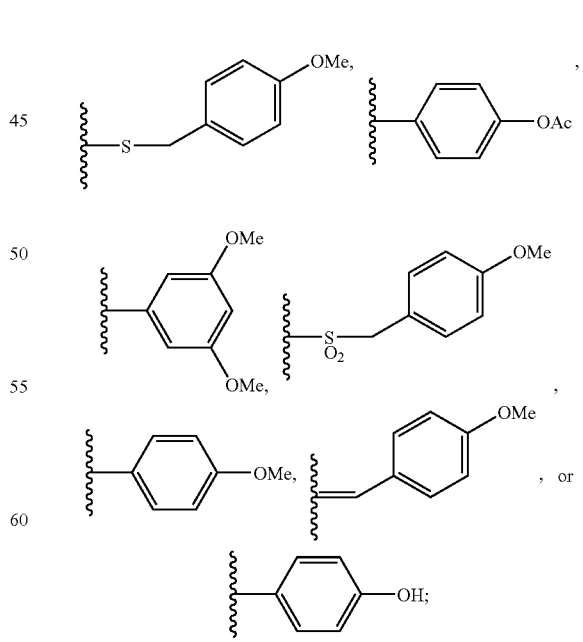

or a compound having the structure:

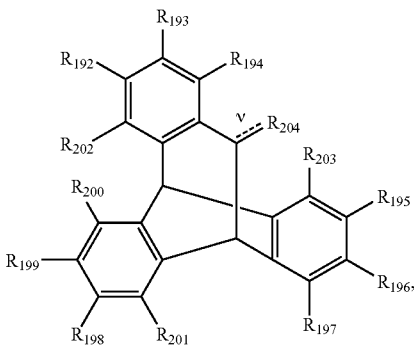

wherein $R_{192}$, $R_{192}$, $R_{193}$, $R_{194}$, $R_{195}$, $R_{196}$, $R_{197}$, $R_{198}$, $R_{199}$, $R_{200}$, $R_{201}$, $R_{202}$, and $R_{203}$ are, independently, H, OH, Br, —OMe, —OAc,

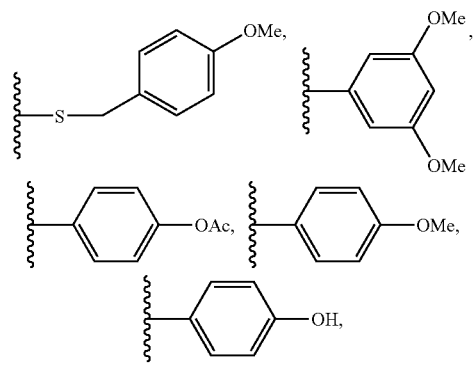

and wherein $R_{204}$ is H, OH, =O, Br, —OAc, —OMe, and wherein bond v is present when $R_{204}$ is =O; or
a compound having the structure:

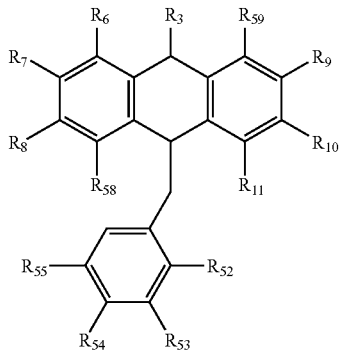

wherein $R_3$, $R_6$, $R_7$, $R_8$, $R_{52}$, $R_{53}$, $R_{54}$, $R_{55}$, and $R_{58}$ are defined as above, $R_9$, $R_{10}$, $R_{11}$, and $R_{59}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X,
where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene,
wherein each occurrence of alkyl, alkenyl, alkynyl, alkylene, alkenylene, and alkynylene is substituted or unsubstituted.

In an embodiment, the composition comprises a compound having the structure:

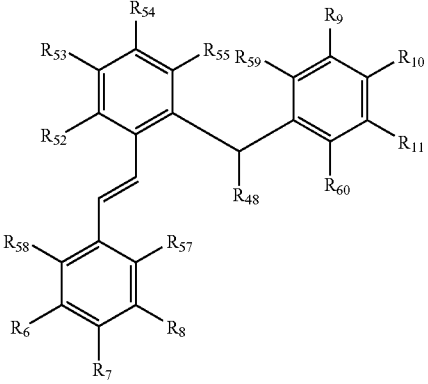

wherein $R_6$, $R_7$, $R_8$, $R_9$, $R_{10}$, $R_{11}$, $R_{52}$, $R_{53}$, $R_{54}$, $R_{55}$, $R_{57}$, $R_{58}$, $R_{59}$, $R_{60}$ are, independently, H, OH, —OMe, —OAc, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$ cycloalkyl, cycloalkenyl, a substituted or unsubstituted aryl, a substituted or unsubstituted heteroaryl, a substituted or unsubstituted heterocyclyl, or —X,
where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene, and
wherein each occurrence of alkyl, alkenyl, alkynyl, alkylene, alkenylene, and alkynylene is substituted or unsubstituted
$R_{48}$ is H, =O, OH, —OAc, —OMe,

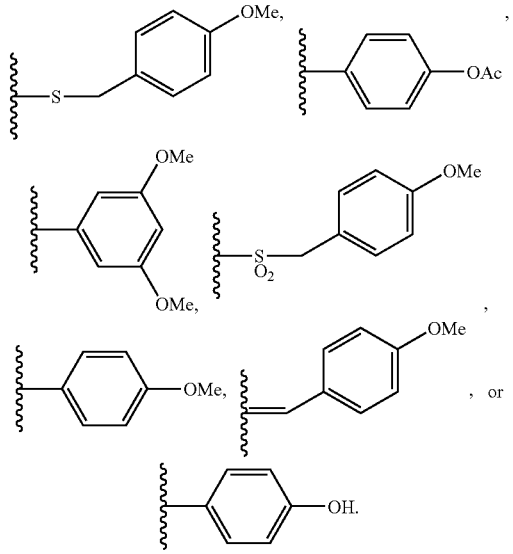

In an embodiment, the composition comprises a compound having the structure:

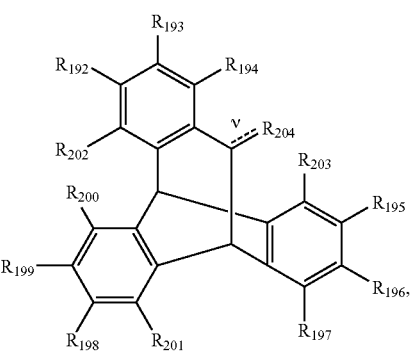

wherein $R_{192}$, $R_{192}$, $R_{193}$, $R_{194}$, $R_{195}$, $R_{196}$, $R_{197}$, $R_{198}$, $R_{199}$, $R_{200}$, $R_{201}$, $R_{202}$, and $R_{203}$ are, independently, H, OH, Br, —OMe, —OAc,

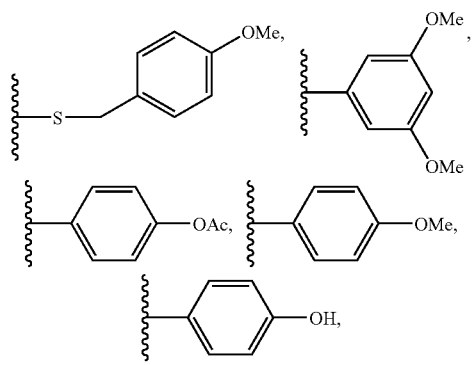

and wherein $R_{204}$ is H, OH, —O, Br, —OAc, —OMe, and wherein bond v is present when $R_{204}$ is =O.

In an embodiment, the composition comprises a compound having the structure:

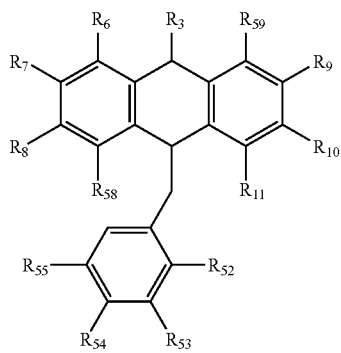

wherein $R_3$, $R_6$, $R_7$, $R_8$, $R_{52}$, $R_{53}$, $R_{54}$, $R_{55}$, and $R_{58}$ are defined as above, $R_9$, $R_{10}$, $R_{11}$, and $R_{59}$, are, independently, H, OH, alkyl, alkenyl, alkynyl, —$OR_{78}$, —$SR_{79}$, —$N(R_{80})_2$, —$S(O)(O)R_{81}$, —$C(O)OR_{82}$, —$R_{83}OR_{84}$, —$R_{83}R_{84}$, cycloalkyl, cycloalkenyl, a substituted or unsubstituted aryl, a substituted or unsubstituted heteroaryl, a substituted or unsubstituted heterocyclyl, or —X,
where X is a halogen, and where $R_{78}$, $R_{79}$, $R_{81}$, $R_{82}$, $R_{84}$ and each occurrence of $R_{80}$ are, independently, H, alkyl, alkenyl, or alkynyl, and where $R_{83}$ is is alkylene, alkenylene or alkynylene,
wherein each occurrence of alkyl, alkenyl, alkynyl, alkylene, alkenylene, and alkynylene is substituted or unsubstituted.

In an embodiment, the composition comprises the compound has the structure:

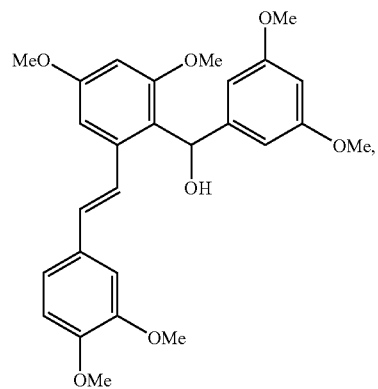

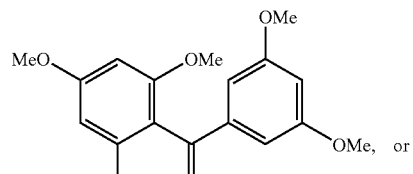

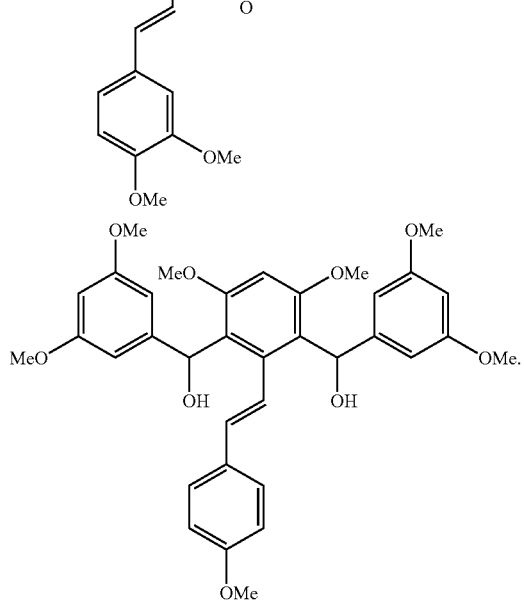

In an embodiment, the composition comprises the compound having the structure:

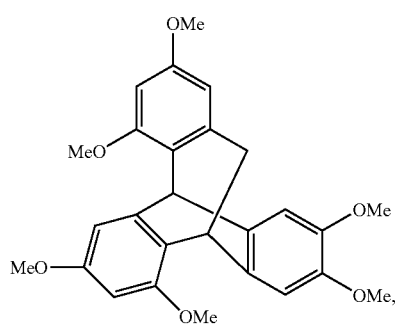

-continued

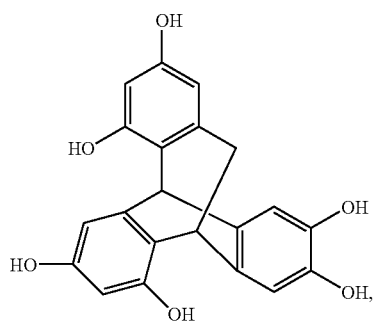

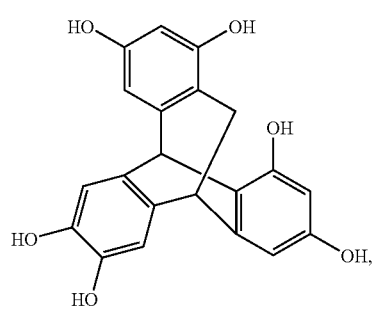

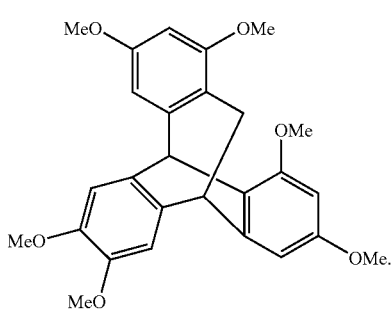

In an embodiment, the composition comprises the compound having the structure:

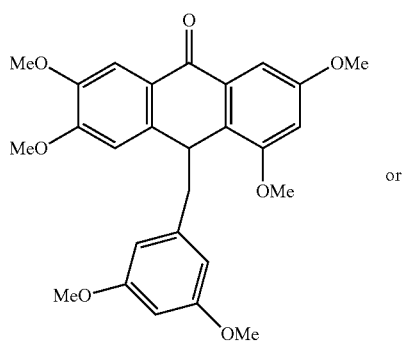

or

-continued

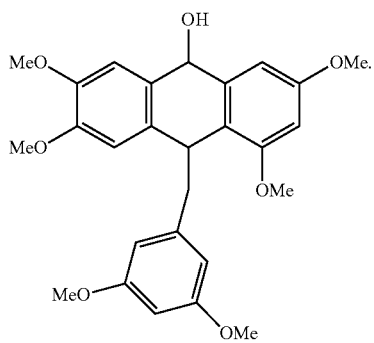

This invention provides a composition, free of extracts, comprising a compound having the structure:

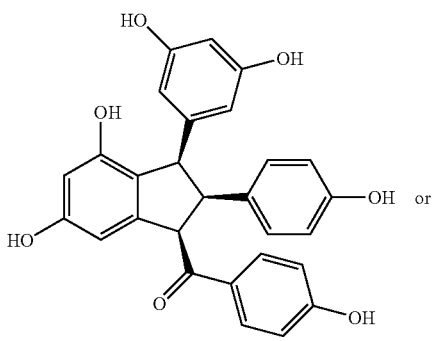

or

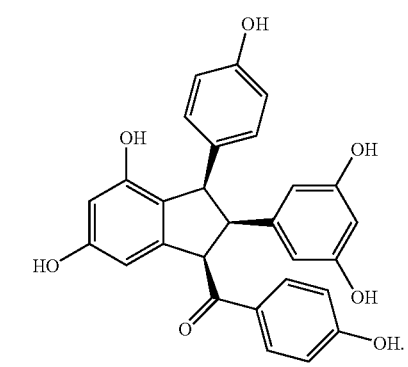

This invention provides a method for reducing a fungal infection of a plant or animal comprising contacting the fungus with one or more of the above compounds in amount effective to reduce the fungal infection.

This invention provides a method for preventing or inhibiting a fungal infection of a plant or animal comprising contacting the plant or animal with one or more of the above compounds in amount effective to prevent or inhibit the fungal infection.

In embodiments, the methods contacting the plant or animal with the compound having the structure:

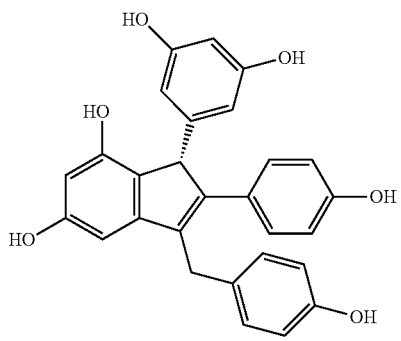 [SMILES: Oc1ccc(CC2=C(c3ccc(O)cc3)[C@@H](c3cc(O)cc(O)c3)c3c(O)cc(O)cc32)cc1]

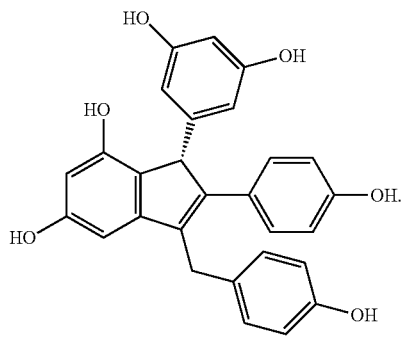 [SMILES: Oc1ccc(CC2=C(c3ccc(O)cc3)[C@@H](c3cc(O)cc(O)c3)c3c(O)cc(O)cc32)cc1]

This invention provides a method for reducing a fungal infection of a plant or animal comprising contacting the fungus with one or more of the above compositions in amount effective to reduce the fungal infection.

This invention provides a method for preventing or inhibiting a fungal infection of a plant or animal comprising contacting the plant or animal with one or more of the above compositions in amount effective to prevent or inhibit the fungal infection.

In embodiments of the instant methods, the fungal infection is of a plant. In an embodiment, the plant is a crop.

In embodiments of the instant method, the composition comprises a compound having the structure:

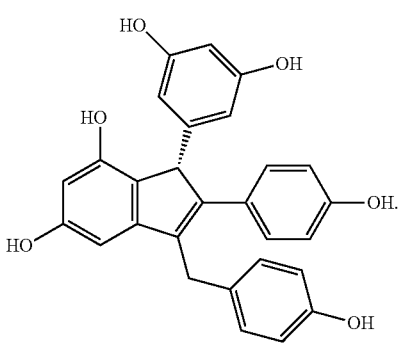 [SMILES: Oc1ccc(CC2=C(c3ccc(O)cc3)[C@@H](c3cc(O)cc(O)c3)c3c(O)cc(O)cc32)cc1]

This invention provides a method for inhibiting fungal growth or fungal proliferation comprising contacting the fungus with one or more of the above compounds in amount effective to inhibit growth or proliferation of the fungus.

This invention provides a method for inhibiting fungal growth or fungal proliferation comprising contacting the fungus with one or more of the above compositions in amount effective to inhibit growth or proliferation of the fungus.

In embodiments, the method inhibits fungal proliferation.

In embodiments of the instant method, the compound has the structure:

This invention provides for use of one or more of the above compounds in the manufacture of a medicament for inhibiting fungal growth or fungal proliferation in a subject.

This invention provides one or more of the above compounds for use in inhibiting fungal growth or fungal proliferation in a subject.

This invention provides for use of the one or more of the above compositions in the manufacture of a medicament for inhibiting fungal growth or fungal proliferation in a subject.

This invention provides one or more of the above compositions for use in inhibiting fungal growth or fungal proliferation in a subject.

This invention provides a method for reducing the transmission of ultraviolet light to a surface exposed thereto comprising contacting the surface with one or more of the above compounds in amount effective to reduce the transmission of ultraviolet light to the surface.

This invention provides a method for reducing the transmission of ultraviolet light to a surface exposed thereto comprising contacting the surface with one or more of the above compositions in amount effective to reduce the transmission of ultraviolet light to the surface.

In embodiments, the ultraviolet light is UV-B.

In embodiments, the surface is the skin of a subject.

In embodiments, the subject is a human.

This invention provides a method for treating a skin cancer in a subject comprising contacting the skin cancer with one or more of the above compounds in amount effective to treat the skin cancer.

This invention provides a method for treating a skin cancer in a subject comprising contacting the skin cancer with one or more of the above compositions in amount effective to treat the skin cancer.

In embodiments, the skin cancer is a malignant melanoma or a basal cell carcinoma.

In embodiments, subject is a human.

This invention provides for use of one or more of the above compounds in the manufacture of a medicament for treating a skin cancer in a subject.

This invention provides one or more of the above compounds for use in the treatment of a skin cancer in a subject.

This invention provides for use of one or more of the above compositions in the manufacture of a medicament for treating a skin cancer in a subject.

This invention provides one or more of the above compositions for use in the treatment of a skin cancer in a subject.

In the fungicidal and fungal-retarding methods described hereinabove it is understood that the compounds and compositions can act on the fungus itself or on the spores of the fungus to achieve their effect. In addition, the compounds and compositions can act on oomycetes to impair their growth or prevent infection by oomycetes, and methods for doing such are also provided herein. The compounds and compositions may be applied for example, in the case of plants and animals, by spraying of, or dipping/immersion in, the compounds or compositions. Alternatively, they may be applied as pharmaceutical compositions comprising a pharmaceutically acceptable carrier.

"Free of plant extract" with regard to a composition as used here means that the composition is absent any amount of resveratrol containing-plant material or resveratrol-based oligomer containing-plant material. Thus only synthetically produced compounds and compositions are free of plant extract. Any compound or compositions isolated from a plant would always contain at least some trace amount of plant material.

A method is provided for reducing the degree of a fungal infection comprising contacting the fungi with a compound described herein an in amount effective to reduce the degree of the fungal infection.

A method is provided for preventing or impairing a fungal infection comprising contacting the fungi with a compound described herein an in amount effective to prevent or impair the fungal infection.

As used herein, "alkyl" includes both branched and straight-chain saturated aliphatic hydrocarbon groups having the specified number of carbon atoms. Thus, $C_1$-$C_n$ as in "$C_1$-$C_n$ alkyl" is defined to include groups having 1, 2, ..., n−1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, propyl, butyl, pentyl, hexyl, and so on. In an embodiment the alkyl is $C_1$ (methyl). In an embodiment the alkyl is a $C_2$-$C_7$ alkyl. In embodiments the alkyl is a $C_1$, $C_2$, $C_3$, $C_4$, $C_5$, $C_6$, $C_7$, $C_8$, $C_9$, or $C_{10}$ alkyl.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "alkenyl" refers to a non-aromatic hydrocarbon radical, straight or branched, containing at least 1 carbon to carbon double bond, and up to the maximum possible number of non-aromatic carbon-carbon double bonds may be present. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl. In an embodiment the alkyl is a $C_2$-$C_7$ alkenyl. In embodiments the alkenyl is a $C_2$, $C_3$, $C_4$, $C_5$, $C_6$, $C_7$, $C_8$, $C_9$, or $C_{10}$ alkenyl. The alkenyl group may be substituted if a substituted alkenyl group is indicated.

The alkenyl group may be substituted if a substituted alkenyl group is indicated.

The term "cycloalkenyl" shall mean cyclic rings of 3 to 10 carbon atoms and at least 1 carbon to carbon double bond (i.e., cyclopropenyl, cyclobutenyl, cyclopenentyl, cyclohexenyl, cycloheptenyl or cycloocentyl).

The term "alkynyl" refers to a hydrocarbon radical straight or branched, containing at least 1 carbon to carbon triple bond, and up to the maximum possible number of non-aromatic carbon-carbon triple bonds may be present. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl. In an embodiment the alkynyl is a $C_2$-$C_7$ alkynyl. In embodiments the alkynyl is a $C_2$, $C_3$, $C_4$, $C_5$, $C_6$, $C_7$, $C_8$, $C_9$, or $C_{10}$ alknyl. The alkynyl group may be substituted if a substituted alkynyl group is indicated.

"Alkylene", "alkenylene" and "alkynylene" shall mean, respectively, a divalent alkane, alkene and alkyne radical, respectively.

As used herein, "aryl" is intended to mean any stable monocyclic, bicyclic or polycyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. In an embodiment the aryl is a substituted or unsubstituted phenyl.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazolyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

The alkyl, alkenyl, alkynyl, cycloalkyl, cycloalkenyl, aryl, heteroaryl and heterocyclyl substituents may be unsubstituted or unsubstituted, unless specifically defined otherwise. In a non-limiting example, a $C_2$-$C_6$ alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, alkynyl, cycloalkyl, cycloalkenyl, aryl, heterocyclyl and heteroaryl groups can be further substituted by replacing one or more hydrogen atoms be alternative non-hydrogen groups. These include, but are not limited to, halo, hydroxy, mercapto, amino, carboxy, cyano and carbamoyl.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. In a non-limiting example, an aryl group may be substituted by an alkenylene and an —OMe group.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds described in the present invention are in racemic form or as individual enantiomers. The enantiomers can be separated using known techniques, such as those described in Pure and Applied Chemistry 69, 1469-1474, (1997) IUPAC.

The instant compounds may be in a salt form. As used herein, a "salt" is salt of the instant compounds which has been modified by making acid or base salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, the term "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

The compounds described herein are useful, being based on resveratrol (see refs. 1a-1d) as, inter alia, antioxidants, for inhibiting lipid peroxidation of low-density lipoprotein, for inhibition of platelet aggregation, for inhibiting cyclooxygenase-1, for inhibiting inflammation, and for inhibiting malignant cell proliferation. In addition, the compounds are therapeutically useful for inhibiting or treating cardiovascular diseases, for example atherosclerosis (see refs. 1a-1d).

The resveratrol-related compounds of this invention are useful for protection of plants, such as crops, from fungal problems. Such antifungal properties of resveratrol have been described in Korean Patent No. 2006114090 and in Adrian et al. (2006) Oxidative Stress and Disease (Ch. 20—Resveratrol in Health and Disease), CRC Press. The compounds are useful in antifungal compositions.

The compositions of this invention may be administered in various forms, including those detailed herein. As used herein, "treatment" of a cardiovascular disease encompasses inducing inhibition, regression, or stasis/prevention of the disorder. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed. In an embodiment, a composition is provided comprising an amount of the compound effective to treat a disease as specified above and a pharmaceutical carrier.

As used herein, a "pharmaceutical carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutical carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds may comprise a single compound or mixtures thereof with anti-cancer compounds, or tumor growth inhibiting compounds, or with other compounds also used to treat neurite damage. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the cancer, all using dosage forms well known to those of ordinary skill in the pharmaceutical arts.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as *acacia*, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds may also be coupled to soluble polymers as targetable drug carriers or as a prodrug. Such polymers include polyvinylpyrrolidone, pyran copolymer, polyhydroxypropylmethacrylamide-phenol, polyhydroxyethylasparta-midephenol, or polyethyleneoxide-polylysine substituted with palmitoyl residues.

Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The instant compounds may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the invention can be coated onto stents for temporary or permanent implantation into the cardiovascular system of a subject.

In embodiments, the compounds of the invention are present in a purity of greater than 70%, 75%, 80%, 85%, 90%, 95%.

In embodiments the purity of the compound is 96%, 97%, 98%, 99% or 100%.

All combinations of the various elements are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Herein the first general synthetic approach capable of accessing all the carbogenic diversity posed by the resveratrol family is disclosed. This solution is based on a new idea for how to selectively generate natural product structures in instances where Nature abandons discrimination to achieve evolutionary advantage [5].

To date, all attempts to prepare resveratrol-based natural products have derived from strategies that parallel their presumed biogenesis, i.e. the generation of radicals or carbocations from 1 through its exposure to different chemicals or enzymes [6-11]. Typically, mixtures of compounds have been observed [6-8] and, in those rare instances when selectivity has been achieved, solely non-natural products have resulted [9,10]. Thus far, in fact, only a highly engineered resveratrol fragment has proven capable of leading to an actual dimeric natural product within this class [11].

Herein a structural solution was considered which might exist for this general chemoselectivity problem, one empowered by the identification of hidden relationships between their seemingly divergent architectures. Upon consideration of natural products such as paucifloral F (7) and diptoindonesin A (8) it was clear that such structures are incongruent with the notion of direct resveratrol oligomerization since they possess three, instead of four, aromatic rings. In fact, there are many members of this family with an odd number of aryl rings. Based on these compounds it was hypothesized that two highly similar building blocks, well removed from resveratrol, and each with three aryl groups arrayed around the same core structure, could controllably lead to every family member by experimentally determining the reagents and reaction conditions to which they are exposed.

Figure 2:
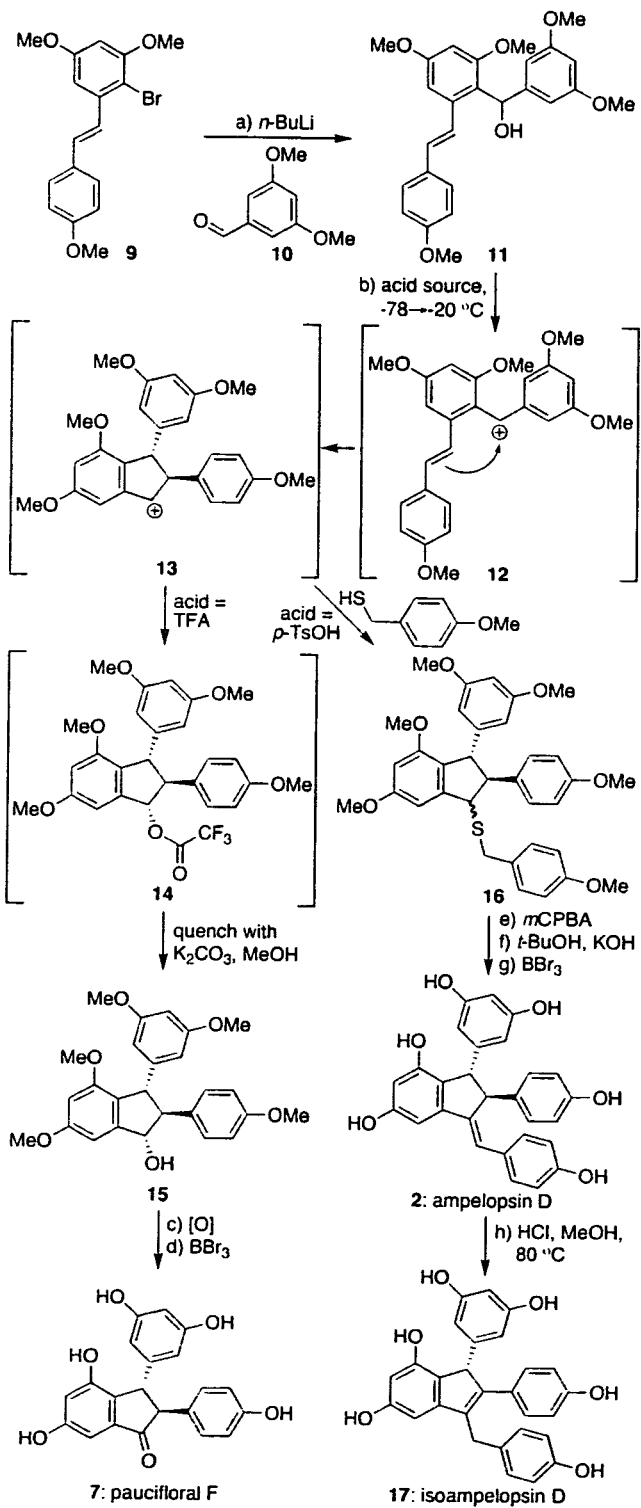
FIG. 2: Total synthesis of three dimeric resveratrol-based natural products (2, 7, and 17) from key building block 11: a) n-BuLi (1.0 equiv), THF, —78° C., 20 min; then 10 (1.0 equiv), —78→25° C., 4 h, 71%; b) for 15: TFA (1.0 equiv), $CH_2Cl_2$, —30→−20° C., 5 h; then $K_2CO_3$ (10 equiv), MeOH, 25° C., 5 min, 75%; for 16: p-TsOH (1.0 equiv), $CH_2Cl_2$, −30→−20° C., h; p-methoxy-α-toluenethiol (3.0 equiv), then concentration to near dryness, 25° C., 12 h, 57%; c) Dess-Martin periodinane (1.2 equiv), $NaHCO_3$ (5.0 equiv), $CH_2Cl_2$, 25° C., 3 h, 97%; d) $BBr_3$ (1.0 M in $CH_2Cl_2$, 10 equiv), $CH_2Cl_2$, 0° C., 6 h, 86%; e) mCPBA (3.0 equiv), $NaHCO_3$ (10 equiv), $CH_2Cl_2$, 0→25° C., 3 h, 78%; f) t-BuOH/$H_2O$/$Cl_4$ (5/1/5), KOH (20 equiv), 80° C., 12 h, 52%; g) $BBr_3$ (1.0 M in $CH_2Cl_2$, 12 equiv), $CH_2Cl_2$, 25° C., 6 h, 76% of 2, 13% of 17; h) conc. HCl (5 equiv), MeOH, 80° C., 2 h, 96%. TFA=trifluoroacetic acid, p-TsOH=p-toluenesulfonic acid, mCBPA=m-chloroperoxybenzoic acid.

One of these compounds is biaryl alcohol 11 (FIG. 2), an adduct synthesized in 71% yield through an aldol reaction between the lithiated form of 9 (prepared in 4 steps in 80% overall yield from 3,5-dimethoxybenzaldehyde, (see Ref. 12) and 3,5-dimethoxybenzaldehyde (10). As shown in Scheme 1, when this key intermediate was treated with a stoichiometric amount of TFA under carefully controlled conditions (−30→−20° C.) in $CH_2Cl_2$, a cascade sequence featuring cation generation, regio- and stereoselective cyclization (in relative terms), and stereoselective cation capture, smoothly afforded intermediate 14 after 4 hours. A terminating quench under basic conditions ($K_2CO_3$, MeOH) then completed the one-pot synthesis of intermediate 15 from 9 in 75% yield, a compound that proved to be just two steps away from paucifloral F (7). Those operations, alcohol oxidation using Dess-Martin periodinane and $BBr_3$-induced global demethylation in $CH_2Cl_2$ at 0° C., [13] proceeded smoothly in 84% overall yield. However, if 11 was exposed to a different proton source, one with a non-nucleophilic counterion such as that possessed by p-TsOH, then it proved possible to arrest the sequence at cation 13 prior to β-hydride elimination and access entirely different cyclic products. Indeed, if a nucleophile such as p-methoxy-α-toluenethiol was added at −30° C. after 11 had been exposed to p-TsOH for 5 hours and the reaction media was then concentrated to near dryness, sulfide 16 was obtained in 57% overall yield. Sulfide 16 could also be accessed in 82% yield from alcohol 15 upon its treatment with p-TsOH and p-methoxy-α-toluenethiol in $CH_2Cl_2$ at 25° C. This new tetra-aryl intermediate could then be converted into the natural product ampelopsin D (2) through a highly selective Ramberg-Backlund reaction [14] under Meyer's modified conditions [15] that afforded permethylated ampelopsin D along with its chromatographically separable Z-olefin isomer in a 5:1 ratio (40% and 7% yield over two steps, respectively), followed by Lewis acid-mediated phenol deprotection using $BBr_3$. This final deprotection step produced a 5:1 mixture of both ampelopsin D (2) and isoampelopsin D (17) which were obtained in pure form in near quantitative yield by treating the product mixture with $Ac_2O$, chromatographically separating the resultant acetates, and using KCN in MeOH to then effect ester hydrolysis. Subsequent treatment of 2 with 5 equivalents of HCl in MeOH at 80° C. then provided the means to effect, in near quantitative yield, the olefin isomerization necessary to access isoampelopsin D (17) [16].

Figure 3:
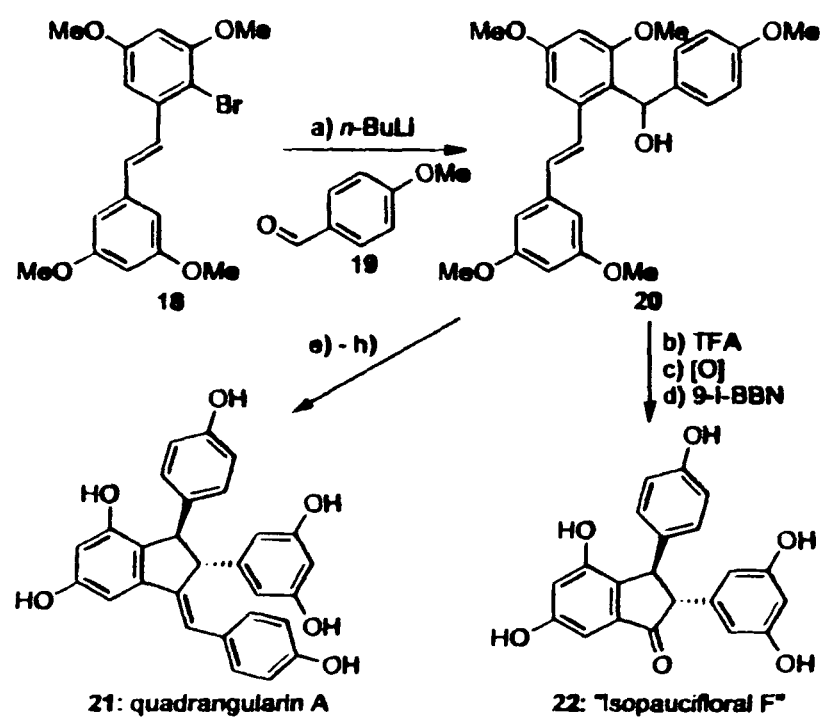
FIG. 3: Total synthesis of two resveratrol-based natural products (21 and 22) from key building block 20. a) n-BuLi (1.0 equiv), THF, −78° C., 20 min; then 19 (1.0 equiv), −78→25° C., 4 h, 71%; b) TFA (1.0 equiv), $CH_2Cl_2$, −30→−20° C., 5 h; then $K_2CO_3$ (10 equiv), MeOH, 25° C., 5 min, 93%; c) Dess-Martin periodinane (1.2 equiv), $NaHCO_3$ (5.0 equiv), $CH_2Cl_2$, 25° C., 3 h, 98%; d) 9-I-BBN (1.0 M in hexanes, 10 equiv), $CH_2Cl_2$, 40° C., 30 min, 72%; e) p-TsOH (1.0 equiv), $CH_2Cl_2$, −30→20° C., 5 h; p-methoxy-α-toluenethiol (3.0 equiv), then concentration to near dryness, 25° C., 12 h, 65%; f) mCPBA (3.0 equiv), $NaHCO_3$ (10 equiv), $CH_2Cl_2$, 0→25° C., 3 h, 70%; g) t-BuOH/$H_2O$/$CCl_4$ (5/1/5), KOH (20 equiv), 80° C., 12 h, 55%; h) $BBr_3$ (1.0 M in $CH_2Cl_2$, 12 equiv), $CH_2Cl_2$, 25° C., 6 h, 75% of 21, 14% of internal alkene isomer. 9-I-BBN=9-iodo-9-borabicyclo[3.3.1]nonane.

The other building block is 20 (FIG. 3), a compound that differs from biaryl alcohol 11 architecturally (in terms of the positioning of two of its three aromatic rings), but behaves in the same manner chemically. Indeed, as indicated in FIG. 3, when this intermediate was exposed to the reaction sequences outlined above, what resulted were total syntheses of quadrangularin A (21) and isopaucifloral F (22) (Isopaucifloral F represents a likely, but not yet isolated, natural product structure) structures which, as expected, display the opposite array of pendant phenol ring systems as those accessed from 11 [17]. Consequently, it would appear, based on these collated results, that any resveratrol-derived structure possessing a single cyclopentane ring system can be obtained cleanly from appropriate triaryl precursors.

What, though, about more complex intermediates such as pallidol (3) and ampelopsin F (4, c.f. FIG. 1), molecules possessing an additional ring appended onto a cyclopentane core? Prior explorations with naturally-derived materials had established that their complexity could arise alongside several other architectures by treating dihydrofuran-bearing substrates, such as vaticanol C (5, c.f. FIG. 1) and hopeaphenol (6, c.f. FIG. 1), with strong acid [16]. It was investigated whether electrophilic activation of the olefins within both ampelopsin D (2) and quadrangularin A (21), followed by a Friedel-Crafts alkylation onto the resultant quinone methide, could accomplish the same objective in a controlled manner.

Figure 4:
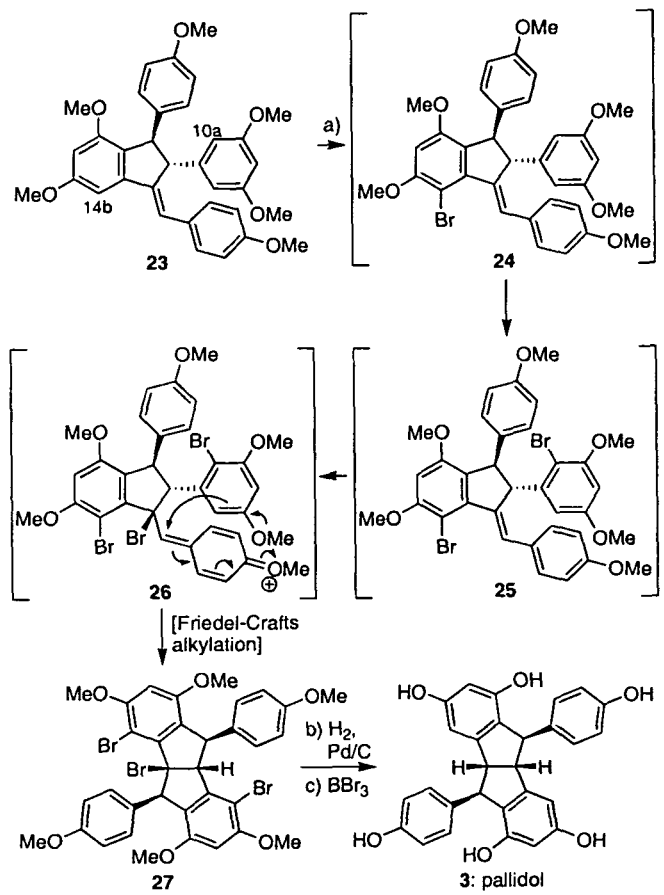
FIG. 4: Sequential, cascade-based halogenation to access pallidol (3): a) $Br_2$ (2.0 equiv), $CH_2Cl_2$, −78° C., 2 h, then slow warming to 25° C., 1 h, 81%; b) Ha, Pd/C (20%, 0.2 equiv), MeOH, 25° C., 24 h, 76%; c) $BBr_3$ (1.0 M in $CH_2Cl_2$, 12 equiv), $CH_2Cl_2$, 0° C., 4 h, then 25° C., 20 h, 83%.
Figure 5:
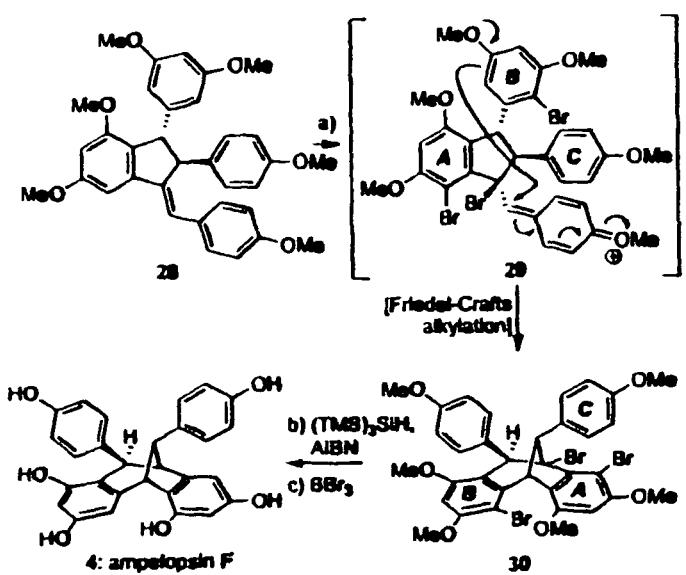
FIG. 5: Sequential, cascade-based halogenation to access ampelopsin F (4): a) $Br_2$ (2.0 equiv), $CH_2Cl_2$, −78° C., 2 h, then slow warming to 25° C., 1 h, 53%; b) $(TMS)_3SiH$ (9.0 equiv), AIBN (1.0 equiv), toluene, 100° C., 8 h, 89%; c) $BBr_3$ (1.0 M in $CH_2Cl_2$, 12 equiv), $CH_2Cl_2$, 0° C., 4 h, then 25° C., 15 h, 90%. TMS=trimethylsilyl, AIBN=2,2'-azobisisobutyronitrile.
Figure 20:
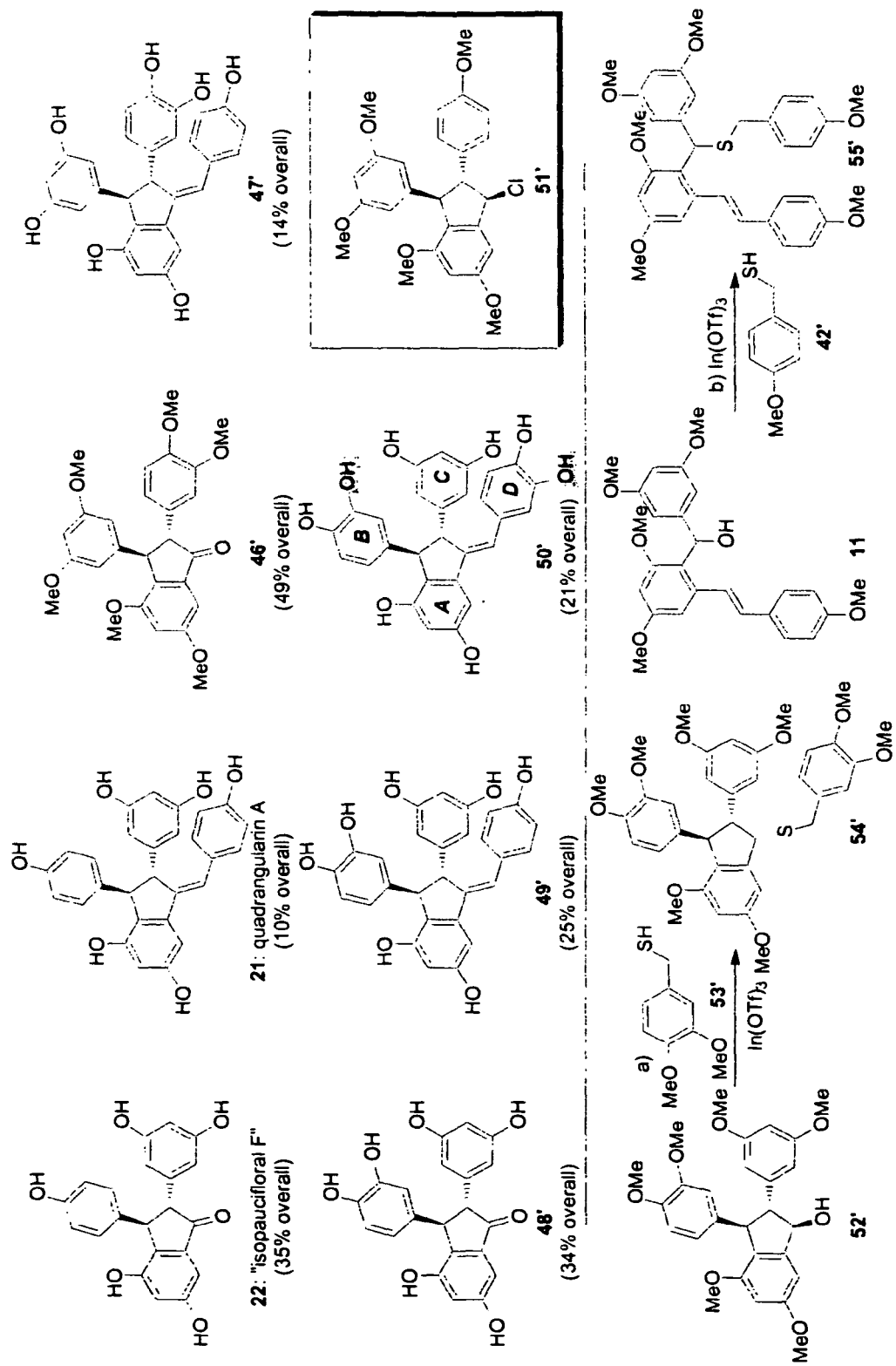
FIG. 20. Additional natural products and natural product-like analogs created through the general pathways defined in FIG. 19, and the discovery of a new reaction to generate thioethers: (a) In(OTf)3 (1.0 equiv), 53' (2.6 equiv), 25° C., 90 min, 85%, 100% based on recovered 52'; (b) $In(OTf)_3$ (1.0 equiv), 42' (3.0 equiv), $CH_2Cl_2$, −10° C., 5 min, 96%.
Figure 21:
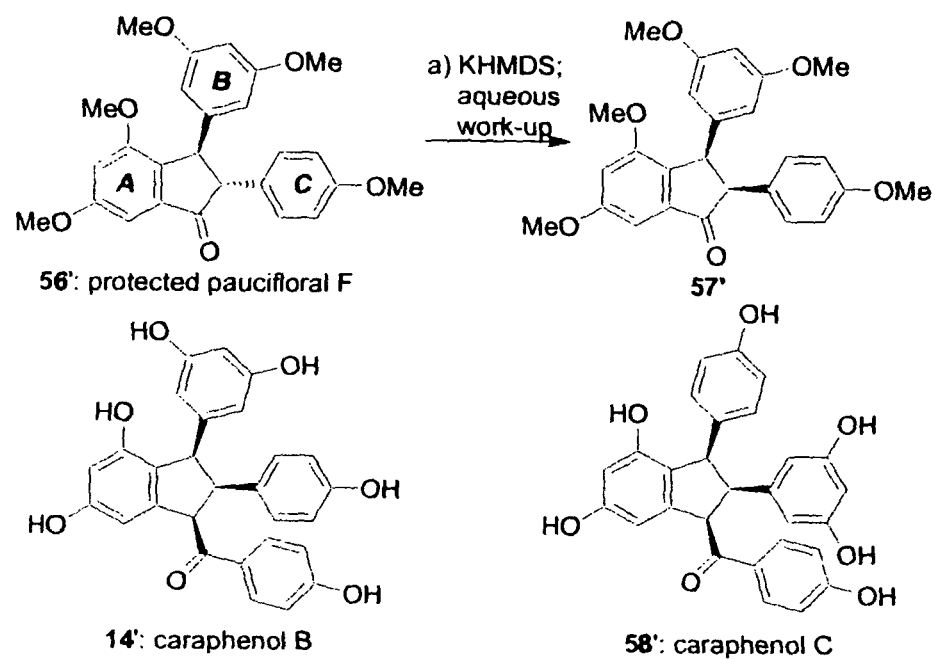
FIG. 21. Synthesis of cis-disposed indane systems: (a) KHMDS (1.1 equiv), THF, −78° C., 5 min, then 25° C., 15 h, 82%.
Figure 22:
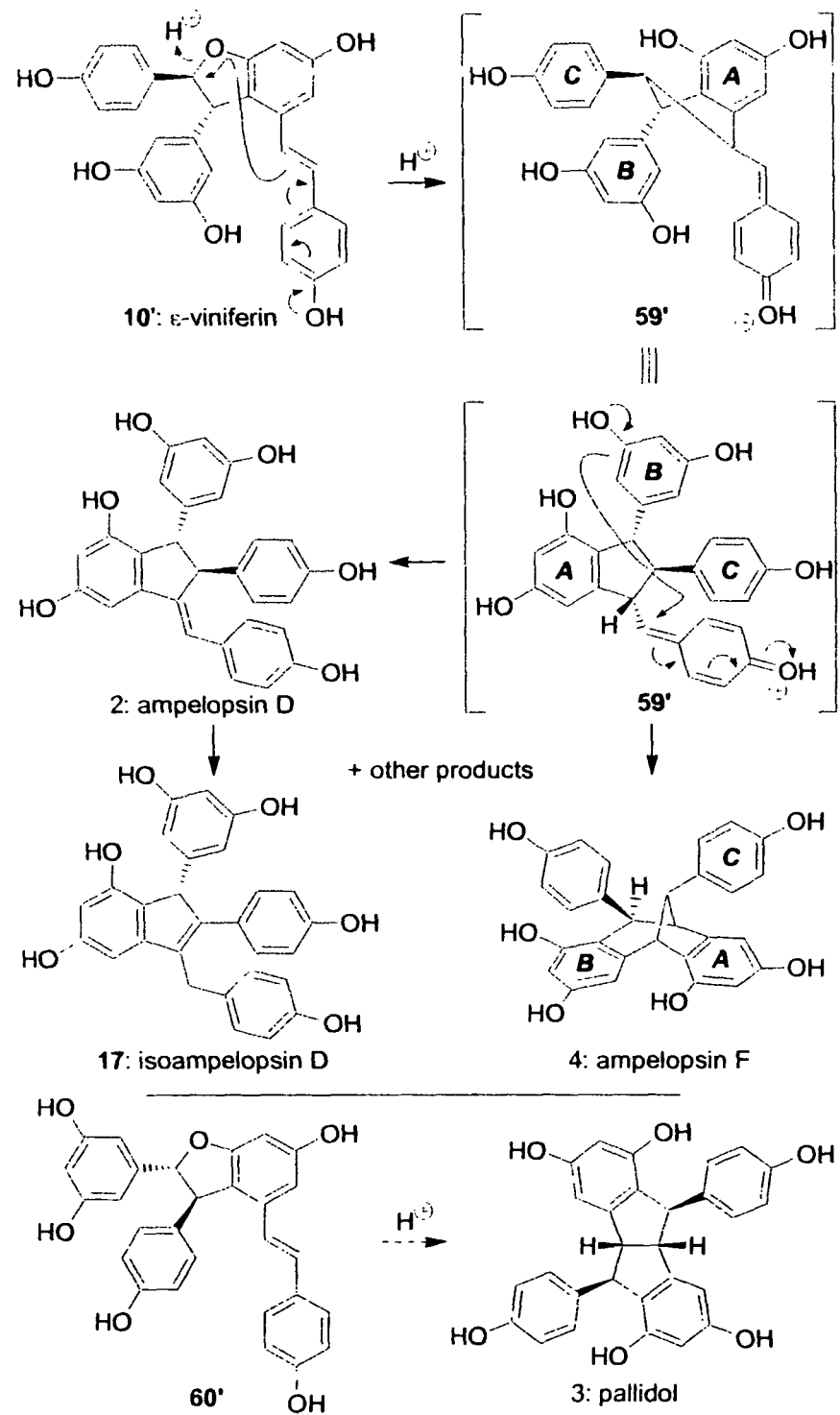
FIG. 22. Known means to access ampelopsin F (4) and other structures from e-viniferin (10').
Figure 23:
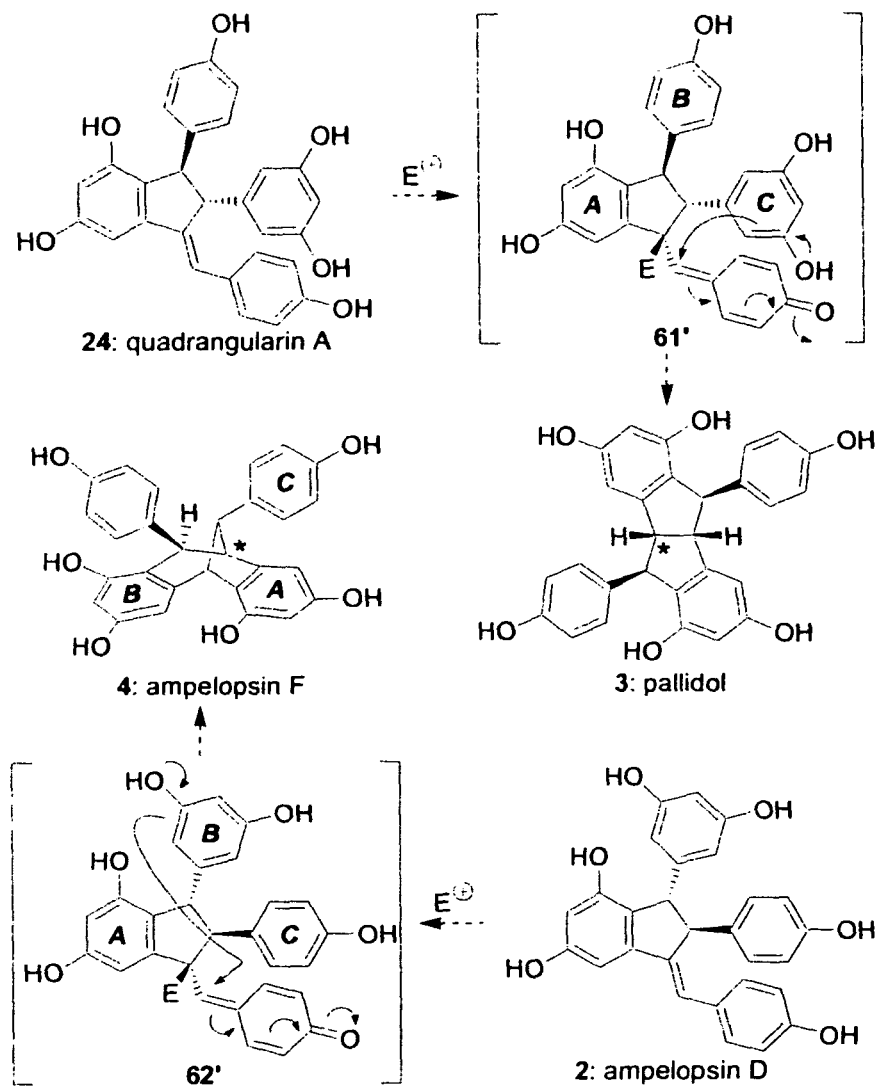
FIG. 23. Attempt to create both pallidol (3) and ampelopsin F (4) via a unique biogenetic connection.
Figure 24:
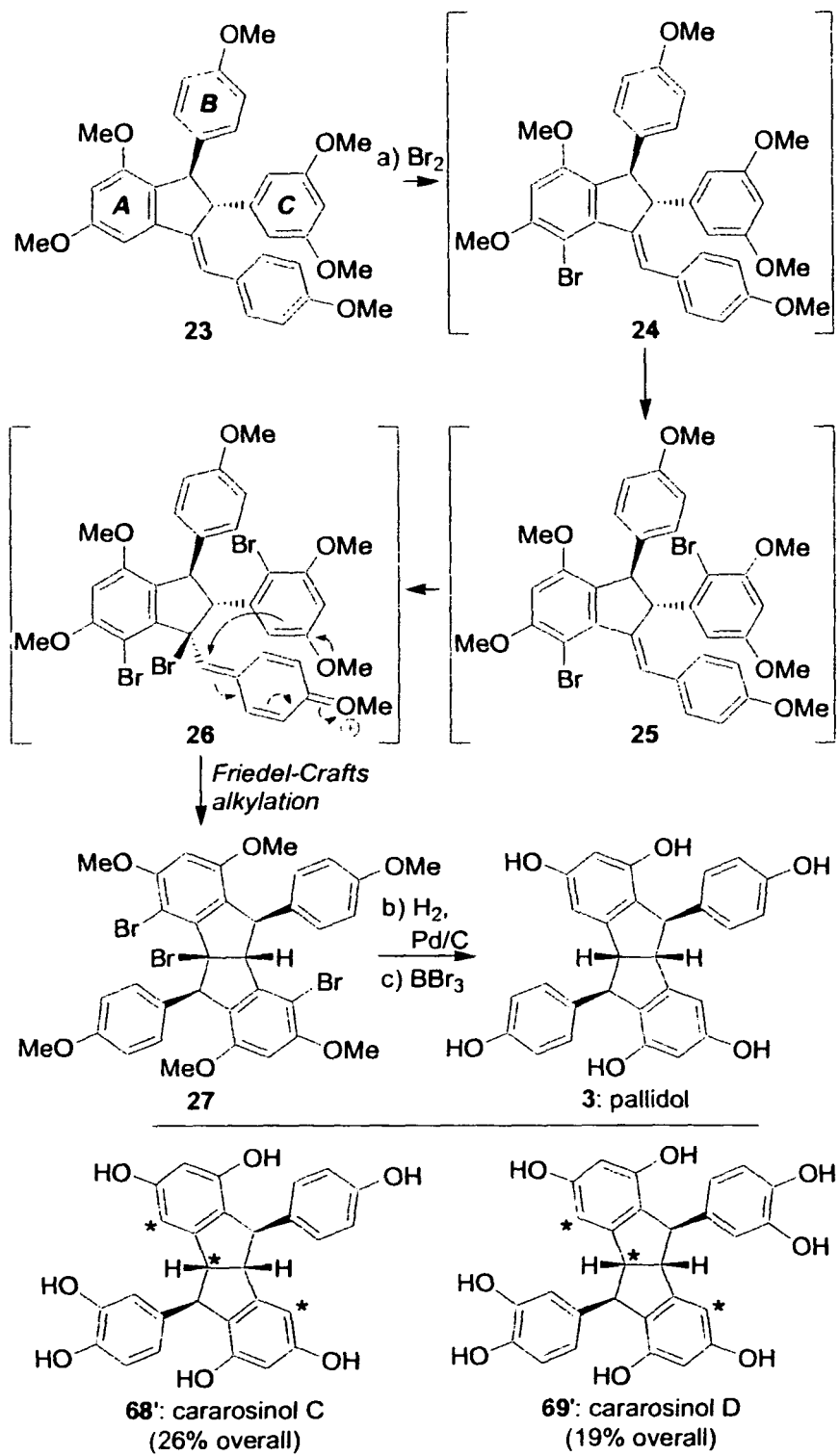
FIG. 24. Sequential, cascade-based halogenation to access pallidol (3), cararosinol C (68'), and cararosinol D (69'):(a) $Br_2$ (2.0 equiv), $CH_2Cl_2$, −78° C., 4 h, then slow warming 25° C., 1 h, 81%; (b) $H_2$, Pd/C (20%, 0.2 equiv), MeOH, 25° C., 12 h, 76%; (c) $BBr_3$ (1.0 M in $CH_2Cl_2$, 12 equiv), $CH_2Cl_2$, 0° C., 4 h, then 25° C., 12 h, 83%.
Figure 25:
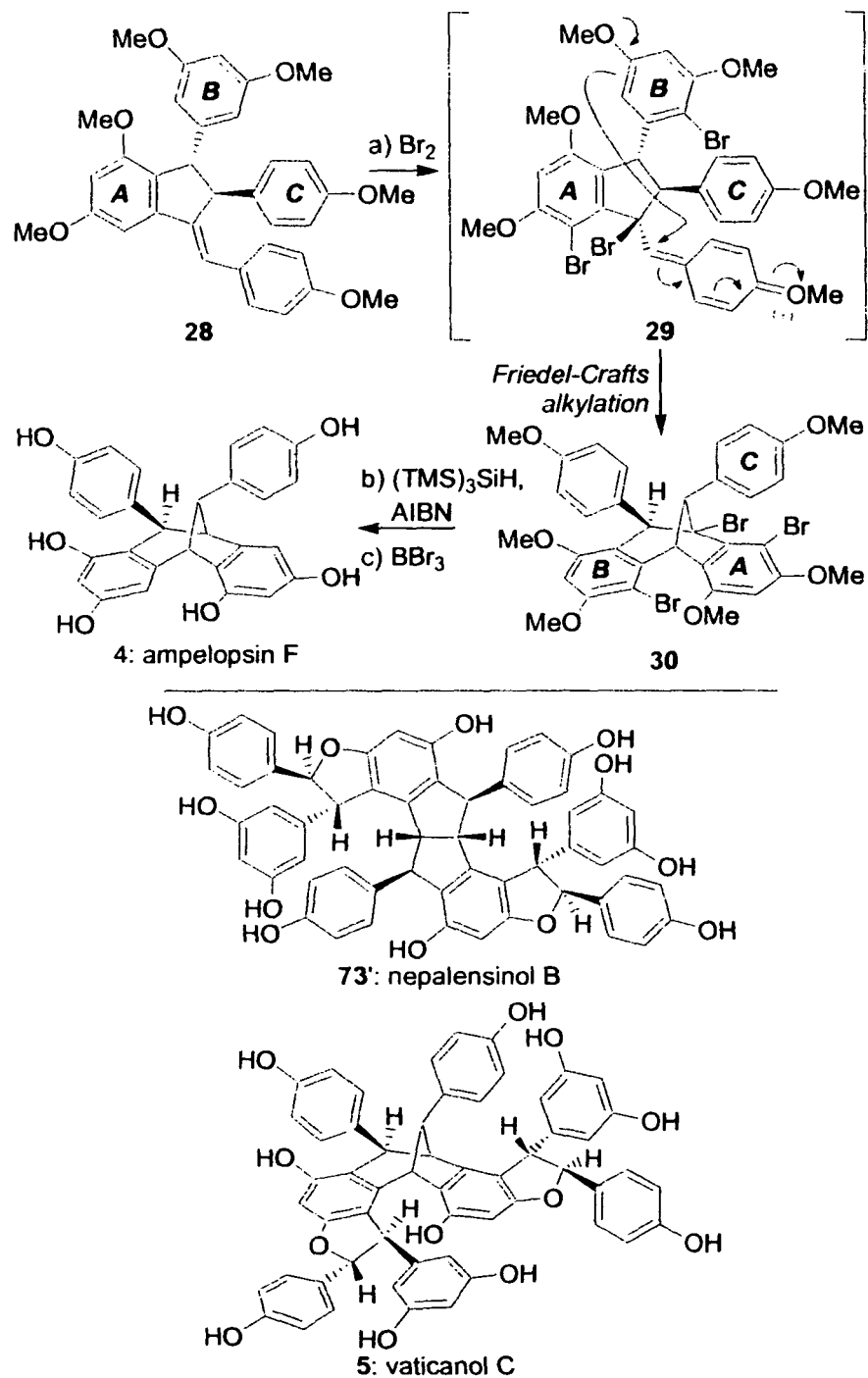
FIG. 25. Sequential, cascade-based halogenations to access ampelopsin F (4): (a) Br$_2$ (2.0 equiv), CH$_2$Cl$_2$, −78° C., 1 h, then slow warming to 25° C., 5 h, 53%; (b) (TMS)$_2$SiH (9.0 equiv), AIBN (1.0 equiv), toluene, 100° C., 5 h, 89%; (c) BBr$_3$ (1.0 M in CH$_2$Cl$_2$, 12 equiv), CH$_2$Cl$_2$, 0° C., 4 h, then 25° C., 12 h, 90%. TMS=trimethylsilyl, AIBN=2,2'-azobisisobutyronitrile.
Figure 26:
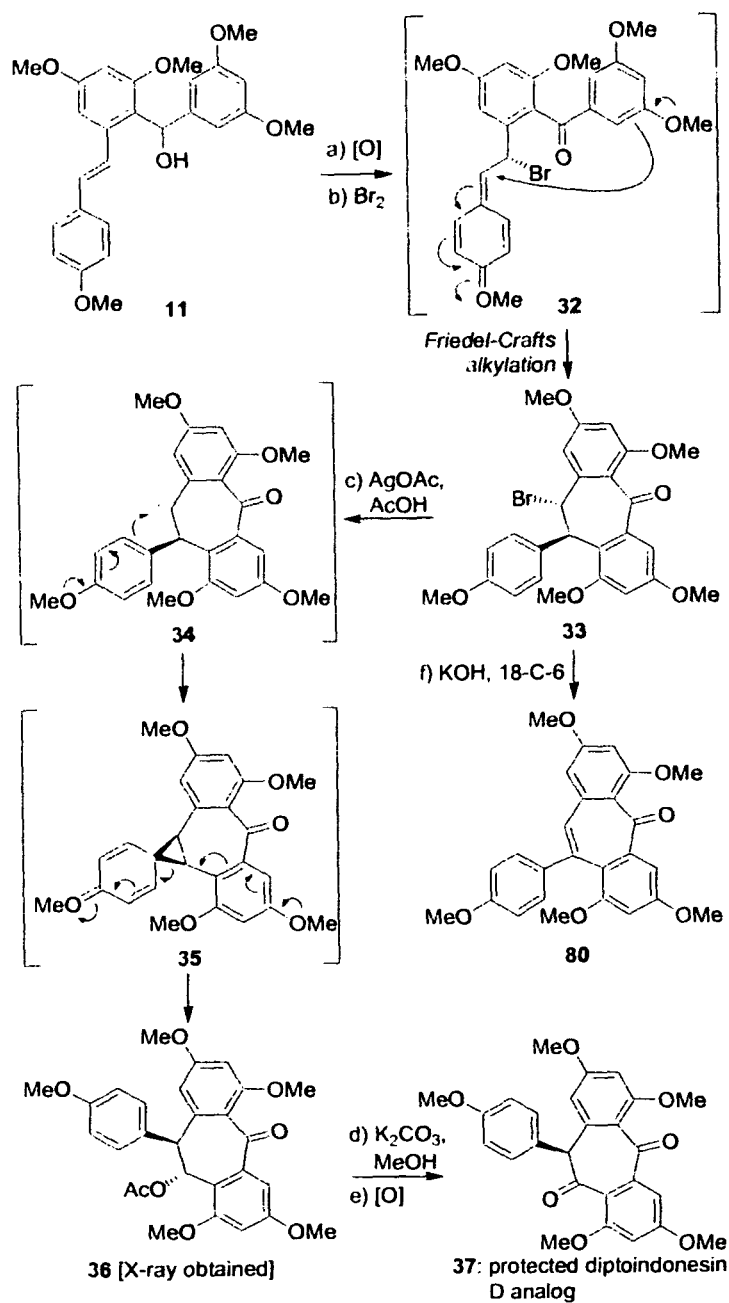
FIG. 26. Synthesis of seven-membered rings via a bromonium-induced cascade sequence followed by an acid-induced phenonium shift to afford non-natural resveratrol-based oligomers (i.e. 37): (a) Dess-Martin periodinane (1.2 equiv), NaHCO$_3$ (10 equiv), CH$_2$Cl$_2$, 25° C., 2 h, 97%; (b) Br$_2$ (1 equiv), CH$_2$Cl$_2$, −78° C., 1 h, then 25° C., 12 h, 50%; (c) AgOAc (3.0 equiv), AcOH, 25° C., 3 h, 62%; (d) K$_2$CO$_3$ (10 equiv), MeOH, 25° C., 12 h, 78%; (e) Dess-Martin periodinane (1.2 equiv), NaHCO$_3$ (10 equiv), CH$_2$Cl$_2$, 25° C., 1.5 h, 99%; (f) KOH (10 equiv), 18-Crown-6 (0.1 equiv), THF, 40° C., 12 h, 92%.
Figure 27:
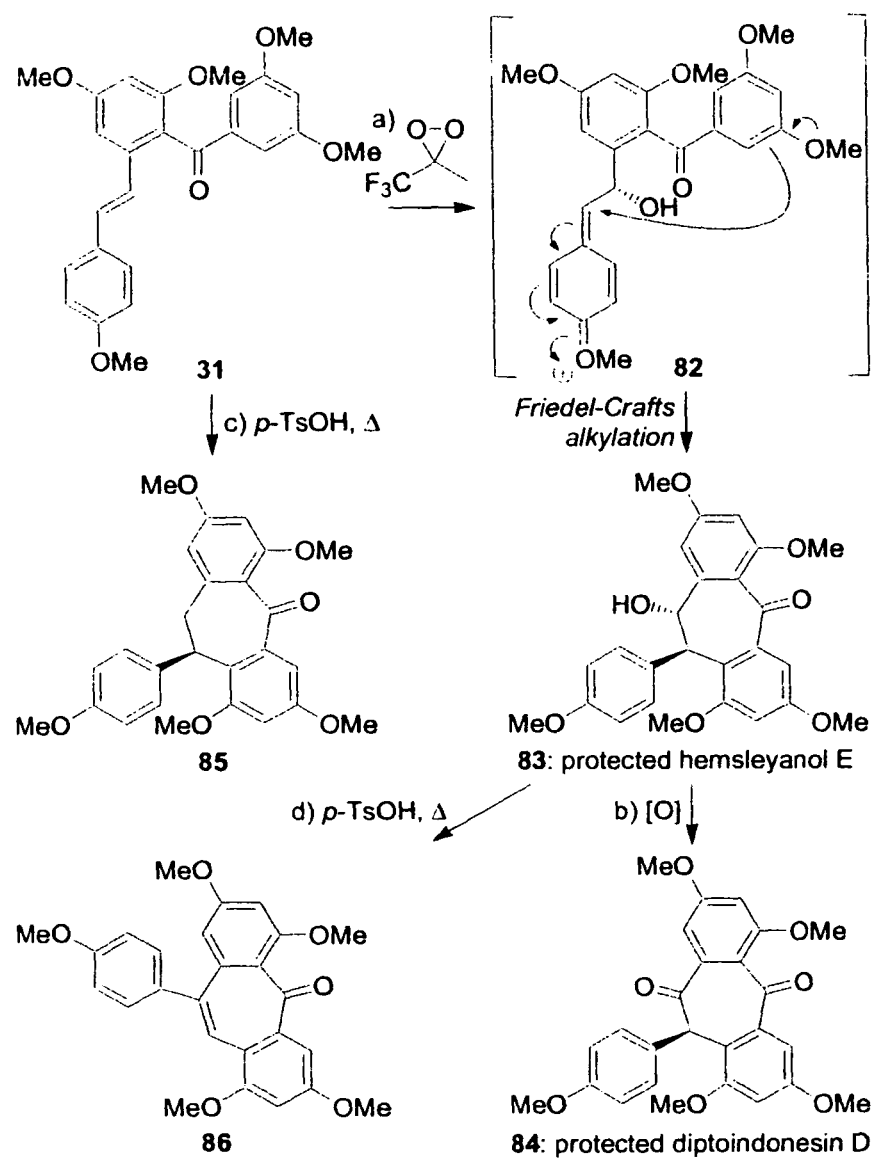
FIG. 27. Total synthesis of diptoindonesin D (8): (a) 1,1,1-trifluoroacetone (excess), NaHCO$_3$ (8.0 equiv), Oxone (5.0 equiv), MeCN/0.0004 M EDTA in H$_2$O (3:1), 25° C., 3 h, 34%; (b) Dess-Martin periodinane (1.2 equiv), NaHCO$_3$ (5.0 equiv), CH$_2$Cl$_2$, 25° C., 1 h, 96%; (c) p-TsOH (10 equiv), toluene, 80° C., 12 h, 96%; (d) p-TsOH (10 equiv), toluene, 65° C., 12 h, 96%.
Figure 28:
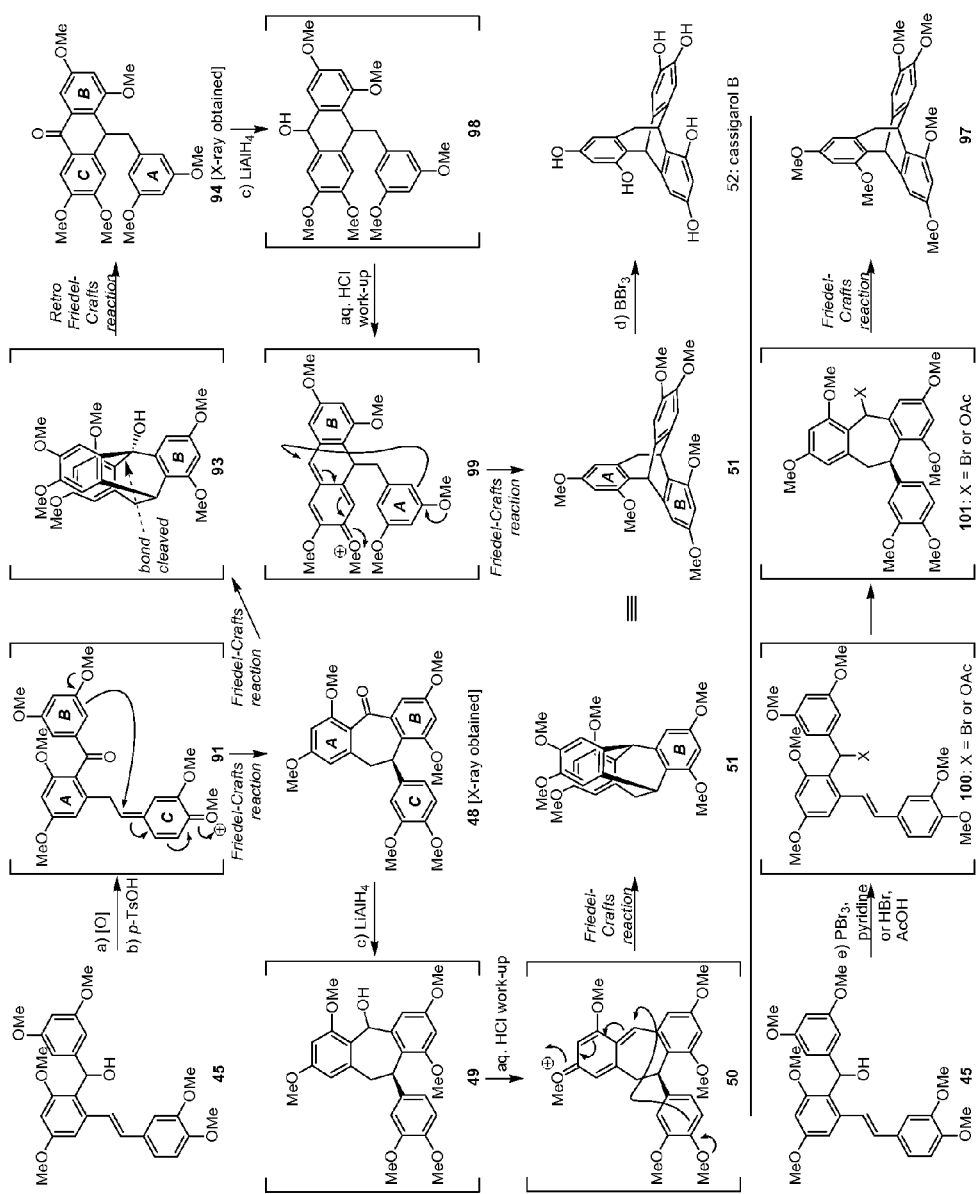
FIG. 28. Total synthesis of cassigarol B (52): (a) Dess-Martin periodinane (1.2 equiv), NaHCO$_3$ (10 equiv), CH$_2$Cl$_2$, 25° C., 1 h, 96%; (b) for 48: p-TsOH (2.0 equiv), toluene, 60° C., 48 h, 85% of 48, 8% 94; for 94: p-TsOH (8.0 equiv), toluene, 60° C., 72 h, 83%; (c) LiAlH$_4$ (5.0 equiv), THF, 25° C., 2 h; aq. HCl (20 equiv), 25° C., 2 h, 91%; (d) BBr$_3$ (1.0 M in CH$_2$Cl$_2$, 10 equiv), CH$_2$Cl$_2$, −78→25° C., 12 h, 87%; (e) HBr (33% in AcOH, 1.0 equiv), CH$_2$Cl$_2$, −78° C., 1 h, then 25° C., 12 h, 74% or PBr$_3$ (1.0 equiv), pyridine, 40° C., 3 h, 58%.
Figure 29:
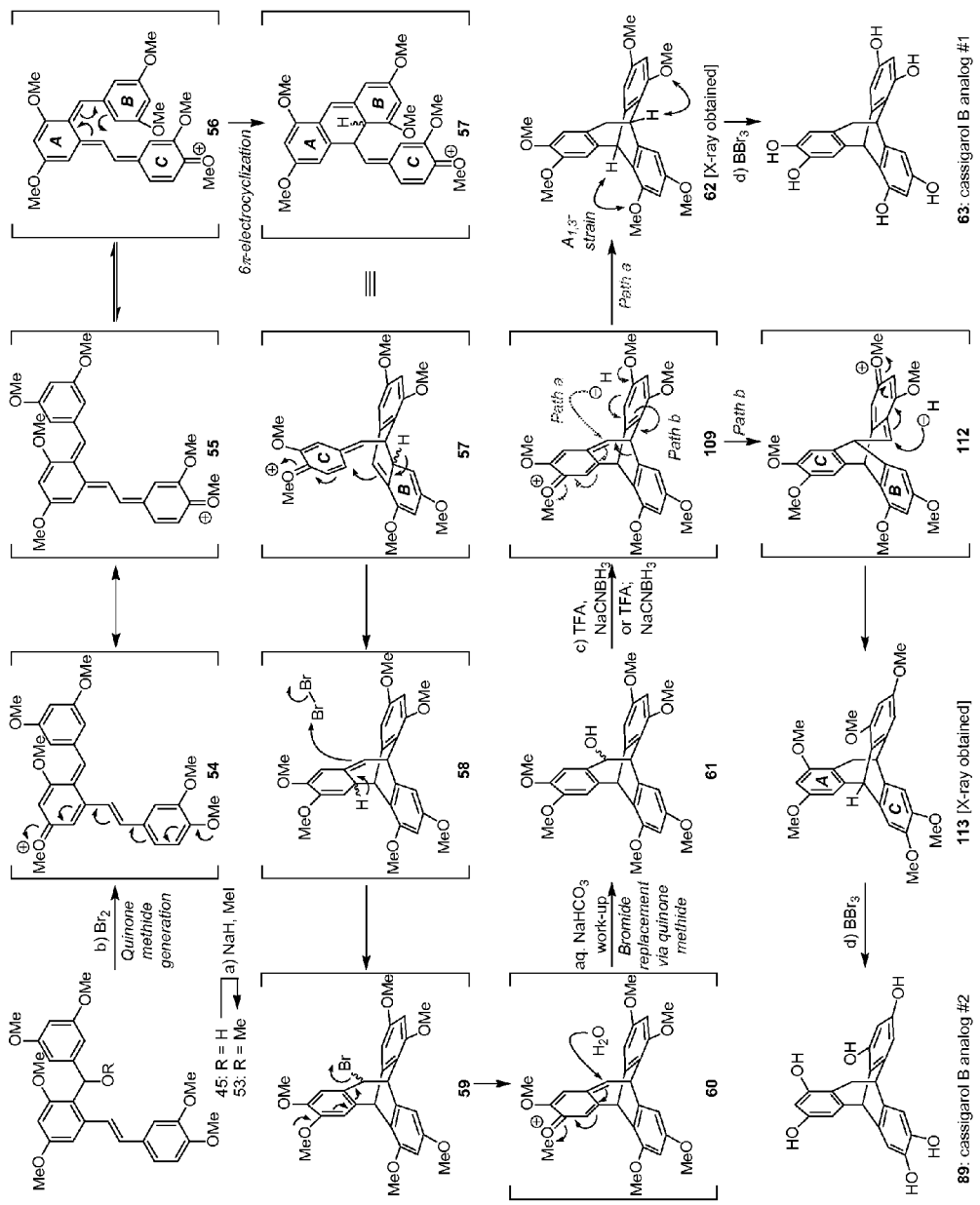
FIG. 29. Selective synthesis of a cassigarol B analogs (63 and 89) via an unique cascade-sequence involving 2 orchestrated C—C bond formations: (a) NaH (10 equiv), THF, 0° C., 30 min, then MeI (5 equiv), THF, 25° C., 4 h, 96% (a) Br$_2$ (1.0 equiv), CH$_2$Cl$_2$, −78° C., 2 h, then slow warming to 25° C., 1 h; aq. NaHCO$_3$, 25° C., 10 min, 52% (b) for 62: TFA (6.0 equiv, added in batches), NaCNBH$_3$ (50 equiv), CH$_2$Cl$_2$, 0° C., 1 h; 25° C., 2 h, 87%; for 113: TFA (12 equiv), CH$_2$Cl$_2$, 0° C., 30 min; 25° C., 3 h, then NaCNBH$_3$ (10 equiv), 25° C., 3 h, 83%; (c) BBr$_3$ (1.0 M in CH$_2$Cl$_2$, 10 equiv), CH$_2$Cl$_2$, −78→25° C., 3 h, 78% for 88, 81% for 89.
Figure 30:
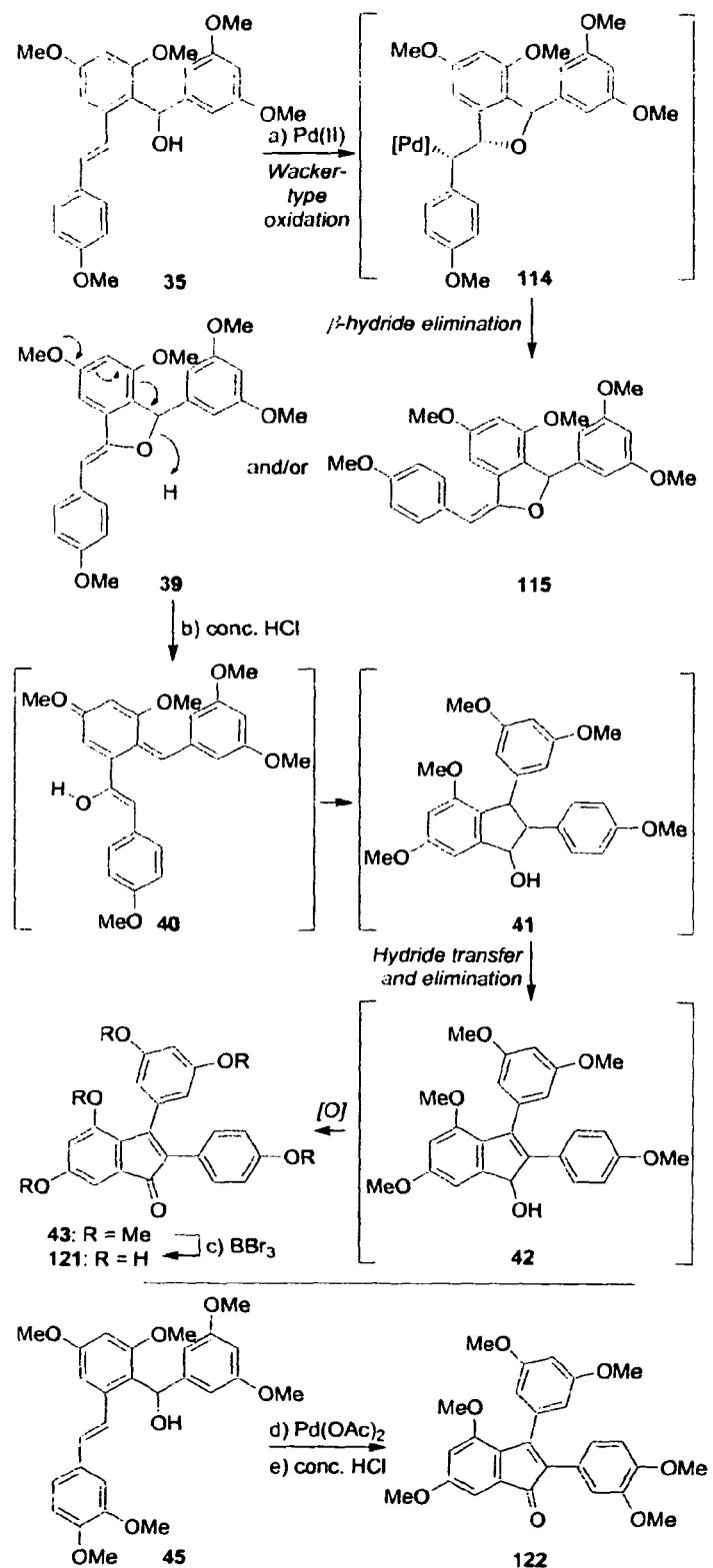
FIG. 30. Creation of a natural product-like structure (121) through the agency of a metal-initiated cascade sequence and an acid-induced Nazarov cyclization: (a) PdCl$_2$ (benzonitrile)$_2$ (1.0 equiv), CuCl$_2$ (1.0 equiv), DMF, 50° C., 1 h, 75% of 115, 22% of 39 or Pd(OAc)$_2$ (0.2 equiv), Cu(OAc)$_2$ (0.2 equiv), O$_2$ atmosphere, i-PrOH, 60° C., 5 h, 87% of 39; (b) conc. HCl (10 equiv), i-PrOH, 25° C., 16 h, 90%; (c) BBr$_3$ (1.0 M in CH$_2$Cl$_2$, 12 equiv), CH$_2$Cl$_2$, −78→25° C., 12 h, 88%; (d) Pd(OAc)$_2$ (0.2 equiv), Cu(OAc)$_2$ (0.2 equiv), O$_2$ atmosphere, i-PrOH, 60° C., 5 h; (e) conc. HCl (10 equiv), i-PrOH, 25° C., 16 h, 72% over two steps.
Figure 31:
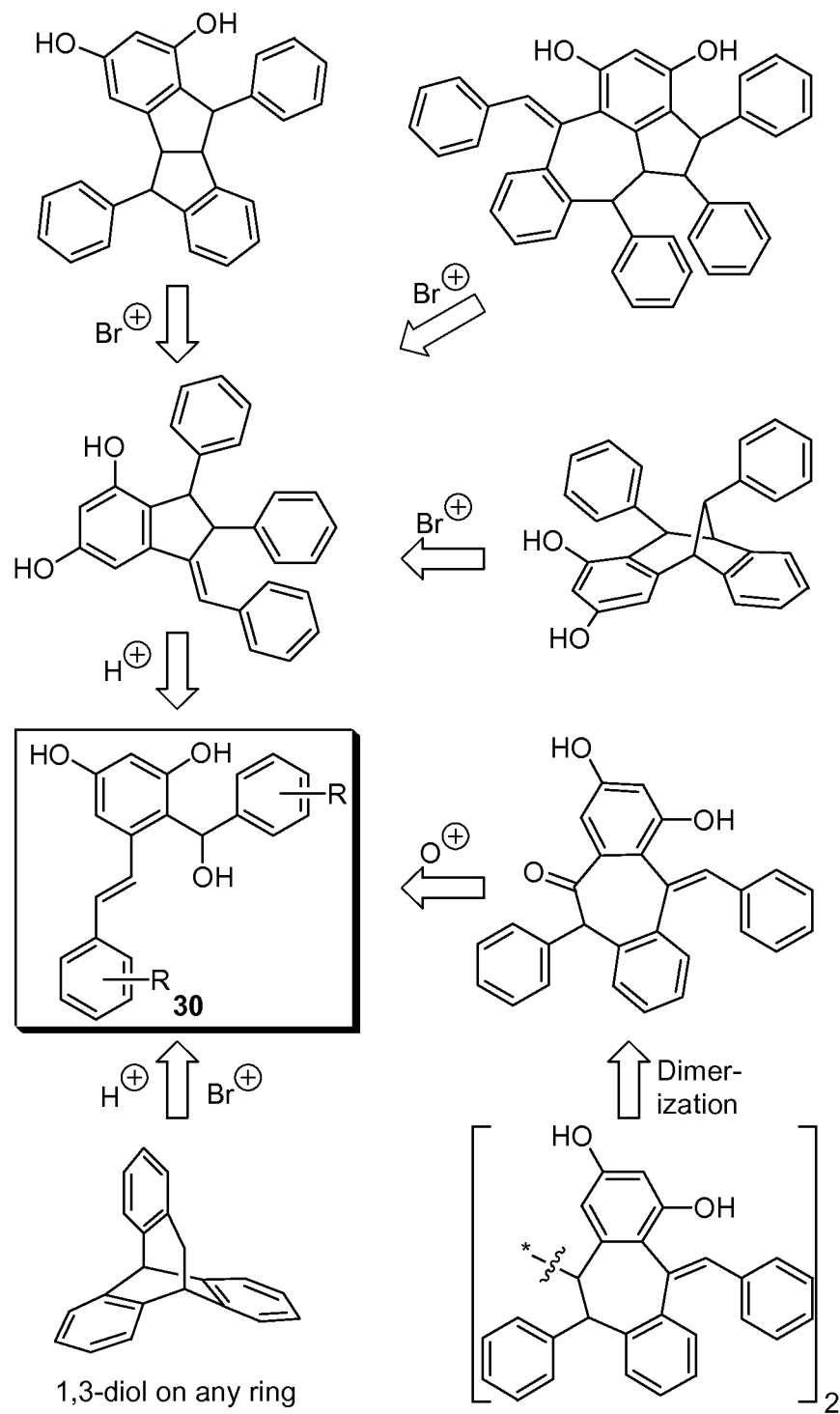
FIG. 31. Towards a universal retrosynthetic analysis for the resveratrol class of natural products.
Figure 32:
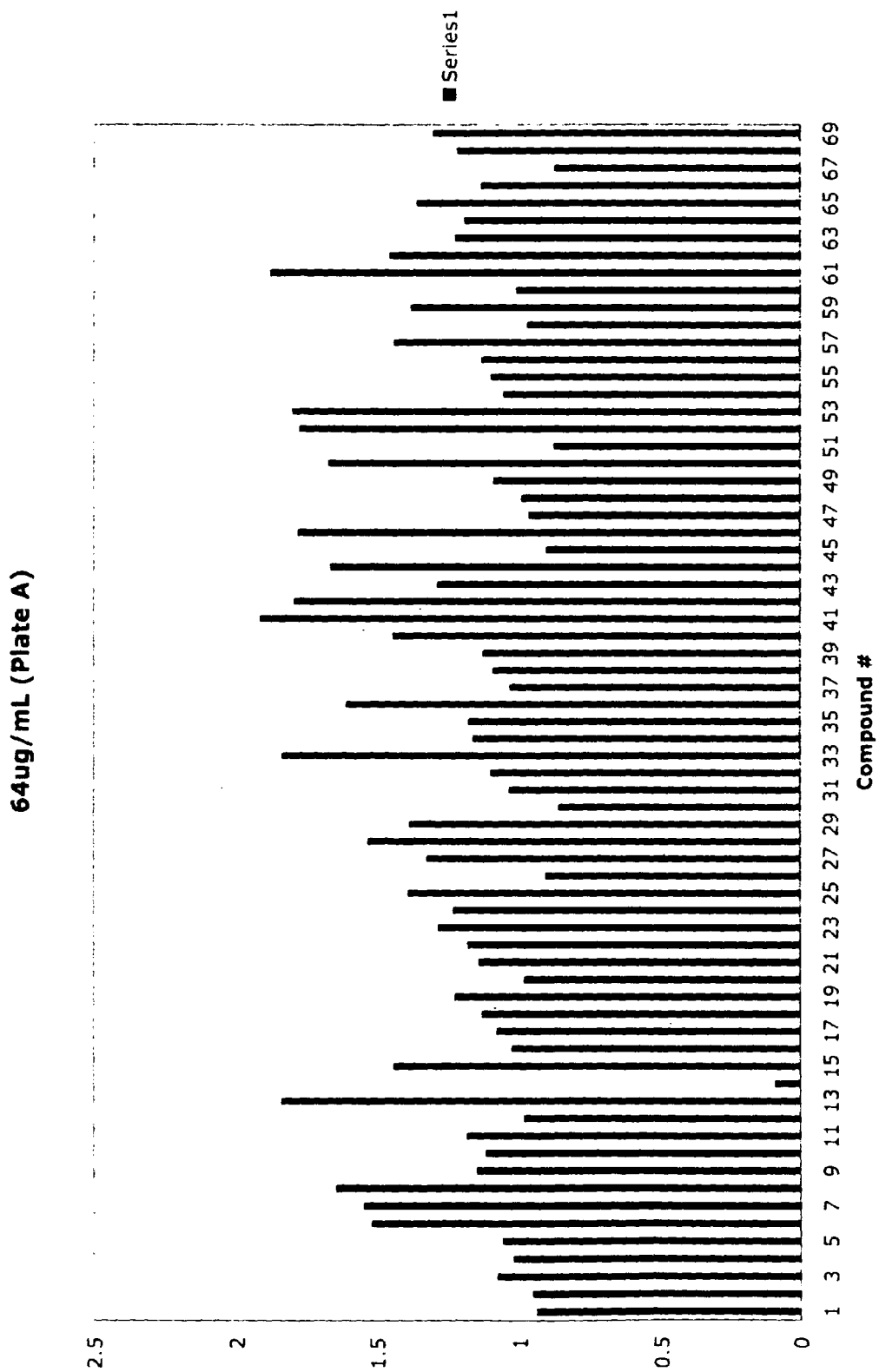
FIGS. 32-35. Antifungal activity of resveratrol-based compounds.
Figure 33:
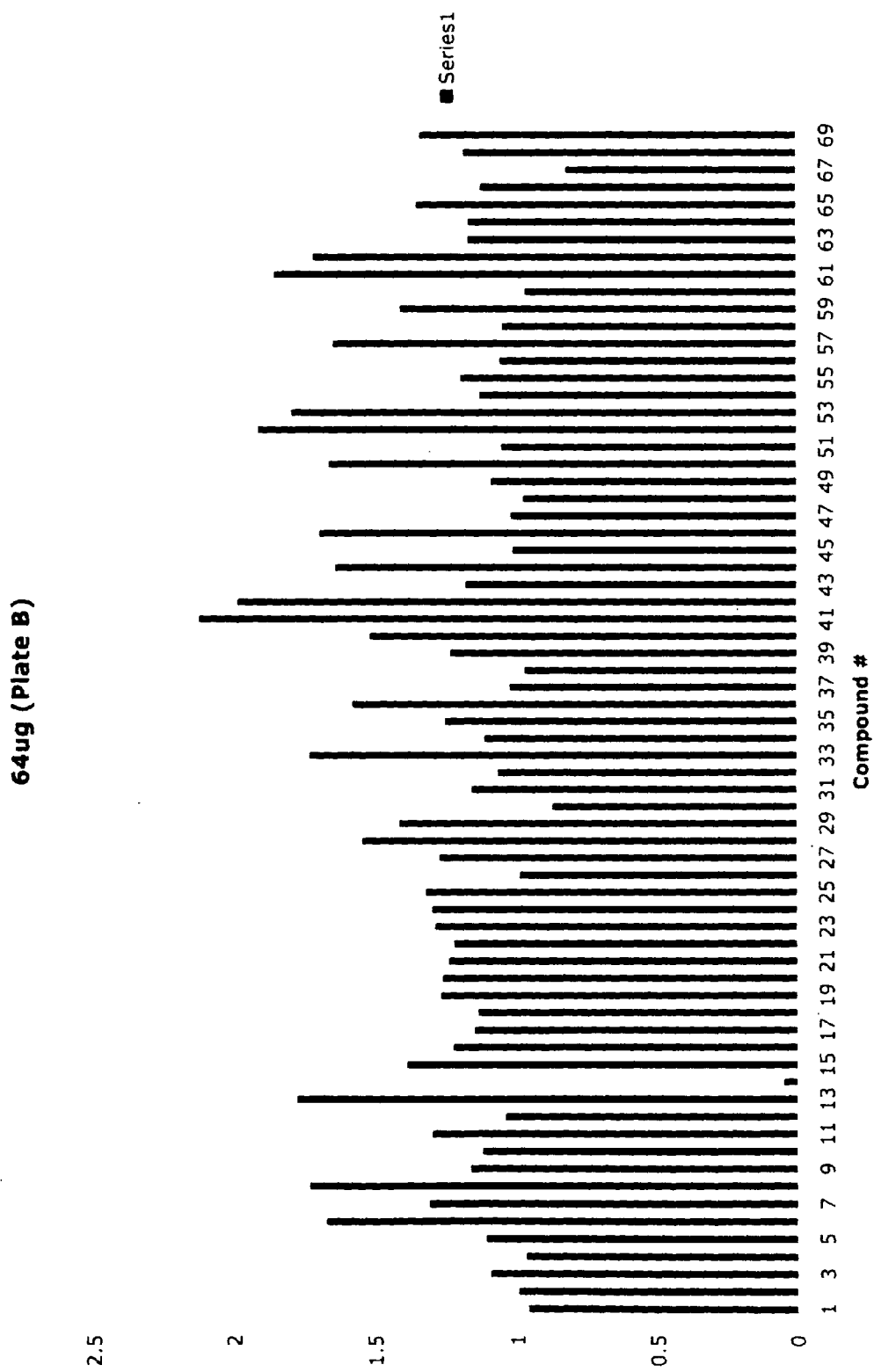
Figure 34:
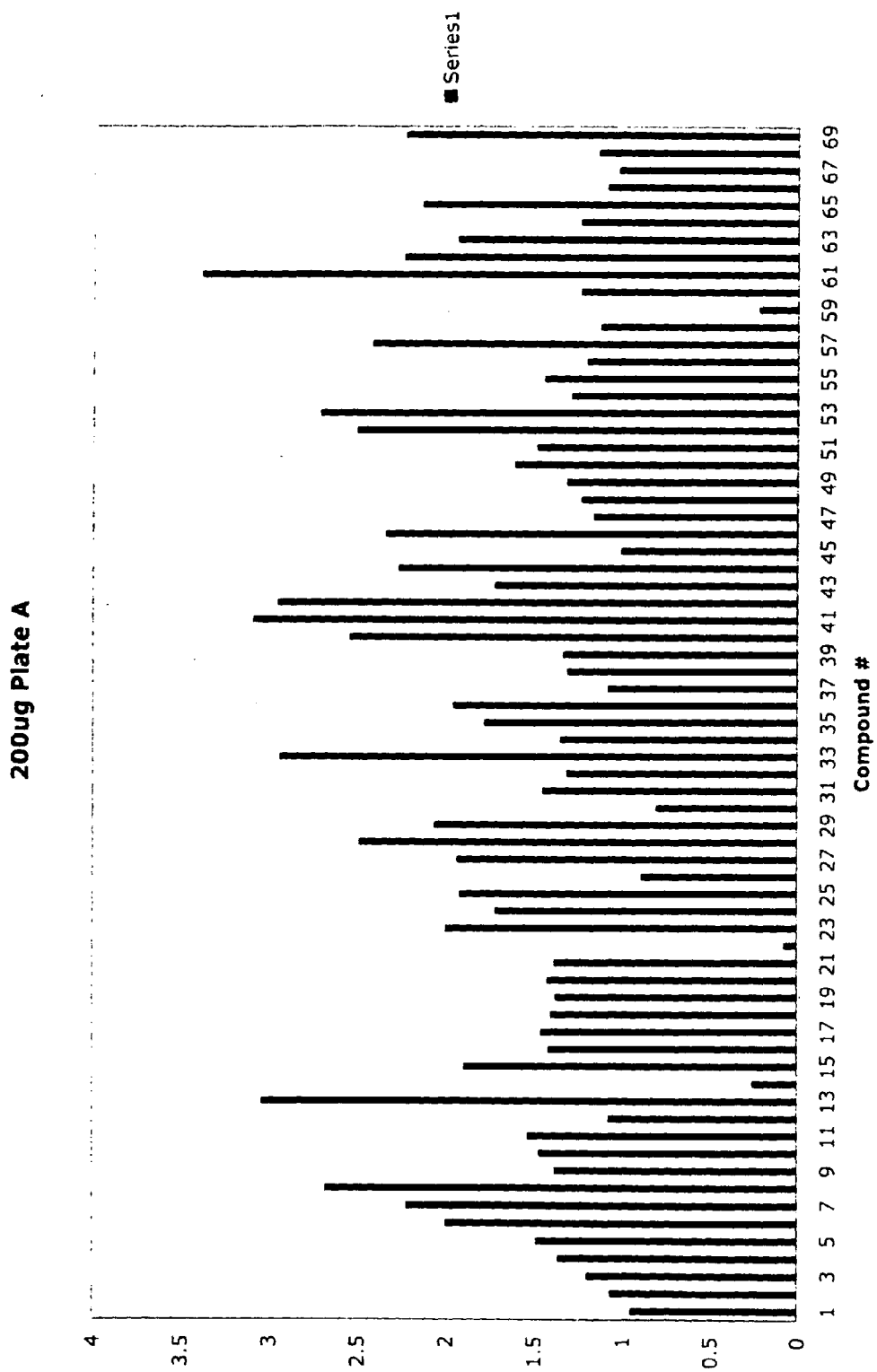
Figure 35:
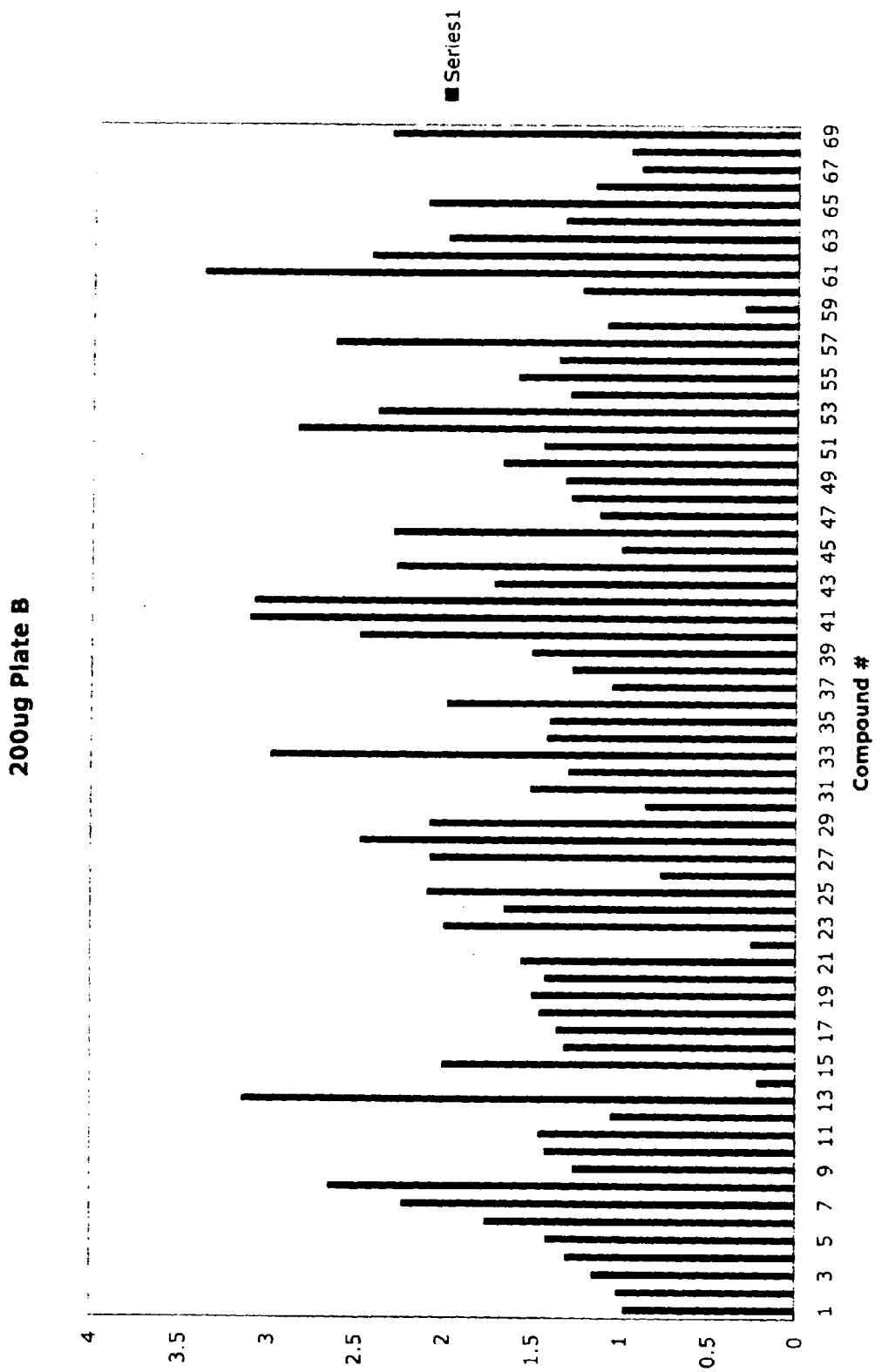
Figure 36:
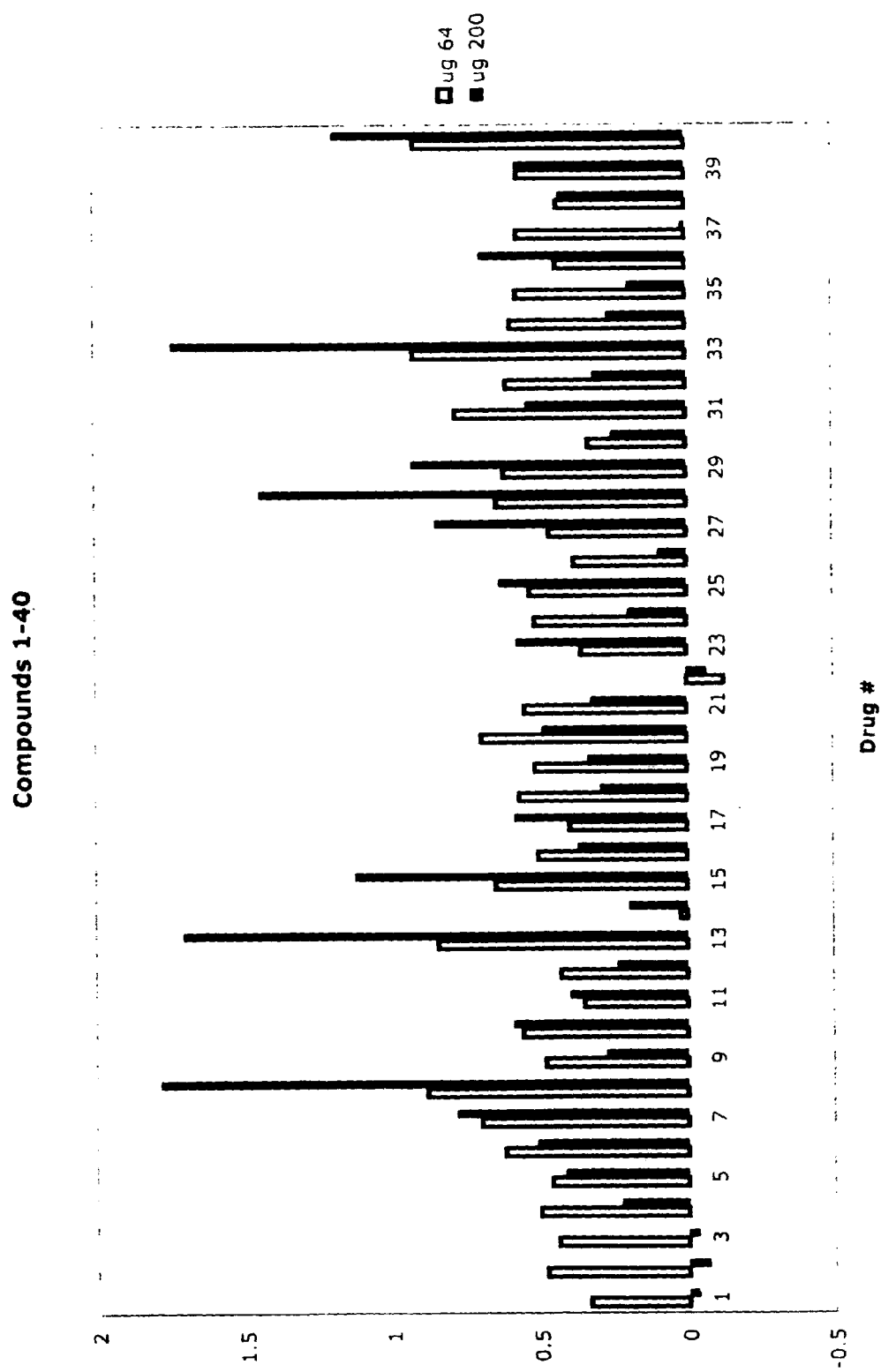
FIG. 36. Antifungal activity of compounds 1-40.

As shown in FIG. 4, that conjecture proved to be correct if bromine was utilized as the activating species. Use of proton as an activating electrophile led in all cases to internal alkenes, such as that possessed by isoampelopsin D (17, c.f. FIG. 1), while all efforts to form epoxides led to intractable mixtures of compounds or unreacted starting material. In the event, exposure of permethylated quadrangularin A (23) to two equivalents of molecular bromine in $CH_2Cl_2$ at −78° C., with slow warming to ambient temperature over several hours, accomplished a highly selective cascade sequence that provided bicycle 27 in 81% yield. Based on a series of control experiments leading to the isolation of both 24 and 25, the course of events is known to involve the initial halogenation of the C-14b position, followed by bromination of the second 3,5-dimethoxybenzene ring system. Though both of these halogens are extraneous in terms of the goal structure [18], each served a critical role in ensuring that the terminating ring closure leading to 27 was stereoselective. Indeed, as revealed by molecular models, the C-10a bromine provided a significant amount of steric bulk to its ring system, forcing the third bromine atom be added solely from the opposite side of the molecule; the C-14b bromide then came into service by preventing rotation of the newly-formed quinone methide (26) away from its initial, perfect positioning for the final closure, thereby assuring that only 27 was formed. From this key intermediate (27), pallidol (3) was then accessed in 63% overall yield via hydrogenative replacement of all three bromides using a catalytic amount of activated Pd/C, followed by $BBr_3$-induced cleavage of all six methyl ethers. Similarly, application of exactly the same reaction conditions to permethylated forms of 49' and 50' (cf. FIG. 20) led to total syntheses of cararosinol C and D (68' and 69', cf. FIG. 24) [33] in the indicated overall yield (the starred positions are the sites of bromine incorporation). As documented in FIG. 5, the same sequence of events with permethylated ampelopsin D (28) afforded the means to selectively access ampelopsin F (4). In this case, radical conditions [$(TMS)_3SiH$, AIBN] were used to replace the three bromine atoms left by the cascade sequence. With the opposite array of ring systems, the second bromine attached to this molecule on the pendant 3,5-dimethoxybenzene ring provided enough steric bulk to ensure that the third bromine ultimately leading to quinone methide 29 came from the same side of the molecule as the adjacent aromatic ring system. Of course, it is worth noting that while an ideal synthetic solution to any molecule would avoid the installation of extra atoms, in these two cases the absence of atom economy would appear to have an atypical benefit, namely the potential to access even greater molecular complexity in the resveratrol class. Indeed, the aryl halides within intermediate 30 are positioned perfectly to attempt construction of the dihydrofuran rings that would lead to vaticanol C (5, c.f. FIG. 1).

Figure 6:
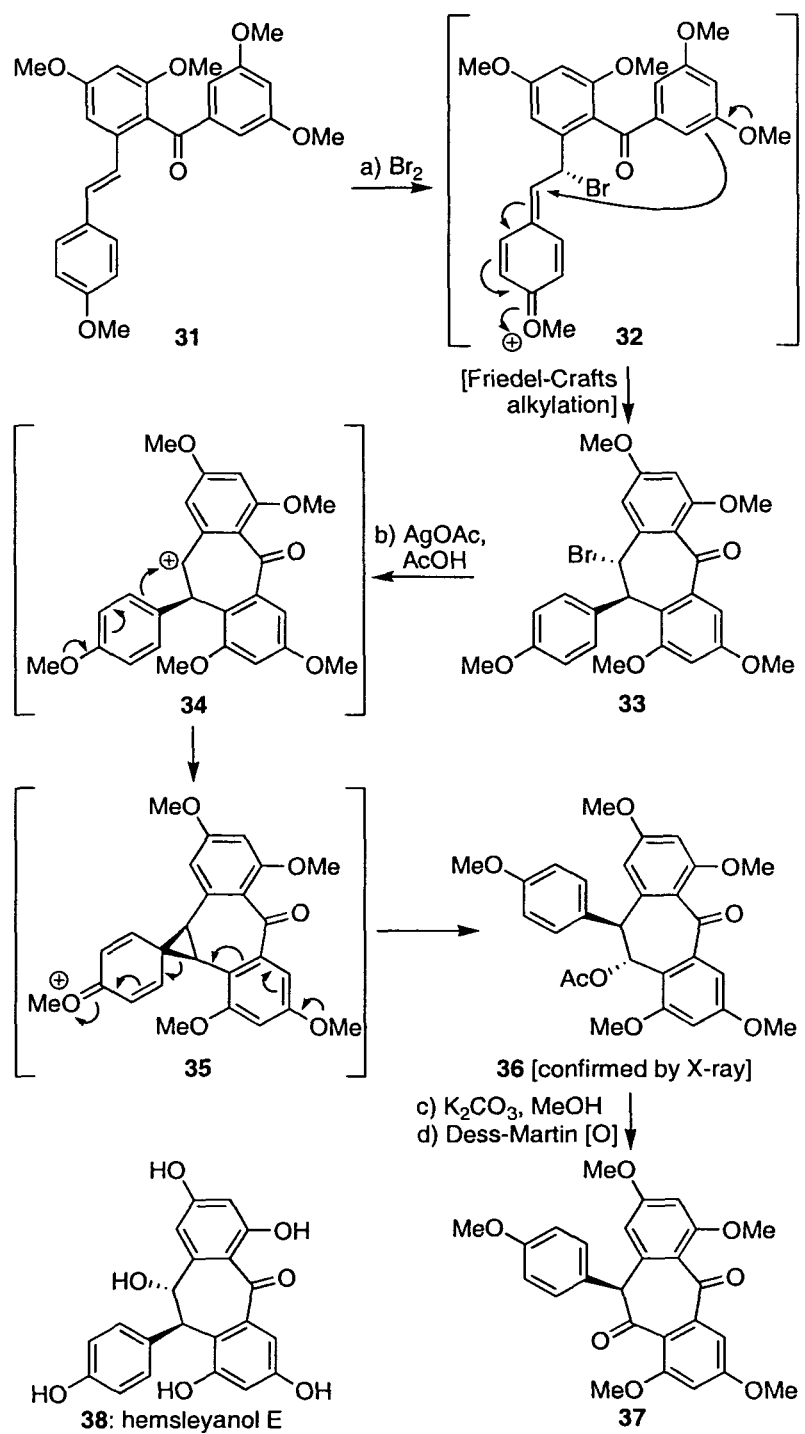
FIG. 6: Alternate use of key intermediate 11 to access the unique architectures of related, but non-natural natural products (such as 37) via a bromonium-induced cascade sequence followed by an acid-induced phenonium shift: a) $Br_2$ (1 equiv), $CH_2Cl_2$, −78° C., 1 h, then 25° C., 12 h, 50%; b) AgOAc (3.0 equiv), AcOH, 25° C., 4 h, 62%; c) $K_2CO_3$ (10 equiv), MeOH, 25° C., 12 h, 78%; d) Dess-Martin periodinane (1.2 equiv), $NaHCO_3$ (5.0 equiv), $CH_2Cl_2$, 25° C., 1 h, 99%.

Finally, the remaining element of carbogenic complexity possessed by the resveratrol family, the seven-membered rings of compounds like diptoindonesin A (8, c.f. FIG. 1), could be obtained through an electrophilic activation-cyclization sequence similar to that just described. In this case, the key starting material is ketone 31 (FIG. 6), the oxidized form of building block 11, which afforded 33 in 50% isolated yield following its exposure to bromine. Though work with this highly sensitive intermediate is only in its initial stages, the halogen handle within 33 is likely to be a key tool for efforts to synthesize the carbon-carbon bond uniting the two halves of hopeaphenol (6, c.f. FIG. 1) and generate the additional oxygen function of both diptoindonesin A (8, c.f. FIG. 1) and the related natural product hemsleyanol E (38) [19].

Figure 7:
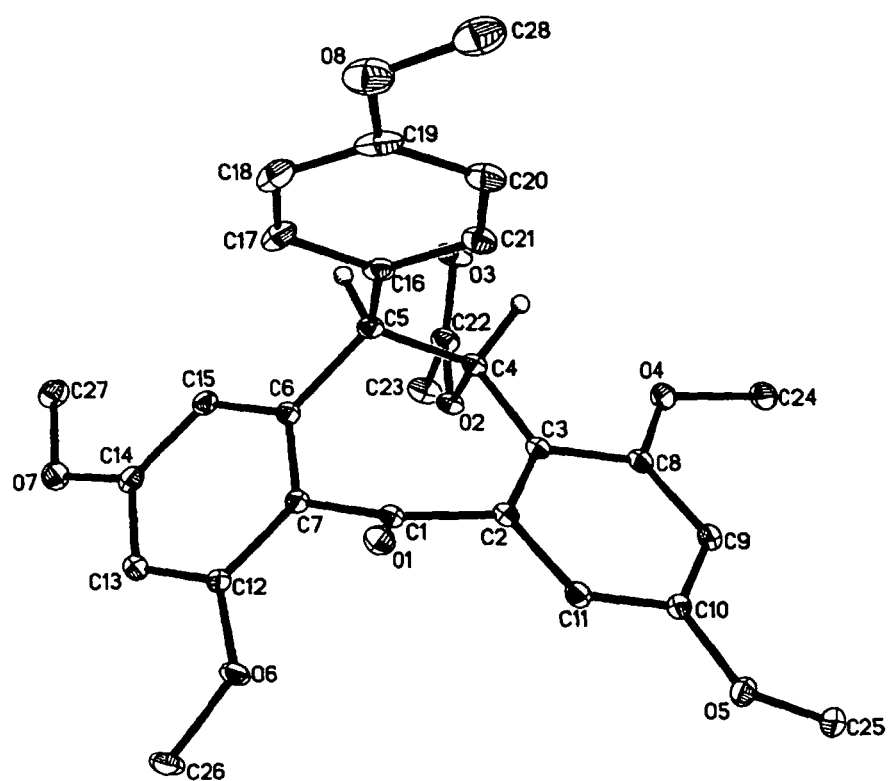
FIG. 7: X-ray crystal structure of acetate 31.
Figure 8:
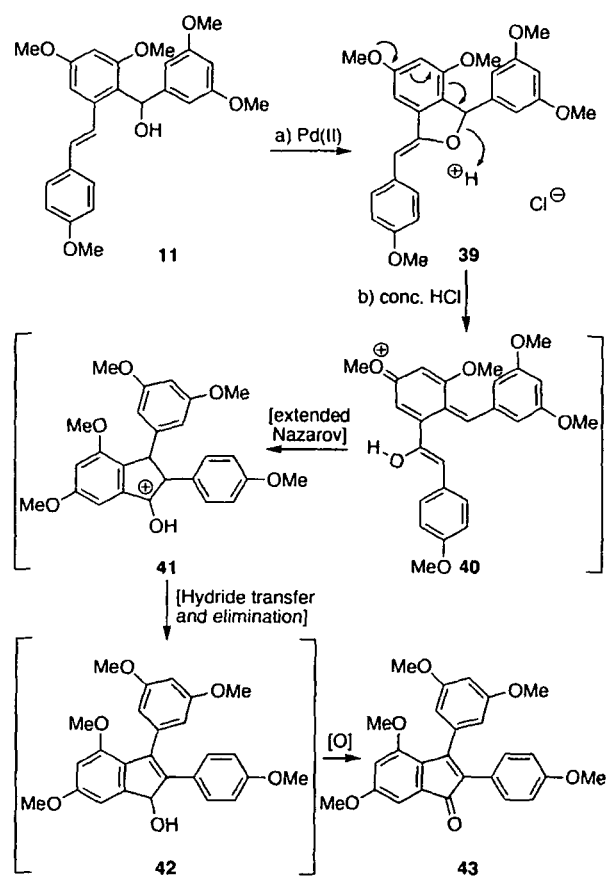
FIG. 8. Creation of natural product-like structures (43) through the agency of a metal-initiated cascade sequence from key intermediate 9: a) $Pd(OTFA)_2$ (1.0 equiv), $CH_2Cl_2$, 0° C., 3 h, 35% based on recovered s.m.; b) conc. HCl (2.0 equiv), MeOH, 50° C., 12 h, 41% based on recovered s.m.
Figure 9:
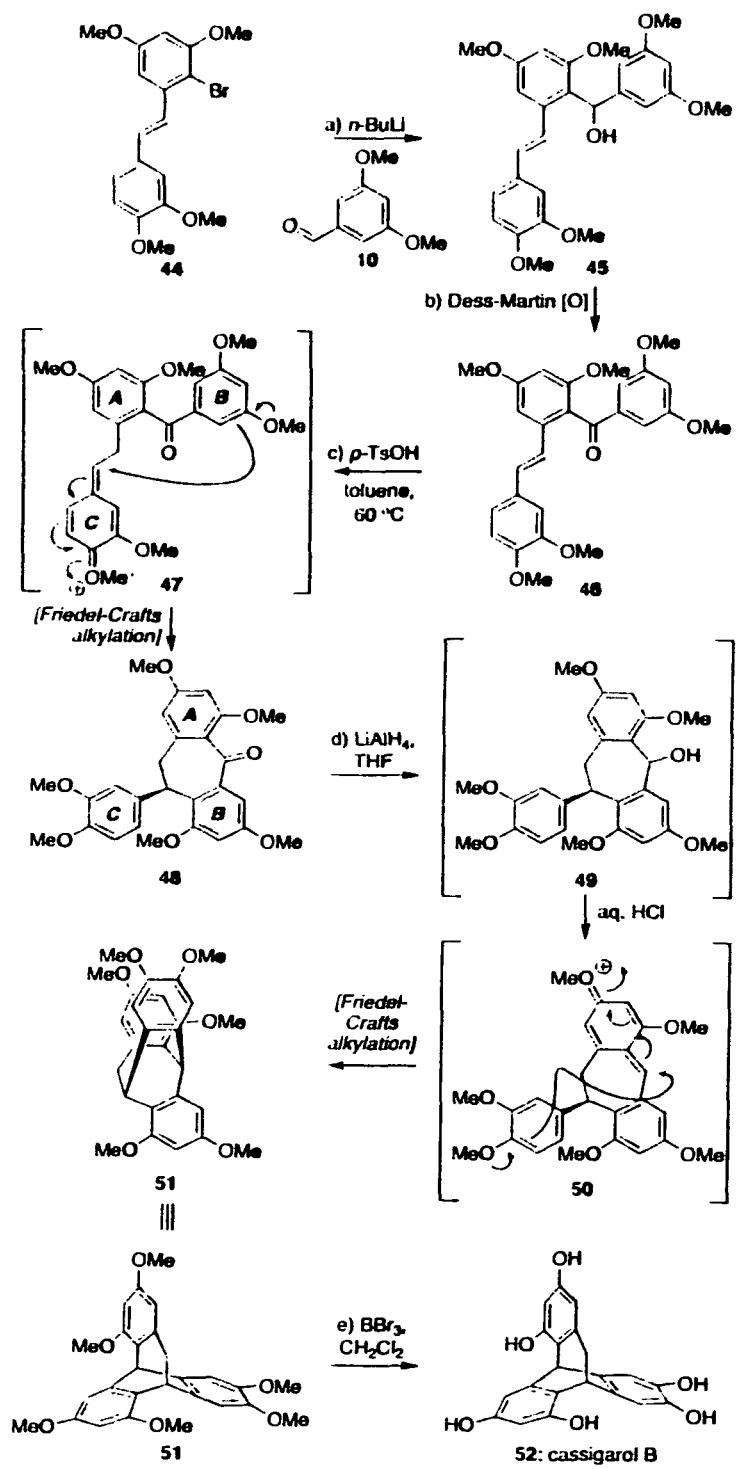
FIG. 9. Synthetic pathway to cassigarol B.

Equally important, this halogen atom has already enabled access to a collection of non-natural analogs through a molecular rearrangement that, despite its facility, does not appear to be employed by Nature in its construction of this molecule class. In fact, there are no molecules known with this particular array of phenols attached to a 7-membered carbocycle. Indeed, exposure of bromide 33 to an excess of AgOAc (3.0 equiv) in AcOH at 25° C. [20] led to the smooth synthesis of acetate 36 in 62% yield, a compound in which the pendant aryl ring had migrated. This unique structure (confirmed by X-ray crystallographic analysis, see FIG. 7) likely resulted from a thermodynamically favored phenonium shift following the generation of cation 34, with the strategically positioned ortho- and para-disposed alkoxy groups within the resultant intermediate (35) then effecting ring opening to provide a single, and new, electrophilic site for a terminating acetate attack.

It is important to note that all evidence indicates that the aryl group has not shifted within 33. Though this compound has proven too difficult to obtain in a pure enough form to verify its connectivities through nOe experiments (due to its sensitivity), the acetate was substituted within structure 36 for chloride with retention of configuration. This compound, along with 36 and 37, possess the four aryl protons of the 3,5-dimethoxybenzene rings tightly and consistently grouped between 6.40 and 6.90 ppm; by contrast, bromide 33 possesses one of these signals as an outlier at 5.76 ppm, presumably the one that is in close proximity to the halogen atom. Subsequent cleavage of the acetate within 36 ($K_2CO_3$, MeOH) then provided a protected regioisomeric analog of hemsleyanol E in 78% yield, and oxidation of the resultant alcohol led to the corresponding diptoindonesin A congener as expressed by structure 37.

In addition, other non-natural structures can also result from 11 if it is exposed to metals instead of electrophiles. For instance, preliminary screens have established that upon treatment of 11 with a stoichiometric amount of $Pd(OTFA)_2$, unique heterocycle 39 could be accessed in an unoptimized yield of 35% (based on the recovery of unreacted 11). This highly sensitive compound likely resulted from palladium coordination with the hydroxyl group within 9, followed by oxygen insertion into the adjacent alkene and a terminating β-hydride elimination. If this new adduct (39) was then exposed to concentrated HCl in MeOH at 50° C. for 12 h, the synthesis of α,β-unsaturated ketone 43 was achieved in 41% yield based on recovered starting material. The mechanism of this final step may reflect an acid-induced ring opening to afford a cationic intermediate well-poised for a Nazarov cyclization [25] with subsequent loss of hydride within 41, followed by aerial oxidation of 42, completing the sequence.

As a final set of entries relating to the ability to access diverse architectures from triaryl intermediates related to resveratrol (1), consider the chemistry of biaryl alcohol 45 (FIG.

9). This molecule, which differs from key compounds 11 and 20 solely by the presence of an extra methoxy group on one of its ring systems, can be readily converted into a number of entirely unique bicyclic architectures upon its exposure to different reaction conditions. For example, if the central biaryl alcohol was oxidized to its ketone congener (46), subsequent exposure of this new compound to p-TsOH in toluene at 80° C. provided a means to access cyclic intermediate 48 in 80% yield via a Friedel-Crafts-like bond-forming event. Though a unique compound in its own right, this material (48) could then be converted into a far more complex adduct, a protected form of cassigarol B (51), through a carefully orchestrated cascade sequence induced by careful treatment with $LiAlH_4$ in THF followed by stirring with concentrated HCl in dioxane. Final exposure of 51 to $BBr_3$ in $CH_2Cl_2$ provided the means to accomplish the first laboratory synthesis of the natural product (52), establishing that the unique architecture of this isolate could, in fact, be related to resveratrol-based building blocks [26].

Figure 10:
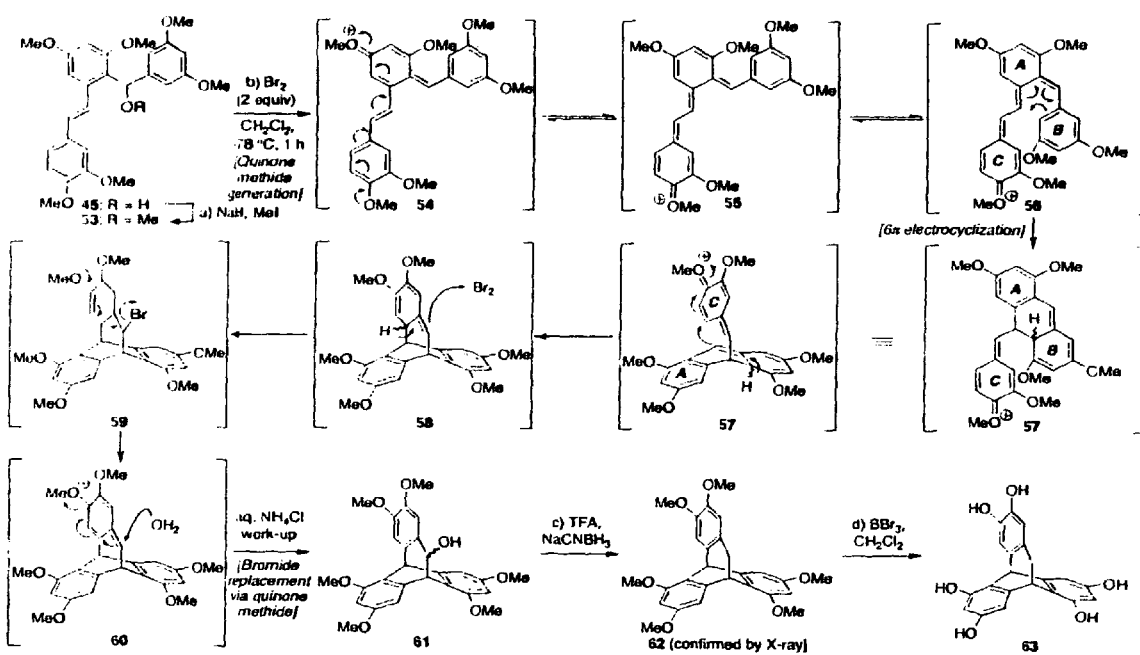
FIG. 10. Synthetic pathway to other bicyclic alocohols.
Figure 11:
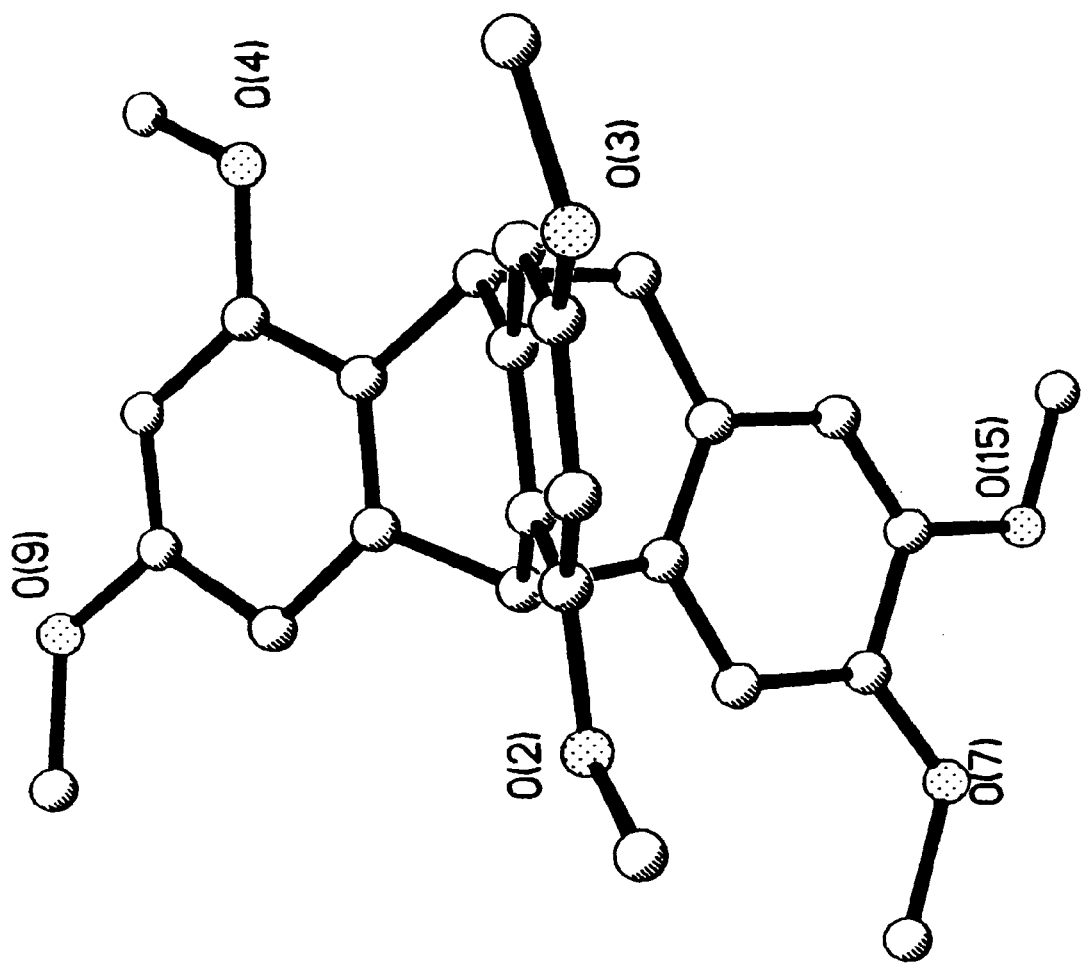
FIG. 11. X-ray crystal structure of acetate 62.

However, if the central biaryl alcohol of 44 was instead methylated (NaH, MeI, THF) to afford intermediate 53 (FIG. 10), it proved possible to access a non-natural structural analog of cassigarol B (63) in which each of the aromatic rings of the original target molecule has been rotated counterclockwise by one turn on the same core carbon skeleton. As shown in FIG. 10, the key element of this unique sequence was achieved by treating 53 with 2 equivalents of $Br_2$ in $CH_2Cl_2$ at −78° C. for 1 h, followed by slow warming to ambient temperature over several hours and subsequent stirring with mild aqueous acid. These conditions achieved the synthesis of alcohol 61 in 43% yield, a product which is the result of a putative mechanistic scenario involving a highly orchestrated sequence of C—C bond forming and cleaving events (3 in all). As indicated, the sequence is believed to begin with expulsion of the central methoxy group to provide a series of equilibrating quinone methides (54, 55, and 56), one of which (56) can funnel to putative intermediate 57 via a 6p-electrocyclization. Of course, though this step is drawn as a pericyclic process, it could also reflect a formal 6 π-like ring formation, using the strategically positioned phenols within the labeled B-ring to achieve C—C bond construction in a stepwise manner. Regardless of which scenario is accurate, rearomatization of 57 through loss of a hydrogen atom, attended by attack of the benzylic carbon onto the aromatic system of the pendant quinone methide, would afford bicyclic compound 58. The use of a related sequence of mechanistic arrows with this intermediate to aromatize its remaining system, with an external electrophile in the form of bromine concluding the movement of electrons, would then lead to 59. Finally, expulsion of that newly installed bromide upon acidic work-up, followed by water capture, would then account for the formation of bicyclic alcohol 61, a compound which was obtained as a 1:1 mixture of stereoisomers (an expected result since both faces of the quinone methide within 60 are equally accessible). Though this mechanistic sequence bears further scrutiny, what is certain is that subsequent removal of the benzylic oxygen function of 61 through its treatment with TFA in the presence of $NaCNBH_3$ provided 62, a molecule whose connectivities have been confirmed by X-ray crystallographic analysis (see FIG. 11). This adduct was then treated with excess $BBr_3$ to provide cassigarol B analog 63 in 49% yield.

Figure 12:
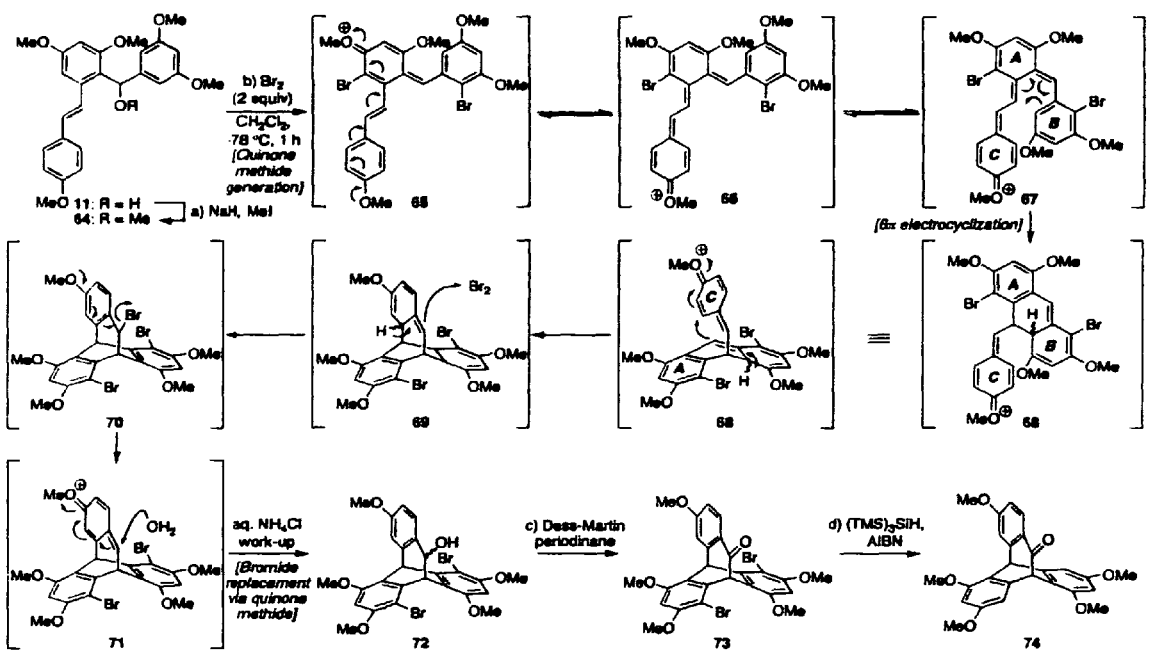
FIG. 12. Synthetic pathway to 72, 73 and 74.
Figure 13:
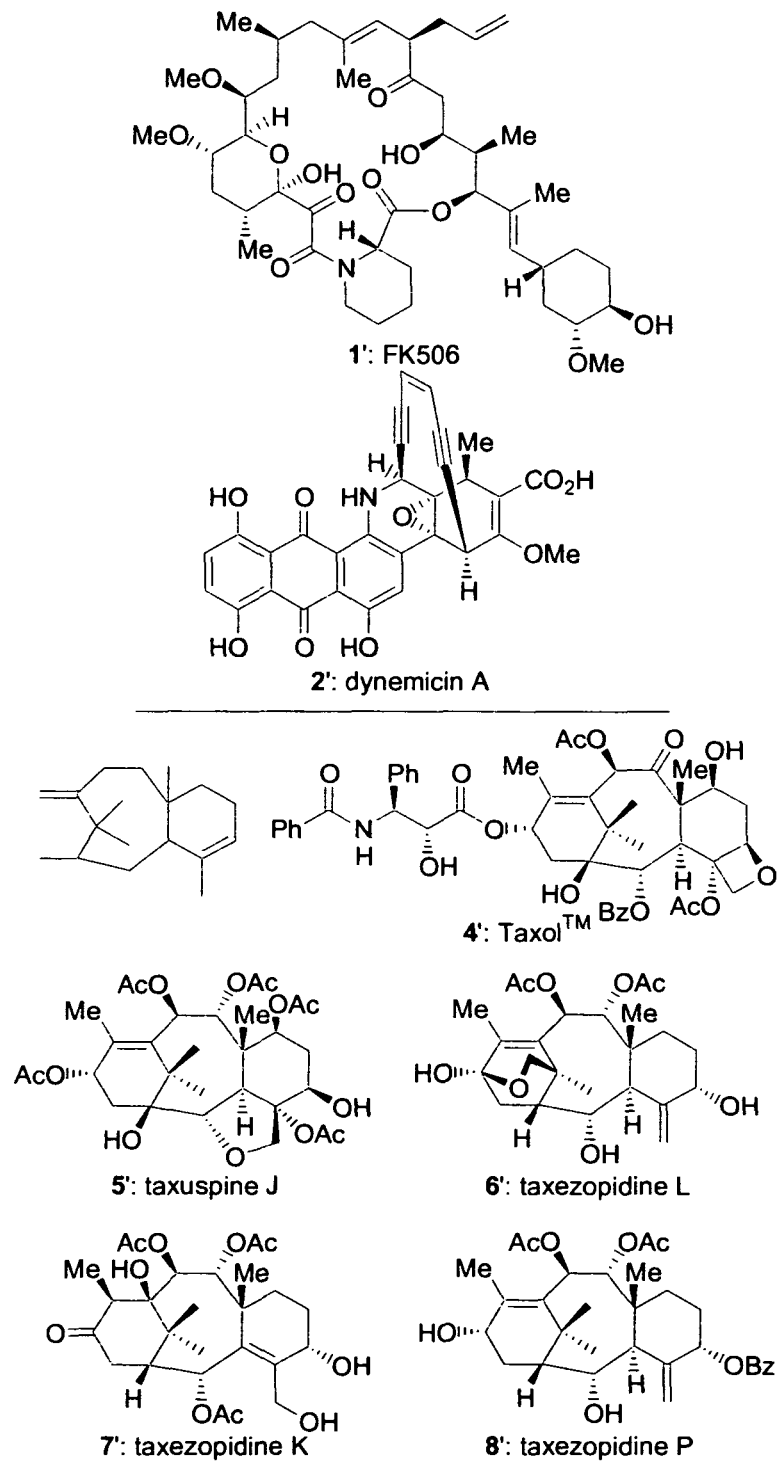
FIG. 13. Examples of structures where Nature demonstrates exquisite control to achieve biological function (1' and 2'), and instances where Nature behaves instead as a combinatorial chemist (4'-8').
Figure 14:
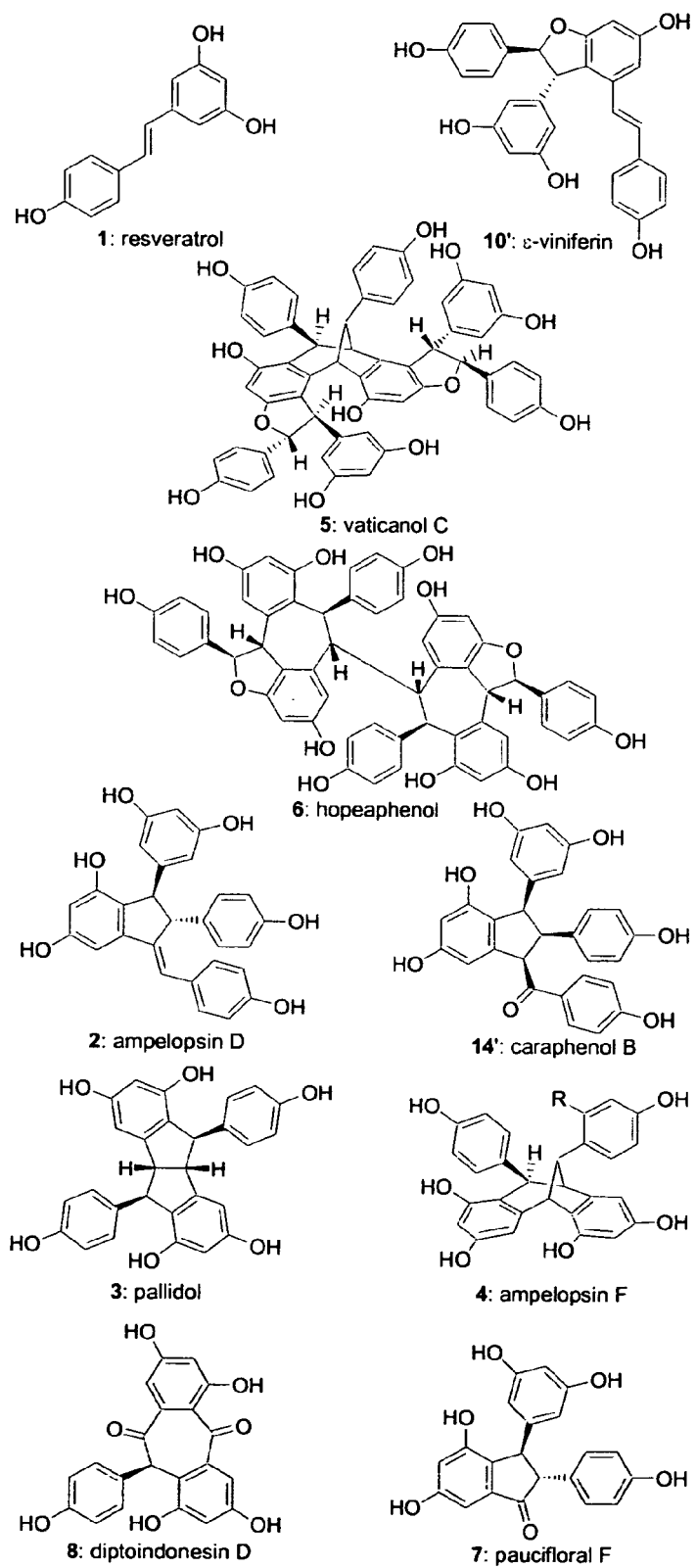
FIG. 14. Selected natural products believed to arise from the union of resveratrol monomers.
Figure 15:
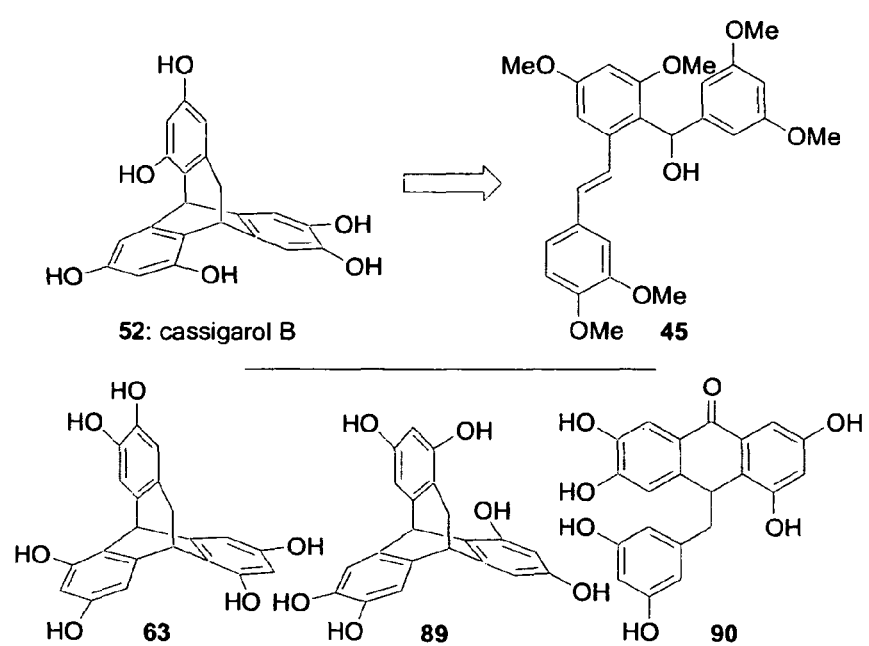
FIG. 15. Additional architectures (52, 63, 89, 90) accessible from our common, non-obvious, synthetic precursors.
Figure 16:
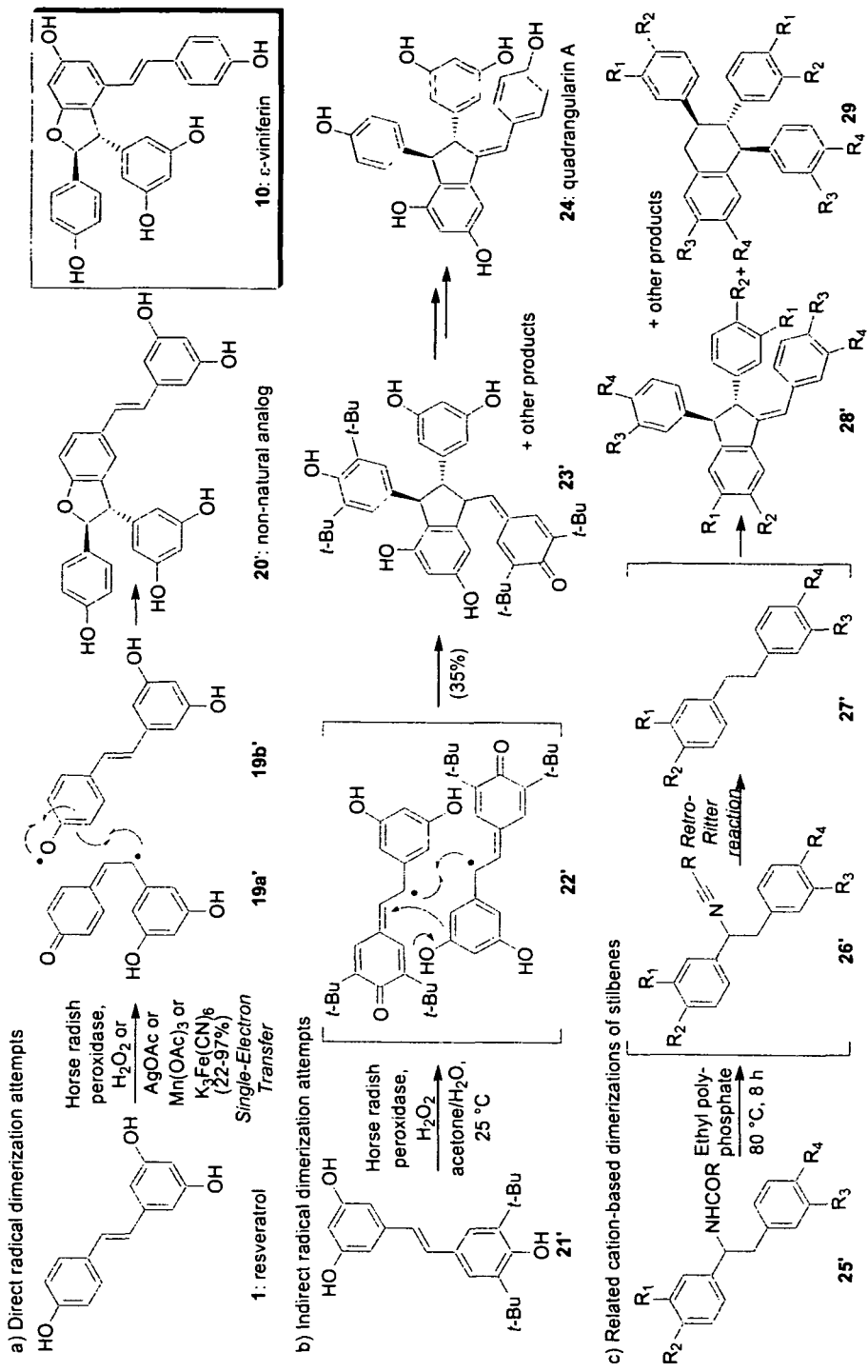
FIG. 16. Previous attempts to achieve the synthesis of resveratrol-based oligomers through selective dimerization reactions.
Figure 17:
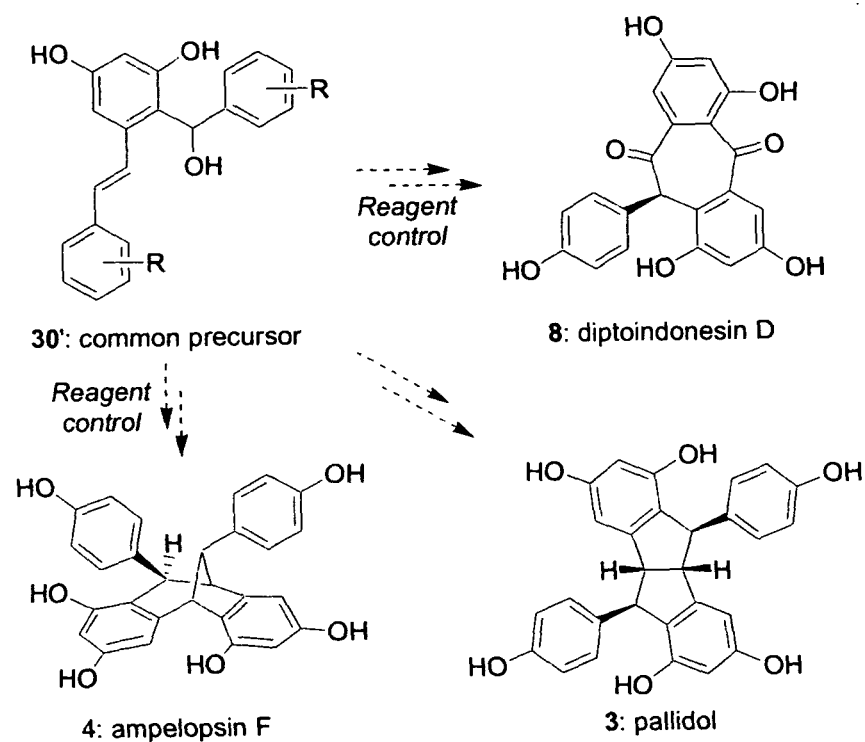
FIG. 17. Idea for the existence of a non-obvious precursor class (30') capable of being converted selectively into all the carbogenic diversity of the resveratrol family.
Figure 18:
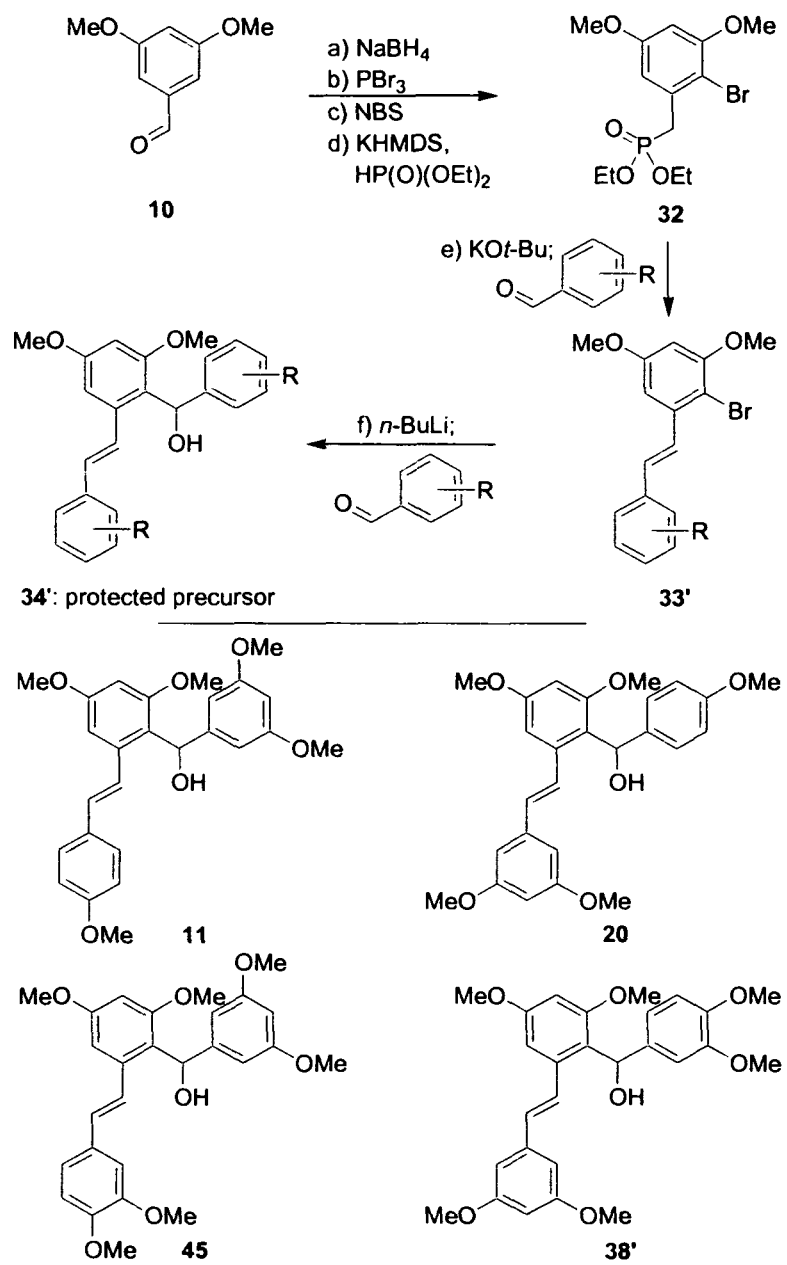
FIG. 18. Generalized synthesis of key precursors (11, 20, 45, and 38'): (a) $NaBH_4$ (2.0 equiv), MeOH, 0° C., 30 min; (b) $PBr_3$ (1.0 equiv), pyridine (0.05 equiv), $Et_2O$, 40° C., 3 h, 93% over two steps; (c) NBS (1.0 equiv), $CH_2Cl_2$, 0° C., 1 h, 95%; (d) HP(O)(OEt)$_2$ (2.0 equiv), KHMDS (0.5 M in toluene, 1.8 equiv), THF, 0° C., 15 min, then add substrate, 25° C., 12 h, 91%; (e) KOt-Bu (1.0 M in THF, 1.0 equiv), THF, −78° C., 20 min, then p-methoxybenzaldehyde (0.95 equiv), −78° C., 1 h, then 25° C., 12 h, 98%; (f) n-BuLi (1.0 equiv), THF, −78° C., 20 min; then p-methoxybenzaldehyde (1.0 equiv), −78→25° C., 4 h, 71%. NBS=N-bromosuccinimide, KHMDS=potassium bis(trimethylsilyl)amide.
Figure 19:
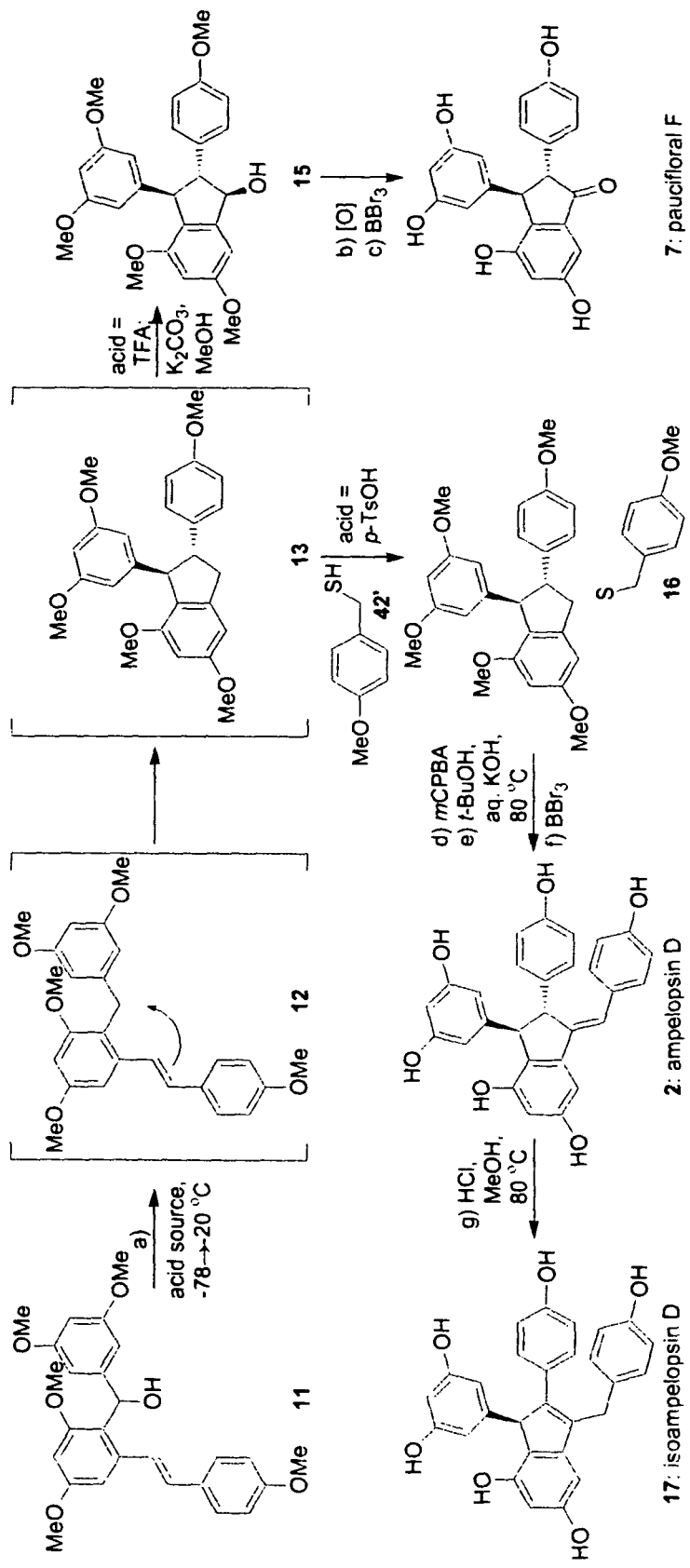
FIG. 19. Total synthesis of three resveratrol-based natural products (2, 7, and 17) from key building block 11: (a) for 15: TFA (1.0 equiv), $CH_2Cl_2$, −30° C. −20° C., 5 h; then $K_2CO_3$ (10 equiv), MeOH, 25° C., 5 min, 75%; for 16: p-TsOH (1.0 equiv), $CH_2Cl_2$, −30° C. −20° C., 5 h; then concentration to near dryness; then 42' (3.0 equiv), 25° C. 12 h, 57%; (b) Dess-Martin periodinane (1.2 equiv), $NaHCO_3$ (5.0 equiv), $CH_2Cl_2$, 25° C., 1 h, 97%; (c) $BBr_3$ (1.0 M in $CH_2Cl_2$, 10 equiv), $CH_2Cl_2$, 0° C., 6 h, 86%; (d) mCPBA (3.0 equiv), $NaHCO_3$ (10 equiv), $CH_2Cl_2$, 0° C.-25° C., 3 h, 78%; (e) t-BuOH/$H_2O$/$CCl_4$ (4/1/4), KOH (powder, 20 equiv), 80° C., 12 h, 52%; (f) $BBr_3$ (1.0 M in $CH_2Cl_2$, 12 equiv), $CH_2Cl_2$, 25° C., 6 h, 76% of 2, 13% of 17; (g) conc. HCl (10 equiv), MeOH, 80° C., 2 h, 95%. TFA=trifluoroacetic acid, p-TsOH=p-toluenesulfonic acid, mCBPA=m-chloroperoxybenzoic acid.

Finally, the unique cascade sequence just described in the preceding paragraph would appear to be a general one given the ability to convert the methylated form of key intermediate 11 (i.e. 64, FIG. 12) to biaryl architecture 72 upon its similar exposure to bromine. As indicated, however, there is one key structural difference with this new adduct: it possesses two bromine atoms attached to its aromatic ring systems, a difference in outcome which we attribute to the unique electronic profile of starting material 64 relative to 53. As indicated, however, these extra halogen atoms can be readily removed, following the oxidation of 72, under radical conditions to afford ketone 74 in 85% overall yield; though not shown, these bromine atoms should also be able to serve as potential sites upon which to incorporate additional complexity through other standard bond-forming reactions.

In exploring the generality of the developed sequences with each of the other three forms of our common building block 20, 45, 38'. It was found that these intermediates all behaved in exactly the same way chemically. Indeed, when building block 20 was subjected to the reaction sequences outlined above, what resulted were total syntheses of quadrangularin A (21) and isopaucifloral F (22), natural products whose pendant phenol ring systems are interchanged, as expected, from those accessed from 11. In a similar vein, natural product-like analogs 46' and 47' were accessed from building block 45, while compounds 48', 49', and 50' were smoothly generated from 38'. Of these adducts, compound 50' is a fully deprotected analog of the natural product gnetulin [27], an isolate that possesses methyl groups on the highlighted phenols.

In order to incorporate the 3,4-dihydroxyphenyl D-ring system of analog 50', a slightly different approach was needed from that described above in that thiol 53' (prepared in situ due to its lability) [28] decomposed in our standard acid-catalyzed cyclization. A solution to this problem was found in a new reaction, one which employs a full equivalent of a lanthanide triflate, such as $In(OTf)_3$ in combination with a highly concentrated solution of sulfide 53', to quickly generate the desired sulfide product from a precursor alcohol (i.e. 52'→54'). Based on initial screening, this reaction is general for any sulfide in combination with a benzylic alcohol, and it would seem that simple triflic acid, while likely present when these lanthanide salts are added to organic solvents [30], cannot account for the transformation.

The natural products and analogs described above are not the only possible indane-based structures that can be reached through these chemistries. Others that possess alternate stereochemistries, such as the more rare cis-disposed aryl rings of caraphenol B and C (14' and 58', respectively) [31] are also accessible. As shown in Figure X, the key operation is a chiral center inversion, achieved by first exposing permethylated paucifloral F (56') to KHDMS for 15 h in THF at 25° C.; a quench of the resultant enolate using water then afforded 57', presumably via selective, kinetic proton capture [32].

An element of molecular complexity possessed by the resveratrol class are seven-membered carbocycles. These systems have also proven accessible from our common, non-obvious, intermediates upon exposure to simple reagents, but only after some minor structural changes have been made to their architectures, namely oxidation of the central biaryl alcohol to the corresponding ketone. Indeed, if compound 31 is reacted with 1,1,1-trifluorodimethyldioxirane, or trifluoromethylmethyldioxirane, (generated in situ using OXONE®, 1,1,1-trifluoroacetone, and $Na_2EDTA$ buffer) [33] in MeCN at ambient temperature, a protected form of the natural product hemsleyanol E (83) [34] is generated in 34% yield.

In addition to the above architectures, The permethylated form of cassigarol B (97) could also be accessed directly in a single step from 45 upon its exposure to either PBr₃ in pyridine at 25° C. or a mixture of 40% HBr in AcOH at 25° C. In both of these cases, we believe that the biaryl alcohol was initially exchanged for either a bromine or an acetate; pure cation generation would be unlikely as this would lead to indane ring synthesis. This group exchange "protected" the benzylic position until Friedel-Crafts cyclization to 101 occurred, but then served as a leaving group to allow the same end-game (via 96) as described above to proceed in the same pot.

In conclusion, herein it is established that the entire array of carbogenic complexity posed by the resveratrol family of natural products, along with several additional isosteres, can be accessed smoothly and selectively from building blocks quite distinct from the compound postulated for their biosynthesis. In all cases, spectral data for synthetic materials perfectly match those of the natural isolates. It should be noted that all molecules reported herein are racemic. Apart from revealing previously hidden structural relationships within the architectural diversity possessed by this compound class, the efficiency of the developed routes (four to seven steps from 9 and 18, each natural product accessed in 7 to 46% overall yield from commercial materials) ensures that the biochemical studies needed to elucidate their full medicinal potential can finally begin in earnest.

Fungicidal Activity

The fungicidal or antifungicide properties of the compounds are readily ascertainable using standard protocols. An example of a suitable protocol for determining the efficacy of compounds for their fungicidal activity against *C. albicans* is as follows. Particular crop-related fungi may be substituted.

Applicants note that in this section of the application only, regarding the testing of resveratrol analogs for fungicidal activity, the following compounds have been ascribed the number identifiers as follows:

1

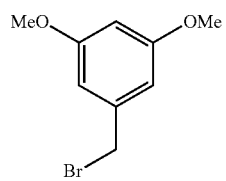

Chemical Formula: $C_9H_{11}BrO_2$
Exact Mass: 229.99
Molecular Weight: 231.09

2

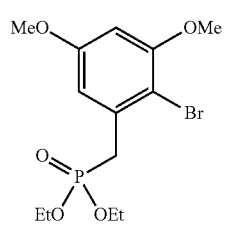

Chemical Formula: $C_{13}H_{20}BrO_5P$
Exact Mass: 366.02
Molecular Weight: 367.17

-continued

3

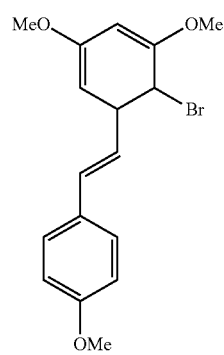

Chemical Formula: $C_{17}H_{17}BrO_3$
Exact Mass: 348.04
Molecular Weight: 349.22

4

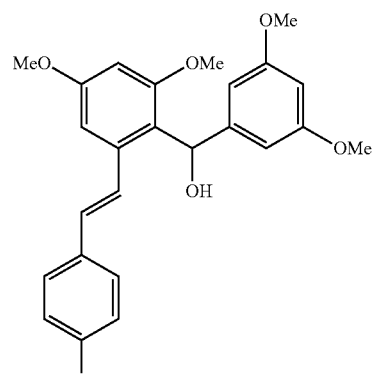

Chemical Formula: $C_{26}H_{28}O_6$
Exact Mass: 436.19
Molecular Weight: 436.5

5

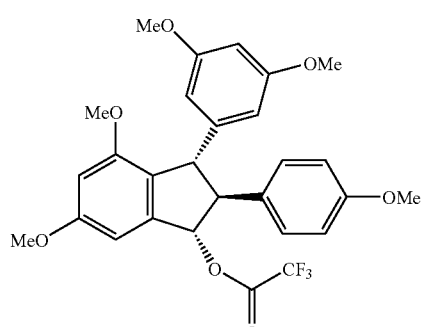

Chemical Formula: $C_{28}H_{27}F_3O_7$
Exact Mass: 532.17
Molecular Weight: 532.5

6

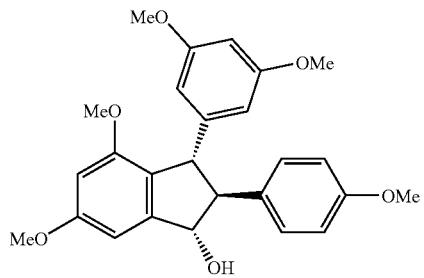

Chemical Formula: $C_{26}H_{28}O_6$
Exact Mass: 436.19
Molecular Weight: 436.5

7

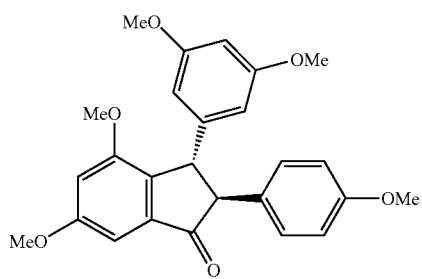

Chemical Formula: C<sub>26</sub>H<sub>26</sub>O<sub>6</sub>
Exact Mass: 434.17
Molecular Weight: 434.48

8

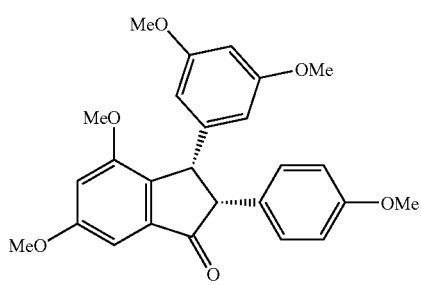

Chemical Formula: C<sub>26</sub>H<sub>26</sub>O<sub>6</sub>
Exact Mas: 434.17
Molecular Weight: 434.48

9

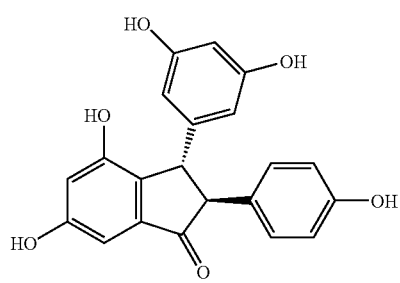

Chemical Formula: C<sub>21</sub>H<sub>16</sub>O<sub>6</sub>
Exact Mass: 364.09
Molecular Weight: 364.35

10

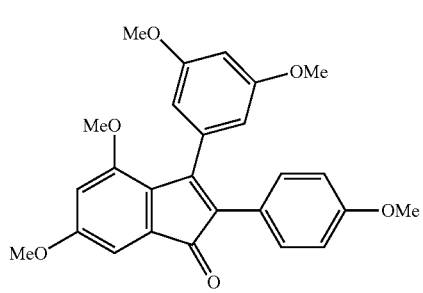

Chemical Formula: C<sub>26</sub>H<sub>24</sub>O<sub>6</sub>
Exact Mass: 432.16
Molecular Weight: 432.47

11

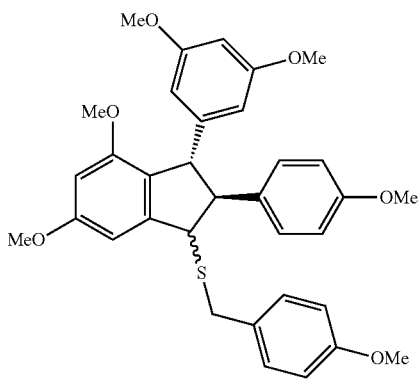

Chemical Formula: C<sub>35</sub>H<sub>40</sub>O<sub>6</sub>S
Exact Mass: 588.25
Molecular Weight: 588.75

12

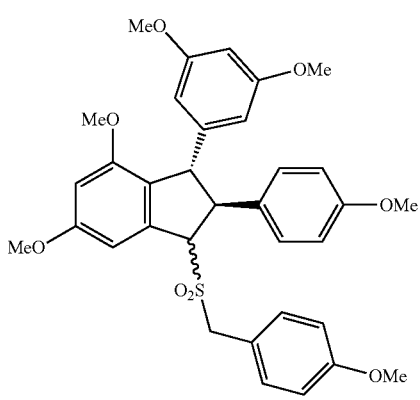

Chemical Formula: C<sub>35</sub>H<sub>40</sub>O<sub>8</sub>S
Exact Mass: 620.24
Molecular Weight: 620.75

13

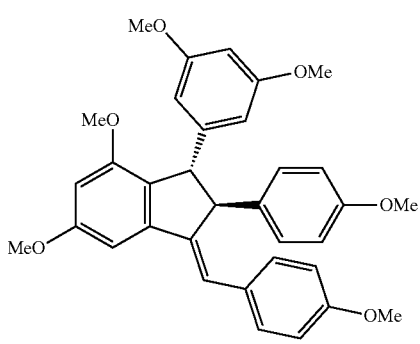

Chemical formula: C<sub>34</sub>H<sub>34</sub>O<sub>6</sub>
Exact Mass: 538.24
Molecular Weight: 538.63

207
-continued

14

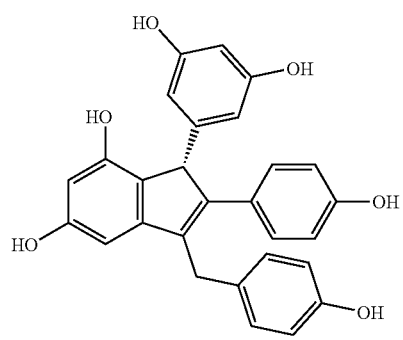

Chemical Formula: $C_{28}H_{22}O_6$
Exact Mass: 454.14
Molecular Weight: 454.47

15

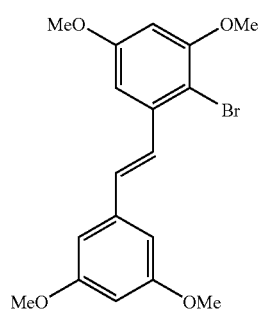

Chemical Formula: $C_{18}H_{19}BrO_4$
Exact Mass: 378.05
Molecular Weight: 379.25

16

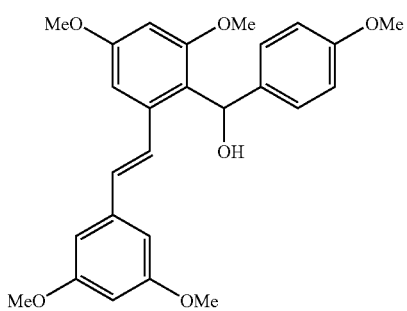

Chemical Formula: $C_{26}H_{28}O_6$
Exact Mass: 436.19
Molecular Weight: 436.5

17

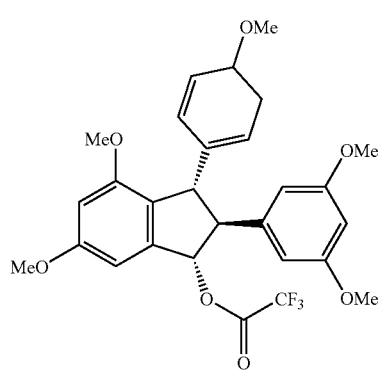

Chemical Formula: $C_{28}H_{27}F_3O_7$
Exact mass: 532.17
Molecular Weight: 532.5

208
-continued

18

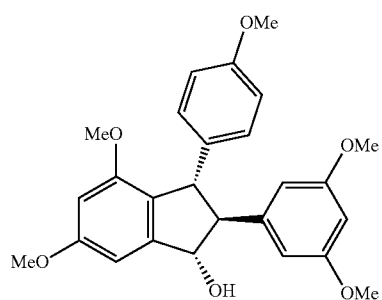

Chemical Formula: $C_{26}H_{28}O_6$
Exact Mass: 436.19
Molecular Weight: 436.5

19

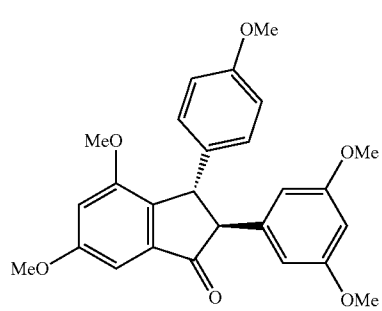

Chemical Formula: $C_{26}H_{26}O_6$
Exact Mass: 434.17
Molecular Weight: 434.48

20

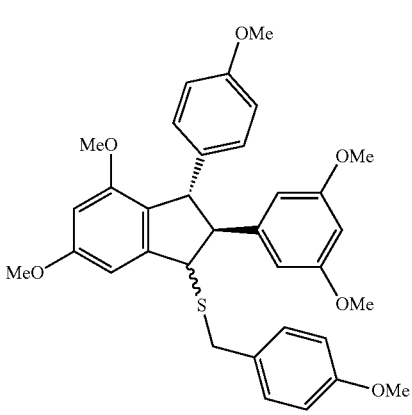

Chemical Formula: $C_{34}H_{36}O_6S$
Exact Mass: 572.22
Molecular Weight: 572.71

21

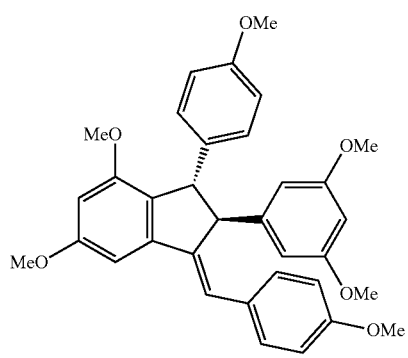

Chemical Formula: $C_{34}H_{34}O_6$
Exact Mass: 538.24
Molecular Weight: 538.63

22

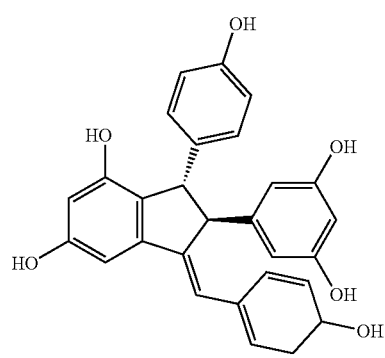

Chemical Formula: $C_{28}H_{22}O_6$
Exact Mass: 454.14
Molecular Weight: 454.47

23

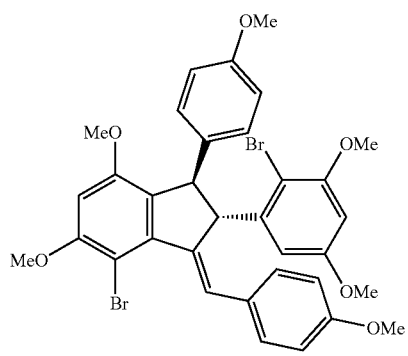

Chemical Formula: $C_{35}H_{36}Br_2O_6$
Exact Mass: 710.09
Molecular Weight: 712.46

24

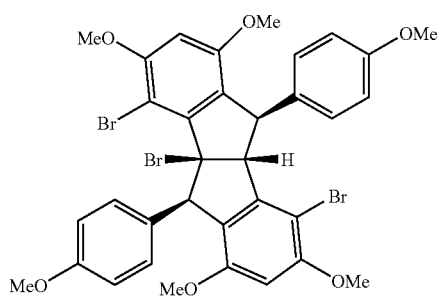

Chemical Formula: $C_{34}H_{31}Br_3O_6$
Exact Mass: 771.97
Molecular Weight: 775.32

25

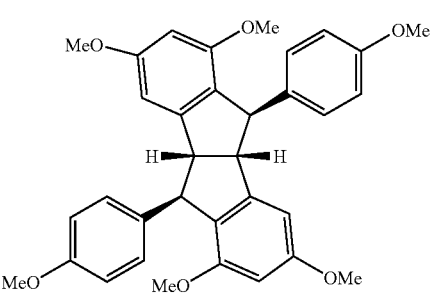

Chemical Formula: $C_{34}H_{34}O_6$
Exact Mass: 538.24
Molecular Weight: 538.63

26

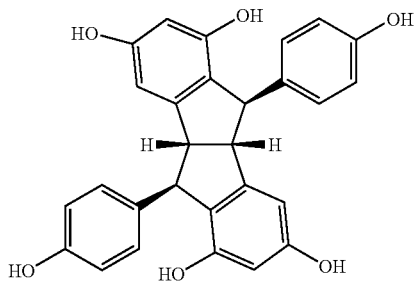

Chemical Formula: $C_{28}H_{22}O_6$
Exact Mass: 454.14
Molecular Weight: 454.47

27

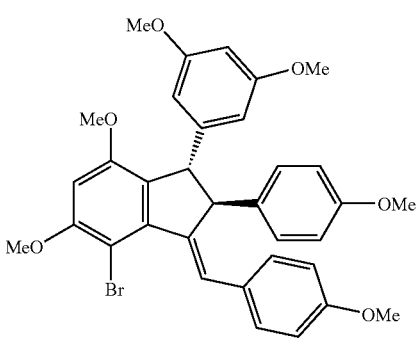

Chemical Formula: $C_{34}H_{33}BrO_6$
Exact Mass: 616.15
Molecular Weight: 617.53

28

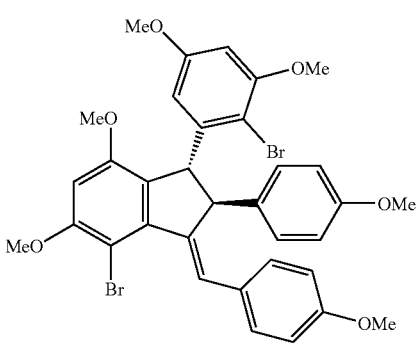

Chemical Formula: $C_{34}H_{32}Br_2O_6$
Exact Mass: 694.06
Molecular Weight: 696.42

29

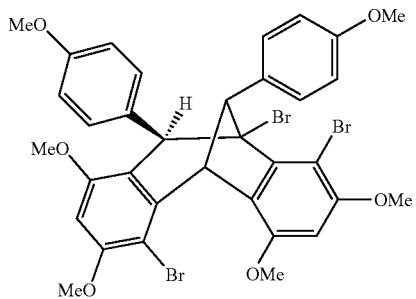

Chemical Formula: $C_{34}H_{31}Br_3O_6$
Exact Mass: 771.97
Molecular Weight: 775.32

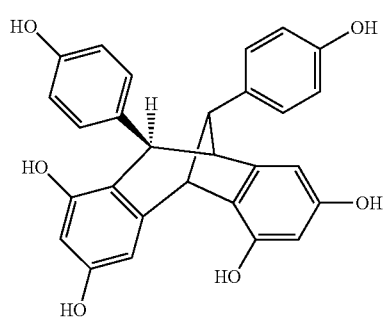

Chemical Formula: $C_{28}H_{22}O_6$
Exact Mass: 454.14
Molecular Weight: 454.47

31

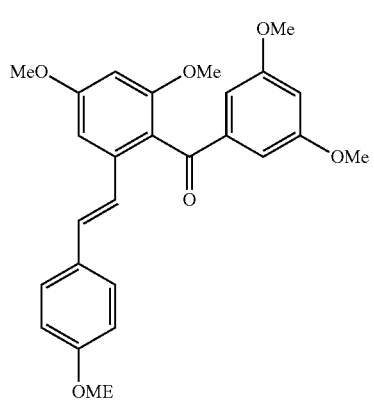

Chemical Formula: $C_{26}H_{26}O_6$
Exact Mass: 434.17
Molecular Weight: 434.48

32

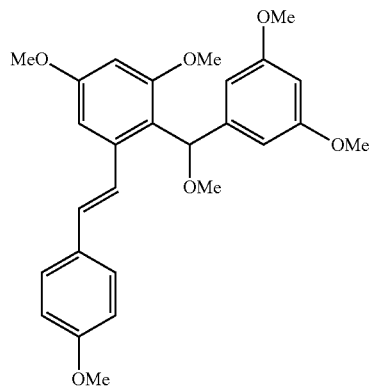

Chemical Formula: $C_{27}H_{30}O_6$
Exact Mass: 450.2
Molecular Weight: 450.52

33

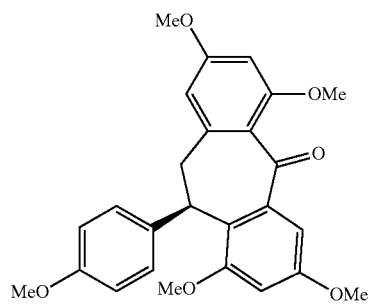

Chemical Formula: $C_{26}H_{26}O_6$
Exact Mass: 434.17
Molecular Weight: 434.48

34

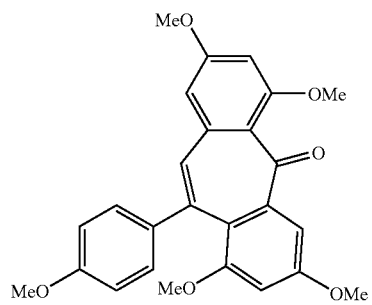

Chemical Formula: $C_{26}H_{24}O_6$
Exact Mass: 432.16
Molecular Weight: 432.47

35

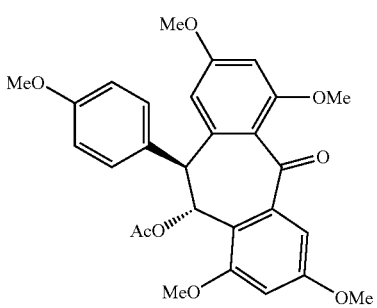

Chemical Formula: $C_{28}H_{28}O_8$
Exact Mass: 492.18
Molecular Weight: 492.52

36
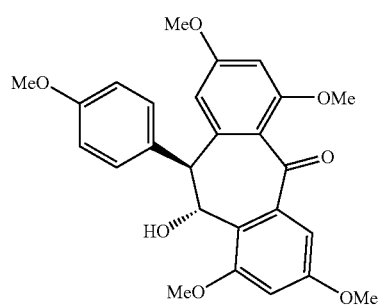
Chemical Formula: $C_{26}H_{26}O_7$
Exact Mass: 450.17
Molecular Weight: 450.48
37
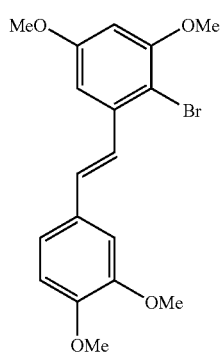
Chemical Formula: $C_{18}H_{19}BrO_4$
Exact Mass: 378.05
Molecular Weight: 379.25
38
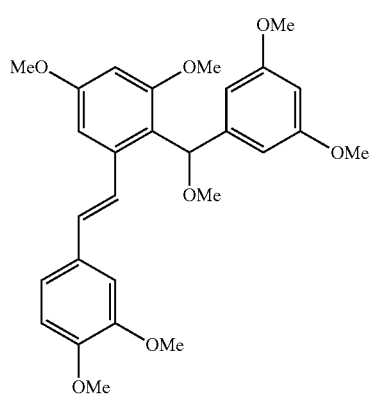
Chemical Formula: $C_{28}H_{32}O_7$
Exact Mass: 480.21
Molecular Weight: 480.55
39
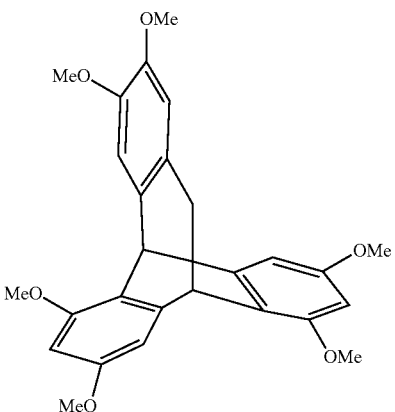
Chemical Formula: $C_{27}H_{28}O_6$
Exact Mass: 448.19
Molecular Weight: 448.51
40
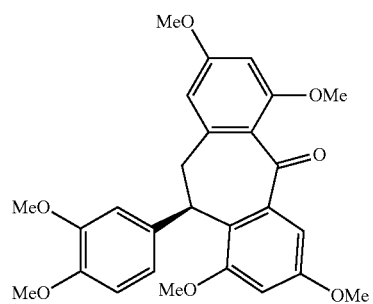
Chemical Formula: $C_{27}H_{28}O_7$
Exact Mass: 464.18
Molecular Weight: 464.51
41
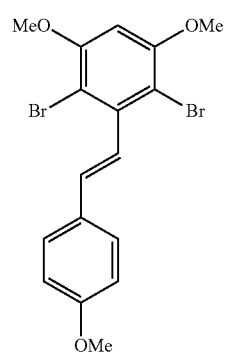
Chemical Formula: $C_{17}H_{16}Br_2O_3$
Exact mass: 425.95
Molecular Weight: 428.12

42
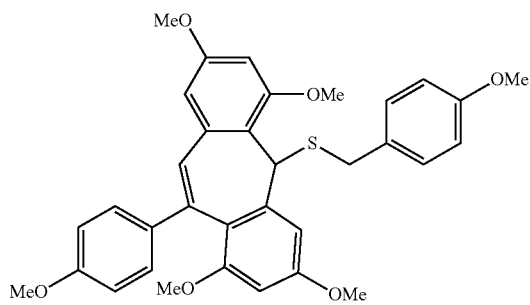
Chemical Formula: C₃₄H₃₄O₆S
Exact Mass: 570.21
Molecular Weight: 570.7
43
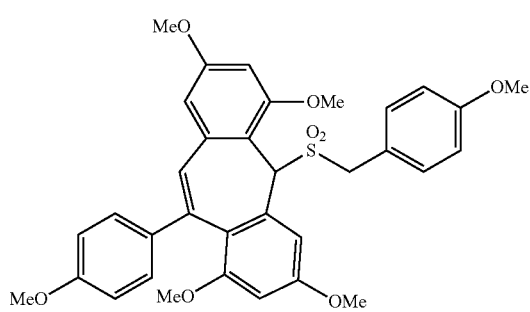
Chemical Formula: C₃₄H₃₄O₈S
Exact Mass: 602.2
Molecular Weight: 602.69
44
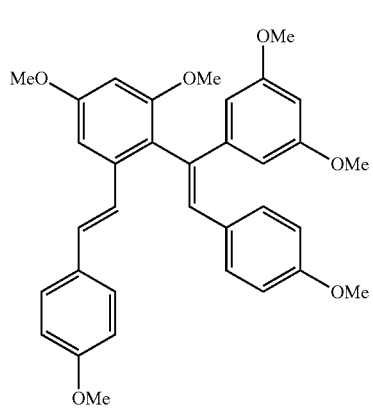
Chemical Formula: C₃₄H₃₄O₆
Exact Mass: 538.24
Molecular Weight: 538.63
45
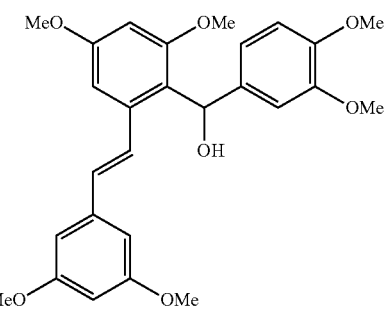
Chemical Formula: C₂₇H₃₀O₇
Exact Mass: 466.2
Molecular Weight: 466.52
46
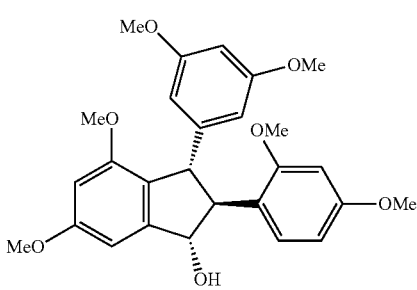
Chemical Formula: C₂₇H₃₀O₇
Exact Mass: 466.2
Molecular Weight: 466.52
47
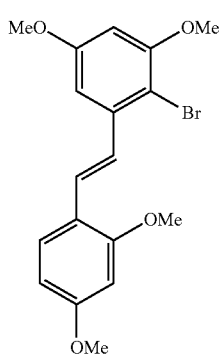
Chemical Formula: C₁₈H₁₉BrO₄
Exact Mass: 378.05
Molecular Weight: 379.25

48
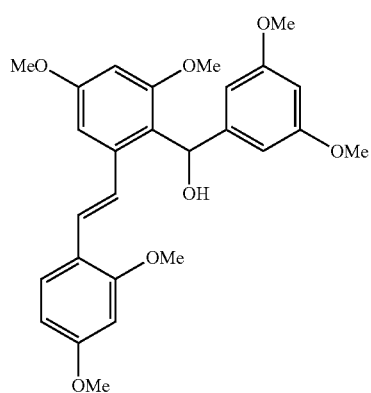
Chemical Formula: C27H30O7
Exact Mass: 466.2
Molecular Weight: 466.52
49
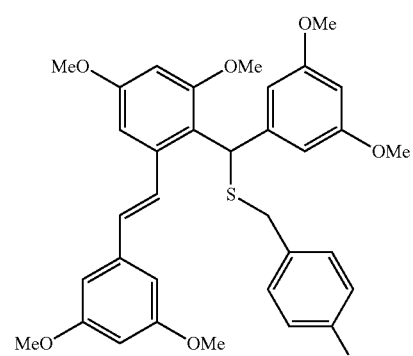
Chemical Formula: C35H38O7S
Exact Mass: 602.23
Molecular Weight: 602.74
50
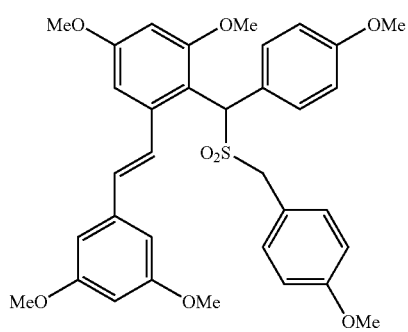
Chemical Formula: C34H36O8S
Exact Mass: 604.21
Molecular Weight: 604.71
51
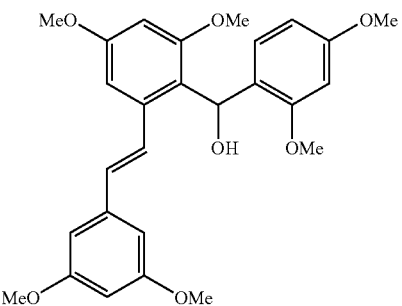
Chemical Formula: C27H30O7
Exact Mass: 466.2
Molecular Weight: 466.52
52
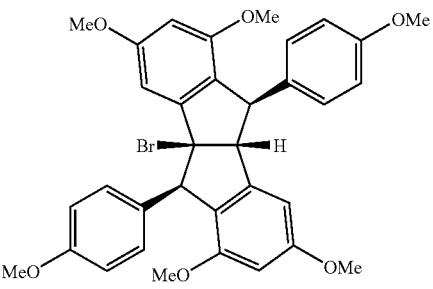
Chemical Formula: C34H33BrO6
Exact Mass: 616.15
Molecular Weight: 617.53
53
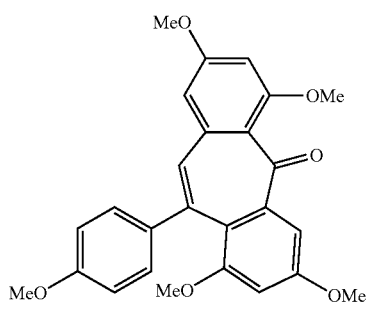
Chemical Formula: C26H24O6
Exact Mass: 432.16
Molecular Weight: 432.47
54
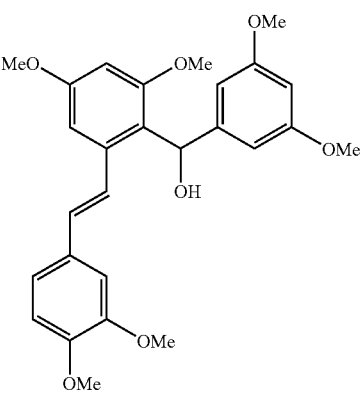
Chemical Formula: C27H30O7
Exact Mass: 466.2
Molecular Weight: 466.52

-continued

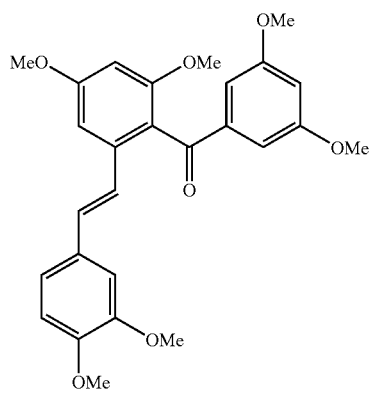

Chemical Formula: C₂₇H₂₈O₇
Exact Mass: 464.18
Molecular Weight: 464.51

55

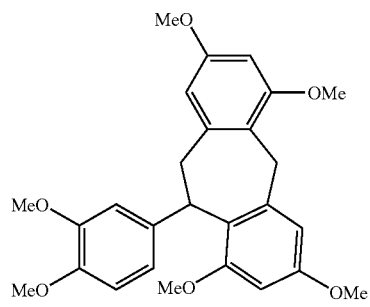

Chemical Formula: C₂₇H₃₀O₆
Exact Mass: 450.2
Molecular Weight: 450.52

56

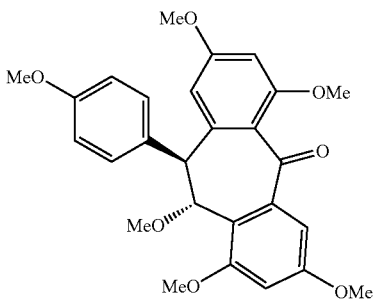

Chemical Formula: C₂₇H₂₈O₇
Exact Mass: 464.18
Molecular Weight: 464.51

57

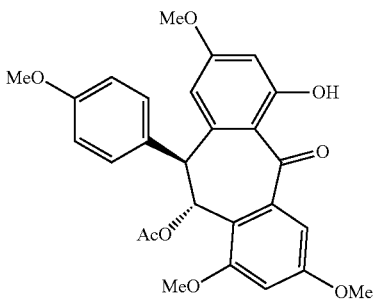

Chemical Formula: C₂₇H₂₈O₈
Exact Mass: 478.16
Molecular Weight: 478.49

58

-continued

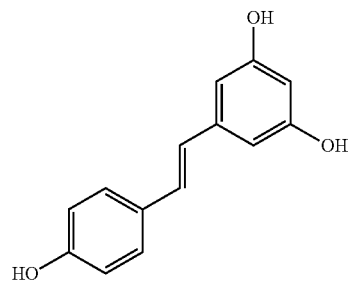

Chemical Formula: C₁₄H₁₂O₃
Exact Mass: 228.08
Molecular Weight: 228.24

59

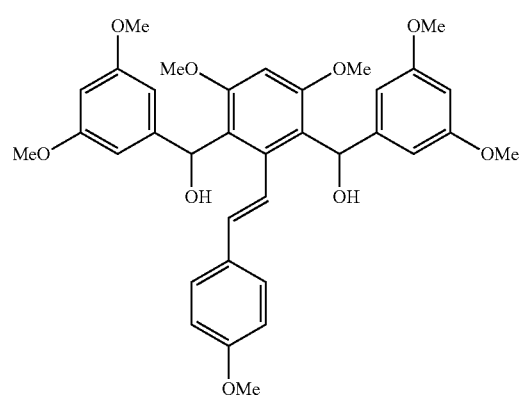

Chemical Formula: C₃₅H₃₈O₉
Exact Mass: 602.25
Molecular Weight: 602.67

60

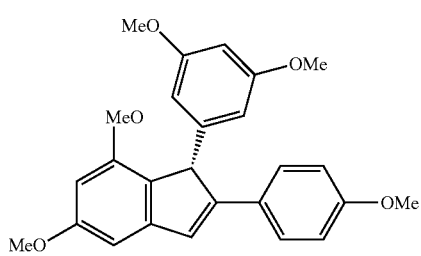

Chemical Formula: C₂₆H₂₆O₅
Exact Mass: 418.18
Molecular Weight: 418.48

61

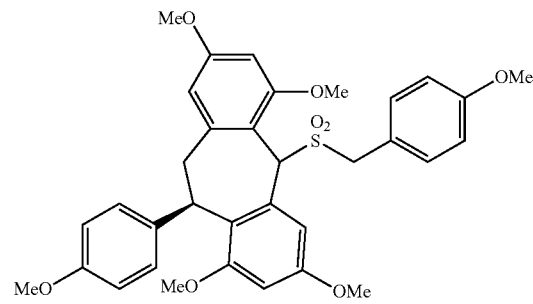

Chemical Formula: C₃₄H₃₆O₈S
Exact Mass: 604.21
Molecular Weight: 604.71

62

63

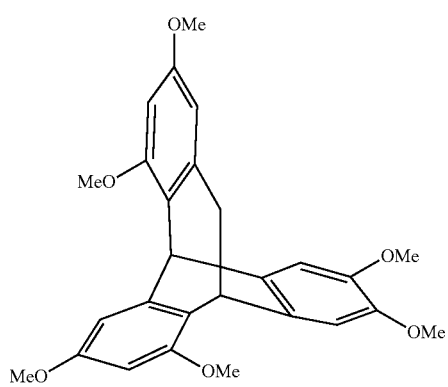

Chemical Formula: $C_{27}H_{26}O_6$
Exact Mass: 448.19
Molecular Weight: 448.51

64

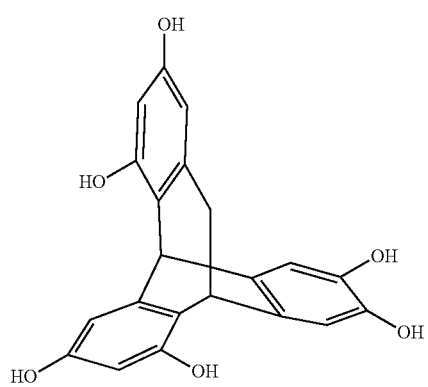

Chemical Formula: $C_{21}H_{16}O_6$
Exact Mass: 364.09
Molecular Weight: 364.35

65

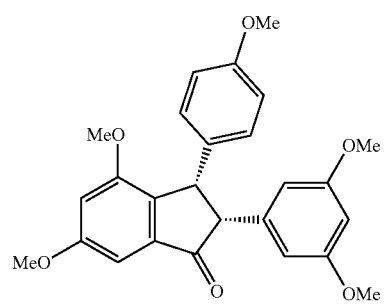

Chemical Formula: $C_{26}H_{26}O_6$
Exact Mass: 434.17
Molecular Weight: 434.48

66

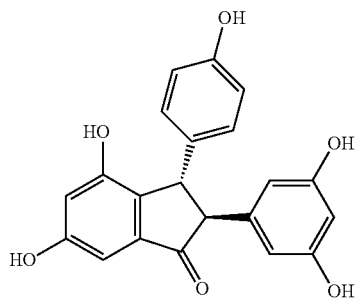

Chemical Formula: $C_{21}H_{16}O_6$
Exact Mass: 364.09
Molecular Weight: 364.35

67

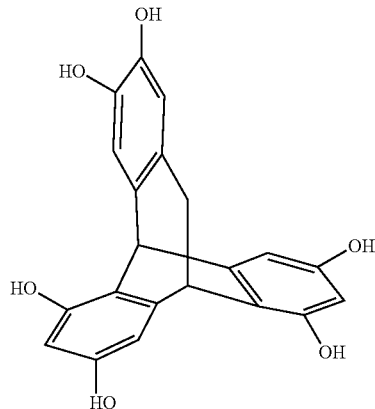

Chemical Formula: $C_{21}H_{16}O_6$
Exact Mass: 364.09
Molecular Weight: 364.35

68

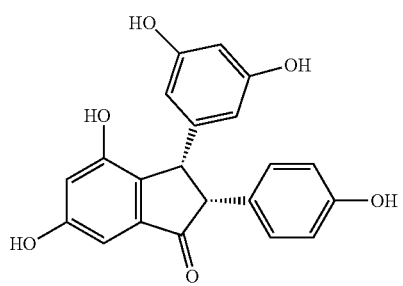

Chemical Formula: $C_{21}H_{16}O_6$
Exact Mass: 364.09
Molecular Weight: 364.35

69

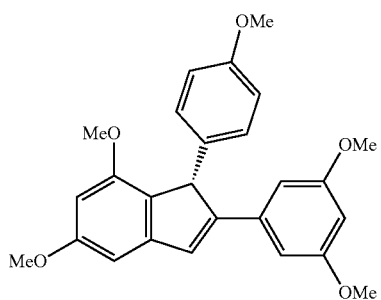

Chemical Formula: $C_{26}H_{26}O_5$
Exact Mass: 418.18
Molecular Weight: 418.48

Materials:
C. albicans strain SC5314
96 well sterile plates with lids
Media—RPMI 1640 with glutamine, without bicarbonate, buffered with MOPS to 7.0, with 2% glucose added
Prospective antifungal compounds
15 ml conicals
Pipettors and tips (yellow and blue)
Sterile loops, tips, test tubes, pipettes,
Spectrophotometer or hemocytometer
35 degree incubator
Tupperware/moist chamber Day 1
Inoculate an overnight culture (5 ml) of the wild type *C. albicans* strain SC5314

Day 2
Plate Preparation

|  |  | Columns | | | | | | | | | | | |
|---|---|---|---|---|---|---|---|---|---|---|---|---|---|
|  |  | 1 | 2 | 3 | 4 | 5 | 6 | 7 | 8 | 9 | 10 | 11 | 12 |
|  | Conc: | 64 | 32 | 16 | 8 | 4 | 2 | 1 | 0.5 | 0.25 | 0.13 | No drug | No cells |
| Rows | 1 CmpndA | | | | | | | | | | | | |
|  | 2 CmpndB | | | | | | | | | | | | |
|  | 3 CmpndC | | | | | | | | | | | | |
|  | 4 CmpndD | | | | | | | | | | | | |
|  | 5 CmpndE | | | | | | | | | | | | |
|  | 6 CmpndF | | | | | | | | | | | | |
|  | 7 CmpndG | | | | | | | | | | | | |
|  | 8 CmpndH | | | | | | | | | | | | |

Set up one microtiter plate in RPMI. For each plate:
1. Use 10 15 ml conicals, labeled 1 to 10.
2. Add 1 ml of the media to each tube.
3. Add 1 ml of media containing 16 μg/ml compound to be tested (8 μl of 2 mg/ml stock) to the tube 1 and mix.
4. Transfer 1 ml from the tube 1 to the tube 2, mix and transfer from tube 2 to 3 etc.
5. Remove 1 ml from tube 10 and dispose, so that all tubes 1 to 10 have 1 ml.
6. Pipette 100 μl from each tube into each well of the appropriate column. (The first tube contains 8 μg/ml of compound but will be diluted by the inoculum to 4 g/ml).
7. Place 100 μl of media in the wells of column 11. Place 200 μl of media in the wells of column 12.

Inoculum Preparation
1) Prepare 1.5 ml of inoculum for each Cmpnd/row to be loaded.
2) For inoculum, 3.3 μl of overnight (usually about 15 OD/ml) into 5 ml of medium usually gives an OD of 0.01 or $10^5$ cells/ml. Then the inoculum is diluted 1/200 (7.5 μl into 1.5 ml of medium)
3) Add 100 μl inoculum to lanes 1-11 of the previously prepared plate.

Incubation and plate reading

1) Put the plate in a Tupperware-type container on top of several damp paper towels. Close the container.
2) Put the container in the shaking 35° C. incubator. Incubate for 48 hr.

Days 3-4
Observe plates for growth by eye; read in plate reader.

Figure 37:
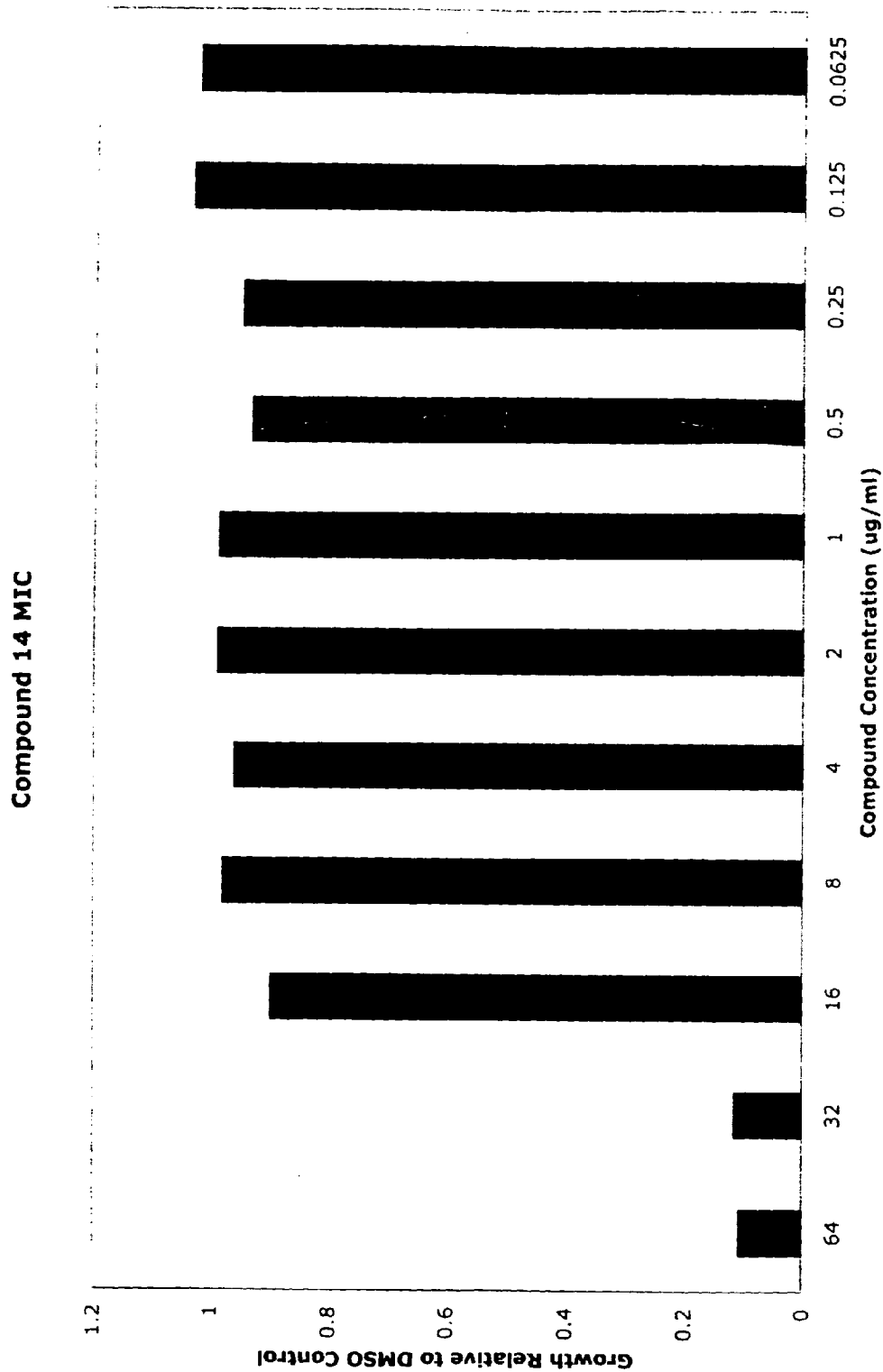
FIG. 37. Mean inhibitor concentration (MIC) of compound 14.

Many of the resveratrol analogs showed fungicidal activity, clearly inhibiting fungal growth relative to control. In fact, the majority of the compounds tested showed inhibition of fungal growth in excess of the inhibition demonstrated by resveratrol (compound 59 in FIGS. 32-36.) The most active tested compound was compound 14 in FIGS. 32-37. The mean inhibitory concentration of compound 14 was tested as set forth in FIG. 37, showing significant fungal growth inhibition at 32 μg/ml. Compound 14 has the structure:

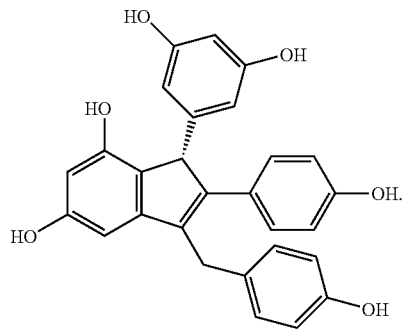 [SMILES: Oc1ccc(CC2=C(c3ccc(O)cc3)[C@@H](c3cc(O)cc(O)c3)c3c(O)cc(O)cc32)cc1]

The compounds described herein are tested for fungicidal activity as described above and are found to have fungicidal activity equal to or better than that exhibited by resveratrol.

UV Protection

Resveratrol is well documented as a potential sunscreen (see PCT International Publication No. WO 01/91695 A2, hereby incorporated by reference in its entirety.) However, the oligomeric and analog forms of resveratrol (the compounds described herein) are expected to have superior thermal and light sensitivity, improved molar absorptivity, as well as larger ranges of absorption in the UV-B range. In addition, apart from their use as sunscreen agents by blocking UV activity, the known ability of resveratrol to interdict reactive-oxygen species suggests that these analogs are a treatment for various forms of skin cancer.

Materials and Methods

General Procedures.

All reactions were carried out under an argon atmosphere with dry solvents under anhydrous conditions, unless otherwise noted. Dry tetrahydrofuran (THF), acetonitrile (MeCN), toluene, benzene, diethyl ether (Et$_2$O) and methylene chloride (CH$_2$Cl$_2$) were obtained by passing commercially available pre-dried, oxygen-free formulations through activated alumina columns. Yields refer to chromatographically and spectroscopically ($^1$H and $^{13}$C NMR) homogeneous materials, unless otherwise stated. Reagents were purchased at the highest commercial quality and used without further purification, unless otherwise stated. Reactions were magnetically stirred and monitored by thin-layer chromatography (TLC) carried out on 0.25 mm E. Merck silica gel plates (60F-254) using UV light as visualizing agent and an ethanolic solution of phosphomolybdic acid and cerium sulfate, and heat as developing agents. SiliCycle silica gel (60, academic grade, particle size 0.040-0.063 mm) was used for flash column chromatography. Preparative thin-layer chromatography (PTLC) separations were carried out on 0.50 mm E. Merck silica gel plates (60F-254). NMR spectra were recorded on Bruker DRX-300, DRX-400, DMX-500 instruments and calibrated using residual undeuterated solvent as an internal reference. The following abbreviations were used to explain the multiplicities: s=singlet, d=doublet, t=triplet, br=broad, AB=AB quartet, app=apparent. IR spectra were recorded on a Perkin-Elmer 1000 series FT-IR spectrometer. High-resolution mass spectra (HRMS) were recorded in the Columbia University Mass Spectral Core facility on a JOEL HX110 mass spectrometer using the MALDI (matrix-assisted laser-desorption ionization) technique.

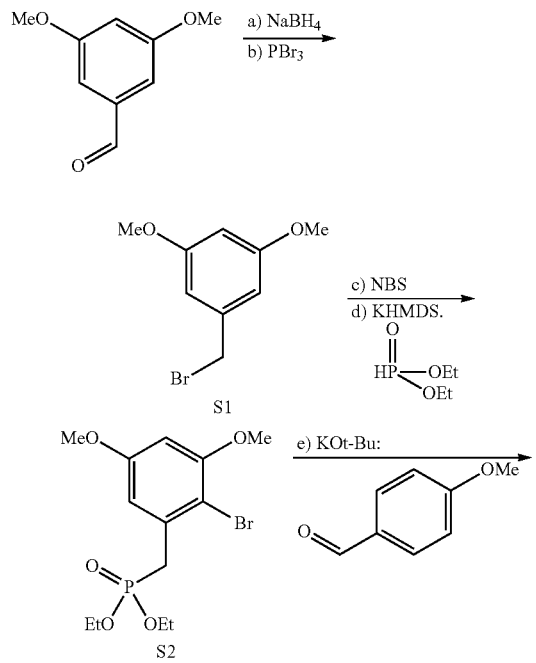

Scheme S1. Synthesis of key halogenated building block 9.

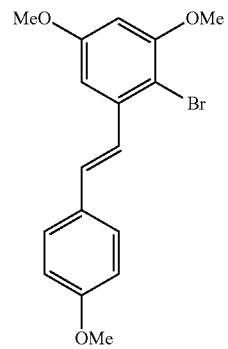

a) NaBH$_4$ (2.0 equiv), MeOH, 0° C., 30 min; b) PBr$_3$ (1.0 equiv), pyridine (0.05 equiv), Et$_2$O, 40° C., 3 h, 93% over two steps; c) NBS (1.0 equiv), CH$_2$Cl$_2$, 0° C., 1 h, 95%; d) HP(O)(OEt)$_2$ (2.0 equiv), KHMDS (0.5M in toluene, 1.8 equiv), THF, 0° C., 15 min, then add substrate, 25° C., 12 h, 91%; e) KOt-Bu (1.0M in THF, 1.0 equiv), THF, -78° C., 20 min, then p-methoxybenzaldehyde (0.95 equiv), -78° C., 1 h, then 25° C., 12 h, 98%;

1-(bromomethyl)-3,5-dimethoxybenzene (S1)

NaBH$_4$ (1.11 g, 30.0 mmol, 2.0 equiv) was added slowly to a solution of 3,5-dimethoxybenzaldehyde (2.44 g, 15.0 mmol, 1.0 equiv) in MeOH (30 mL) at 0° C. After 30 min of stirring at 0° C., the reaction contents were quenched by the slow addition of water (20 mL), poured into water (10 mL), and extracted with EtOAc (3×20 mL). The combined organic layers were then washed with water (20 mL) and brine (20 mL), dried (MgSO$_4$), and concentrated to afford the desired alcohol intermediate (2.43 g, 99% yield) as a white solid which was carried forward without further purification. Next, pyridine (0.017 mL, 0.212 mmol, 0.05 equiv) and PBr$_3$ (0.400 mL, 4.25 mmol, 1.0 equiv) were added sequentially and slowly to a portion of this newly-formed alcohol (0.715 g, 4.25 mmol, 1.0 equiv) in Et$_2$O (20 mL) at 25° C., and the resultant mixture was heated at 40° C. for 3 h. Upon completion, the reaction contents were quenched carefully with ice water (15 mL), poured into water (10 mL), and extracted with Et$_2$O (3×20 mL). The combined organic layers were then washed with water (15 mL) and brine (15 mL), dried (MgSO$_4$), and concentrated to afford alkyl halide 81 (1.50 g, 93% yield) as an amorphous white solid which was carried forward without additional purification. 81: R$_f$=0.66 (silica gel, EtOAc/hexanes, 1:1); IR (film) v$_{max}$ 3002, 2960, 2838, 1597, 1465, 1429, 1348, 1325, 1300, 1264, 1206, 1158, 1064, 992, 931, 836, 693, 650; $^1$H NMR (300 MHz, CDCl$_3$) δ 6.54 (d, J=2.1 Hz, 2H), 6.39 (t, J=2.1 Hz, 1H), 4.42 (s, 2H), 3.80 (s, 6H); $^{13}$C NMR (75 MHz, CDCl$_3$) δ 160.9, 139.7, 107.0 (2C), 100.6, 55.4 (2C), 33.6; HRMS (MALDI-FTMS) calculated for C$_9$H$_{11}$BrO$_2$+ [M$^+$]229.9942. found 229.9937.

Diethyl 2-bromo-3,5-diamthoxybeasylphosphonat (S2)

To a solution of alkyl bromide S1 (1.34 g, 5.80 mmol, 1.0 equiv) in CH$_2$Cl$_2$ (60 mL) at 0° C. was added solid NBS (0.516 g, 2.89 mmol, 0.5 equiv) in a single portion. After stirring the resultant solution for 30 min at 0° C., a second aloquot of NBS was added (0.516 g, 2.89 mmol, 0.5 equiv) and the reaction was stirred for an additional 30 min at 0° C. Upon completion, the reaction mixture was quenched with saturated aqueous NaHCO$_3$ (10 mL), poured into H$_2$O (20 mL), and extracted with EtOAc (3×70 mL). The combined organic layers were then washed with water (20 mL) and brine (20 mL), dried (MgSO$_4$), and concentrated to give the desired halogenated intermediate (1.70 g, 95% yield) as a white solid which was carried forward without additional purification. Next, a portion of this newly formed aryl bromide (1.00 g, 3.22 mmol, 1.0 equiv) was dissolved in THF (5 mL) and added dropwise at 0° C. to a THF solution of the anion of diethylphosphite which had been prepared by adding KHMDS (11.6 mL, 0.5 M in toluene, 5.80 mmol, 1.8 equiv) to a solution of diethylphosphite (0.830 mL, 6.44 mmol, 2.0 equiv) in THF (20 mL) at 0° C. and stirring for 15 min. After 5 min of stirring at 0° C., the reaction contents were warmed to 25° C. and stirred for 12 h. Upon completion, the reaction mixture was quenched with saturated aqueous NH$_4$Cl (10 mL), poured into water (15 mL), and extracted with EtOAc (3×40 mL). The combined organic layers were then washed with water (15 mL) and brine (15 mL), dried (MgSO$_4$), and concentrated. The resultant light yellow product was left under high vacuum for 24 h to remove any residual diethylphosphite, ultimately affording phosphonate S2 (1.07 g, 91% yield) as a white solid. S2: R$_f$=0.15 (silica gel, EtOAc/hexanes, 1:1); IR (film) $v_{max}$ 2981, 2938, 2907, 2837, 1592, 1456, 1418, 1331, 1253, 1204, 1165, 1079, 1052, 1024, 961, 852, 782, 650; $^1$H NMR (300 MHz, CDCl$_3$) δ 6.67 (t, J=2.7 Hz, 1H), 6.39 (t, J=2.4 Hz, 1H), 4.15 (dd, J=6.9, 6.0 Hz, 2H), 4.06 (dd, J=6.9, 6.0 Hz, 2H), 3.86 (s, 3H), 3.80 (s, 3H), 3.43 (d, J=22.2 Hz, 2H), 1.36 (t, J=6.9 Hz, 3H), 1.27 (t, J=6.9 Hz, 3H); $^{13}$C NMR (75 MHz, CDCl$_3$) δ 159.3, 156.8, 133.7, 133.6, 107.4, 107.3, 99.8, 62.3, 62.2, 56.3, 55.5, 34.7, 16.4, 16.3; HRMS (MALDI-FTMS) calcd for C$_{13}$H$_{21}$BrO$_5$P$^+$ [M+H$^+$] 367.0310. found 367.0301.

(E)-2-bromo-1,5-diethoxy-3-(4-methoxystyryl)bensene (9)

KOt-Bu (5.71 mL, 1.0 M in THF, 5.71 mmol, 1.05 equiv) was added dropwise over the course of 5 min to a solution of phosphonate S2 (2.00 g, 5.44 mmol, 1.0 equiv) in THF (25 mL) at −78° C. After 20 min of stirring at −78° C., a solution of anisaldehyde (0.704 g, 5.17 mmol, 0.95 equiv) in THF (5 mL) was added at −78° C. The resultant solution was stirred at −78° C. for 1 h, and then at 25° C. for 12 h. Upon completion, the reaction mixture was quenched with saturated aqueous NH$_4$Cl (15 mL), poured into water (10 mL), and extracted with EtOAc (3×40 mL). The combined organic layers were then washed with water (10 mL) and brine (10 mL), dried (MgSO$_4$), and concentrated to give resveratrol derivative 9 (1.86 g, 98% yield) as a white powder which was carried forward without additional purification. 9: R$_f$=0.61 (silica gel, EtOAc/hexanes, 1:1); IR (film) $v_{max}$ 3002, 2937, 2836, 1719, 1589, 1511, 1454, 1415, 1341, 1286, 1252, 1203, 1163, 1082, 1023, 962, 827; 1H NMR (300 MHz, CDCl$_3$) δ 7.50 (d, J=8.7 Hz, 2H), 7.41 (d, J=16.2 Hz, 1H), 6.98 (d, J=16.2 Hz, 1H), 6.91 (d, J=9.0 Hz, 2H), 6.80 (d, J=2.7 Hz, 1H), 6.42 (d, J=2.7 Hz, 1H), 3.88 (s, 3H), 3.86 (s 3H), 3.83 (s, 3H); $^{13}$C NMR (75 MHz, CDCl$_3$) δ 159.6, 159.5, 156.8, 138.9, 131.1, 129.7, 128.1, 125.8, 114.1, 104.9, 102.4, 98.7, 56.3, 55.5, 55.3; HRMS (MALDI-FTMS) calcd for C$_{17}$H$_{17}$BrO$_3$$^+$ [M$^+$] 348.0361. found 348.0362.

(E)-(2,4-dimethoxy-6-(4-methoxystyryl)phenyl-(3,5-dimethoxyphenyl)methanol (11)

n-BuLi (2.91 mL, 1.6 M in THF, 4.65 mmol, 1.05 equiv) was added slowly over the course of 5 min to a solution of resveratrol derivative 9 (1.62 g, 4.65 mmol, 1.05 equiv) in THF (10 mL) at −78° C., ultimately yielding a light yellow solution. After 20 min of stirring at −78° C., a solution of 3,5-dimethoxybenzaldehyde (0.734 g, 4.42 mmol, 1.0 equiv) in THF (40 mL) was added slowly at −78° C., and the resultant mixture was stirred for 1 h at −78° C., warmed slowly to 25° C., and stirred for an additional 4 h at 25° C. Upon completion, the reaction contents were quenched with saturated aqueous NH$_4$Cl (20 mL), poured into water (20 mL), and extracted with EtOAc (3×40 mL). The combined organic layers were then washed with water (20 mL) and brine (20 mL), dried (MgSO$_4$), and concentrated. The resultant light yellow oil was purified by flash column chromatography (silica gel, EtOAc/hexanes, 2:1) to give aldol adduct 11 (1.43 g, 71% yield) as a white solid. 11: R$_f$=0.40 (silica gel, EtOAc/hexanes, 1:1); IR (film) $v_{max}$ 3509, 3001, 2938, 2837, 1604, 1511, 1458, 1307, 1244, 1204, 1175, 1153, 1059, 1032, 966, 930, 833, 736; 1H NMR (300 MHz, CDCl$_3$) δ 7.36 (d, J=8.7 Hz, 2H), 7.28 (d, J=16.2 Hz, 1H), 6.88 (d, J=16.2 Hz, 1H), 6.86 (d, J=8.7 Hz, 2H), 6.74 (d, J=2.1 Hz, 1H), 6.54 (d, J=2.0 Hz, 2H), 6.45 (d, J=2.1, 1 H), 6.33 (t, J=2.4, 1H), 6.22 (d, J=9 Hz, 1H), 3.86 (s, 3H), 3.80 (s, 3H), 3.78 (s, 1H), 3.74 (s, 6H), 3.72 (s, 3H); $^{13}$C NMR (75 MHz, CDCl$_3$) δ 160.5, 159.8, 159.4, 158.6, 147.5, 138.7, 131.5, 129.9, 127.8, 124.4, 121.7, 114.0, 103.8, 103.1, 98.6, 98.3, 70.0, 55.7, 55.3, 55.1; HRMS (MALDI-FTMS) calcd for C$_{26}$H$_{28}$O$_6$$^+$ [M$^+$]436.1886. found 436.1870.

3-(3,5-dimethoxyphenyl)-4,6-dimethoxy-2-(4-methoxyphenyl)-2,3-dihydro-1H-inden-1-ol (15)

To a solution of aldol adduct 11 (0.150 g, 0.344 mmol, 1.0 equiv) in CH$_2$Cl$_2$ (10 mL) at −78° C. was added in a single portion a solution of TFA (0.027 mL, 0.344 mmol, 1.0 equiv) in CH$_2$Cl$_2$ (0.2 mL). The resultant dark purple reaction mixture was then warmed slowly to −20° C. over the course of 30 min and stirred for 5 h at −20° C. Upon completion, the reaction mixture was quenched sequentially with solid K$_2$CO$_3$ (0.475 g, 3.44 mmol, 10 equiv) and MeOH (10 mL), warmed to 25° C., and stirred for 15 min at 25° C. The reaction contents were then poured into water (15 mL) and extracted with EtOAc (3×40 mL). The combined organic layers were washed with water (15 mL) and brine (15 mL), dried (MgSO$_4$), and concentrated. The resultant brown oil was purified by flash column chromatography (silica gel, EtOAc/hexanes, 2:1) to give alcohol 15 (0.113 g, 75% yield) as an amorphous white solid. 15: R$_f$=0.41 (silica gel, EtOAc/hexanes, 1:1); IR (film) $v_{max}$ 2935, 1597, 1512, 1463, 1304, 1248, 1203, 1151, 1060, 829; $^1$H NMR (300 MHz, CDCl$_3$) δ 7.09 (d, J=8.7 Hz, 2H), 6.83 (d, J=8.7 Hz, 2H), 6.65 (d, J=2.1 Hz, 1H), 6.42 (d, J=2.1 Hz, 1H), 6.27 (t, J=2.3 Hz, 1H), 6.17 (d, J=2.4 Hz, 2H), 5.13 (app t, J=5.7 Hz, 1H), 4.19 (d, J=6.9 Hz, 1H), 3.86 (s, 3H), 3.79 (s, 3H), 3.68 (s, 3H), 3.59 (s, 3H), 3.18 (d, J=6.6 Hz, 1H); $^{13}$C NMR (75 MHz, CDCl$_3$) δ 161.7, 160.4, 158.5, 157.1, 146.9, 146.3, 134.0, 128.7, 122.9, 113.9, 105.5, 99.7, 99.4, 99.3, 98.0, 82.5, 66.1, 55.6, 55.3, 55.2, 54.7; HRMS (MALDI-FTMS) calculated for C$_{26}$H$_{21}$O$_6$$^+$ [M$^+$] 436.1886. found 436.1870.

Paucifloral P (7)

Dess-Martin periodinane (0.152 g, 0.358 mmol, 1.2 equiv) was added in a single portion to a solution of alcohol 13 (0.130 g, 0.298 mmol, 1.0 equiv) in CH$_2$Cl$_2$ (8 mL) at 25° C., and the resultant slurry was stirred for 1 h at 25° C. Upon completion, the reaction contents were quenched with saturated aqueous Na$_2$SO$_3$ (1.5 mL) followed by stirring the resultant biphasic system vigorously for 5 min at 25° C. The reaction contents were then poured into saturated aqueous NaHCO$_3$ (5 mL) and extracted with EtOAc (3×10 mL). The combined organic layers were washed with water (5 mL) and brine (5 mL), dried (MgSO$_4$), and concentrated to afford permethylated paucifloral F (0.122 g, 97% yield) as a light yellow oil which was carried forward without additional purification. R$_f$=0.45 (silica gel, EtOAc/hexanes, 1:1); IR (film) v$_{max}$ 1696, 1614, 1514, 1474, 1347, 1155, 1082, 1005, 842; 1H NMR (300 MHz, CDCl$_3$) δ 7.02 (d, J=8.7 Hz, 2H), 6.90 (d, J=2.1 Hz, 1H), 6.84 (d, J=8.7 Hz, 2H), 6.70 (d, J=2.1 Hz, 1H), 6.32 (app t, J=2.4 Hz, 1H), 6.16 (d, J=2.4 Hz, 2H), 4.44 (d, J=2.7 Hz, 1H), 3.88 (s, 3H), 3.78 (s, 3H), 3.71 (s, 3H), 3.69 (s, 3H), 3.65 (d, J=3.0 Hz, 1H); $^{13}$C NMR (75 MHz, CDCl$_3$) δ 205.9, 162.0 (2C), 160.8, 158.6, 157.8, 145.9, 138.7, 137.6, 131.5, 128.8, 114.2 (2C), 106.4, 105.1 (2C), 98.1, 96.4, 64.1, 55.8, 55.6, 55.2, 51.9. Finally, a solution of this newly synthesized ketone (0.035 g, 0.081 mmol, 1.0 equiv) in CH$_2$Cl$_2$ (3 mL) was added dropwise to a commercially-prepared solution of BBr$_3$ (0.770 mL, 1.0 M in CH$_2$Cl$_2$, 0.810 mmol, 10 equiv) at 0° C., and the resultant solution was stirred for 6 h at 0° C. Upon completion, the reaction mixture was quenched with water (5 mL), poured into water (10 mL), and extracted with EtOAc (3×20 mL). The combined organic layers were then washed with water (5 mL) and brine (5 mL), dried (MgSO$_4$), and concentrated. The resultant light pink product was purified by flash column chromatography (silica gel, CH$_2$Cl$_2$/MeOH, 9:1) to give paucifloral F (0.025 g, 86% yield) as an amorphous white solid. 7: R$_f$=0.06 (silica gel, CH$_2$Cl$_2$/MeOH, 9:1); IR (film) v$_{max}$ 3334, 1696, 1614, 1514, 1474, 1347, 1155, 1082, 1005, 842; 1H NMR (300 MHz, Acetone-d$_6$) δ 8.75 (s, 1H), 8.49 (s, 1H), 8.27 (s, 1H), 8.07 (s, 2H), 6.96 (d, J=8.7 Hz, 2H), 6.78 (d, J=8.7 Hz, 2H), 6.72 (s, 2H), 6.19 (app t, J=2.1 Hz, 1H), 6.02 (d, J=2.1 Hz, 2H), 4.38 (d, J=2.7 Hz, 1H), 3.50 (d, J=2.7 Hz, 1H); $^{13}$C NMR (75 MHz, Acetone-d) δ 205.5, 160.2, 159.5, 157.2, 156.7, 147.3, 140.0, 134.8, 131.8, 129.6, 116.3, 110.2, 106.3, 101.6, 100.5, 65.3, 52.1; HRMS (MALDI-FTMS) calcd for C$_{21}$H$_{17}$O$_6$S [M+H$^+$] 365.1025. found 365.1055. All spectroscopic data for this synthetic material match those reported by Ito and co-workers for natural paucifloral F (7) [21].

Sulfide 16

Solid p-TsOH (0.039 g, 0.229 mmol, 1.0 equiv) was added in a single portion to a solution of aldol adduct 11 (0.100 g, 0.229 mmol, 1.0 equiv) in CH$_2$Cl$_2$ (10 mL) at −50° C. The resultant mixture was then warmed slowly to −30° C. over the course of 20 min and stirred for an additional 5 h at −30° C. Once this operation was complete, the reaction contents were warmed to 0° C., p-methoxy-α-toluenethiol (0.096 mL, 0.687 mmol, 3.0 equiv) was added in a single portion, and the resultant mixture was concentrated to a minimum volume (approximately 0.2 mL). The resultant solution was then stirred for 12 h at 25° C. Upon completion, the reaction mixture was quenched with saturated aqueous NaHCO$_3$ (5 mL), poured into water (5 mL), and extracted with EtOAc (3×10 mL). The combined organic layers were then washed with water (10 mL) and brine (10 mL), dried (MgSO$_4$), and concentrated. The resulted yellow product was purified by flash column chromatography (silica gel, EtOAc/hexanes, 1:1) to give a sulfide 16 (0.075 g, 57%) as a light yellow oil. Alternatively, p-methoxy-α-toluenethiol (0.240 mL, 1.72 mmol, 3.0 equiv) and p-TsOH (0.099 g, 0.573 mmol, 1.0 equiv) were added to a highly concentrated solution of alcohol 15 (0.250 g, 0.573 mmol, 1.0 equiv) in CH$_2$Cl$_2$ (0.5 mL) at 25° C. The resulting yellow-green solution was stirred for 24 h at 25° C. under the strict exclusion of light. Upon completion, the reaction mixture was quenched with saturated aqueous NaHCO$_3$ (5 mL), poured into water (5 mL), and extracted with EtOAc (3×10 mL). The combined organic layers were then washed with water (10 mL) and brine (10 mL), dried (MgSO$_4$), and concentrated. The resultant light green product was purified by flash column chromatography (silica gel, EtOAc/hexanes, 1:3) to give a sulfide 16 (0.269 g, 82%) as a light yellow oil. 16: R$_f$=0.71 (silica gel, EtOAc/hexanes, 1:1); IR (film) v$_{max}$ 2995, 2934, 2831, 1607, 1512, 1463, 1421, 1326, 1303, 1249, 1203, 1175, 1154, 1061, 1035, 934, 830; $^1$H NMR (300 MHz, CDCl$_3$, 1:1 mixture of diastereomers) δ7.13 (d, J=8.4 Hz, 2H), 7.07 (d, J=8.7 Hz, 2H), 7.04 (d, J=9.0 Hz, 2H), 7.03 (d, J=8.4 Hz, 2H), 6.84 (d, J=2.4 Hz, 2H), 6.80 (d, J 2.7 Hz, 2H), 6.79 (s, 1H), 6.77 (s, 1H), 6.74 (d, J=8.7 Hz, 2H), 6.53 (d, J=1.5 Hz, 1H), 6.45 (d, J=1.5 Hz, 1H), 6.36 (br m, 3H), 6.28 (br m, 2H), 6.18 (br m, 4H), 4.55 (s, 1H), 4.53 (d, J=2.7 Hz, 1H), 4.22 (app t, J=7.2 Hz, 3H), 3.82 (s, 3H), 3.81 (s, 3H), 3.80 (s, 3H), 3.79 (s, 3H), 3.77 (s, 3H), 3.76 (s, 3H), 3.69 (s, 3H), 3.68 (s, 6H), 3.61 (s, 3H), 3.57 (s, 6H); $^{13}$C NMR (75 MHz, CDCl$_3$, 1:1 mixture of diastereomers) δ 161.5, 161.3, 160.5, 160.3, 158.5, 157.0, 156.8, 147.1, 146.5, 146.2, 145.3, 135.7, 133.5, 130.3, 130.0, 129.8, 128.6, 124.1, 123.7, 113.9, 113.8, 113.7, 113.3, 105.5, 100.8, 100.4, 98.9, 98.5, 98.1, 97.9, 64.6, 60.3, 57.2, 56.7, 55.5, 55.2, 54.0, 53.7, 36.0, 34.9; HRMS (MALDI-FTMS) calcd for C$_{31}$H$_{35}$O$_6$S [M−H$^+$]571.2154. found 571.2168.

Ampelopsin D (2)

Solid NaHCO$_3$ (0.257 g, 3.06 mmol, 5.0 equiv) and mCPBA (55%, 0.317 g, 1.84 mmol, 3.0 equiv) were added sequentially to a solution of sulfide 16 (0.350 g, 0.612 mmol, 1.0 equiv) in CH$_2$Cl$_2$ (20 mL) at 0° C. to give a milk-colored slurry. After warming this mixture to 25° C. and stirring for 3 h, the reaction contents were quenched with saturated aqueous NaHCO$_3$ (15 mL), poured into water (10 mL), and extracted with EtOAc (3×20 mL). The combined organic layers were then washed with water (20 mL) and brine (20 mL), dried (MgSO$_4$), and concentrated. The resultant off-white solid was purified by flash column chromatography (silica gel, EtOAc/hexanes, 1:1) to give the desired sulfone intermediate (0.289 g, 78%) as a yellow-pink oil. Next, finely powdered KOH (0.186 g, 3.31 mmol, 20 equiv) was added in a single portion to a solution of a portion of this newly synthesized adduct (0.100 g, 0.166 mmol, 1.0 equiv) in a mixture of CCl$_4$/t-BuOH/H$_2$O (5/5/1, 3.8 mL/3.8 mL/0.79 mL) at 25° C. The resultant slurry was then stirred for 12 h at 80° C. Upon completion, the reaction mixture was quenched with saturated aqueous NH$_4$Cl (2 mL), poured into water (5 mL), and extracted with EtOAc (3×10 mL). The combined organic layers were then washed with water (5 mL) and brine (5 mL), dried (MgSO$_4$), and concentrated. The resultant light yellow oil was purified by flash column chromatography (silica gel, EtOAc/hexanes, 1:1) to give both the desired alkene (28, 0.042 g, 52%) as a yellow oil along with a small portion of its exocyclic olefinic regioisomer (0.013 g, 15%) as a light yellow oil. 28: R$_f$=0.53 (silica gel, EtOAc/hexanes, 1:1); IR (film) v$_{max}$ 2995, 2934, 2836, 1606, 1509, 1463, 1288, 1248, 1203, 1175, 1152, 1065, 1036, 827; $^1$H NMR (300 MHz, CDCl$_3$) δ 7.20 (d, J=8.7 Hz, 2H), 7.18 (d, J=8.4 Hz, 2H), 7.09 (s, 1H), 6.85 (d, J=1.8 Hz, 1H), 6.80 (d, J=8.4 Hz, 2H), 6.72 (d, J=8.7 Hz, 2H), 6.33 (d, J=1.8 Hz, 1H), 6.29 (d, J=2.1 Hz, 1H), 6.27 (d, J=2.1 Hz, 1H), 4.36 (s, 1H), 4.25 (s, 1H), 3.93 (s, 3H), 3.76 (s, 3H), 3.73 (s, 3H), 3.71 (s, 6H), 3.62 (s, 3H); $^{13}$C NMR (75 MHz, CDCl$_3$) δ 161.5, 160.6, 158.4, 158.0, 157.6, 148.1, 145.6, 142.7, 137.3, 130.0, 129.6, 127.9, 126.0, 122.1, 114.1, 113.7, 105.3, 99.1, 97.5, 94.9, 58.0, 57.9, 55.6, 55.2 (2C); HRMS (MALDI-FTMS) calculated for C$_{34}$H$_{34}$O$_{60}$

[M+]538.2355. found 538.2357. Finally, permethylated ampelopsin D (28, 0.050 g, 0.090 mmol, 1.0 equiv) was added as a solution in $CH_2Cl_2$ (5 mL) at 25° C. to a freshly-prepared solution of $BBr_3$ [made by dissolving solid $BBr_3$ (0.271 g, 1.08 mmol, 12 equiv) in $CH_2Cl_2$ (5 mL) at 25° C. in dry box], and the resulting solution was stirred for 6 h at 25° C. Upon completion, the reaction mixture was quenched with saturated aqueous $NaHCO_3$ (15 mL), poured into water (15 mL), and extracted with EtOAc (3×15 mL). The combined organic layers were then washed with water (20 mL) and brine (20 mL), dried ($MgSO_4$), and concentrated. The resultant light yellow solid was purified by flash column chromatography (silica gel, $CH_2Cl_2$/MeOH, 9:1) to afford a 5/1 mixture of ampelopsin D and isoampelopsin D (0.041 g combined, 89% overall) as colorless oils. These regioisomers were obtained individually in near quantitative yield (95%) following acetylation [$Ac_2O$, pyridine], chromatographic separation via flash column chromatography, and acetate hydrolysis [cat. KCN, MeOH]. 2: $R_f$=0.03 (silica gel, $CH_2Cl_2$/MeOH, 9:1); IR (film) $v_{max}$ 3339, 1604, 1511, 1465, 1374, 1335, 1238, 1147, 1010, 834, 650; $^1$H NMR (300 MHz, acetone-$d_6$) δ 8.30 (br s, 1H), 8.20 (br s, 1H), 8.11 (br s, 1H), 7.97 (br s, 2H), 7.85 (br s, 1H), 7.18 (d, J=8.7 Hz, 2H), 7.12 (d, J 8.7 Hz, 2H), 7.04 (app t, J=0.6 Hz, 1H), 6.81 (d, J=1.8 Hz, 1H), 6.75 (d, J=8.4 Hz, 2H), 6.66 (d, J=8.7 Hz, 2H), 6.30 (d, J=2.1 Hz, 1H), 6.11 (m, 3H), 4.29 (s, 1H), 4.15 (s, 1H); $^{13}$C NMR (75 MHz, acetone-$d_6$) δ 159.7, 159.3, 157.3, 156.7, 156.1, 149.3, 147.6, 143.1, 137.4, 131.0, 129.7, 128.8, 123.8, 122.7, 116.3, 116.0, 106.5, 103.8, 101.3, 98.4, 59.5, 58.7; HRMS (MALDI-FTMS) calcd for $C_{28}H_{22}O_6$, [M+]454.1416. found 454.1448. All spectroscopic data for this synthetic material match those reported by Niwa and co-workers for natural ampelopsin D (2) (22).

Isoampelopsin D (17)

Concentrated HCl (50 mL, 0.600 mmol, 5.5 equiv.) was added to a solution of ampelopsin D (2, 5.0 mg, 0.110 mmol, 1.0 equiv) in MeOH (0.5 mL) at 25° C., and the resultant mixture was stirred at 80° C. for 12 h. Upon completion, the reaction mixture was quenched with water (3 mL) and extracted with EtOAc (3×10 mL). The combined organic layers were then washed with water (5 mL) and brine (5 mL), dried ($MgSO_4$), and concentrated. The resulted light yellow product was purified by flash column chromatography (silica gel, $CH_2Cl_2$/MeOH, 9:1) to give isoampelopsin D 17 (4.8 mg, 96%) as a colorless oil. 17: $R_f$=0.13 (silica gel, $CH_2Cl_2$/MeOH, 9:1); IR (film) $v_{max}$ 3411, 2810, 1680, 1628, 1511, 1443, 1371, 1333, 1206, 1149, 1055, 1006, 833; $^1$H NMR (300 MHz, methanol-$d_4$) δ 7.11 (d, J=8.4 Hz, 2H), 7.07 (d, J=8.7 Hz, 2H), 6.73 (d, J=8.7 Hz, 2H), 6.66 (d, J=8.7 Hz, 2H), 6.17 (d, J=2.1 Hz, 1H), 6.06 (d, J=1.5 Hz, 1H), 6.06 (d, J=2.1 Hz, 2H), 5.99 (t, J=2.1 Hz, 1H), 4.80 (s, 1H), 3.84 (s, 2H); $^{13}$C NMR (75 MHz, methanol-$d_4$) δ 158.9, 158.7, 157.5, 156.5, 154.0, 150.4, 149.9, 144.0, 136.6, 132.1, 131.1, 130.2, 128.9, 125.4, 116.3, 115.8, 108.1, 101.4, 100.7, 56.7, 32.2; HRMS (MALDI-FTMS) calcd for $C_{28}H_{22}O_6$·[M+]454.1416. found 454.1428. All spectroscopic data for this synthetic material match those reported by Niwa and co-workers for natural isoampelopsin (15) [22].

Total Synthesis of Quadrangularin A (21) and Isopaucifloral F (22)

These two natural products were synthesized from intermediate 82 exactly as described above for ampelopsin D (2) and paucifloral F (6) by substituting 3,5-dimethoxybenzaldehyde in the Horner-Wadsworth-Emmons reaction leading to intermediate 18. Only the final deprotection leading to isopaucifloral F (22) in Scheme 2 is fundamentally different from the steps outlined above, so only this procedure is defined specifically on the ensuing pages.

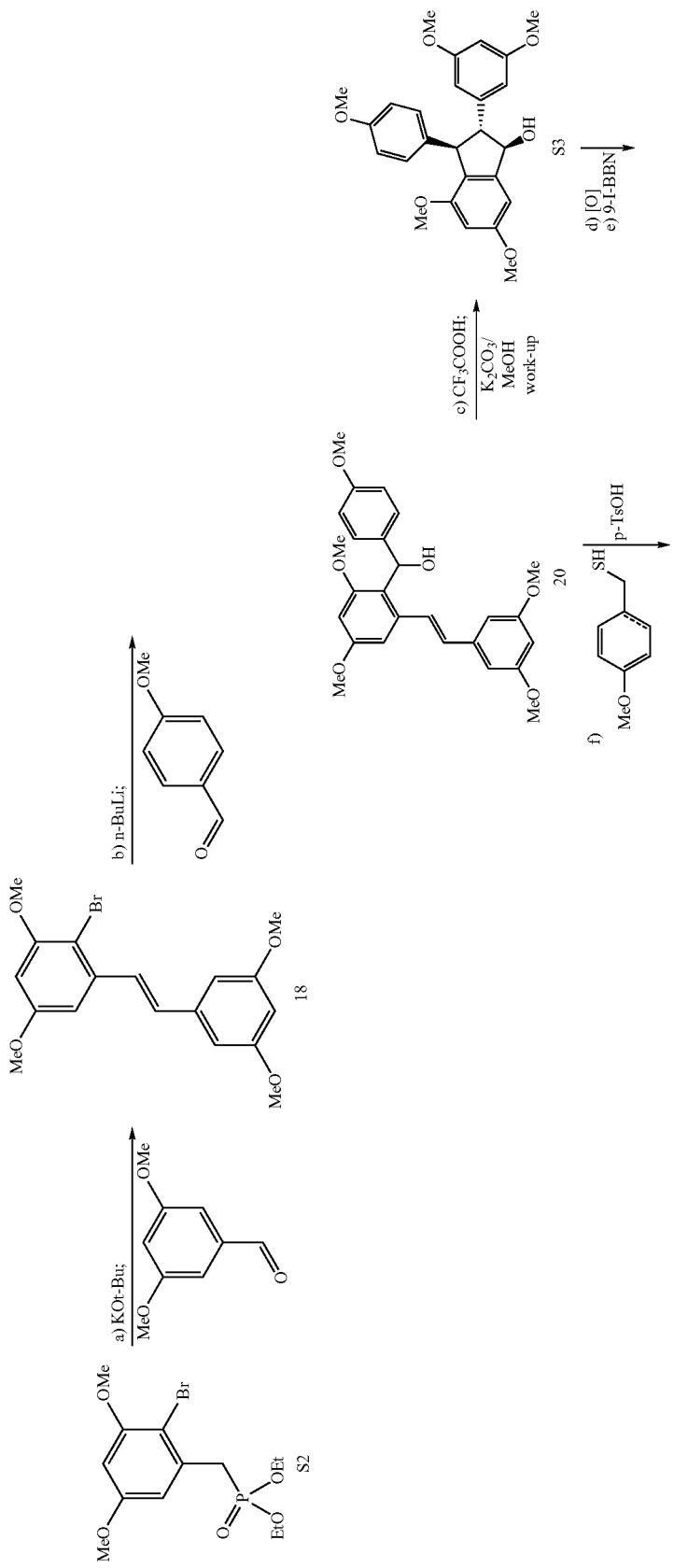

-continued

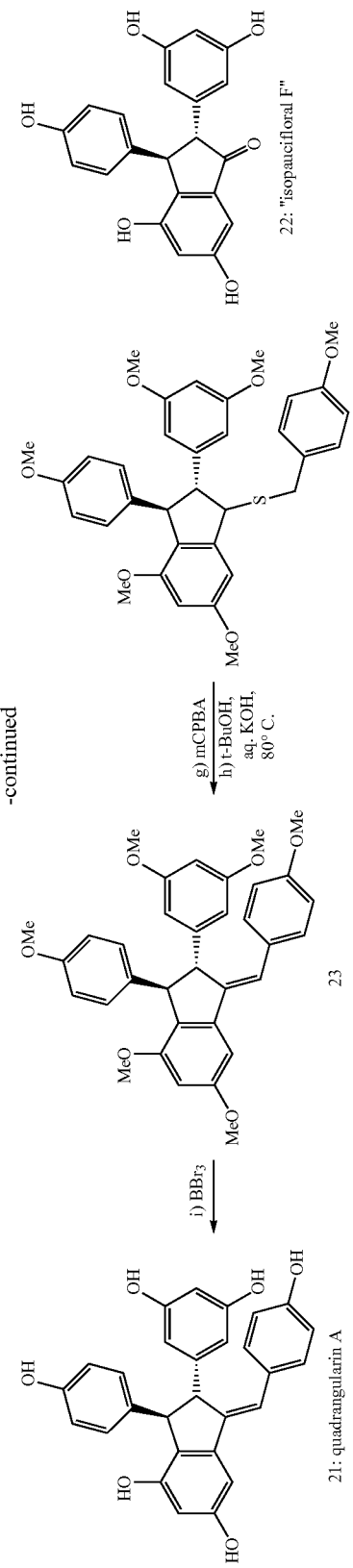

a) KOt-Bu (1.0M in THF, 1.0 equiv), THF, -78° C., 20 min, then 3,5-dimethoxybenzaldehyde (0.95 equiv), -78° C., 1 h, then 25° C., 12 h, 98%; b) n-BuLi (1.0 equiv), THF, -78° C., 20 min; then p-methoxybenzaldehyde (1.0 equiv), -78 → 25° C., 4 h, 71%; c) TFA (1.0 equiv), CH$_2$Cl$_2$, -30 → -20° C., 5 h; then K$_2$CO$_3$ (10 equiv), MeOH, 25° C., 5 min 93%; d) Dess-Martin periodinane (1.2 equiv), NaHCO$_3$ (5.0 equiv), CH$_2$Cl$_2$, 25° C., 3 h, 98%; e) 9-I-BBN (1.0M in hexanes, 1 equiv), CH$_2$Cl, 40° C., 30 min, 72%; f) p-TsOH (1.0 equiv), CH$_2$Cl$_2$, -30 → -20° C., 5 h; p-methoxybenzenethiol (3.0 equiv), CH$_2$Cl$_2$, -30 → -20° C., 12 h, 65%; g) mCPBA (3.0 equiv), NaHCO$_3$ (10 equiv), CH$_2$Cl$_2$, 0 → 25° C., 3 h, 70%; f) t-BuOH/H$_2$O/CCl$_4$ (5/1/5), KOH (powder, 20 equiv), 80° C., 12 h, 55%; g) BBr$_3$ 1.0M in CH$_2$Cl$_2$, 12 equiv), CH$_2$Cl$_2$, 25° C., 6 h, 75% of 15, 14% of internal alkene isomer, 9-I-BBN = 9-iodo-9-borabicyclo[3.3.1]nonane.

18: $R_f$=0.55 (silica gel, EtOAc/hexanes, 1:1); IR (film) $v_{max}$ 3001, 2957, 2938, 2837, 1592, 1457, 1418, 1353, 1288, 1230, 1204, 1155, 1083, 1022, 959, 829, 650; $^1$H NMR (300 MHz, CDCl$_3$) δ 7.50 (d, J=15.9 Hz, 1H), 6.94 (d, J=15.9, 1H), 6.80 (d, J=2.7 Hz, 1H), 6.71 (d, J=2.4 Hz, 2H), 6.43 (d, J=2.7 Hz, 1H), 6.42 (t, J=2.1 1H), 3.88 (s, 3H), 3.85 (s, 3H), 3.83 (s, 6H); $^{13}$C NMR (75 MHz, CDCl$_3$) δ 160.9, 159.5, 156.8, 138.9, 138.5, 131.5, 128.4, 104.9, 102.7, 100.3, 99.1, 56.3, 55.5, 55.3; HRMS (MALDI-FTMS) calcd for $C_{18}H_{19}BrO_4$+ [M+]378.0467. found 378.0484.

20: $R_f$=0.45 (silica gel, EtOAc/hexanes, 1:1); IR (film) $v_{max}$ 3508, 3001, 2938, 2837, 1599, 1510, 1459, 1425, 1323, 1283, 1246, 1203, 1152, 1064, 1035, 964, 835, 799, 736; $^1$H NMR (300 MHz, CDCl$_3$) δ 7.36 (d, J=15.9 Hz, 1H), 7.24 (d, J=8.4 Hz, 2H), 6.84 (d, J=15.9 Hz, 1H), 6.82 (d, J=8.7 Hz, 2H), 6.74 (d, J=2.4 Hz, 1H), 6.56 (d, J=2.1 Hz, 2H), 6.48 (d, J=2.4 Hz, 1H), 6.38 (t, J=2.1 Hz, 1H), 6.23 (d, J=9.9 Hz, 1H), 3.87 (s, 3H), 3.80 (s, 6H), 3.77 (s, 3H), 3.73 (s, 3H); $^{13}$C NMR (75 MHz, CDCl$_3$) δ 160.9, 159.8, 158.8, 158.3, 139.1, 138.2, 136.8, 132.0, 127.1, 126.9, 122.3, 113.4, 104.6, 103.3, 100.3, 99.1, 69.8, 55.7, 55.4, 55.3, 55.2; HRMS (MALDI-FTMS) calcd for $C_{26}H_{28}O_6$+ [M+] 436.1886. found 436.1870. S3: $R_f$=0.48 (silica gel, EtOAc/hexanes, 1:1); IR (film) $v_{max}$ 3475, 2934, 2837, 1596, 1512, 1463, 1429, 1304, 1245, 1203, 1149, 1046, 935, 831, 735; $^1$H NMR (300 MHz, CDCl$_3$) δ 6.95 (d, J=8.7 Hz, 2H), 6.75 (d, J=8.7 Hz, 2H), 6.65 (d, J=1.8 Hz, 1H), 6.41 (d, J=2.1 Hz, 1H), 6.34 (app t, J=2.7 Hz, 1H), 6.32 (d, J=2.1 Hz, 2H), 5.18 (t, J=6.0 Hz, 1H), 4.26 (d, J=7.2 Hz, 1H), 3.85 (s, 3H), 3.76 (s, 3H), 3.73 (s, 3H), 3.54 (s, 3H), 3.13 (t, J=6.9 Hz, 1H); $^{13}$C NMR (75 MHz, CDCl$_3$) δ 161.6, 160.8, 157.7, 157.1, 146.1, 144.2, 136.5, 128.2, 123.3, 113.3, 105.8, 99.7, 99.2, 98.5, 82.2, 67.5, 55.6, 55.2, 55.1, 53.3; HRMS (MALDI-FTMS) calcd for $C_{26}H_{28}O_6$+ [M+]436.1886. found 436.1870.

Permethylated Isopaucifloral F $R_f$=0.45 (silica gel, EtOAc/hexanes, 1:1); IR (film) $v_{max}$ 3001, 2935, 2837, 1713, 1596, 1511, 1462, 1431, 1305, 1247, 1204, 1151, 1065, 1036, 835; $^1$H NMR (300 MHz, CDCl$_3$) δ 6.94 (d, J=8.7 Hz, 2H), 6.89 (d, J=2.1 Hz, 1H), 6.79 (d, J=8.7 Hz, 2H), 6.69 (d, J=2.1 Hz, 1H), 6.36 (app t, J=2.1 Hz, 1H), 6.24 (d, J=2.1 Hz, 1H), 4.51 (d, J=2.4 Hz, 1H), 3.88 (s, 3H), 3.78 (s, 3H), 3.74 (s, 6H), 3.66 (s, 3H), 3.61 (d, J=2.7 Hz, 1H); $^{13}$C NMR (75 MHz, CDCl$_3$) δ 205.4, 161.9, 161.0, 158.1, 157.7, 141.5, 138.5, 138.4, 135.4, 127.9, 113.8, 106.6, 106.0, 98.9, 96.4, 77.2, 65.3, 55.8, 55.6, 55.3, 55.2, 50.9; HRMS (MALDI-FTMS) calcd for $C_{26}H_{26}O_6$+ [M+]434.1742. found 434.1746.

Isopaucifloral F (22)

9-I-BBN (1.61 mL, 1.0 M in hexanes, 1.61 mmol, 7.0 equiv) was added dropwise to a solution of permethylated isopaucifloral F (0.100 g, 0.240 mmol, 1.0 equiv) in CH$_2$Cl$_2$ (10 mL) at 25° C. The reaction solution turned a red color immediately, and was immediately heated at 40° C. for 30 min with continued stirring. Upon completion, the reaction mixture was cooled to 25° C., quenched with water (15 mL) and extracted with EtOAc (3×20 mL). The combined organic layers were then washed with water (15 mL) and brine (15 mL), dried (MgSO$_4$), and concentrated. The resultant red oil was purified by flash column chromatography (silica gel, CH$_2$Cl$_2$/MeOH, 9:1) to afford isopaucifloral F (0.063 g, 721) as colorless oil. 22: $R_f$=0.06 (silica gel, CH$_2$Cl$_2$/MeOH, 9:1); IR (film) $v_{max}$ 3349, 1691, 1602, 1512, 1418, 1342, 1251, 1149; $^1$H NMR (300 MHz, CDCl$_3$) δ 8.13 (s, 3H), 7.35 (s, 2H), 6.89 (d, J=8.7 Hz, 2H), 6.74 (d, J=8.7 Hz, 2H), 6.71 (d, J=2.1 Hz, 1H), 6.24 (t, J=2.1 Hz, 1H), 6.11 (d, J=2.1 Hz, 2H), 4.48 (d, J=2.4 Hz, 1H), 3.42 (d, J=2.7 Hz, 1H); $^{13}$C NMR (75 MHz, CDCl$_3$) δ 205.1, 160.2, 159.6, 156.8, 156.6, 143.3, 140.1, 135.7, 135.3, 128.9, 116.1, 110.3, 107.0, 102.1, 100.7, 66.3, 51.4; HRMS (MALDI-FTMS) calcd for $C_{21}H_{16}O_6$+ [M+]364.0947. found 364.0961.

S4: $R_f$=0.55 (silica gel, EtOAc/hexanes, 1:1); IR (film) $v_{max}$ 2999, 2936, 2836, 1595, 1511, 1446, 1428, 1329, 1302, 1247, 1206, 1175, 1153, 1090, 1067, 1035, 830, 736; $^1$H NMR (300 MHz, CDCl$_3$) δ 7.03 (d, J=8.7 Hz, 2H), 6.92 (d, J=8.7 Hz, 2H), 6.74 (d, J=8.4 Hz, 4H), 6.55 (d, J=1.2 Hz, 1H), 6.35 (d, J=1.8 Hz, 2H), 6.26 (d, J=1.8 Hz, 2H), 4.29 (d, J=6.9 Hz, 1H), 4.24 (d, J=7.5 Hz, 1H), 3.83 (s, 3H), 3.78 (s, 3H), 3.76 (s, 3H), 3.73 (s, 6H), 3.53 (s, 3H); $^{13}$C NMR (75 MHz, CDCl$_3$) δ 161.1, 160.7, 158.5, 157.8, 157.0, 145.9, 145.1, 136.8, 130.3, 130.1, 129.1, 128.3, 124.1, 113.7, 113.3, 105.8, 100.4, 99.0, 98.6, 66.4, 56.2, 56.0, 55.6, 55.3, 34.9, 29.7; HRMS (MALDI-FTMS) calcd for $C_{34}H_{36}O_6S$+ [M+] 572.2233. found 572.2233.

23: $R_f$=0.50 (silica gel, EtOAc/hexanes, 1:1); IR (film) $v_{max}$ 2995, 2925, 2831, 1593, 1509, 1462, 1246, 1202, 1151, 1061, 1035; $^1$H NMR (300 MHz, CDCl$_3$) δ 7.24 (d, J=9.0 Hz, 2H), 7.12 (s, 1H), 7.05 (d, J=8.7 Hz, 2H), 6.85 (d, J=2.1 Hz, 1H), 6.77 (d, J=8.7 Hz, 2H), 6.75 (d, J=8.7 Hz, 2H), 6.45 (d, J=2.1 Hz, 2H), 6.33 (d, J=2.1 Hz, 1H), 6.31 (app t, J=2.1 Hz, 1H), 4.32 (d, J=4.2 Hz, 2H), 3.93 (s, 3H), 3.75 (s, 3H), 3.74 (s, 3H), 3.74 (s, 6H), 3.61 (s, 3H); $^{13}$C NMR (75 MHz, CDCl$_3$) δ 161.4, 160.9, 158.4, 157.8, 157.4, 147.7, 145.2, 142.2, 137.9, 130.0, 129.7, 127.8, 126.8, 122.4, 113.7, 105.3, 99.1, 97.6, 94.8, 59.2, 56.8, 55.5, 55.2 (3C); HRMS (MALDI-FTMS) calcd for $C_{34}H_{34}O_6$+ [M−2H+] 538.2374. found 538.2355.

Quadrangularin A (21)

16: $R_f$=0.03 (silica gel, CH$_2$Cl$_2$/MeOH, 9:1); IR (film) $v_{max}$ 3306, 1603, 1511, 1459, 1339, 1242, 1149, 1004, 833, 650; $^1$H NMR (300 MHz, MeOH-d$_3$) δ 7.13 (d, J=8.7 Hz, 2H), 6.98 (s, 1H), 6.88 (d, J=8.7 Hz, 2H), 6.70 (d, J=1.8 Hz, 1H), 6.62 (d, J=8.7 Hz, 2H), 6.60 (d, J=8.7 Hz, 2H), 6.22 (d, J=2.1 Hz, 2H), 6.17 (d, J=1.8 Hz, 1H), 6.09 (t, J=2.1 Hz, 1H), 4.17 (br s, 1H), 4.03 (br s, 1H); $^{13}$C NMR (75 MHz, MeOH-d$_3$) δ 159.7 (2C), 157.4, 156.5, 156.2, 149.7, 147.7, 143.4, 138.5, 131.2 (2C), 130.3, 128.9 (2C), 125.4, 123.1, 116.0 (4C), 106.6 (2C), 103.8, 101.5, 98.4, 61.2, 58.1; HRMS (MALDI-FTMS) calcd for $C_{28}H_{22}O_6$+ [M+]454.1416. found 454.1440. All spectroscopic data for this synthetic material match those reported by Pals and co-workers for natural quadrangularin A (21) [23].

Monobrominated Intermediate 24

Solid NBS (3.2 mg, 0.018 mmol, 1.0 equiv) was added in a single portion to a solution of permethylated quadrangularin A (23, 10 mg, 0.018 mmol, 1.0 equiv) in THF (5 mL) at −78° C. The resultant solution was stirred for 5 min at −78° C. and then was slowly warmed to 25° C. over the course of 3 h. Upon completion, the reaction mixture was quenched with saturated aqueous NaHCO$_3$ (5 mL), poured into water (5 mL), and extracted with EtOAc (3×5 mL). The combined organic layers were then washed with water (5 mL) and brine (5 mL), dried (MgSO$_4$), and concentrated. The resultant brown residue was purified by flash column chromatography (silica gel, EtOAc/hexanes, 1:1) to afford bromide 24 (8.0 mg, 72%) as a light yellow oil. 24: $R_f$=0.50 (silica gel, EtOAc/hexanes, 1:1); IR (film) $v_{max}$ 2934, 1592, 1511, 1460, 1330, 1252, 1204, 1177, 1157, 1034, 829, 732; $^1$H NMR (300 MHZ, CDCl$_3$): 8.07 (s, 1H), 7.16 (d, J=8.7 Hz, 2H), 7.05 (d, J=8.7 Hz, 2H), 6.75 (d, J=3.9 Hz, 2H), 6.72 (d, J=3.9 Hz, 2H), 6.44 (d, J=2.1 Hz, 2H), 6.34 (s, 2H), 6.31 (m, 1H), 4.26 (s, 2H), 3.93 (s, 3H), 3.74 (s, 3H), 3.74 (s, 6H), 3.72 (s, 3H), 3.64 (s, 3H); $^{13}$C NMR (75 MHz, CDCl$_3$) δ 161.0, 158.7, 157.9, 157.0, 156.0, 147.9, 142.0, 141.2, 137.0, 136.8, 130.3, 130.1, 129.8, 129.0, 128.4, 127.8, 113.7, 105.2, 98.0, 97.3, 96.3, 59.0, 56.9, 56.3, 55.9, 55.5, 55.2; HRMS (MALDI-FTMS) calcd for C$_{34}$H$_{33}$BrO$_6^+$ [M$^+$] 616.1461. found 616.1439.

Dibrominated Intermediate 25

A solution of Br$_2$ (2.90 L, 0.056 mmol, 1.0 equiv) in CH$_2$Cl$_2$ (0.5 mL) was added dropwise to a solution of permethylated quadrangularin A (23, 0.030 g, 0.056 mmol, 1.0 equiv) in CH$_2$Cl$_2$ (3.0 mL) at −78° C. The resultant solution was stirred at −78° C. for 2 h, warmed slowly to 25 OC over the course of 1 h, and stirred for an additional 1 h at 25° C. Upon completion, the reaction mixture was quenched with saturated aqueous NaHCO$_3$ (5 mL), poured into water (5 mL), and extracted with EtOAc (3×15 mL). The combined organic layers were then washed with water (15 mL) and brine (15 mL), dried (MgSO$_4$), and concentrated. The resultant product was purified by flash column chromatography (silica gel, EtOAc/hexanes, 1:1) to give bromide 25 (0.033 g, 83%) as a light yellow oil. 25: R$_f$=0.50 (silica gel, EtOAc/hexanes, 1:1); IR (film) ν$_{max}$ 2954, 1586, 1511, 1460, 1330, 1252, 1177, 1034; $^1$H NMR (300 MHz, CDCl$_3$) δ 8.08 (s, 1H), 7.27 (d, J=2.4 Hz, 1H), 7.16 (d, J=8.7 Hz, 2H), 7.10 (d, J=8.7 Hz, 2H), 6.76 (d, J=8.7 Hz, 2H), 6.70 (d, J=8.7 Hz, 2H), 6.38 (d, J=2.7 Hz, 1H), 6.33 (d, J=1.8 Hz, 2H), 4.71 (s, 1H), 4.15 (s, 1H), 3.92 (s, 3H), 3.91 (s, 3H), 3.74 (s, 3H), 3.72 (s, 3H), 3.62 (s, 3H), 3.60 (s, 3H); $^{13}$C NMR (75 MHz, CDCl$_3$) δ 159.6, 158.9, 157.8, 157.0, 156.9, 156.0, 146.1, 142.2, 141.4, 136.8, 130.2, 129.6, 129.2, 128.4, 113.9, 113.3, 105.3, 104.4, 98.0, 97.1, 96.5, 58.3, 56.9, 56.3, 55.5, 55.2, 55.1, 54.3; HRMS (MALDI-FTMS) calcd for C$_{34}$H$_{32}$Br$_2$O$_6^+$ [M$^+$] 694.0566. found 694.0540.

Cascade Product 27

A solution of Br$_2$ (8.60 µL, 0.167 mmol, 2.0 equiv) in CH$_2$Cl$_2$ (0.1 mL) was added dropwise to a solution of permethylated quadrangularin A (23, 0.045 g, 0.083 mmol, 1.0 equiv) in CH$_2$Cl$_2$ (4.5 mL) at −78° C. The resultant solution was stirred at −78° C. for 2 h, warmed slowly to 25 OC over the course of 1 h, and stirred for an additional 1 h at 25° C. Upon completion, the reaction mixture was quenched with saturated aqueous NaHCO$_3$ (3 mL), poured into water (5 mL), and extracted with EtOAc (3×5 mL). The combined organic layers were then washed with water (5 mL) and brine (5 mL), dried (MgSO$_4$), and concentrated. The resultant yellow-orange oil was purified by flash column chromatography (silica gel, EtOAc/hexanes, 1:1) to give trihalogenated adduct 27 (0.052 g, 81%) as a pale yellow oil. 27: R$_f$=0.40 (silica gel, EtOAc/hexanes, 1:1); IR (film) ν$_{max}$ 3434, 2956, 2919, 2862, 2091, 1643, 1511, 1462, 1330, 1247, 1211, 1175, 1149, 1111, 1083, 1036, 998; $^1$H NMR (300 MHz, CDCl$_3$) δ 7.49 (d, J=8.7 Hz, 2H), 6.80 (br d, J=8.7 Hz, 6H), 6.39 (s, 1H), 6.27 (s, 1H), 5.59 (s, 1H), 5.10 (s, 1H), 4.53 (s, 1H), 3.91 (s, 3H), 3.87 (s, 3H), 3.77 (s, 6H), 3.62 (s, 3H), 3.55 is, 3H); $^{13}$C NMR (75 MHz, CDCl$_3$) δ 158.2, 157.9, 157.5, 156.9, 155.8, 155.3, 145.9, 144.3, 136.3, 135.4, 129.7, 126.5, 126.2, 113.0, 99.5, 98.4, 97.1, 96.2, 78.1, 70.9, 56.8, 56.6, 55.6, 55.1, 51.5; HRMS (MALDI-FTMS) calcd for C$_{34}$H$_{32}$Br$_3$O$_6^+$ [M+H$^+$] 772.9746. found 772.9756.

Pallidol (3)

Activated Pd/C (10%, 13.7 mg, 0.013 mmol, 0.5 equiv) was added in a single portion to a solution of tribromide 27 (20.0 mg, 0.026 mmol, 1.0 equiv) in MeOH (2.5 mL) at 25° C., and then H$_2$ gas was bubbled slowly and continuously through the solution for 24 h. Upon completion, the reaction mixture was filtered through Celite to remove insoluble particulates (using several washes of EtOAc to ensure quantitative transfer), poured into water (5 mL), and extracted with EtOAc (3×5 mL). The combined organic layers were then washed with water (5 mL) and brine (5 mL), dried (MgSO$_4$), and concentrated. The resultant colorless oil was purified by flash column chromatography (silica gel, EtOAc/hexanes, 1:1) to give permethylated pallidol (10.6 mg, 76%) as an amorphous white solid. Next, a portion of this newly synthesized adduct (5.0 mg, 0.009 mmol, 1.0 equiv) was dissolved in CH$_2$Cl$_2$ (0.5 mL) and treated with BBr$_3$ (0.108 mL, 1.0 M solution in CH$_2$Cl$_2$, 0.108 mmol, 12 equiv) at 0° C. The resultant red mixture was stirred for 4 h at 0° C., and then stirred for an additional 20 h at 25° C. Upon completion, the reaction mixture was quenched with water (5 mL), poured into water (5 mL), and extracted with EtOAc (3×5 mL). The combined organic layers were then washed with water (5 mL) and brine (5 mL), dried (MgSO$_4$), and concentrated. The resultant product was purified by preparative TLC (silica gel, CH$_2$Cl$_2$/MeOH, 9:1) to give pallidol (3.4 mg, 83%) as an off-white solid. 3: R$_f$=0.01 (silica gel, CH$_2$Cl$_2$/MeOH, 9:1); IR (film) ν$_{max}$ 3368, 2957, 2919, 2850, 1601, 1512, 1459, 1333, 1244, 1168, 1124, 1036, 985, 833; $^1$H NMR (300 MHz, acetone-d$_6$) δ 8.03 (app d, J=5.7 Hz, 4H), 7.79 (s, 2H), 6.98 (d, J=8.4 Hz, 4H), 6.70 (d, J=8.4 Hz, 4H), 6.62 (s, 2H), 6.19 (d, J=1.5 Hz, 2H), 4.56 (br s, 2H), 3.79 (br s, 2H); $^{13}$C NMR (75 MHz, acetone-d$_6$) δ 159.3, 156.3, 155.3, 150.3, 137.7, 129.0, 123.2, 115.8, 103.3, 102.5, 60.5, 53.9; HRMS (MALDI-FTMS) calcd for C$_{28}$H$_{22}$O$_6^+$ [M$^+$]454.1414. found 454.1416. All spectroscopic data for the permethylated form of this synthetic material in DMSO-d$_6$ match those reported by Zaman and co-workers for the same naturally-derived compound [24].

Ampelopsin F (4)

A solution of Br$_2$ (2.87 L, 0.056 mmol, 2.0 equiv) in CH$_2$Cl$_2$ (0.1 mL) was added dropwise to a solution of permethylated ampelosin D (28, 15.0 mg, 0.028 mmol, 1.0 equiv) in CH$_2$Cl$_2$ (1.5 mL) at −78° C. The resultant solution was stirred at −78° C. for 2 h, warmed slowly to 25° C. over the course of 1 h, and stirred for an additional 1 h at 25° C. Upon completion, the reaction was quenched with saturated aqueous NaHCO$_3$ (3 mL), poured into water (3 mL), and extracted with EtOAc (3×5 mL). The combined organic layers were then washed with water (5 mL) and brine (5 mL), dried (MgSO$_4$), and concentrated. The resultant light yellow residue was purified by flash column chromatography (silica gel, EtOAc/hexanes, 1:1) to afford tribromide 30 (11.5 mg, 53%) as a light yellow oil. Next, solid AIBN (0.8 mg, 0.005 mmol, 1.0 equiv) was added in a single portion at 25° C. to a solution of tribromide 30 (4.0 mg, 0.005 mmol, 1.0 equiv) and (TMS)$_3$SiH (0.0143 mL, 0.046 mmol, 9.0 equiv) in toluene (0.7 mL) that had been carefully degassed by bubbling argon for 20 min directly into the solvent. The resultant solution was then heated at 100° C. for 8 h. Upon completion, the reaction contents were cooled to 25 OC, concentrated, and purified directly by flash column chromatography (silica gel, EtOAc/hexanes, 1:1) to afford permethylated ampelopsin F (2.4 mg, 89%) as a light yellow oil. Finally, after repeating the previous reaction, this newly synthesized adduct (3.0 mg, 0.006 mmol, 1.0 equiv) was dissolved in CH$_2$Cl$_2$ (0.5 mL) and treated with BBr$_3$ (0.083 mL, 1.0 M solution in CH$_2$Cl$_2$, 0.083 mmol, 12 equiv) at 0° C. The resultant red mixture was stirred for 4 h at 0° C., and then stirred for an additional 15 h at 25° C.

Upon completion, the reaction mixture was quenched with water (3 mL), poured into water (3 mL), and extracted with EtOAc (3×5 mL). The combined organic layers were then washed with water (5 mL) and brine (5 mL), dried (MgSO$_4$), and concentrated. The resultant orange-red residue was purified by flash column chromatography (silica gel, CH$_2$Cl$_2$/MeOH, 9:1) to afford ampelopsin F (2.5 mg, 90%) as an off-white solid. 4: R$_f$=0.13 (silica gel, CH$_2$Cl$_2$/MeOH, 9:1); IR (film) ν$_{max}$ 3361, 2953, 2920, 2847, 1598, 1496, 1471, 1330, 1240, 1165, 1121, 1035, 985, 833; 1H NMR (300 MHz, acetone-d$_6$) δ 8.04 (s, 1H), 7.98 (s, 1H), 7.97 (s, 1H), 7.91 (s, 1H), 7.83 (s, 1H), 7.40 (s, 1H), 7.09 (d, J=8.4 Hz, 2H), 6.78 (d, J=8.4 Hz, 2H), 6.76 (d, J=8.4 Hz, 2H), 6.57 (d, J=8.7 Hz, 2H), 6.52 (d, J=1.8 Hz, 1H), 6.44 (d, J=1.8 Hz, 1H), 6.15 (d, J=2.1 Hz, 1H), 6.07 (d, J=1.8 Hz, 1H), 4.19 (d, J=0.6 Hz, 1H), 4.13 (d, J=0.6 Hz, 1H), 3.65 (br s, 1H), 3.36 (br s, 1H); $^{13}$C NMR (75 MHz, acetone-d$_6$) δ 158.6, 157.8, 157.2, 156.2, 156.0, 153.1, 147.6, 147.4, 138.4, 135.5, 129.9, 129.3, 127.8, 115.6, 115.5, 113.4, 105.7, 104.2, 101.9, 101.6, 58.2, 50.5, 49.7, 47.2; HRMS (MALDI-FTMS) calcd for C$_{28}$H$_{22}$O$_6$, [M$^+$] 454.1416. found 454.1402. All spectroscopic data for this synthetic material match those reported by Niwa and co-workers for natural ampelopsin F (4) [22].

Ketone 31

Solid NaHCO$_3$ (3.30 g, 39.4 mmol, 10 equiv) and Dess-Martin periodinane (1.67 g, 3.94 mmol, 1.0 equiv) were added sequentially in single portions to a solution of alcohol 11 (1.72 g, 3.94 mmol, 1.0 equiv) in CH$_2$Cl$_2$ (30 mL) at 25° C., and the resultant slurry was stirred for 2 h at 25° C. Upon completion, the reaction contents were quenched with saturated aqueous Na$_2$SO$_3$ (10 mL) followed by stirring the resultant biphasic system vigorously for 5 min at 25° C. The reaction contents were then poured into saturated aqueous NaHCO$_3$ (10 mL) and extracted with EtOAc (3×30 mL). The combined organic layers were washed with water (30 mL) and brine (30 mL), dried (MgSO$_4$), and concentrated to afford ketone 31 (1.66 g, 97% yield) as a white solid. 31: R$_f$=0.45 (silica gel, EtOAc/hexanes, 1:1); IR (film) ν$_{max}$ 3003, 2938, 2838, 1668, 1595, 1512, 1456, 1426, 1351, 1316, 1301, 1273, 1252, 1204, 1175, 1157, 1118, 1080, 1065, 1032, 989, 971, 928, 831, 782, 765, 736, 703; $^1$H NMR (300 MHz, CDCl$_3$) δ 7.27 (d, J=8.7 Hz, 2H), 6.99 (d, J=2.4 Hz, 2H), 6.98 (d, J=16.2 Hz, 1H), 6.84 (d, J=2.1 Hz, 1H), 6.80 (d, J=8.7 Hz, 2H), 6.74 (d, J=15.9 Hz, 1H), 6.63 (app t, J=2.4 Hz, 1H), 6.42 (d, J=2.4 Hz, 1H), 3.91 (s, 3H), 3.79 (s, 6H), 3.78 (s, 3H), 3.68 (s, 3H); $^{13}$C NMR (75 MHz, CDCl$_3$) δ 197.3, 161.3, 160.8, 159.5, 158.4, 140.4, 137.7, 131.0, 129.6, 128.0, 123.1, 121.4, 114.0, 107.3, 105.7, 101.1, 97.7, 55.8, 55.5 (2C), 55.3; HRMS (MALDI-FTMS) calcd for C$_{26}$H$_{26}$O$_6$, [M$^+$]434.1729. found 434.1725.

7-Membered Ring Bromide 33

A solution of Br$_2$ (0.024 mL, 0.460 mmol, 1.0 equiv) in CH$_2$Cl$_2$ (0.4 mL) was added dropwise to a solution of ketone 31 (0.200 g, 0.460 mmol, 1.0 equiv) in CH$_2$Cl$_2$ (0.2 mL) at −78° C. The reaction mixture was then stirred for 1 h at −78° C., warmed slowly to 0° C. over the course of 1 h, and then stirred for 3 h at 0° C. and an additional 12 h at 25° C. Upon completion, the reaction mixture was quenched with saturated aqueous NaHCO$_3$ (2 mL), poured into water (1 mL), and extracted with EtOAc (3×10 mL). The combined organic layers were then washed with water (10 mL) and brine (10 mL), dried (MgSO$_4$), and concentrated to afford bromide 33 (0.118 g, 50%) as a white solid that was utilized immediately in subsequent chemistry. [Note: this product is especially light sensitive, so it must be kept away from sunlight at all times].

7-Membered Ring Acetate 36

Solid AgOAc (0.073 g, 0.438 mmol, 3.0 equiv) was added in a single portion to a solution of bromide 33 (0.075 g, 0.146 mmol, 1.0 equiv) in neat AcOH (5 mL) at 25° C. The reaction flask was then wrapped with aluminum foil to protect its contents from light, and stirring was continued at 25 OC for 3 h. Upon completion, the reaction mixture was neutralized with saturated aqueous NaHCO$_3$ (3 mL), poured into water (3 mL), and extracted with EtOAc (3×10 mL). The combined organic layers were then washed with water (10 mL) and brine (10 mL), dried (MgSO$_4$), and concentrated. The resultant yellow oily residue was purified by flash column chromatography (silica gel, EtOAc/hexanes, 1:1) to give acetate 36 (0.045 g, 62%) as a crystalline white solid. 36: R$_f$=0.25 (silica gel, EtOAc/hexanes, 1:1); IR (film) ν$_{max}$ 3001, 2939, 2837, 1732, 1669, 1600, 1512, 1460, 1315, 1235, 1152, 1100, 1059, 1034, 963, 834, 792, 735; $^1$H NMR (300 MHz, CDCl$_3$) δ 6.87 (d, J=5.4 Hz, 1H), 6.83 (d, J=7.5 Hz, 2H), 6.82 (d, J=2.7 Hz, 1H), 6.63 (d, J=8.7 Hz, 2H), 6.47 (d, J=2.4 Hz, 1H), 6.45 (d, J=2.1 Hz, 1H), 6.30 (d, J=2.1 Hz, 1H), 4.81 (d, J=5.4 Hz, 1H), 3.84 (s, 3H), 3.81 (s, 3H), 3.79 (s, 3H), 3.69 (s, 3H), 3.67 (s, 3H), 1.95 (s, 3H); $^{13}$C NMR (75 MHz, CDCl$_3$) δ 194.2, 170.3, 162.2, 160.6, 159.5, 158.9, 158.0, 143.1, 141.3, 131.2, 129.3, 122.6, 115.0, 113.4, 107.8, 103.2, 101.8, 97.9, 69.7, 56.0, 55.6, 55.4, 55.1, 51.6, 21.2; HRMS (MALDI-FTMS) calcd for C$_{28}$H$_{29}$O$_8$, [M+H$^+$]493.1862. found 493.1847.

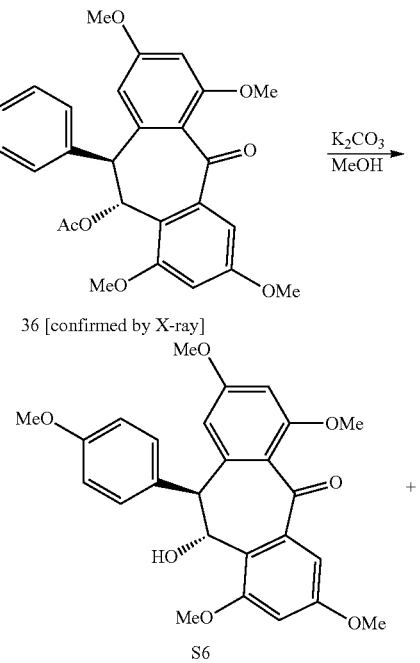

Scheme S3.

36 [confirmed by X-ray]

S6

-continued

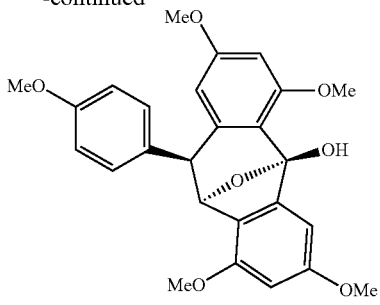

S7

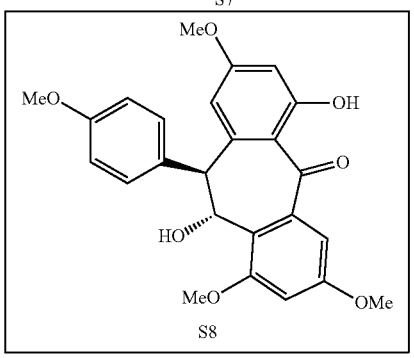

S8

Generation of a mixture of both open, as well as lactol, forms of the acetate cleavage product of 36. Interestingly, if the phenol adjacent to the carbocyclic ketone is unprotected, the lactol is not observed under the same cleavage conditions (i.e. S8 was formed cleanly). As such, this step highlights an element of unique reactivity instigated entirely by protecting groups.

Permethylated Hemsleyanol Analog 6/87

Finely powdered $K_2CO_3$ (0.121 g, 0.873 mmol, 10 equiv) was added in a single portion to a solution of acetate 36 (0.043 g, 0.087 mmol, 1.0 equiv) in MeOH (8 mL) at 25° C., and the resultant slurry was stirred for 12 h at 25° C. Upon completion, the reaction contents were neutralized with saturated aqueous $NH_4Cl$ (5 mL), poured into water (5 mL), and extracted with EtOAc (3×10 mL). The combined organic layers were then washed with water (5 mL) and brine (5 mL), dried ($MgSO_4$), and concentrated. The resultant colorless residue was purified by flash column chromatography (silica gel, EtOAc/hexanes, 1:1) to give an inseparable mixture of alcohol 86 and lactol 87 (2.5/1, 0.039 g, 78% combined). S6 and S7: $R_f$=0.16 (silica gel, EtOAc/hexanes, 1:1); IR (film) $v_{max}$ 3469, 2933, 2839, 1664, 1600, 1511, 1460, 1312, 1249, 1211, 1149, 1096, 1057, 1036, 987, 935, 833, 735; $^1H$ NMR (300 MHz, $CDCl_3$) δ 6.89 (d, J=8.7 Hz, 2.8H), 6.85 (d, J=2.4 Hz, 1H), 6.67 (d, J=8.7 Hz, 2.8H), 6.60 (d, J=2.4 Hz, 1H), 6.52 (d, J=2.1 Hz, 1.8H), 6.44 (d, J=2.1 Hz, 1H), 6.32 (d, J=2.1 Hz, 0.4H), 6.04 (d, J=1.8 Hz, 0.8H), 5.88 (d, J=5.4 Hz, 1H), 5.54 (d, J=5.7 Hz, 0.4H), 4.76 (d, J=6.0 Hz, 0.4H), 4.66 (d, J=6.0 Hz, 1H), 3.96 (s, 1.2H), 3.87 (s, 3H), 3.85 (s, 3H), 3.81 (s, 3H), 3.78 (s, 4.2H), 3.71 (s, 1.2H), 3.69 (s, 4.2H), 3.58 (s, 1.2H); $^{13}C$ NMR (75 MHz, $CDCl_3$) δ 194.3, 162.0, 161.6, 160.1, 159.8, 159.2, 158.7, 158.4, 157.8, 155.4, 154.3, 151.8, 141.1, 140.8, 140.4, 131.9, 131.5, 128.9, 123.3, 120.9, 119.8, 117.8, 113.5, 108.2, 107.8, 104.8, 103.5, 102.5, 97.8, 97.2, 97.0, 94.8, 79.3, 67.5, 56.1, 55.9, 55.4, 55.3, 55.2, 55.0, 54.7, 53.6, 47.8; HRMS (MALDI-FTMS) calcd for $C_{26}H_{27}O_7$, $[M+H^{30}]$ 451.1757. found 451.1756.

Tetramethylated Hemsleyanol 3 Analog S8

Acetate 36 (0.050 g, 0.102 mmol, 1.0 equiv) was dissolved in neat AcOH (8 mL) at 25° C., and the resulted solution was stirred for 12 h at 25° C. Upon completion, the reaction mixture was quenched with water (5 mL), poured into water (5 mL), and extracted with EtOAc (3×15 mL). The combined organic layers were then washed with brine (10 mL), dried ($MgSO_4$), and concentrated to afford the desired mono-deprotected intermediate (0.045 g, 93%) as a colorless oil which was carried forward without any additional purification. Next, solid KCN (0.6 mg, 0.009 mmol, 0.1 equiv) was added in a single portion to a solution of newly-formed compound (0.045 g, 0.090 mmol, 1.0 equiv) in MeOH (8 mL) at 25° C., and then resultant mixture was heated at 65° C. for 3 h. Upon completion, the reaction was quenched with water (5 mL), poured into water (5 mL) and extracted with EtOAc (3×10 mL). The combined organic layers were then washed with brine (5 mL), dried ($MgSO_4$), and concentrated. The resultant light yellow product was purified by flash column chromatography (silica gel, EtOAc/hexanes, 1:1) to give alcohol S8 (0.037 g, 89%) as a colorless oil. 38: $R_f$=0.19 (silica gel, EtOAc/hexanes, 1:1); IR (film) $v_{max}$ 3468, 3001, 238, 2831, 1606, 1579, 1511, 1462, 1416, 1351, 1298, 1253, 1206, 1151, 1055, 1035, 935, 841, 796, 726; $^1H$ NMR (300 MHz, $CDCl_3$) δ 13.70 (s, 1H), 6.95 (d, J=2.4 Hz, 1H), 6.71 (d, J=8.7 Hz, 2H), 6.58 (d, J=8.7 Hz, 2H), 6.42 (d, J=2.7 Hz, 1H), 6.29 (d, J=2.4 Hz, 1H), 6.27 (dd, J=2.7, 0.6 Hz, 1H), 5.76 (dd, J=5.7, 2.4 Hz, 1H), 4.88 (d, J=6.1 Hz, 1H), 3.81 (s, 3H), 3.77 (s, 3H), 3.68 (s, 3H), 3.45 (s, 3H); $^{13}C$ NMR (75 MHz, $CDCl_3$) δ 198.2, 166.6, 165.0, 160.0, 157.9, 156.8, 143.6, 141.0, 132.7, 129.5, 121.5, 115.0, 113.2, 112.6, 105.7, 102.2, 100.0, 67.0, 57.3, 55.9, 55.4, 55.3, 55.2, 55.1; HRMS (MALDI-FTMS) calcd for $C_{25}H_{24}O_7$, $[M^+]$ 436.1522. found 436.1544.

Permethylated Diptoindonesin A Analog 37

Dess-Martin periodinane (0.049 g, 0.115 mmol, 1.0 equiv) and solid $NaHCO_3$ (0.097 g, 1.15 mmol, 10 equiv) were added sequentially in single portions to a solution of alcohol 86 and lactol 87 (0.052 g, 0.115 mmol, 1.0 equiv) in $CH_2Cl_2$ (10 mL) at 25° C., and the resultant slurry was stirred for 1.5 h at 25° C. Upon completion, the reaction contents were quenched with saturated aqueous $Na_2SO_3$ (3 mL) followed by stirring the resultant biphasic system vigorously for 5 min at 25° C., poured into water (5 mL), and extracted with EtOAc (3×15 mL). The combined organic layers were then washed with saturated aqueous $NaHCO_3$ (3×10 mL), dried ($MgSO_4$), and concentrated to give the desired permethylated diptoindonesin A analog (0.051 g, 99%) as a light yellow oil. 37: $R_f$=0.33 (silica gel, EtOAc/hexanes, 1:1); IR (film) $v_{max}$ 3008, 2939, 2837, 1668, 1592, 1512, 1462, 1327, 1295, 1250, 1211, 1157, 1070, 1023, 974, 928, 832, 732; $^1H$ NMR (300 MHz, $CDCl_3$) δ 6.98 (d, J=2.4 Hz, 1H), 6.91 (d, J=8.1 Hz, 2H), 6.69 (d, J=9.2 Hz, 2H), 6.64 (d, J=2.4 Hz, 1H), 6.52 (d, J=2.1 Hz, 1H), 6.47 (d, J=2.1 Hz, 1H), 5.18 (s, 1H), 3.90 (s, 3H), 3.86 (s, 3H), 3.85 (s, 3H), 3.81 (s, 3H), 3.70 (s, 3H); $^{13}C$ NMR (75 MHz, $CDCl_3$) δ 195.3, 192.5, 163.0, 162.6, 161.1, 159.9, 158.4, 141.9, 136.7, 129.9, 129.4, 122.5, 116.8, 113.8, 105.8, 105.4, 104.0, 98.8, 66.7, 56.8, 56.1, 55.7, 55.5, 55.1; HRMS (MALDI-FTMS) calcd for $C_{26}H_{25}O_7$, $[M+H^+]$449.1556. found 449.1619.

(Z)-3-(3,5-dimethoxyphenyl)-4,6-diethoxy-1-(4-methoxybenzylidene)-1,3-dihydro-isobenzofuran (39)

Solid $NaHCO_3$ (0.010 g, 0.115 mmol, 1.0 equiv) and $Pd(OTFA)_2$ (0.038 g, 0.115 mmol, 1.0 equiv) was added sequentially in single portions to a solution of aldol adduct 11

(0.050 g, 0.115 mmol, 1.0 equiv) in $CH_2Cl_2$ (5 mL) at 0° C., and the resultant slurry was stirred for 3 h at 0° C. Upon completion, the reaction mixture was quenched with saturated aqueous $NaHCO_3$ (5 mL), poured into water (5 mL), and extracted with EtOAc (3×5 mL). The combined organic extracts were then filtered though Celite to remove insoluble particulates and concentrated directly. The resultant brown residue was purified by flash column chromatography (silica gel, EtOAc/hexanes, 1:1) to afford recovered 11 (0.030 g) and dihydroisobenzofuran 39 (0.007 g, 35% based on recovered s.m.) as a light yellow oil. [Note: compound 39 is incredibly unstable and should be used immediately in subsequent chemistry with minimal exposure to oxygen]. 39: $R_f$=0.53 (silica gel, EtOAc/hexanes, 1:1); IR (film) $v_{max}$ 2951, 2928, 2875, 1718, 1600, 1503, 1462, 1428, 1358, 1314, 1244, 1206, 1155, 1111, 1055, 1036, 833; $^1H$ NMR (300 MHz, $CDCl_3$, 1:1 mixture of alkene isomers) δ 7.68 (d, J=9.0 Hz, 2H), 7.67 (d, J=8.7 Hz, 2H), 6.88 (d, J 8.7 Hz, 2H), 6.86 (d, J=9.0 Hz, 2H), 6.63 (d, J=2.1 Hz, 1H), 6.62 (s, 1H), 6.54 (d, J 2.1 Hz, 1H), 6.49 (d, J 2.1 Hz, 1H), 6.46 (s, 1H), 6.39 (app t, J=2.1 Hz, 1H), 6.35 (dd, J=6.6, 2.1 Hz, 1H), 6.32 (s, 1H), 6.31 (d, J=2.1 Hz, 1H), 6.22 (s, 1H), 5.87 (s, 1H), 3.88 (s, 3H), 3.84 (s, 3H), 3.82 (s, 3H), 3.80 (s, 3H), 3.79 (s, 3H), 3.74 (s, 6H), 3.71 (s, 3H), 3.68 (s, 6H); $^{13}C$ NMR (75 MHz, $CDCl_3$) δ 162.2, 160.7, 160.6, 160.4, 160.2, 157.5, 156.2, 155.3, 154.2, 151.9, 143.5, 142.4, 137.3, 133.2, 129.2, 129.1, 127.3, 126.6, 113.8, 113.7, 110.0, 105.2, 105.1, 101.0, 100.1, 99.6, 99.5, 99.4, 96.7, 96.1, 94.5, 86.1, 77.2, 73.4, 55.7, 55.5, 55.4, 55.3, 55.2, 55.0.

α,β-Unsaturated Ketone 43

Concentrated HCl (0.010 ml, 0.12 mmol, 7.5 equiv) was added in a single portion to a solution of 39 (0.007 g, 0.016 mmol, 1.0 equiv) in MeOH (2.5 mL) at 25° C., and the resultant mixture was heated at 50° C. for 12 h; the solution turned dark violet after 1 h. Upon completion, the reaction mixture was quenched with saturated aqueous $NaHCO_3$ (5 mL), poured into water (5 mL), and extracted with EtOAc (3×5 mL). The combined organic layers were then washed with water (5 mL) and brine (5 mL), dried ($MgSO_4$), and concentrated. The resultant product was purified by flash column chromatography (silica gel, EtOAc/hexanes, 1:1) to give recovered 39 (0.003 g) in addition to unsaturated ketone 43 (0.0016 g, 41% based on recovered s.m.) as a dark purple oil. 43: $R_f$=0.53 (silica gel, EtOAc/hexanes, 1:1); IR (film) $v_{max}$ 2926, 1704, 1600, 1509, 1460, 1310, 1249, 1204, 1154, 1061, 833; $^1H$ NMR (300 MHz, $CDCl_3$) δ 7.12 (d, J=8.7 Hz, 2H), 6.86 (d, J=1.8 Hz, 1H), 6.75 (d, J=8.7 Hz, 2H), 6.49 (d, J=2.1 Hz, 2H), 6.44 (d, J=2.1 Hz, 2H), 3.86 (s, 3H), 3.76 (s, 3H), 3.70 (s, 6H), 3.61 (s, 3H); $^{13}C$ NMR (75 MHz, $CDCl_3$) δ 162.5, 160.2, 158.7, 156.6, 154.7, 137.0, 134.1, 130.6, 123.6, 113.4, 106.6, 104.1, 102.8, 101.0, 55.9, 55.8, 55.4, 55.2; HRMS (MALDI-FTMS) calcd for $C_{26}H_{24}O_6^+$ [M+H$^+$] 432.1573. found 432.1578.

Brominated Building Block 44

KOt-Bu (1.85 mL, 1.0 M in THF, 1.85 mmol, 1.05 equiv) was added dropwise over the course of 5 min to a solution of phosphonate 82 (0.650 g, 1.77 mmol, 1.0 equiv) in THF (20 mL) at −78° C. After 20 min of stirring at −78° C., a solution of 3,4-dimethoxybenzaldehyde (0.279 g, 1.68 mmol, 0.95 equiv) in THF (5 mL) was added at −78° C. The resultant solution was stirred at −78° C. for 1 h, and then at 25° C. for 12 h.

Upon completion, the reaction mixture was quenched with saturated aqueous $NH_4Cl$ (10 mL), poured into water (5 mL), and extracted with EtOAc (3×10 mL). The combined organic layers were then washed with water (10 mL) and brine (10 mL), dried ($MgSO_4$), and concentrated to give resveratrol derivative 44 (0.646 g, 96% yield) as a white powder which was carried forward without additional purification. 44: $R_f$=0.48 (silica gel, EtOAc/hexanes, 1:1); $^1H$ NMR (300 MHz, $CDCl_3$) δ 7.38 (d, J=16.1 Hz, 1H), 7.08 (m, 2H), 6.96 (d, J=16.1 Hz, 1H), 6.86 (d, J=8.7 Hz, 1H), 6.79 (d, J=2.3 Hz, 1H), 6.41 (d, J=1.9 Hz, 1H), 3.95 (s, 3H), 3.90 (s, 3H), 3.87 (s, 3H), 3.85 (s, 3H); $^{13}C$ NMR (75 MHz, $CDCl_3$) δ 159.5, 156.8, 149.3, 149.1, 138.8, 131.4, 130.0, 126.0, 120.3, 111.2, 109.1, 104.8, 102.4, 98.7, 56.3, 55.9, 55.8, 55.5.

(E)-(2,4-dimethoxy-6-(3,4-diethoxystyryl)phenyl-(3,5-dimethoxyphenyl)methanol (45)

n-BuLi (1.5 mL, 1.6 M in THF, 2.4 mmol, 1.50 equiv) was added slowly over the course of 5 min to a solution of intermediate 44 (0.620 g, 1.63 mmol, 1.0 equiv) in THF (10 mL) at −78° C., ultimately yielding a light yellow solution. After 20 min of stirring at −78° C., a solution of 3,5-dimethoxybenzaldehyde (0.295 g, 1.63 mmol, 1.0 equiv) in THF (10 mL) was added slowly at −78° C., and the resultant mixture was stirred for 1 h at −78° C., warmed slowly to 25° C., and stirred for an additional 4 h at 25° C. Upon completion, the reaction contents were quenched with saturated aqueous $NH_4Cl$ (10 mL), poured into water (10 mL), and extracted with EtOAc (3×15 mL). The combined organic layers were then washed with water (10 mL) and brine (10 mL), dried ($MgSO_4$), and concentrated. The resultant light yellow oil was purified by flash column chromatography (silica gel, EtOAc/hexanes, 1:2) to give aldol adduct 45 (0.463 g, 61% yield) as a white solid. 45: $R_f$=0.26 (silica gel, EtOAc/hexanes, 1:1); $^1H$ NMR (300 MHz, $CDCl_3$) δ 7.31 (s, 1H), 7.01 (m, 2H), 6.90 (d, J=16.1 Hz, 1H), 6.88 (app s, 1H), 6.78 (d, J=2.3 Hz, 1H), 6.57 (m, 2H), 6.50 (d, J=2.4 Hz, 1H), 6.37 (app t, J=2.3 Hz, 1H), 6.27 (d, J=9.5 Hz, 1H), 3.95 (s, 3H), 3.94 (s, 3H), 3.92 (s, 3H), 3.79 (s, 3H), 3.78 (app s, 6H); $^{13}C$ NMR (75 MHz, $CDCl_3$) δ 161.0, 160.4, 159.2, 149.5, 148.1, 139.1, 132.2, 130.7, 125.1, 122.3, 120.6, 111.5, 109.1, 104.4, 103.6, 99.2, 98.6, 70.3, 56.4, 56.3, 56.2, 55.8, 55.6.

Ketone 46

Dess-Martin periodinane (0.049 g, 0.116 mmol, 1.2 equiv) was added in a single portion to a solution of alcohol 45 (0.045 g, 0.097 mmol, 1.0 equiv) in $CH_2Cl_2$ (5 mL) at 25° C., and the resultant slurry was stirred for 1 h at 25° C. Upon completion, the reaction contents were quenched with saturated aqueous $Na_2SO_3$ (1.5 mL) followed by stirring the resultant biphasic system vigorously for 5 min at 25° C. The reaction contents were then poured into saturated aqueous $NaHCO_3$ (5 mL) and extracted with EtOAc (3×5 mL). The combined organic layers were washed with water (5 mL) and brine (5 mL), dried ($MgSO_4$), and concentrated to afford the desired ketone intermediate (0.043 g, 96% yield) as a light yellow solid which was carried forward without additional purification. 46: $R_f$=0.33 (silica gel, EtOAc/hexanes, 1:1); 1H NMR (300 MHz, $CDCl_3$) δ 6.99 (d, J=2.4 Hz, 2H), 6.93 (m, 2H), 6.80 (d, J=1.8 Hz, 1H), 6.78 (d, J=1.8 Hz, 1H), 6.61 (m, 1H), 6.63 (app t, J=2.4 Hz, 1H), 6.42 (d, J=1.8 Hz, 1H), 3.91 (s, 3H), 3.86 (s, 3H), 3.83 (s, 3H), 3.79 (s, 6H), 3.69 (s, 3H); $^{13}C$ NMR (75 MHz, $CDCl_3$) δ 197.1, 161.2, 160.7, 158.3, 149.1, 148.9, 140.4, 137.5, 131.1, 129.9, 123.3, 121.2, 120.0, 111.0, 109.1, 107.1, 105.4, 101.1, 97.7, 55.7 (2C), 55.6 (2C), 55.4 (2C).

Cyclized Intermediate 48

Solid p-TsOH (0.082 g, 0.432 mmol, 2.0 equiv) was added in a single portion to a solution of ketone 46 (0.100 g, 0.216 mmol, 1.0 equiv) in toluene (5 mL) at room temperature. The resulting heterogeneous mixture was warmed to 60° C. and stirred for 48 h. Upon completion, the reaction mixture was quenched with saturated aqueous $NaHCO_3$ (5 mL), poured into water (5 mL), and extracted with EtOAc (3×10 mL). The combined organic layers were then washed with water (10 mL) and brine (10 mL), dried ($MgSO_4$), and concentrated. The resultant yellow product was purified by flash column chromatography (silica gel, EtOAc/hexanes, 1:1) to give a carbocycle 48 (0.080 g, 80%) as a light yellow solid. 48: $R_f$=0.27 (silica gel, EtOAc/hexanes, 1:1); IR (film) $v_{max}$ 2930, 1653, 1600, 1514, 1458, 1340, 1207, 1138; 1H NMR (300 MHz, $CDCl_3$) δ 7.15 (d, J=2.4 Hz, 1H), 6.60 (d, J=8.4 Hz, 1H), 6.53 (d, J=2.9 Hz, 1H), 6.41 (dd, J=8.1, 1.8 Hz, 1H), 6.28 (d, J=2.1 Hz, 1H), 6.25 (d, J=1.8 Hz, 1H), 5.71 (d, J=2.1 Hz, 1H), 4.64 (dd, J=6.9, 2.7 Hz, 1H), 3.89 (s, 3H), 3.79 (s, 3H), 3.78 (s, 3H), 3.58 (app s, 6H), 3.54 (s, 3H); $^{13}$C NMR (75 MHz, $CDCl_3$) δ 196.7, 161.8, 158.8, 158.6, 157.8, 148.0, 146.7, 141.1, 138.9, 136.3, 125.1, 123.4, 119.8, 111.1, 110.3, 105.9, 103.9, 103.2, 97.1, 55.9, 55.6, 55.4, 55.3, 43.1, 40.9.

Permethylated Cassigarol 8 (51)

Solid $LiAlH_4$ (4.0 mg, 0.107 mmol, 3.0 equiv) was added to a solution of compound 48 (17.0 mg, 0.036 mmol, 1.0 equiv) in THF (30 mL) at 0° C. After 30 min of stirring at 0 SC, the reaction contents were warmed to 25° C. and stirred for an additional 1 h. Next, HCl (4 mL, 1 M in $H_2O$) was added and the resultant slurry was stirred at 25° C. for 6 h. Upon completion, the reaction contents were then quenched with saturated aqueous $NaHCO_3$ (5 mL), poured into water (5 mL), and extracted with EtOAc (3×10 mL). The combined organic layers were then washed with water (10 mL) and brine (10 mL), dried ($MgSO_4$), and concentrated to afford permethylated cassigarol B (10.0 mg, 60% yield) as an amorphous white solid. 51: $R_f$=0.53 (silica gel, EtOAc/hexanes, 1:1); $^1$H NMR (300 MHz, $CDCl_3$) δ 6.94 (s, 1H), 6.87 (s, 1H), 6.53 (d, J=2.2 Hz, 1H), 6.29 (d, J=2.2 Hz, 1H), 6.24 (d, J=2.4 Hz, 1H), 6.02 (d, J=2.3 Hz, 1H), 5.52 (s, 1H), 4.57 (dd, J=6.9, 3.5 Hz, 1H), 3.91 (s, 3H), 3.86 (s, 3H), 3.85 (s, 3H), 3.83 (s, 3H), 3.77 (s, 3H), 3.65 (s, 3H), 3.14 (d, J=3.4 Hz, 2H); $^{13}$C NMR (75 MHz, $CDCl_3$) δ 158.9, 158.5, 156.2, 155.9, 147.7, 147.1, 146.9, 137.3, 137.2, 134.0, 123.0, 121.4, 109.9, 109.2, 107.8, 102.1, 96.4, 96.3, 56.1, 55.5, 55.4, 41.9, 36.4, 36.2.

Cassigarol B (52)

To a solution of carbocycle 51 (3.0 mg, 0.007 mmol, 1.0 equiv) in $CH_2Cl_2$ (1 mL) was added dropwise a commercially-prepared solution of $BBr_3$ (0.08 mL, 1.0 M in $CH_2Cl_2$, 0.080 mmol, 12 equiv) at –78° C., and the resultant solution was stirred for 2 h at –78° C. and allowed to slowly warm to 25° C. and stir for an additional 12 h. Upon completion, the reaction mixture was quenched with water (5 mL), poured into water (10 mL), and extracted with EtOAc (3×10 mL). The combined organic layers were then washed with water (5 mL) and brine (5 mL), dried ($MgSO_4$), and concentrated. The resultant light pink product was purified by preparative thin layer chromatography (silica gel, $CH_2Cl_2$/MeOH, 9:1) to give cassigarol B (2.5 mg, 76% yield) as an amorphous white solid. 52: Rt=0.10 (silica gel, MeOH/$CH_2Cl_2$, 1:9); $^1$H NMR (400 MHz, DMSO-$d_6$) δ 9.13 (s, 1H), 9.12 (s, 1H), 8.87 (s, 1H), 8.74 (s, 1H), 8.56 (br s, 1H), 8.52 (br s, 1H), 6.67 (s, 1H), 6.55 (s, 1H), 6.09 (d, J=2.0 Hz, 1H), 6.04 (d, J=2.0 Hz, 1H), 6.00 (d, J=2.0 Hz, 1H), 5.70 (d, J=2.0 Hz, 1H), 5.03 (s, 1H), 4.18 (m, 1H), 2.79 (m, 2H); $^{13}$C NMR (100 MHz, DMSO-$d_6$) δ 155.5, 155.2, 153.3, 153.2, 147.9, 142.4, 142.1, 136.8, 136.0, 132.8, 120.3, 117.8, 113.4, 112.4, 108.7, 103.2, 99.6, 99.5, 41.1, 36.2, 35.4.

Methylated Biaryl Alcohol 53

To a mixture of sodium hydride (0.070 g, 3.00 mmol, 2.0 equiv) in THF (10 mL) was added a solution of alcohol 45 (0.700 g, 1.50 mmol, 1.0 equiv) in THF (5 mL) dropwise at 0° C. After 20 min of stirring at 0° C., iodomethane (0.700 mL, 7.51 mmol, 5 equiv) was added in a single portion and the resulting solution stirred for an additional 30 minutes at 0° C. Next, the reaction contents were warmed to 25° C. and left to stir for an additional 3 h. Upon completion, the reaction contents were quenched by the slow addition of saturated aqueous $NH_4Cl$ (15 mL), poured into water (10 mL), and extracted with EtOAc (3×15 mL). The combined organic layers were then washed with water (10 mL) and brine (10 mL), dried ($MgSO_4$), and concentrated. Trituration of the resulting oil with hexanes (3×5 mL) to remove mineral oil afforded the desired intermediate (0.706 g, 98% yield) as a white amorphous solid. 53: $R_f$=0.34 (silica gel, EtOAc/hexanes, 1:1); $^1$H NMR (300 MHz, $CDCl_3$) δ 7.42 (d, J=16.1 Hz, 1H), 6.86 (m, 2H), 6.78 (app t, J=2.6 Hz, 1H), 6.74 (d, J=16.1 Hz, 1H), 6.57 (m, 2H), 6.44 (d, J=2.3 Hz, 1H), 6.27 (app t, J=2.2 Hz, 1H), 6.10 (s, 1H), 3.89 (s, 3H), 3.87 (app s, 6H), 3.85 (s, 3H), 3.69 (s, 6H), 3.33 (s, 3H); $^{13}$C NMR (75 MHz, $CDCl_3$) δ 160.5, 159.9, 159.5, 149.0, 148.7, 146.1, 139.4, 131.1, 128.4, 126.4, 120.1, 119.7, 111.0, 108.6, 104.2, 102.5, 97.9, 97.4, 75.9, 56.4, 55.9, 55.7, 55.3, 55.1 (2C).

Cascade product 61

A solution of $Br_2$ (1.07 μL, 0.020 mmol, 1.0 equiv) in $CH_2Cl_2$ (0.5 mL) was added dropwise to a solution of intermediate 53 (10.0 mg, 0.020 mmol, 1.0 equiv) in $CH_2Cl_2$ (0.5 mL) at –78° C. The resultant dark green solution was stirred at –78° C. for 2 h, warmed slowly to 25° C. over the course of 6 h, and stirred for an additional 6 h at 25° C. Upon completion, the reaction mixture was quenched with saturated aqueous $NaHCO_3$ (5 mL), poured into $H_2O$ (5 mL), and extracted with EtOAc (3×10 mL). The combined organic layers were then washed with water (10 mL) and brine (10 mL), dried ($MgSO_4$), and concentrated to give a crude oil which was purified directly by preparative thin layer chromatography (silica gel, EtOAc/hexanes, 1:1) to give the desired alcohol intermediate (4.0 mg, 43% yield) as a white solid. 61: $R_f$=0.16 (silica gel, EtOAc/hexanes, 1:1); 1H NMR (300 MHz, $CDCl_3$) δ 6.90 (s, 1H), 6.82 (s, 1H), 6.67 (d, J=2.1 Hz, 1H), 6.56 (d, J=2.1 Hz, 1H), 6.34 (d, J=2.1 Hz, 1H), 6.31 (d, J=2.1 Hz, 1H), 5.10 (s, 1H), 4.78 (m, 2H), 3.93 (s, 3H), 3.86 (app s, 6H), 3.82 (s, 3H), 3.79 (s, 3H), 3.77 (s, 3H), 1.79 (d, J=11.4 Hz, 1H).

Permethylatad cassigarol B Analog 62

To a solution of intermediate 61 (6.5 mg, 0.014 mmol, 1.0 equiv) in $CH_2Cl_2$ (4.7 mL) was added $NaBH_3CN$ (8.9 mg, 1.42 mmol, 100 equiv) at 0° C. to afford a cloudy suspension. A solution of TFA in $CH_2Cl_2$ (0.618 M) was then added dropwise in 3 equal portions (0.044 mL, 0.028 mmol, 2.0 equiv), with 10 min breaks between each portion. The resulting suspension was stirred at 0° C. for 30 minutes, and slowly warmed to room temperature and stirred for an additional 2 h.

The reaction contents were quenched with saturated aqueous NaHCO$_3$ (5 mL), poured into water (5 mL), and extracted with EtOAc (3×5 mL). The combined organic layers were then washed with water (5 mL) and brine (5 mL), dried (MgSO$_4$), and concentrated. The resultant oil was purified by flash column chromatography (silica gel, EtOAc/hexanes, 1:1) to give the desired intermediate (5.7 mg, 91% yield) as a white crystalline solid. 62: R$_f$=0.52 (silica gel, EtOAc/hexanes, 1:1); m.p.=228.0-229.0° C.; $^1$H NMR (300 MHz, CDCl$_3$) δ 6.88 (s, 1H), 6.80 (s, 1H), 6.65 (d, J=2.1 Hz, 1H), 6.54 (d, J=2.1 Hz, 1H), 6.33 (d, J=2.4 Hz, 1H), 6.29 (d, J=2.1 Hz, 1H), 5.08 (s, 1H), 4.77 (AB, J=18.6, 4.5 Hz, 2H), 3.95 (s, 3H), 3.84 (app s, 6H), 3.82 (m, 2H), 3.79 (s, 3H), 3.77 (s, 3H), 3.75 (s, 3H).

Cassigarol B Analog 63

To a solution of carbocycle 62 (3.0 mg, 0.007 mmol, 1.0 equiv) in CH$_2$Cl$_2$ (0.5 mL) was added dropwise a commercially-prepared solution of BBr$_3$ (0.067 mL, 1.0 M in CH$_2$Cl$_2$, 0.067 mmol, 10 equiv) at −78° C., and the resultant solution was stirred for 2 h at −78° C. and allowed to slowly warm to room temperature overnight. Upon completion, the reaction mixture was quenched with water (5 mL), poured into water (10 mL), and extracted with EtOAc (3×10 mL). The combined organic layers were then washed with water (5 mL) and brine (5 mL), dried (MgSO$_4$), and concentrated. The resultant light pink product was purified by preparative thin layer chromatography (silica gel, CH$_2$Cl$_2$/MeOH, 9:1) to give the isomeric cassigarol B product (1.2 mg, 49% yield) as an amorphous white solid. 63: Rt=0.09 (silica gel, CH$_2$Cl$_2$/MeOH, 9:1); $^1$H NMR (400 MHz, acetone-d$_6$) δ 6.80 (s, 1H), 6.42 (d, J=2.1 Hz, 1H), 6.39 (d, J=2.0 Hz, 1H), 6.34 (s, 1H), 6.23 (d, J=2.0 Hz, 1H), 6.20 (d, J=2.2 Hz, 1H), 4.94 (s, 1H), 4.49 (m, 1H), 2.98 (d, J=4.1 Hz, 2H).

methylated biaryl alcohol 64

To a mixture of sodium hydride (0.021 g, 0.917 mmol, 2.0 equiv) in THF (5 mL) was added a solution of alcohol 11 (0.200 g, 0.458 mmol, 1.0 equiv) in THF (5 mL) dropwise at 0° C. After 20 min of stirring at 0° C., iodomethane (0.184 mL, 4.58 mmol, 5.0 equiv) was added in a single portion and the resulting solution stirred for an additional 30 min at 0° C. Next, the reaction contents were warmed to 25° C. and left to stir for an additional 3 h. Upon completion, the reaction contents were quenched with saturated aqueous NH$_4$Cl (10 mL), poured into water (10 mL), and extracted with EtOAc (3×10 mL). The combined organic layers were then washed with water (10 mL) and brine (10 mL), dried (MgSO$_4$), and concentrated. Trituration of the resultant oil with hexanes (3×5 mL) to remove mineral oil afforded the desired intermediate (0.200 g, 97% yield) as a white amorphous solid. 64: R$_f$=0.60 (silica gel, EtOAc/hexanes, 1:1); $^1$H NMR (300 MHz, CDCl$_3$) δ 7.52 (d, J=16.2 Hz, 1H), 7.31 (d, J=8.7 Hz, 2H), 6.85 (d, J=8.7 Hz, 2H), 6.77 (d, J=2.4 Hz, 1H), 6.76 (d, J=16.2 Hz, 1H), 6.59 (app t, J=1.5 Hz, 2H), 6.46 (d, J=2.0 Hz, 1H), 6.29 (app t, J=1.8 Hz, 1H), 6.11 (s, 1H), 3.89 (s, 3H), 3.86 (s, 3H), 3.83 (s, 3H), 3.73 (s, 3H), 3.37 (s, 3H).

Cascade Product 72

A solution of Br$_2$ (1.14 L, 0.022 mmol, 1.0 equiv) in CH$_2$Cl$_2$ (0.5 mL) was added dropwise to a solution of methylated biaryl alcohol 64 (10.0 mg, 0.022 mmol, 1.0 equiv) in CH$_2$Cl$_2$ (0.5 mL) at −78° C. The resultant red solution was stirred at −78° C. for 2 h, warmed slowly to 25° C. over the course of 6 h, and stirred for an additional 6 h at 25° C. Upon completion, the reaction mixture was quenched with saturated aqueous NaHCO$_3$ (5 mL) during which a color change from red to yellow was observed, poured into H$_2$O (5 mL), and extracted with EtOAc (3×10 mL). The combined organic layers were then washed with water (10 mL) and brine (10 mL), dried (MgSO$_4$), and concentrated to give a crude oil which was purified directly by preparative thin layer chromatography (silica gel, EtOAc/hexanes, 1:1) to give the desired halogenated intermediate (3.3 mg, 24% yield) as a white solid. 72: R$_f$=0.37 (silica gel, EtOAc/hexanes, 1:1); $^1$H NMR (300 MHz, CDCl$_3$) δ 7.28 (d, J=8.4 Hz, 1H), 7.00 (d, J=2.7 Hz, 1H), 6.72 (dd, J=8.4, 2.7 Hz, 1H), 6.41 (s, 1H), 6.36 (s, 1H), 5.93 (s, 1H), 5.66 (d, J=4.8 Hz, 1H), 4.87 (dd, J=8.4, 4.5 Hz, 1H), 3.92 (s, 3H), 3.91 (s, 3H), 3.88 (s, 3H), 3.86 (s, 3H), 3.81 (s, 3H), 1.88 (d, J=8.4 Hz, 1H).

Brominated Ketone 73

Dess-Martin periodinane (0.033 g, 0.009 mmol, 2.0 equiv) was added in a single portion to a solution of alcohol 72 (2.0 mg, 0.005 mmol, 1.0 equiv) and solid NaHCO$_3$ (10.0 mg, 0.110 mmol, 12 equiv) in CH$_2$Cl$_2$ (0.4 mL) at 25° C., and the resultant slurry was stirred for 1 h at 25° C. Upon completion, the reaction contents were quenched with saturated aqueous Na$_2$SO$_3$ (1.5 mL) followed by stirring the resultant biphasic system vigorously for 5 min at 25° C. The reaction contents were then poured into saturated aqueous NaHCO$_3$ (5 mL) and extracted with EtOAc (3×5 mL). The combined organic layers were washed with water (5 mL) and brine (5 mL), dried (MgSO$_4$), and concentrated to afford ketone 73 (2.0 mg, 98% yield) as a light yellow oil which was carried forward without additional purification. 73: R$_f$=0.40 (silica gel, EtOAc/hexanes, 1:1); $^1$H NMR (300 MHz, CDCl$_3$) δ 7.98 (d, J=8.7 Hz, 1H), 7.05 (d, J=2.7 Hz, 1H), 6.73 (dd, J=8.7, 2.7 Hz, 1H), 6.39 (app s, 1H), 6.36 (app s, 1H), 6.26 (s, 1H), 6.17 (s, 1H), 3.92 (s, 3H), 3.91 (s, 3H), 3.88 (app s, 6H), 3.87 (s, 3H).

Ketone 74

Solid AIBN (0.8 mg, 0.005 mmol, 1.0 equiv) was added in a single portion at 25° C. to a solution of dibromide 73 (2.0 mg, 0.005 mmol, 1.0 equiv) and (TMS)$_3$SiH (12.8 mL, 0.045 mmol, 9.0 equiv) in toluene (0.5 mL) that had been carefully degassed by bubbling argon for 20 min directly into the solvent. The resultant solution was then heated at 100° C. for 3 h. Upon completion, the reaction contents were cooled to 25° C., concentrated, and purified directly by preparative thin layer chromatography (silica gel, EtOAc/hexanes, 1:1) to afford the desired product (1.7 mg, 85%) as a light yellow oil. 74: R$_f$=0.55 (silica gel, EtOAc/hexanes, 1:1); $^1$H NMR (300 MHz, CDCl$_3$) δ 7.99 (d, J=8.7 Hz, 1H), 6.93 (d, J=2.7 Hz, 1H), 6.71 (m, 2H), 6.64 (d, J=2.1 Hz, 1H), 6.32 (d, J=2.4 Hz, 1H), 6.31 (d, J=2.1 Hz, 1H), 5.51 (s, 1H), 5.39 (s, 1H), 3.86 (s, 3H), 3.85 (app s, 6H), 3.80 (s, 3H), 3.79 (s, 3H).

General Procedure to Access Key Triaryl Intermediates (34')

n-BuLi (2.91 mL, 1.6 M in THF, 4.65 mmol, 1.05 equiv) was added slowly over the course of 5 min to a solution of resveratrol derivative 33' (1.62 g, 4.65 mmol, 1.05 equiv) in THF (10 mL) at −78° C., ultimately yielding a light yellow solution. After 20 min of stirring at −78° C., a solution of the appropriate aldehyde (4.42 mmol, 1.0 equiv) in THF (40 mL) was added slowly at −78° C., and the resultant mixture was stirred for 1 h at −78° C., warmed slowly to 25° C., and stirred for an additional 4 h at 25° C. Upon completion, the reaction contents were quenched with saturated aqueous NH$_4$Cl (20 mL), poured into water (20 mL), and extracted with EtOAc (3×40 mL). The combined organic layers were then washed with water (20 mL) and brine (20 mL), dried (MgSO$_4$), and concentrated. The resultant light yellow oils crystallized upon standing and were then triturated with EtOAc (3×10 mL) to give the desired triaryl intermediates as white solids.

(E)-[2,4-dimethoxy-6-(3,5-dimethoxystyryl)phenyl]-(3,4-dimethoxyphenyl)methanol (38')

75% yield, R$_f$=0.47 (silica gel, EtOAc/hexanes, 1:1); IR (film) $v_{max}$ 3487, 2987, 2930, 2830, 1591, 1511, 1455, 1200, 1136, 1026 cm$^{-1}$; $^1$H NMR (300 MHz, CDCl$_3$) δ 7.35 (d, J=15.9 Hz, 1H), 7.03 (d, J=1.5 Hz, 1H), 6.83 (d, J=15.9 Hz, 1H), 6.74 (d, J=10.2 Hz, 1H), 6.73 (app s, 1H), 6.68 (ddd, J=8.4, 1.7, 0.9 Hz, 1H), 6.55 (d, J=2.4 Hz, 2H), 6.48 (d, J=2.4 Hz, 1H), 6.37 (t, J=2.4 Hz, 1H), 6.21 (d, J=10.2 Hz, 1H), 3.87 (s, 3H), 3.83 (s, 3H), 3.82 (s, 3H), 3.78 (s, 6H), 3.75 (d, J=10.2 Hz, 1H), 3.73 (s, 3H); $^{13}$C NMR (75 MHz, CDCl$_3$) δ 161.4, 160.3, 159.2, 149.1, 148.1, 139.5, 138.7, 137.8, 132.4, 127.7, 122.5, 118.1, 109.8, 105.1, 103.7, 100.6, 99.5, 70.3, 56.2, 55.8, 55.7; HRMS (FAB) calcd for C$_{27}$H$_{30}$O$_7{}^+$ [M$^+$] 466.1992. found 466.1983.

Synthesis of Natural Product-Like Compounds 46' and 47'

These two compounds were synthesized from intermediate 45 exactly as described above for ampelopsin D (2) and paucifloral F (7); as such, only data for selected compounds is provided.

Scheme S2. Synthesis of natural product-like architectures 46 and 47.$^a$

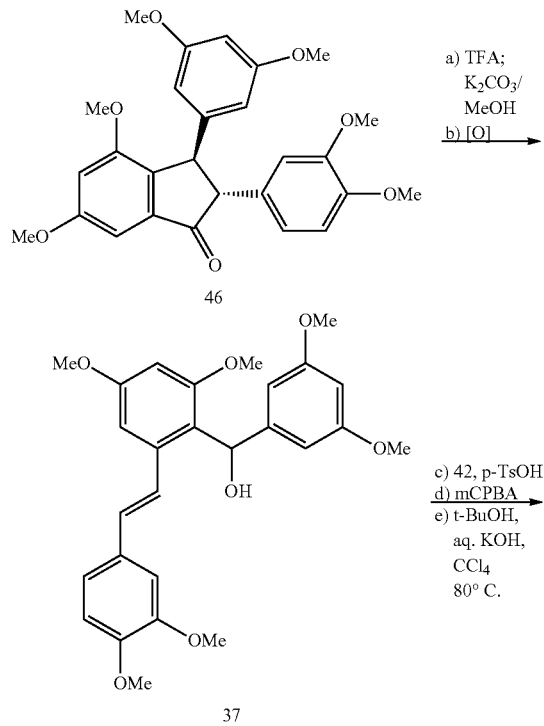

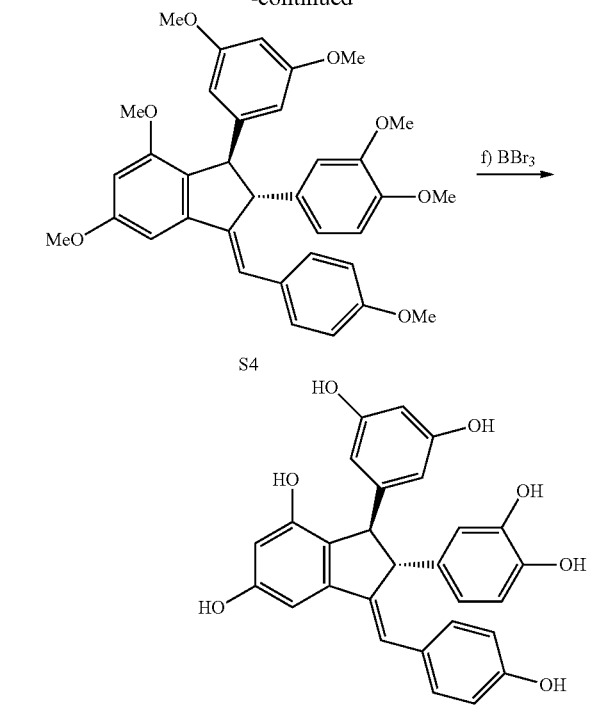

$^a$Reagents and conditions: (a) TFA (1.0 equiv), CH$_2$Cl$_2$, -30→20° C., 5 h; then K$_2$CO$_3$ (10 equiv), MeOH, 25° C., 5 min, 93%; (b) Dess-Martin periodinane (12 equiv), NaHCO$_3$ (5.0 equiv), CH$_2$Cl$_2$, 25° C. 3 h, 98%; (c) p-TsOH (10 equiv), CH$_2$Cl$_2$, -30, →20° C., 5 h; p-methoxybenzenethiol (42. 3.0 equiv), then concentration to near dryness, 25° C., 12 h, 82%; (d) mCPBA (3.0 equiv), NaHCO$_3$ (10 equiv), CH$_2$Cl$_2$, 0→25° C., 3 h, 73%; (e) t-BuOH/H$_2$O/CCl$_4$ (5/1/5), KOH (powder, 20 equiv). 80° C., 12 h, 68%; (f) BBr$_3$ (1.0M in CH$_2$Cl$_2$, 12 equiv), CH$_2$Cl$_2$, 25° C., 6 h, 63% of 47. 20% of internal alkene isomer.

46': R$_f$=0.39 (silica gel, EtOAc/hexanes, 1:1); IR (film) $v_{max}$ 2998, 2935, 2835, 2056, 1733, 1593, 1511, 1486, 1463, 1428, 1329, 1300, 1251, 1236, 1202, 1177, 1154, 1095, 1066, 1030, 935, 827, 757, 733, 694 cm$^{-1}$; $^1$H NMR (300 MHz, CDCl$_3$) δ 7.19 (d, J=8.7 Hz, 2H), 7.09 (s, 1H), 6.83 (d, J 1.8 Hz, 1H), 6.79-6.70 (m, 5H), 6.32-6.26 (m, 4H), 4.34 (app s, 1H), 4.26 (app s, 1H), 3.92 (s, 3H), 3.82 (s, 3H), 3.79 (s, 6H), 3.73 (s, 3H), 3.70 (s, 6H), 3.62 (s, 3H); $^{13}$C NMR (75 MHz, CDCl$_3$) δ 161.5, 160.7, 160.6, 158.4, 157.5, 149.0, 148.2, 147.4, 145.5, 142.7, 137.7, 130.0, 129.7, 126.2, 122.2, 118.7, 113.7, 111.4, 110.6, 105.3, 99.1, 97.6, 95.0, 58.4, 57.9, 55.9, 55.8, 55.6, 55.3, 55.1; HRMS (FAB) calcd for C$_{35}$H$_{35}$O$_7{}^+$ [M$^+$] 568.2461. found 568.2479.

47': R$_f$=0.03 (silica gel, MeOH/CH$_2$Cl$_2$, 1:9); IR (film) $v_{max}$ 3317, 2923, 2851, 1660, 1651, 1604, 1511, 1462, 1455, 1373, 1338, 1248, 1153, 1111, 1008, 832, 693, 662 cm$^{-1}$ $^1$H NMR (300 MHz, CDCl$_3$) δ 7.20 (d, J=8.7 Hz, 2H), 7.02 (s, 1H), 6.78 (d, J=1.8 Hz, 1H), 6.74-6.72 (m, 2H), 6.66 (d, J=8.7 Hz, 2H), 6.30 (d, J=1.8 Hz, 1H), 6.14 (d, J=2.4 Hz, 1H), 6.11-6.09 (m, 3H), 4.21 (app s, 1H), 4.16 (app s, 1H); $^{13}$C NMR (75 MHz, CDCl$_3$) δ 159.9, 158.3, 157.1, 150.4, 148.7, 147.1, 145.4, 144.1, 139.4, 132.2, 131.1, 123.8, 120.4, 117.4, 117.3, 117.0, 115.7, 108.8, 107.5, 104.8, 102.3, 99.4, 60.9, 59.8; HRMS (FAB) calcd for C$_{27}$H$_{27}$O$_7{}^+$ [M$^+$]470.1366. found 470.1375.

Synthesis of Natural Product-Like Compounds 48' and 49'

These two compounds were synthesized from intermediate 38' exactly as described above for ampelopsin D (2) and paucifloral F (7); as such, only data for selected compounds is provided.

pound decomposes relatively quickly even under an Argon atmosphere, precluding several attempts at obtaining a $^{13}C$ spectrum].

S6: $R_f$=0.51 (silica gel, EtOAc/hexanes, 1:1); IR (film) $v_{max}$ 2960, 2919, 2850, 1595, 1463, 1426, 1261, 1117, 1094, 1027 cm$^{-1}$; $^1$H NMR (300 MHz, CDCl$_3$) δ 7.21 (d, J=8.7 Hz, 2H), 7.09 (s, 1H), 6.82 (d, J=1.8 Hz, 1H), 6.73 (d, J=8.7 Hz,

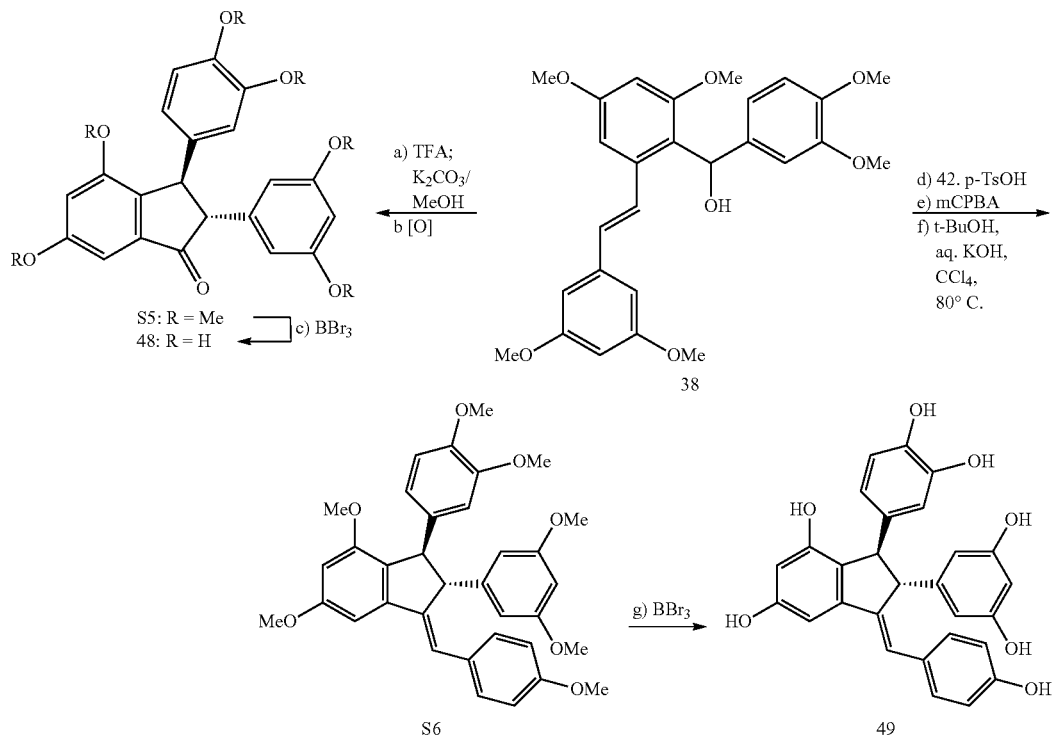

Scheme S3'. Synthesis of natural product-like architectures 48' and 49'.

$^a$Reagents and conditions: (a) TFA (1.0 equiv), CH$_2$Cl$_2$, -30→20° C., 5 h: then K$_2$CO$_3$ (10 equiv), MeOH, 25° C., 5 min, 83%; (b) Dess-martin periodinane (1.2 equiv), NaHCO$_3$ (5.0 equiv), CH$_2$Cl$_2$, 25° C., 1 h, 97%; (c) BBr$_3$ (1.0M in CH$_2$Cl$_2$, 12 equiv), CH$_2$Cl$_2$, 25° C., 12 h, 72%; (d) p-TsOH (1.0 equiv), CH$_2$Cl$_2$, -30→20° C., 5h; p-methoxybenzenethiol (3.0 equiv), then concentration to near dryness, 25° C., 12 h, 65%; (e) mCPBA (3.0 equiv), NaHCO$_3$ (10 equiv), CH$_2$Cl$_2$, 0° C., 15 min. 94%; (f) i-BuOH/H$_2$O/CCl$_4$ (5/1/5), KOH (powder, 20 equiv), 80° C., 12 h, 55%; (g) BBr$_3$ (1.0M in CH$_2$Cl$_2$, 14 equiv), CH$_2$Cl$_2$, 25° C., 2 h, 75%.

S5: $R_f$=0.46 (silica gel, EtOAc/hexanes, 1:1); IR (film) $v_{max}$ 3002, 2936, 2837, 1710, 1593, 1513, 1460, 1304, 1203, 1148, 1028, 730 cm$^{-1}$; $^1$H NMR (300 MHz, CDCl$_3$) δ 6.89 (d, J 2.0 Hz, 1H), 6.73 (d, J=8.8 Hz, 1H), 6.68 (d, J=2.0 Hz, 1H), 6.53 (dd, J=8.8, 2.0 Hz, 1H), 6.53 (d, J=2.8 Hz, 1H), 6.35 (t, J=2.4 Hz, 1H), 6.23 (d, J=2.4 Hz, 2H), 4.48 (d, J=2.8 Hz, 1H), 3.86 (s, 3H), 3.83 (s, 3H), 3.87 (s, 3H), 3.83 (s, 3H), 3.75 (s, 3H), 3.72 (s, 6H), 3.65 (s, 3H), 3.61 (d, J=2.8 Hz, 1H); $^{13}$C NMR (75 MHz, CDCl$_3$) δ 205.8, 162.5, 161.4, 158.2, 149.3, 148.0, 141.9, 139.0, 138.6, 136.4, 119.3, 111.5, 110.8, 107.0, 106.5, 99.4, 96.9, 65.7, 56.2, 56.0, 55.71, 55.70. HRMS (FAB) calcd for $C_{21}H_{28}O_7{}^+$ [M+$^+$] 464.1835. found 464.1842.

48': $R_f$=0.13 (silica gel, DCM/MeOH, 9:1); IR (film) $v_{max}$ 3418, 1683, 1615, 1495, 1374, 1154; $^1$H NMR (400 MHz, acetone-d$_6$) δ 6.74 (d, J=2.1 Hz, 1H), 6.73 (d, J=3.1 Hz, 1H), 6.72 (d, J=8.0 Hz, 1H), 6.51 (d, J=2.4 Hz, 1H), 6.43 (dd, J=8.1, 2.1 Hz, 1H), 6.25 (t, J=2.4 Hz, 1H), 6.13 (d, J=2.4 Hz, 2H), 4.44 (d, J=2.4 Hz, 1H), 3.43 (d, J=2.4 Hz, 1H); $^{13}$C NMR (75 MHz, acetone-d$_6$) δ 205.8, 165.8, 163.0, 158.9, 154.0, 145.0, 143.8, 142.0, 140.5, 124.8, 120.5, 115.2, 109.6, 102.5, 102.1, 100.1, 97.8, 60.0, 47.9; HRMS (FAB) calcd for $C_{21}H_{16}O_7{}^+$ [M$^+$] 380.0896. found 380.0884. [Note: this com- 2H), 6.69 (s, 1H), 6.67 (d, J=1.8 Hz, 1H), 6.64 (d, J=1.8 Hz, 1H), 6.61 (d, J=2.1 Hz, 1H), 6.41 (d, J=2.1 Hz, 2H), 6.30 (d, J=2.1 Hz, 1H), 6.28 (t, J=2.1 Hz, 1H), 4.31 (app s, 1H), 4.28 (app s, 1H), 3.91 (s, 3H), 3.80 (s, 3H), 3.75 (s, 3H), 3.73 (s, 3H), 3.72 (s, 6H), 3.65 (s, 3H); $^{13}$C NMR (75 MHz, CDCl$_3$) δ 6161.9, 161.4, 158.9, 157.9, 149.1, 148.1, 147.7, 145.6, 142.9, 138.9, 130.4, 130.1, 127.2, 122.8, 119.1, 114.2, 111.6, 110.9, 105.8, 99.6, 98.1, 95.4, 59.5, 57.5, 56.2, 56.0, 55.6; HRMS (FAB) calcd for $C_{35}H_{37}O_7{}^+$ [M+H$^+$] 569.2539. found 569.2520.

49': $R_f$=0.03 (silica gel, CH$_2$Cl$_2$/MeOH, 9:1); IR (film) $v_{max}$ 3394, 2956, 2917, 2849, 1363, 1260; $^1$H NMR (300 MHz, acetone-d$_6$) δ 7.22 (d, J=8.7 Hz, 2H), 7.04 (s, 1H), 6.79 (d, J=2.1 Hz, 1H), 6.69 (d, J=8.7 Hz, 2H), 6.67 (d, J=8 Hz, 1H), 6.53 (d, J=1.8 Hz, 2H), 6.50 (dd, J 8.1, 2.4 Hz, 1H), 6.31 (app t, J=2.4 Hz, 3H), 6.20 (t, J=2.1 Hz, 1H), 4.22 (app s, 1H) 4.15 (app. s, 1H); $^{13}$C NMR (75 MHz, acetone-d$_6$) δ 159.20, 159.16, 156.8, 156.7, 155.4, 148.6, 146.9, 145.2, 143.7, 142.2, 138.3, 130.5, 124.0, 122.4, 118.7, 115.5, 115.4, 114.3, 105.8, 103.3, 101.1, 97.9, 60.2, 57.3; HRMS (FAB) calcd for $C_{28}H_{22}O_7{}^+$ [M$^+$]470.1366. found 470.1366.

Synthesis of Natural Product-Like Compound 50'

This compound was synthesized from intermediate 52' (prepared in the above sequence) exactly as described above for ampelopsin D (2) and paucifloral F (7) except for the step incorporating the sulfide fragment and the final deprotection, so only these procedures are defined specifically below. The synthesis of sulfide 53' is also described, along with physical data for the starting material (i.e. 52').

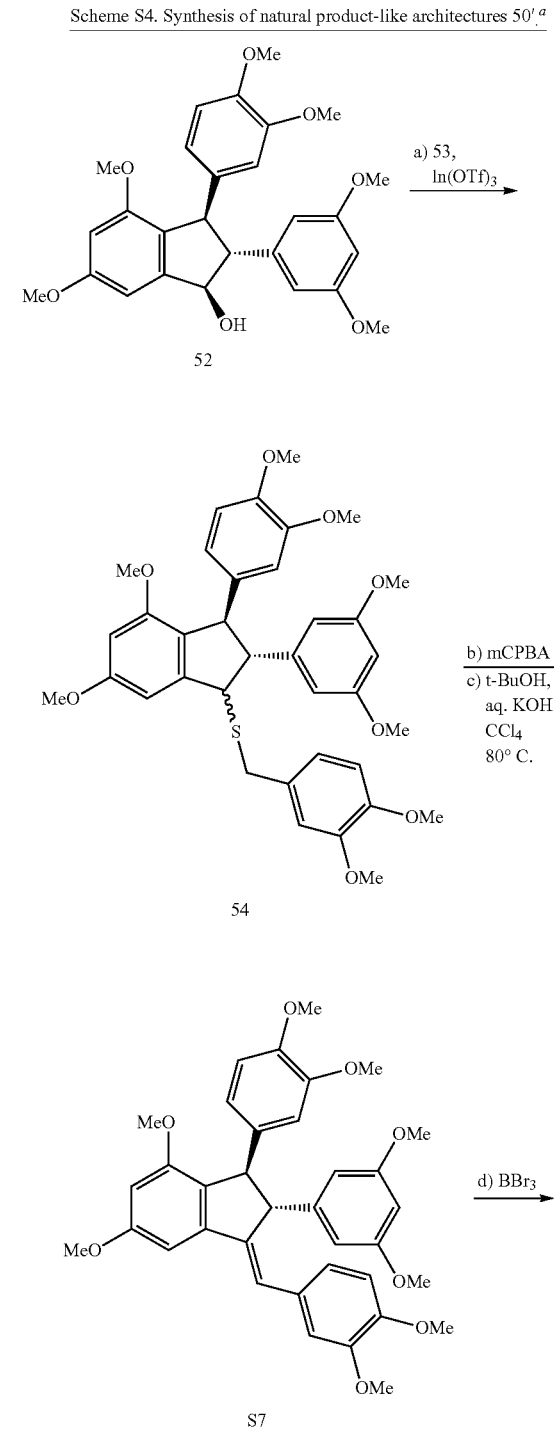

Scheme S4. Synthesis of natural product-like architectures 50'.[a]

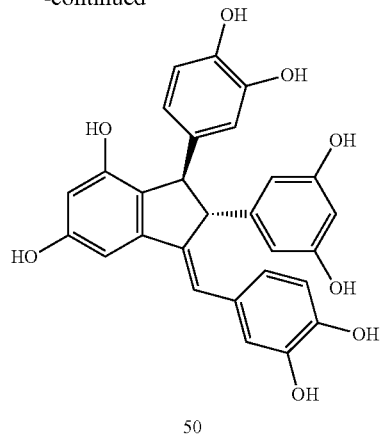

[a]Reagents and conditions: (a) In(OTf)$_3$ (1.0 equiv), 53 (2.6 equiv), 25° C., 90 min, 85%, 100% based on recovered 52; (b) mCPBA (3.0 equiv), NaHCO$_3$ (10 equiv), CH$_2$Cl$_2$, 0° C., 15 min, 94%; (c) t-BuOH/H$_2$O/CCl$_4$ (5/1/5), KOH (powder, 20 equiv), 80° C., 12 h, 55%; (d) BBr$_3$ (1.0M in CH$_2$Cl$_2$, 12 equiv), CH$_2$Cl$_2$, 25° C., 6 h, 82%.

52': $R_f$=0.24 (silica gel, EtOAc/hexanes, 1:1); IR (film) $v_{max}$ 3495, 3000, 2937, 2937, 1594, 1513, 1461, 1201, 1147, 1045, 1027, 729 cm$^{-1}$; $^1$H NMR (300 MHz, CDCl$_3$) δ 6.69 (d, J=8.1 Hz, 1H), 6.64 (d, J=1.8 Hz, 1H), 6.57 (d, J=1.8 Hz, 1H), 6.41 (d, J=2.1 Hz, 1H), 6.33 (t, J=2.1 Hz, 1H), 6.31 (d, J=2.1 Hz, 2H), 5.18 (t, J=6.6 Hz, 1H), 4.23 (d, J=7.2 Hz, 1H), 3.85 (s, 3H), 3.83 (s, 3H), 3.72 (s, 6H), 3.55 (s, 3H), 3.13 (t, J=6.9 Hz, 1H), 2.25 (d, J=6.6 Hz, 1H); $^{13}$C NMR (75 MHz, CDCl$_3$) δ 162.0, 161.2, 157.5, 148.9, 147.6, 146.6, 144.6, 137.3, 123.5, 119.8, 111.4, 111.0, 107.5, 106.3, 100.1, 99.8, 99.0, 82.4, 67.8, 56.2, 56.0, 55.7 (2C), 54.3; HRMS (FAB) calcd for C$_{27}$H$_{30}$O$_7$·[M$^+$] 466.1992. found 466.1983.

3,4-dimethoxytoluenethiol (53')

NaBH$_4$ (0.455 g, 12.0 mmol, 1.95 equiv) was added slowly to a solution of 3,4-dimethoxybenzaldehyde (1.00 g, 6.15 mmol, 1.0 equiv) in MeOH (10 mL) at 0° C. After 30 min of stirring at 0° C., the reaction contents were quenched by the slow addition of water (10 mL), poured into water (10 mL), and extracted with EtOAc (3×15 mL). The combined organic layers were then dried (MgSO$_4$) and concentrated to afford desired alcohol intermediate (1.00 g, 99% yield) as a colorless liquid. Moving forward without any additional purification, this intermediate (1.00 g, 5.95 mmol, 1.0 equiv) was dissolved in water/acetone (1:1, 15 mL). Thiourea (0.910 g, 12.0 mmol, 2.0 equiv) was then added at 25° C., the solution was acidified by addition of 5 N HCl (7 mL), and the resultant mixture was stirred at 25° C. for 12 h. Upon completion, the contents were poured into water and extracted with EtOAc (3×15 mL) to remove excess thiourea. Following separation of the aqueous layer, it was brought to an alkaline pH by the addition of crushed NaOH (1 g), transferred to a sealed tube, and heated at 100° C. for 3 h. Upon completion, the contents were cooled to 25° C. and acidified with concentrated HCl (~2 mL), and poured into water (10 mL) and extracted with EtOAc (3×15 mL). The combined organic layers were then washed with water (15 mL) and brine (15 mL), dried (MgSO$_4$), and concentrated to give 53' (1.06 g, 97%) as a colorless oil which was used without additional purification. 53': $R_f$=0.57 (silica gel, EtOAc/hexanes, 1:1); IR (film) $v_{max}$ 3000, 2934, 2834, 1514, 1464, 1263, 1027 cm$^{-1}$; $^1$H NMR (300 MHz, CDCl$_3$) δ 6.87 (s, 1H), 6.86 (app d, J=8.1 Hz, 1H), 6.80 (d, J=8.1 Hz, 1H), 3.89 (s, 3H), 3.72 (d, J=7.2 Hz, 2H), 1.76 (t, J=7.2 Hz, 1H), $^{13}$C NMR (75 MHz, CDCl$_3$) δ 149.3, 148.3, 133.9, 120.4, 111.7, 111.6, 56.0, 55.9, 28.9. HRMS (FAB) calcd for C$_9$H$_{12}$O$_2$S$^+$ [M$^+$] 184.0558. found 184.0567.

Sulfide 54'

To a neat mixture of 52' (0.100 g, 0.214 mmol, 1.0 equiv) and In(OTf)$_3$ (0.120 g, 0.214 mmol, 1.0 equiv) at 25° C. was added thiol 53' (0.10 mL, 0.617 mmol, 2.6 equiv) in a single portion. The resultant viscous red mixture was protected from light and stirred for 90 min at 25° C. Upon completion, the reaction contents were dissolved in EtOAc (2.0 mL), quenched with saturated aqueous NaHCO$_3$ (15 mL), filtered through Celite, and extracted with EtOAc (3×20 mL). The combined organic layers were washed with water (15 mL) and brine (15 mL), dried (MgSO$_4$), and concentrated. The resultant yellow solid was purified by flash column chromatography (silica gel, EtOAc/hexanes, 1:9→1:1) to give recovered 52' (0.150 g) along with sulfide 54' (0.118 g, 87% yield, 100% yield based on recovered s.m.) as a white amorphous solid. 54': R$_f$=0.39 (silica gel, EtOAc/hexanes, 1:1); IR (film) $v_{max}$ 2997, 2935, 2835, 1595, 1514, 1463, 1261, 1150 cm$^{-1}$; $^1$H NMR (300 MHz, CDCl$_3$, 3:2 mixture of diastereomers) major diastereomer δ 6.72 (d, J=1.8 Hz, 1H), 6.70 (d, J=9.6 Hz, 1H), 6.68 (d, J=8.1 Hz, 1H), 6.64 (d, J=2.1 Hz, 1H), 6.55 (dd, J=9.6, 2.8 Hz, 1H) 6.54 (dd, J=8.1, 1.5 Hz, 1H), 6.46 (d, J=2.1 Hz, 1H), 6.42 (d, J=2.1 Hz, 2H), 6.35 (t, J=2.1 Hz, 1H), 6.32 (d, J=2.1 Hz, 2H), 4.27 (d, J=6.0 Hz, 2H), 3.84 (s, 3H), 3.84 (s, 3H), 3.83 (s, 3H), 3.76 (s, 3H), 3.73 (s, 3H), 3.72 (s, 6H), 3.63 (m, 2H), 3.55 (s, 3H), 3.38 (app t, J=6.0 Hz, 1H); $^1$H NMR (300 MHz, CDCl$_3$, 3:2 mixture of diastereomers) minor diastereomer δ 6.73 (d, J=1.8 Hz, 1H), 6.69 (d, J=7 Hz, 1H), 6.69 (d, J=2.1 Hz, 1H), 6.63 (d, J=2.1 Hz, 1H), 6.62 (dd, J=7.1, 2.1 Hz, 1H), 6.56 (dd, J=8.1, 1.8 Hz, 1H), 6.56 (d, J=8.1 Hz, 1H), 6.35 (d, J=2.1 Hz, 2H), 6.34 (t, J=3.0 Hz, 1H), 6.24 (d, J=3.0 Hz, 1H), 4.59 (d, J 6.0 Hz, 1H), 4.49 (d, J=6.0 Hz, 1H), 3.58 (app t, J=9.0 Hz, 1H), 3.83 (s, 3H), 3.82 (s, 3H), 3.81 (s, 3H), 3.80 (s, 3H), 3.73 (s, 6H), 3.72 (s, 3H), 3.56 (s, 3H); $^{13}$C NMR (75 MHz, CDCl$_3$, 3:2 mixture of diastereomers) δ 159.5, 159.2, 158.8, 158.3, 155.0, 146.9, 146.8, 146.4, 145.9, 145.3, 145.1, 143.9, 143.2, 141.3, 135.3, 134.3, 128.8, 128.7, 122.3, 122.0, 119.1, 117.4, 117.0, 109.9, 108.7, 108.6, 108.5, 105.4, 103.7, 98.8, 98.4, 96.9, 96.5, 64.1, 59.6, 54.8, 53.8, 53.7, 53.4, 52.3, 50.7, 34.6, 33.8; HRMS (FAB) calcd for C$_{36}$H$_{40}$O$_8$S$^+$ [M$^+$] 632.2444. found 632.2441.

S7: R$_f$=0.50 (silica gel, EtOAc/hexanes, 1:1); IR (film) $v_{max}$ 2952, 2923, 2851, 1732, 1593, 1514, 1463, 1261, 1151 cm$^{-1}$; $^1$H NMR (400 MHz, CDCl$_3$) δ 7.11 (s, 1H), 6.87 (dd, J=8.4, 1.6 Hz, 1H), 6.83 (d, J=1.6 Hz, 1H), 6.76 (d, J=1.6 Hz, 1H), 6.71 (d, J=8.4 Hz, 1H), 6.63 (d, J=8.4 Hz, 1H), 6.68 (d, J=2.0 Hz, 1H), 6.64 (dd, J=8.2, 2.0 Hz, 1H), 6.43 (d, J=2.4 Hz, 2H), 6.31 (d, J=2.0 Hz, 1H), 6.28 (t, J=2.4 Hz, 1H), 4.32 (app s, 1H), 4.29 (app s, 1H), 3.91 (s, 3H), 3.81 (s, 3H), 3.80 (s, 3H), 3.76 (s, 3H), 3.70 (s, 6H), 3.60 (s, 3H), 3.54 (s, 3H); $^{13}$C NMR (75 MHz, CDCl$_3$) δ 161.4, 161.1, 157.4, 148.6, 148.5, 148.0, 147.6, 147.3, 145.1, 142.3, 138.4, 130.0, 126.7, 122.8, 122.2, 110.9, 110.5, 105.4, 99.2, 97.6, 949, 59.2, 57.1, 55.7, 55.5, 55.2; HRMS (FAB) calcd for C$_{36}$H$_{38}$O$_8$$^+$ [M$^+$] 598.2567. found 598.2573.

Gnetulin Analog (50')

To a solution of 37 (11.0 mg, 0.023 mmol, 1.0 equiv) in CH$_2$Cl$_2$ (1 mL) at –78° C. was added dropwise a commercial solution of BBr$_3$ (0.330 mL, 1.0M in CH$_2$Cl$_2$, 0.330 mmol, 14.3 equiv). After 10 min of stirring at –78° C., the solution was quickly warmed to 25° C. and stirred for an additional 2 h. Upon completion, the reaction mixture was quenched with water (5 mL), poured into water (10 mL), and extracted with EtOAc (3×10 mL).

The combined organic layers were washed with water (10 mL) and brine (10 mL), dried (MgSO$_4$), and concentrated. The resultant pale pink solid was purified by preparative TLC on Et$_3$N-deactivated plates (CH$_2$Cl$_2$/MeOH, 9:1) to give 50' along with a small, and inseparable, amount of its internal alkene regioisomer (7.4 mq, 83% yield) as a pale yellow oil. [Note: under the reaction conditions, almost no alkene isomerization was observed; this event occurs only upon final purification]. 50': R$_f$=0.06 (silica gel, CH$_2$Cl$_2$/MeOH, 9:1); IR (film) $v_{max}$ 3416, 2919, 2847, 1630, 1384, 1105, 1064 cm$^{-1}$; $^1$H NMR (300 MHz, acetone-d$_6$) δ 6.97 (s, 1H), 6.93 (d, J=2.1 Hz, 1H), 6.78 (d, J=1.8 Hz, 1H), 6.74 (m, 1H), 6.67 (d, J=7.5 Hz, 1H), 6.57 (d, J=8.7 Hz, 1H), 6.49 (dd, J=8.1, 2.1 Hz, 1H), 6.39 (d, J=2.1 Hz, 1H), 6.33 (d, J=2.4 Hz, 2H), 6.30 (d, J=2.1 Hz, 1H), 6.18 (t, J=2.1 Hz, 1H), 4.22 (s, 1H), 4.19 (s, 1H); $^{13}$C NMR (75 MHz, acetone-d$_6$) δ 161.4, 160.8, 157.7, 150.7, 147.4, 147.2, 144.5, 140.6, 133.8, 132.2, 125.1, 124.0, 122.3, 120.9, 117.6 (2C), 116.7, 108.2, 105.5, 103.4, 100.1, 62.4, 59.7; HRMS (FAB) calcd for C$_{28}$H$_{22}$O$_8$$^+$ [M$^+$] 486.1315. found 486.1327.

Chloride 51'

Solid BiCl$_3$ (0.076 g, 0.240 mmol, 1.05 equiv) was added in a single portion to a solution of alcohol 15 (0.100 g, 0.229 mmol, 1.0 equiv) in CH$_2$Cl$_2$ (10 mL) at –78° C. The resultant reaction mixture was then warmed slowly to –30° C. over the course of 1 h and stirred for 3 h at –30° C. Upon completion, the reaction mixture was quenched with saturated aqueous NaHCO$_3$ (10 mL), poured into water (10 mL), and extracted with EtOAc (3×20 mL). The combined organic layers were then washed with water (20 mL) and brine (20 mL), dried (MgSO$_4$), and concentrated. The resultant yellow oil was purified by flash column chromatography (silica gel, EtOAc/hexanes, 1:4) to give chloride 51' (0.090 g, 86% yield) as a light yellow oil. 51': R$_f$=0.58 (silica gel, EtOAc/hexanes, 1:1); IR (film) $v_{max}$ 2924, 2853, 1727, 1608, 1596, 1514, 1490, 1463, 1428, 1332, 1305, 1251, 1203, 1179, 1146, 1095, 1066, 1035, 927, 827, 788, 699 cm$^{-1}$; $^1$H NMR (300 MHz, CDCl$_3$) δ 7.08 (d, J=8.7 Hz, 2H), 6.84 (d, J=9.0 Hz, 2H), 6.64 (d, J=1.8 Hz, 1H), 6.42 (d, J=2.1 Hz, 1H), 6.30 (t, J=2.4 Hz, 1H), 6.22 (d, J=2.4 Hz, 2H), 5.27 (d, J=6.0 Hz, 1H), 4.28 (d, J=6.3 Hz, 1H), 3.87 (s, 3H), 3.79 (s, 3H), 3.69 (s, 6H), 3.59 (s, 3H), 3.56 (t, J=6.6 Hz, 1H); $^{13}$C NMR (75 MHz, CDCl$_3$) δ 161.8, 160.4, 158.7, 156.9, 146.3, 144.5, 133.6, 128.4, 123.7, 114.1, 105.6, 100.1, 98.3, 77.2, 68.4, 65.7, 56.1, 55.6, 55.4, 55.2; HRMS (FAB) calcd for C$_{26}$H$_{26}$O$_5$Cl$^+$ [M$^+$] 454.1547. found 454.1554.

Sulfide 55'

4-methoxytoluenethiol (42', 0.014 mL, 0.100 mmol, 3.0 equiv) and In(OTf)$_3$ (0.019 g, 0.033 mmol, 1.0 equiv) were added sequentially in single portions to a solution of biaryl alcohol 11 (0.015 g, 0.033 mmol, 1.0 equiv) in CH$_2$Cl$_2$ (0.5 mL) at –50° C. The resultant mixture was then warmed to –10° C. over the course of 5 min with constant stirring. Upon completion, the reaction contents were quenched with saturated aqueous NaHCO$_3$ (2 mL), poured into water (2 mL), and extracted with EtOAc (3×5 mL). The combined organic layers were washed with water (5 mL) and brine (5 mL), dried (MgSO$_4$), and concentrated. The resultant yellow solid was purified by flash column chromatography (silica gel, EtOAc/hexanes, 1:9→1:1) to give 55' (0.018 g, 96% yield) as a white amorphous solid. 55': R$_f$=0.63 (silica gel, EtOAc/hexanes, 1:2); IR (film) $v_{max}$ 3000, 2935, 2835, 1597, 1511, 1250, 1154 cm$^{-1}$; $^1$H NMR (300 MHz, CDCl$_3$) δ 7.24 (d, J=8.4 Hz, 2H), 7.21 (d, J=15.9 Hz, 1H), 7.20 (d, J=8.4 Hz, 2H), 6.85 (d, J=8.4 Hz, 2H), 6.78 (d, J=8.4 Hz, 2H), 6.75 (d, J=15.9 Hz, 1H), 6.69 (d, J=2.4 Hz, 1H), 6.65 (dd, J=2.1, 0.6 Hz, 2H), 6.38 (d, J=2.4 Hz, 1H), 6.28 (t, J=2.1 Hz, 1H), 5.70 (br s, 1H), 3.84 (s, 3H), 3.82 (s, 3H), 3.76 (s, 3H), 3.71 (s, 6H), 3.69 (s, 3H), 3.68 (s, 2H); $^{13}$C NMR (75 MHz, CDCl$_3$) 160.9, 159.8, 159.7, 159.0, 144.8, 139.5, 130.9, 130.8, 130.5, 129.7, 128.3, 126.1, 121.7, 114.4, 114.2, 114.1, 106.8, 103.2, 98.6, 98.4, 56.2, 55.7, 55.7 (4C), 37.2; HRMS (FAB) calcd for $C_{34}H_{36}O_6S^+$ [M$^+$] 572.2233. found 572.2225.

Ketone 57'

To a solution of permethylated paucifloral F (56', 0.150 g, 0.345 mmol, 1.0 equiv) in THF (20 mL) at −78° C. was added a solution of KHMDS (0.759 mL, 0.5 M in toluene 0.380 mmol, 1.1 equiv) in a single portion. The resultant bright yellow reaction mixture was then warmed slowly to 25° C. over the course of 3 h and stirred for 12 h at 25° C. Upon completion, the reaction mixture was quenched with water (15 mL), poured into water (15 mL), and extracted with EtOAc (3×25 mL). The combined organic layers were washed with brine (15 mL), dried (MgSO$_4$), and concentrated. The resultant dark purple oil was purified by flash column chromatography (silica gel, EtOAc/hexanes, 1:3) to give ketone 57' (0.123 g, 82% yield) as light yellow oil. 57': R$_f$=0.43 (silica gel, EtOAc/hexanes, 1:1); IR (film) v$_{max}$ 3002, 2938, 2837, 1717, 1610, 1512, 1496, 1463, 1430, 1358, 1309, 1249, 1204, 1180, 1154, 1066, 1039, 965, 934, 834, 807, 791, 736, 702 cm$^{-1}$; $^1$H NMR (300 MHz, CDCl$_3$) δ 6.99 (d, J=1.8 Hz, 1H), 6.92 (d, J=9.0 Hz, 2H), 6.74 (d, J=2.1 Hz, 1H), 6.57 (d, J=9.0 Hz, 2H), 6.07 (t, J=2.1 Hz, 1H), 5.82 (br s, 2H), 4.62 (s, 1H), 3.91 (s, 3H), 3.67 (s, 3H), 3.64 is, 3H), 3.55 (s, 6H), 2.99 (s, 1H); $^{13}$C NMR (75 MHz, CDCl$_3$) δ 206.9, 161.9, 159.8, 158.7, 158.3, 141.6, 137.3, 135.5, 132.3, 128.1, 112.8, 107.4, 107.2, 98.5, 96.8, 85.5, 77.2, 56.6, 55.8, 55.7, 55.2; HRMS (MALDI-FTMS) calcd for $C_{26}H_2O_6^+$ [M$^+$]433.1651. found 433.1667.

Total Synthesis of Cararosinol C (68') and Cararosinol D (69')

These two compounds were synthesized from intermediates S6 and S7 exactly as described above for pallidol (3) with some alteration in solvent and reaction times as noted below; as such, only data for selected compounds are provided.

Scheme S5. Total synthesis of cararosinol C (68') and cararosinol D (69').$^a$

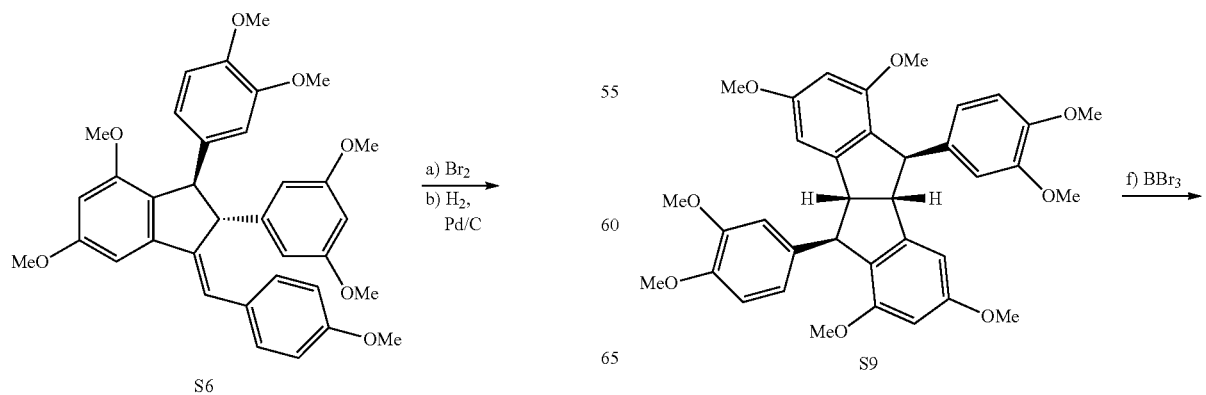

-continued

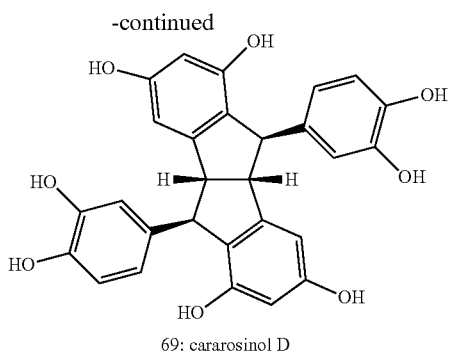

69: cararosinol D

*a* Reagents and conditions: (a) Br₂ (2.0 equiv), CH₂Cl₂, -78° C., 60 min, 10 min with O₂ atmosphere, 97%; (b) H₂, Pd/C (20%, 0.2 equiv). THF, 25° C., 24 h, 94%; (c) BBr₃ (1.0M in CH₂Cl₂, 12 equiv). CH₂Cl₂, 0° C., 10 min, then 25° C., 3 h, 97%; (d) Br₂ (2.0 equiv), CH₂Cl₂, -78° C. 60 min. 10 min with O₂ atmosphere, 97%; (e) H₂, Pd/C (20%, 0.2 equiv), THF, 25° C., 24 h, 83%; (f) BBr₃ (1.0M in CH₂Cl₂, 12 equiv), CH₂Cl₂, 0° C., 10 min, then 25° C., 3 h, 95%.

88: $R_f$=0.32 (silica gel, EtOAc/hexanes, 1:1 IR (film) $v_{max}$ 2928, 2934, 1602, 1508, 1141 cm⁻¹; ¹H NMR (300 MHz, CDCl₃) δ 7.06 (d, J=8.7 Hz, 2H), 6.79 (d, J=8.4 Hz, 2H), 6.71 (d, J=2.1 Hz, 1H), 6.68 (app s, 1H), 6.62 (dd, J=8.1, 1.5 Hz, 2H), 6.49 (d, J=8.4 Hz, 1H), 6.26 (app d, J=1.8 Hz, 2H), 4.59 (app d, J=3.3 Hz, 1H), 4.00 (app dd, J=10.5, 6.3 Hz, 1H), 3.85 (s, 6H), 3.83 (s, 3H), 3.82 (s, 3H), 3.76 (s, 3H), 3.62 (s, 3H), 3.60 (s, 3H); ¹³C NMR (75 MHz, CDCl₃) 161.7, 161.6, 157.4, 149.2, 149.1, 148.9, 138.9, 138.4, 138.3, 128.6, 128.5, 125.3, 119.3, 114.1, 111.6, 111.4, 101.0, 100.8, 100.7, 98.1, 98.0, 60.1, 56.5, 56.4, 56.3, 56.1, 56.0, 55.8, 55.6, 54.2, 53.9; HRMS (FAB) calcd for $C_{35}H_{36}O_7$ [M⁺]568.2567. found 568.2472.

Cararosinol C (68')

$R_f$=0.11 (silica gel, CH₂Cl₂/MeOH, 9:1); IR (film) $v_{max}$ 3285, 2933, 1698, 1599, 1512, 1463, 1355, 1257, 1129, 1043, 838 cm⁻¹; ¹H NMR (300 MHz, acetone-d₆) δ 6.95 (d, J=8.4 Hz, 2H), 6.68 (d, J=8.4 Hz, 2H), 6.67 (d, J=8.7 Hz, 1H), 6.58 (d, J=2.1 Hz, 2H), 6.57 (d, J=2.0 Hz, 1H), 6.16 (br s, 2H), 4.53 (s, 1H), 4.48 (s, 1H), 3.79 (d, J=6.0 Hz, 1H), 3.76 (d, J=6.6 Hz, 1H) ¹³C NMR (75 MHz, acetone-d₆) 159.3 (2C), 156.3, 155.3 (2C), 150.3 (2C), 145.6, 143.9, 138.7, 137.8, 129.0, 123.2 (2C), 119.5, 115.9, 115.8, 115.1, 103.3, 103.2, 102.5 (2C), 60.6, 60.5, 54.1, 54.0; LRMS (FAB) calcd for $C_{20}H_{22}O_7Na⁺$ [M+Na⁺]493.13. found 493.33. All spectroscopic data for this synthetic material in acetone-d₆ match those reported by Yang and co-workers for the same naturally-derived compound [32].

S9: $R_f$=0.31 (silica gel, EtOAc/hexanes, 1:1); IR (film) $v_{max}$ 3003, 2935, 1595, 1508, 1460, 1265, 1141; ¹H NMR (400 MHz, CDCl₃) δ 6.74 (d, J=8 Hz, 2H), 6.72 (d, J=2.0 Hz, 2H), 6.68 (d, J=1.6 Hz, 2H), 6.63 (dd, J=8 Hz, 2.0 Hz, 2H), 6.26 (d, J=1.6 Hz, 2H), 4.58 (s, 2H), 4.01 (s, 2H), 3.85 (s, 6H), 3.823 (s, 6H), 3.818 (s, 6H), 3.43 (s, 6H); ¹³C NMR (75 MHz, CDCl₃) 157.4, 149.0, 138.8, 128.6, 125.1, 119.3, 111.5, 111.4, 102.4, 100.8, 98.0, 89.2, 60.0, 56.3, 56.0, 55.7, 54.3, 50.0; HRMS (FAB) calcd for $C_{36}H_{38}O_8⁺$ [M⁺]598.2567. found 598.2596.

Cararosinol D (69')

$R_f$=0.01 (silica gel, CH₂Cl₂/MeOH, 9:1); IR (film) $v_{max}$ 3399, 2923, 1604, 1462, 1378, 1260, 1103, 1023, 801; ¹H NMR (300 MHz, acetone-d₆) δ 6.67 (d, J=7.8 Hz, 2H), 6.58 (d, J=1.8 Hz, 2H), 6.52 (dd, J=7.8, 1.8 Hz, 2H), 6.16 (d, J=1.8 Hz, 2H), 4.47 (s, 1H), 3.76 (s, 1H); ¹³C NMR (75 MHz, acetone-d₆) 159.2, 155.4, 150.3, 145.6, 143.9, 138.8, 123.2, 119.4, 115.9, 115.1, 103.2, 102.5, 60.5, 54.1. All spectroscopic data for this synthetic material in acetone-d₆ match those reported by Yang and co-workers for the same naturally-derived compound [32].

7-Membered Ring Bromide 3

Solid NaHCO₃ (3.30 g, 39.4 mmol, 10 equiv) and Dess-Martin periodinane (1.67 g, 3.94 mmol, 1.0 equiv) were added sequentially in single portions to a solution of alcohol 11 (1.72 g, 3.94 mmol, 1.0 equiv) in CH₂Cl₂ (30 mL) at 25° C., and the resultant slurry was stirred for 2 h at 25° C. Upon completion, the reaction contents were quenched with saturated aqueous Na₂SO₃ (10 mL) followed by stirring the resultant biphasic system vigorously for 5 min at 25° C. The reaction contents were then poured into saturated aqueous NaHCO₃ (10 mL) and extracted with EtOAc (3×30 mL). The combined organic layers were washed with water (30 mL) and brine (30 mL), dried (MgSO₄), and concentrated to afford the desired ketone (31, 1.66 g, 97% yield) as a white solid. 31: $R_f$=0.45 (silica gel, EtOAc/hexanes, 1:1); IR (film) $v_{max}$ 3003, 2938, 2838, 1668, 1595, 1512, 1456, 1426, 1351, 1316, 1301, 1273, 1252, 1204, 1175, 1157, 1118, 1080, 1065, 1032, 989, 971, 928, 831, 782, 765, 736, 703 cm⁻¹; ¹H NMR (300 MHz, CDCl₃) δ 7.27 (d, J=8.7 Hz, 2H), 6.99 (d, J=2.4 Hz, 2H), 6.98 (d, J=16.2 Hz, 1H), 6.84 (d, J=2.1 Hz, 1H), 6.80 (d, J=8.7 Hz, 2H), 6.74 (d, J=15.9 Hz, 1H), 6.63 (app t, J=2.4 Hz, 1H), 6.42 (d, J=2.4 Hz, 1H), 3.91 (s, 3H), 3.79 (s, 6H), 3.78 (s, 3H), 3.68 (s, 3H); ¹³C NMR (75 MHz, CDCl₃) δ 197.3, 161.3, 160.8, 159.5, 158.4, 140.4, 137.7, 131.0, 129.6, 128.0, 123.1, 121.4, 114.0, 107.3, 105.7, 101.1, 97.7, 55.8, 55.5 (2C), 55.3; HRMS (FAB) calcd for $C_{26}H_{26}O_6⁺$ [M⁺] 434.1729. found 434.1725. Next, a solution of Br₂ (0.024 mL, 0.460 mmol, 1.0 equiv) in CH₂Cl₂ (0.4 mL) was added dropwise to a solution of the newly-formed ketone (31, 0.200 g, 0.460 mmol, 1.0 equiv) in CH₂Cl₂ (0.2 mL) at −78° C. The reaction mixture was then stirred for 1 h at −78° C., warmed slowly to 0° C. over the course of 1 h, and then stirred for 3 h at 0° C. and an additional 12 h at 25° C. Upon completion, the reaction mixture was quenched with saturated aqueous NaHCO₃ (2 mL), poured into water (1 mL), and extracted with EtOAc (3×10 mL). The combined organic layers were then washed with water (10 mL) and brine (10 mL), dried (MgSO₄), and concentrated to afford bromide 33 (0.118 g, 50%) as a white solid that was utilized immediately in subsequent chemistry. [Note: this product is especially light sensitive, so it must be kept away from sunlight at all times]. 33: Rt=0.36 (silica gel, EtOAc/hexanes, 1:1); IR (film) $v_{max}$ 2932, 2829, 1659, 1602, 1511, 1450, 911, 832 cm⁻¹; ¹H NMR (300 MHz, CDCl₃) δ 7.27 (d, J=2.7 Hz, 1H), 6.75 (d, J=8.7 Hz, 2H), 6.57 (d, J=8.7 Hz, 2H), 6.57 (d, J=2.7 Hz, 1H), 5.74 (d, J=2.1 Hz, 1H), 5.25 (d, J=5.1 Hz, 1H), 5.12 (d, J=5.4 Hz, 1H), 3.90 (s, 3H), 3.83 (s, 3H), 3.69 (s, 3H), 3.58 (s, 3H), 3.53 (s, 3H).

Alkene 80

To a solution of bromide 33 (0.119 g, 0.231 mmol, 1.0 equiv) in THF (10 mL) at 25° C. was sequentially added finely powdered KOH (0.129 g, 2.31 mmol, 10.0 equiv) and 18-crown-6 (0.006 g, 0.023 mmol, 0.1 equiv) in single portions; the reaction was then wrapped in aluminum foil to protect the contents from light. The resultant mixture was heated at 40° C. for 12 h. Upon completion, the reaction contents were quenched with saturated aqueous NH₄Cl (15 mL), poured into water (10 mL), and extracted with EtOAc (3×20 mL). The combined organic layers were then washed with water (10 mL) and brine (10 mL), dried (MgSO$_4$), and concentrated. The resultant yellow oily residue was purified by flash column chromatography (silica gel, EtOAc/hexanes, 1:1) to give alkene 80 (0.092 g, 92%) as an amorphous white solid. 80: R$_f$=0.39 (silica gel, EtOAc/hexanes, 1:1); IR (film) ν$_{max}$ 2996, 2932, 1669, 1593, 1565, 1508, 1454, 1328 cm$^{-1}$; $^1$H NMR (400 MHz, CDCl$_3$) δ 7.22 (d, J=8.8 Hz, 2H), 6.95 (s, 1H), 6.84 (d, J=8.7 Hz, 2H), 6.83 (d, J=2.1 Hz, 1H), 6.50 (app d, J=1.8 Hz, 2H), 6.46 (d, J=1.5 Hz, 1H), 3.90 (s, 3H), 3.86 (s, 3H), 3.85 (s, 3H), 3.82 (s, 3H), 3.47 (s, 3H); $^{13}$C NMR (75 MHz, CDCl$_3$) δ 195.2, 161.4, 161.1, 158.7, 158.6, 157.6, 147.4, 140.0, 137.5, 137.2, 127.5, 116.6, 113.2, 103.6, 101.9, 100.3, 98.7, 56.1, 55.8, 55.7, 55.5, 55.3; HRMS (FAB) calcd for C$_{26}$H$_{25}$O$_6$+ [M+H$^+$] 433.1651. found 433.1659.

Cyclized Alcohol 83

A solution of ketone 31 (0.500 g, 1.15 mmol, 1.0 equiv) in MeCN (10 mL) at 25° C. was treated sequentially with an aqueous solution of the disodium salt of EDTA (6 mL, 0.0004 M), excess 1,1,1-trifluoroacetone (2 mL), Oxone® (3.50 g, 5.75 mmol, 5.0 equiv), and solid NaHCO$_3$ (0.774 g, 11.5 mmol, 8.0 equiv). The resulting suspension was allowed to stir at 25° C. for 3 h. Upon completion, the reaction mixture was quenched with saturated aqueous NH$_4$Cl (15 mL), poured into water (30 mL), and extracted with Et$_2$O (3×30 mL). The combined organic layers were then washed with water (10 mL) and brine (10 mL), dried (MgSO$_4$), and concentrated. The resultant red oily residue was purified by flash column chromatography (silica gel, EtOAc/hexanes, 1:1) to give 83 (0.176 g, 34%) as a pale yellow solid. [Note: this compound exists as an equilibrium mixture of both alcohol and lactol forms in a 6:1 ratio, respectively]. 83: R$_f$=0.14 (silica gel, EtOAc/hexanes, 1:1); IR (film) ν$_{max}$ 3442, 2996, 2955, 2939, 1666, 1651, 1650, 1600, 1511, 1454, 1153 cm$^{-1}$; $^1$H NMR (400 MHz, CDCl$_3$) δ 7.16 (d, J=2.4 Hz, 1H), 6.72 (d, J=8.8 Hz, 2H), 6.61 (d, J=8.0 Hz, 2H), 6.54 (d, J=2.8 Hz, 1H), 6.35 (d, J=2.0 Hz, 1H), 5.79 (d, J=1.8 Hz, 1H), 4.99 (dd, J=6.3, 1.8 Hz, 1H), 4.87 (d, J=6.3 Hz, 1H), 3.88 (s, 3H), 3.82 (s, 3H), 3.71 (s, 3H), 3.59 (s, 3H), 3.52 (s, 3H), 2.37 (d, J=2.0 Hz, 1H); $^{13}$C NMR (75 MHz, CDCl$_3$) δ 195.7, 161.5, 159.2, 158.1, 157.8, 141.5, 141.1, 133.6, 129.2, 121.8, 119.9, 113.2, 112.8, 104.1, 103.4, 98.7, 78.4, 56.1, 56.0, 55.5, 55.4, 55.1, 49.6; HRMS (FAB) calcd for C$_{26}$H$_{27}$O$_7$+ [M+H$^+$] 451.1757. found 451.1768.

Cyclized Ketone 85

To a solution of ketone 31 (0.200 g, 0.461 mmol, 1.0 equiv) in toluene (10 mL) at 25° C. was added solid p-TsOH (0.875 g, 4.61 mmol, 10.0 equiv) and the resultant mixture was heated at 80° C. for 12 h. Upon completion, the reaction mixture was quenched with saturated aqueous NaHCO$_3$ (20 mL), poured into water (20 mL), and extracted with EtOAc (3×20 mL). The combined organic layers were then washed with water (15 mL) and brine (15 mL), dried (MgSO$_4$), and concentrated. The resultant brown oily residue was purified by flash column chromatography (silica gel, EtOAc/hexanes, 1:1) to give cyclized ketone 85 (0.192 g, 96%) as a white solid. 85: R$_f$=0.43 (silica gel, EtOAc/hexanes, 1:1); IR (film) ν$_{max}$ 3003, 2942, 2835, 1666, 1594, 1508, 1458, 1318 cm$^{-1}$; $^1$H NMR (300 MHz, CDCl$_3$) δ 7.13 (d, J=2.7 Hz, 1H), 6.70 (d, J=8.7 Hz, 2H), 6.60 (d, J=8.7 Hz, 2H), 6.53 (d, J=2.7 Hz, 1H), 6.26 (d, J=2.1 Hz, 1H), 5.70 (d, J=2.1 Hz, 1H), 4.65 (dd, J=6.9, 2.7 Hz, 1H), 3.88 (s, 3H), 3.79 (s, 3H), 3.70 (s, 3H), 3.58 (s, 3H), 3.52 (s, 3H), 3.51 (dd, J=13.5, 3.0 Hz, 1H), 2.93 (dd, J=13.5, 6.9 Hz, 1H); $^{13}$C NMR (75 MHz, CDCl$_3$) δ 197.0, 161.7, 158.9, 158.6, 157.7, 157.3, 141.3, 138.8, 135.9, 128.4, 125.2, 123.4, 112.9, 105.8, 103.8, 103.2, 97.2, 55.9, 55.87, 55.3, 55.1, 42.7, 40.9; HRMS (FAB) calcd for C$_{26}$H$_{27}$O$_6$+ [M+H$^+$] 435.1808. found 435.1802.

Alkene 86

To a solution of alcohol 83 (10.0 mg, 0.222 mmol, 1.0 equiv) in toluene (3 mL) was added solid p-TsOH (0.422 g, 2.22 mmol, 10 equiv) as a single portion and the resultant mixture was heated at 65° C. for 12 h. Upon completion, the reaction mixture was quenched with saturated aqueous NaHCO$_3$ (10 mL), poured into water (10 mL), and extracted with EtOAc (3×10 mL). The combined organic layers were then washed with water (10 mL) and brine (10 mL), dried (MgSO$_4$), and concentrated to afford pure alkene 86 (9.6 mg, 96%) as a white solid. 86: R$_f$=0.37 (silica gel, EtOAc/hexanes, 1:1); IR (film) ν$_{max}$ 2927, 2908, 1682, 1651, 1594, 1594, 1559, 1505, 1454 cm$^{-1}$; $^1$H NMR (300 MHz, CCl$_3$) δ 7.39 (d, J=8.4 Hz, 2H), 7.37 (s, 1H), 6.92 (d, J=8.3 Hz, 2H), 6.84 (d, J=2.0 Hz, 1H), 6.58 (d, J=2.0 Hz, 1H), 6.54 (d, J 2.0 Hz, 1H), 6.28 (d, J=2.0 Hz, 1H), 3.90 (app s, 9H), 3.85 (s, 3H), 3.64 (s, 3H); $^{13}$C NMR (75 MHz, CDCl$_3$) δ 195.3, 160.9, 160.5, 159.0, 157.8, 157.3, 144.7, 138.9, 138.6, 136.7, 130.4, 123.5, 117.6, 116.3, 113.6, 105.0, 100.9, 99.9, 99.2, 56.3, 56.0, 55.7, 55.3 (2C); HRMS (FAB) calcd for C$_{26}$H$_{25}$O$_6$+ [M+H$^+$] 433.1651. found 433.1645.

Permethylated Diptoindonesin D (84)

Dess-Martin periodinane (0.113 g, 0.266 mmol, 1.2 equiv) and solid NaHCO$_3$ (0.093 g, 1.11 mmol, 5.0 equiv) were added sequentially in single portions to a solution of alcohol 83 (0.100 g, 0.222 mmol, 1.0 equiv) in CH$_2$Cl$_2$ (10 mL) at 25 SC, and the resultant slurry was stirred for 1 h at 25° C. Upon completion, the reaction contents were quenched with saturated aqueous Na$_2$SO$_3$ (3 mL) followed by stirring the resultant biphasic system vigorously for 5 min at 25° C., poured into water (5 mL), and extracted with EtOAc (3×15 mL). The combined organic layers were then washed with saturated aqueous NaHCO$_3$ (3×10 mL), dried (MgSO$_4$), and concentrated to give permethylated diptoindonesin D (84, 0.095 g, 96%) as a light yellow oil. 84: R$_f$=0.25 (silica gel, EtOAc/hexanes, 1:1); IR (film) ν$_{max}$ 2932, 2834, 1676, 1650, 1593, 1460, 1508 cm$^{-1}$; $^1$H NMR (400 MHz, CDCl$_3$) δ 7.19 (d, J=2.4 Hz, 1H), 6.81 (d, J=8.8 Hz, 2H), 6.67 (d, J=8.8 Hz, 2H), 6.66 (d, J=2.4 Hz, 1H), 6.60 (d, J=2.4 Hz, 1H), 6.58 (d, J=2.4 Hz, 1H), 5.97 (s, 1H), 3.89 (s, 3H), 3.85 (app s, 6H), 3.81 (s, 3H), 3.69 (s, 3H); $^{13}$C NMR (75 MHz, CDCl$_3$) δ 196.4, 193.7, 162.9, 160.6, 159.6, 158.4, 157.9, 146.2, 137.0, 129.9, 128.7, 120.8, 113.9, 111.8, 106.2, 103.6, 103.3, 101.0, 56.7, 56.2, 55.7, 55.6, 55.1, 54.9; LRMS (APCI+) calcd for C$_{21}$H$_{16}$O$_6$+ [M+H$^+$] 449. found 449.

Cyclised Product 92

Dess-Martin periodinane (0.109 g, 0.258 mmol, 1.2 equiv) and solid NaHCO$_3$ (0.180 g, 2.15 mmol, 10 equiv) were added sequentially in single portions to a solution of alcohol 37' (0.100 g, 0.215 mmol, 1.0 equiv) in CH$_2$Cl$_2$ (10 mL) at 25° C., and the resultant slurry was stirred for 1 h at 25° C. Upon completion, the reaction contents were quenched with saturated aqueous Na$_2$SO$_3$ (3 mL) followed by stirring the resultant biphasic system vigorously for 5 min at 25° C., poured into water (5 mL), and extracted with EtOAc (3×15 mL). The combined organic layers were then washed with saturated aqueous NaHCO$_3$ (3×10 mL), dried (MgSO$_4$), and concentrated to give the desired ketone (0.098 g, 96%) as a white solid. R$_f$=0.46 (silica gel, EtOAc/hexanes, 1:1); IR (film) v$_{max}$ 2923, 2948, 2857, 1647, 1559, 1505, 1454 cm$^{-1}$; $^1$H NMR (300 MHz, CDCl$_3$) δ 6.99 (d, J=2.4 Hz, 1H), 6.93 (m, 2H), 6.80 (d, J=1.8 Hz, 1H), 6.78 (d, J=1.8 Hz, 1H), 6.61 (m, 1H), 6.63 (app t, J=2.4 Hz, 1H), 6.42 (d, J=1.8 Hz, 1H), 3.91 (s, 3H), 3.86 (s, 3H), 3.83 (s, 3H), 3.79 (s, 6H), 3.69 (s, 3H); $^{13}$C NMR (75 MHz, CDCl$_3$) δ 197.1, 161.2, 160.7, 158.3, 149.1, 148.9, 140.4, 137.5, 131.1, 129.9, 123.3, 121.2, 120.0, 111.0, 109.1, 107.1, 105.4, 101.1, 97.7, 55.7 (2C), 55.6 (2C), 55.4 (2C). Next, p-TsOH (0.082 g, 0.860 mmol, 2.0 equiv) was added in a single portion to a solution of the newly-generated ketone (0.200 g, 0.43 mmol, 1.0 equiv) in toluene (10 mL) at 25° C. and the resultant mixture was heated at 60° C. for 48 h. Upon completion, the reaction contents were quenched with oily residue was purified by flash column chromatography (silica gel, EtOAc/hexanes, 1:1) to give cyclized ketone 94 (0.454 g, 83%) as a white crystalline solid. 94: R$_f$=0.36 (silica gel, EtOAc/hexanes, 1:1); m.p.=167-168° C.; IR (film) v$_{max}$ 2951, 2925, 1650, 1598, 1508, 1459, 1267, 1207 cm$^{-1}$; $^1$H NMR (400 MHz, CDCl$_3$) δ 7.66 (s, 1H), 7.34 (d, J=1.6 Hz, 1H), 6.74 (d, J=2.4 Hz, 1H), 6.35 (s, 1H), 6.26 (t, J=2.0 Hz, 1H), 5.89 (d, J=2.0 Hz, 2H), 4.56 (dd, J=8.4, 3.6 Hz, 1H), 3.99 (s, 3H), 3.96 (s, 3H), 3.91 (s, 3H), 3.70 (s, 3H), 3.63 (s, 6H); 3.31 (dd, J=12.8, 3.6 Hz, 1H), 2.55 (dd, J=12.8, 8.4 Hz, 1H); $^{13}$C NMR (75 MHz, CDCl$_3$) δ 183.3, 160.2, 159.4, 157.1, 152.2, 148.2, 141.1, 139.3, 133.7, 127.1, 125.2, 110.4, 108.3, 107.8, 103.4, 100.2, 98.6, 56.0, 55.9, 55.7 (2C), 55.2, 53.4, 46.0, 39.3; HRMS (FAB) calcd for C$_{27}$H$_{29}$O$_7$+[M+H$^+$] 465.1913. found 465.1917.

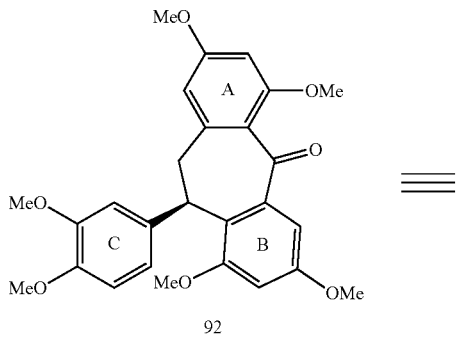
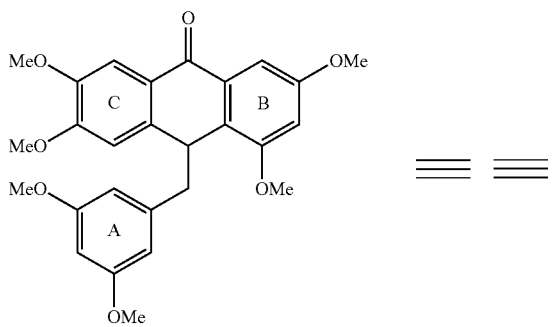

Figure S2. X-ray crystal structures of 92 and 94.

saturated aqueous NaHCO$_3$ (20 mL), poured into water (20 mL), and extracted with EtOAc (3×20 mL). The combined organic layers were then washed with water (15 mL) and brine (15 mL), dried (MgSO$_4$), and concentrated. The resultant brown oily residue was purified by flash column chromatography (silica gel, EtOAc/hexanes, 1:1) to give cyclized ketone 92 (0.454 g, 85%) as a white crystalline solid. 92: R$_f$=0.24 (silica gel, EtOAc/hexanes, 1:1); m.p.=80-82° C.; IR (film) v$_{max}$ 3002, 2930, 1653, 1600, 1514, 1458, 1340, 1207, 1138 cm$^{-1}$; $^1$H NMR (300 MHz, CDCl$_3$) δ 7.15 (d, J=2.4 Hz, 1H), 6.60 (d, J=8.4 Hz, 2H), 6.53 (d, J=2.9 Hz, 1H), 6.41 (dd, J=8.1, 1.8 Hz, 1H), 6.28 (d, J=2.1 Hz, 1H), 5.71 (d, J=2.1 Hz, 1H), 4.64 (dd, J=6.9, 2.7 Hz, 1H), 3.89 (s, 3H), 3.79 (s, 3H), 3.78 (s, 3H), 3.58 (app s, 6H), 3.54 (s, 3H); $^{13}$C NMR (75 MHz, CDCl$_3$) δ 196.7, 161.8, 158.8, 158.6, 157.8, 148.0, 146.7, 141.1, 138.9, 136.3, 125.1, 123.4, 119.8, 111.1, 110.3, 105.9, 103.9, 103.2, 97.1, 55.9, 55.6, 55.4, 55.3, 43.1, 40.9; HRMS (FAB) calcd for C$_{27}$H$_{29}$O$_7$+ [M+H$^+$]465.1913. found 465.1924.

Cyclized Ketone 94

Solid p-TsOH (0.655 g, 3.448 mmol, 8.0 equiv) was added in a single portion to solution of the ketone derived from 37' (0.200 g, 0.431 mmol, 1.0 equiv) in toluene (10 mL) at 25° C. and the resultant was mixture heated to 60° C. for 48 h. Upon completion, the reaction contents were quenched with saturated aqueous NaHCO$_3$ (20 mL), poured into water (20 mL), and extracted with EtOAc (3×20 mL). The combined organic layers were then washed with water (15 mL) and brine (15 mL), dried (MgSO$_4$), and concentrated. The resultant brown Permethylated Cassigarol B (51)

Solid LiAlH$_4$ (0.041 g, 1.08 mmol, 5.0 equiv) was added in a single portion to a solution of cyclized ketone 48 (0.100 g, 0.22 mmol, 1.0 equiv) in THF (10 mL) at 0° C. The resulting slurry was stirred at 0° C. for 1 h, then slowly warmed to 25° C. and stirred for an additional 1 h. Upon completion, the reaction contents were quenched with 1 N HCl (10 mL) and stirred vigorously for an additional 2 h at 25° C. Next, saturated aqueous NaHCO$_3$ (15 mL) was added, and the reaction mixture poured into water (10 mL) and extracted with EtOAc (3×20 mL). The combined organic layers were then washed with water (15 mL) and brine (15 mL), dried (MgSO$_4$), and concentrated. The resultant light yellow oily residue was purified by flash column chromatography (silica gel, EtOAc/hexanes, 1:1) to give permethylated cassigarol B (51, 0.088 g, 91%) as a white solid. Alternatively, permethylated cassigarol B could be prepared in 73% yield by the identical procedure starting from biaryl ketone 94. Additionally, permethylated cassigarol B (51) could be prepared by the slow, dropwise addition of HBr (33% in HOAc, 7.8 µL, 0.043 mmol, 1.0 equiv) to a solution of alcohol 45 (0.020 g, 0.043 mmol, 1.0 equiv) in CH$_2$Cl$_2$ (2 mL) at −78° C. The solution was stirred at −78° C. for 1 h, then slowly warmed to 25° C. and stirred for an additional 12 h. Upon completion, the reaction contents were quenched by the addition of saturated aqueous NaHCO$_3$ (10 mL), poured into water (10 mL), and extracted with EtOAc (3×20 mL). The combined organic layers were then washed with water (15 mL) and brine (15 mL), dried (MgSO$_4$), and concentrated. The resultant dark oily residue was purified by flash column chromatography (silica gel, EtOAc/hexanes, 1:1) to give permethylated cassigarol B (51, 0.016 g, 74%) as a white solid. Finally, permethylated cassigarol B (51) could also be prepared by the addition of PBr$_3$ (4.0 µL, 0.043 mmol, 1.0 equiv) to a solution of alcohol 45 (0.020 g, 0.043 mmol, 1.0 equiv) in CH$_2$Cl$_2$ (2 mL) at 25° C. The resultant red solution was warmed to 40° C. and then stirred for an additional 3 h at 40° C. Upon completion, the reaction mixture was quenched with water (5 mL), poured into water (5 mL), and extracted with EtOAc (3×5 mL). The combined organic layers were then washed with water (5 mL) and brine (5 mL), dried (MgSO$_4$), and concentrated. The resultant dark oily residue was purified by flash column chromatography (silica gel, EtOAc/hexanes, 1:1) to give permethylated cassigarol B (51, 0.012 g, 58%) as a white solid. 51: R$_f$=0.39 (silica gel, EtOAc/hexanes, 1:1); IR (film) v$_{max}$ 3005, 2932, 2828, 1606, 1508, 1444, 1207, 1138 cm$^{-1}$; $^1$H NMR (300 MHz, CDCl$_3$) δ 6.94 (s, 1H), 6.87 (s, 1H), 6.53 (d, J=2.2 Hz, 1H), 6.29 (d, J=2.2 Hz, 1H), 6.24 (d, J=2.4 Hz, 1H), 6.02 (d, J=2.3 Hz, 1H), 5.52 (s, 1H), 4.57 (dd, J=6.9, 3.5 Hz, 1H), 3.91 (s, 3H), 3.86 (s, 3H), 3.85 (s, 3H), 3.83 (s, 3H), 3.77 (s, 3H), 3.65 (s, 3H), 3.14 (d, J=3.4 Hz, 2H); $^{13}$C NMR (75 MHz, CDCl$_3$) δ 158.9, 158.5, 156.2, 155.9, 147.7, 147.1, 146.9, 137.3, 137.2, 134.0, 123.0, 121.4, 109.9, 109.2, 107.8, 102.1, 96.4, 96.3, 56.1, 55.5, 55.4, 55.1, 41.9, 36.4, 36.2; HRMS (FAB) calcd for C$_{27}$H$_{28}$O$_6$· [M$^+$] 448.1886. found 448.1882.

Cassigarol B (52)

Permethylated cassigarol B (51, 15.0 mg, 0.0334 mmol, 1.0 equiv) was dissolved in CH$_2$Cl$_2$ (1.0 mL) and treated with BBr$_3$ (0.40 mL, 1.0 M in CH$_2$Cl$_2$, 0.40 mmol, 12 equiv) at −78° C. The resultant red solution was stirred for 1 h at −78° C., allowed to warm slowly to 25° C. and then stirred for an additional 10 h at 25° C. Upon completion, the reaction mixture was quenched with water (5 mL), poured into water (5 mL), and extracted with EtOAc (3×5 mL). The combined organic layers were then washed with water (5 mL) and brine (5 mL), dried (MgSO$_4$), and concentrated. The resultant product was purified by preparative TLC (silica gel, CH$_2$Cl$_2$/MeOH, 9:1) to give cassigarol B (52, 10.6 mg, 87%) as an off-white solid. 52: R$_f$=0.11 (silica gel, CH$_2$Cl$_2$/MeOH, 9:1); IR (film) V ax 3300, 2945, 2927, 1682, 1600, 1454, 1328, 1296 cm$^{-1}$; $^1$H NMR (300 MHz, DMSO-d$_6$) δ 9.13 (s, 1H), 9.12 (s, 1H), 8.87 (s, 1H), 8.74 (s, 1H), 8.56 (br s, 1H), 8.52 (br s, 1H), 6.67 (s, 1H), 6.55 (s, 1H), 6.09 (d, J=2.0 Hz, 1H), 6.04 (d, J=2.0 Hz, 1H), 6.00 (d, J=2.0 Hz, 1H), 5.70 (d, J 2.0 Hz, 1H), 5.03 (s, 1H), 4.18 (m, 1H), 2.79 (m, 2H); $^{13}$C NMR (75 MHz, acetone-d$_6$) δ 155.5, 155.2, 153.3, 153.2, 147.9, 142.5, 142.2, 136.9, 136.0, 132.8, 120.3, 117.9, 113.4, 112.4, 108.7, 103.2, 99.6, 99.5, 41.1, 36.2, 35.4; HRMS (FAB) calcd for C$_{21}$H$_{16}$O$_6$· [M$^+$] 364.0947. found 364.0964. All spectroscopic data for the free phenol form of this synthetic material in DMSO-d$_6$ match those reported by Kozawa and co-workers for the same naturally-derived compound (26).

Methyl Ether 53

NaH (60% dispersion in mineral oil, 0.086 g, 2.14 mmol, 2.0 equiv) was added in a single portion to a solution of alcohol 45 (0.500 g, 1.07 mmol, 1.0 equiv) in THF (15 mL) at 0° C. After stirring for 30 min at 0° C., MeI (0.33 mL, 5.35 mmol, 5.0 equiv) was added dropwise at 0 OC. The resulting mixture was then warmed slowly to 25° C. and stirred for an additional 4 h. Upon completion, the reaction mixture was quenched with saturated aqueous NH$_4$Cl (15 mL), poured into water (10 mL), and extracted with EtOAc (3×20 mL). The combined organic layers were then washed with water (10 mL) and brine (10 mL), dried (MgSO$_4$), and concentrated. The resultant oil was then triturated with hexanes (3×10 mL) to remove residual mineral oil, yielding 53 (0.494 g, 98%) as a pale yellow solid. 53: R$_f$=0.34 (silica gel, EtOAc/hexanes, 1:1); IR (film) v$_{max}$ 2999, 2955, 2933, 1670, 1591, 1514, 1451, 1261, 1157 cm$^{-1}$; $^1$H NMR (300 MHz, CDCl$_3$) δ 7.42 (d, J=16.1 Hz, 1H), 6.86 (m, 2H), 6.78 (app t, J=2.6 Hz, 2H), 6.74 (d, J=16.1 Hz, 1H), 6.57 (m, 2H), 6.44 (d, J=2.3 Hz, 1H), 6.27 (app t, J=2.2 Hz, 2H), 6.10 (s, 1H), 3.89 (s, 3H), 3.87 (app s, 6H), 3.85 (s, 3H), 3.69 (s, 6H), 3.33 (s, 3H); $^{13}$C NMR (75 MHz, CDCl$_3$) δ 160.5, 159.9, 159.5, 149.0, 148.7, 146.1, 139.4, 131.1, 128.4, 126.4, 120.1, 119.7, 111.0, 108.6, 104.2, 102.5, 97.9, 97.4, 75.9, 56.4, 55.9, 55.7, 55.3, 55.1 (2C); HRMS (FAB) calcd for C$_{28}$H$_{32}$O$_7$· [M$^+$] 480.2148. found 480.2151.

Alcohol 61

A solution of Br$_2$ (10.7 µL, 0.200 mmol, 1.0 equiv) in CH$_2$Cl$_2$ (1.0 mL) was added dropwise to a solution of methyl ether 53 (0.100 g, 0.200 mmol, 1.0 equiv) in CH$_2$Cl$_2$ (5.0 mL) at −78° C. The resultant dark green solution was stirred at −78° C. for 2 h, warmed slowly to 25° C. over the course of 6 h, and stirred for an additional 6 h at 25° C. Upon completion, the reaction mixture was quenched with saturated aqueous NaHCO$_3$ (15 mL), poured into water (5 mL), and extracted with EtOAc (3×15 mL). The combined organic layers were then washed with water (10 mL) and brine (10 mL), dried (MgSO$_4$), and concentrated. The resultant crude brown oil was purified by flash column chromatography (silica gel, EtOAc/hexanes, 1:1) to give cyclized alcohol 61 (0.047 g, 52% yield) as a white solid. 61: R$_f$=0.18 (silica gel, EtOAc/hexanes, 1:1); IR (film) v$_{max}$ 3471, 2996, 2948, 2927, 1606, 1587, 1458, 1268, 1194, 1151 cm$^{-1}$; $^1$H NMR (300 MHz, CDCl$_3$) δ 6.90 (s, 1H), 6.82 (s, 1H), 6.67 (d, J=2.1, 1H), 6.56 (d, J=2.1, 1H), 6.34 (d, J=2.1, 1H), 6.31 (d, J=2.1, 1 H), 5.10 (s, 1H), 4.78 (m, 2H), 3.93 (s, 3H), 3.86 (app s, 6H), 3.82 (s, 3H), 3.79 (s, 3H), 3.77 (s, 3H), 1.79 (d, J=11.4 Hz, 1H); $^{13}$C NMR (75 MHz, CDCl$_3$) δ 159.4, 159.1, 157.2, 155.4, 148.0, 147.8, 147.4, 138.5, 134.7, 129.5, 126.1, 117.5, 115.6, 110.2, 105.8, 102.2, 97.1, 96.2, 69.4, 56.0, 55.9, 55.6, 55.5, 55.3, 45.8, 45.5; HRMS (FAB) calcd for C$_{27}$H$_{29}$O$_7$· [M+H$^+$] 465.1913. found 465.1928.

Permethylated Cassigarol B Analog #1 (62)

To a solution of alcohol 61 (6.5 mg, 0.014 mmol, 1.0 equiv) in CH$_2$Cl$_2$ (4.7 mL) at 0° C. was added NaCNBH$_3$ (0.089 mg, 1.42 mmol, 100 equiv) in a single portion to give a cloudy suspension. A solution of TFA in CH$_2$Cl$_2$ (0.132 mL TFA diluted with CH$_2$Cl$_2$ to a final volume of 0.6 mL, 0.084 mmol, 6.0 equiv) was added dropwise over the course of 10 min. The resultant suspension was stirred at 0° C. for 30 min and then slowly warmed to 25° C. and stirred for an additional 1 h. Upon completion, the reaction contents were quenched with saturated aqueous NaHCO$_3$ (5 mL), poured into water (5 mL), and extracted with EtOAc (3×5 mL). The combined organic layers were then washed with water (5 mL) and brine (5 mL), dried (MgSO$_4$), and concentrated. The resultant oil yellow oil was purified by flash column chromatography (silica gel, EtOAc/hexanes, 1:1) to give 62 (5.5 mg, 87%) as a white crystalline solid. 62: R$_f$=0.43 (silica gel, EtOAc/hexanes, 1:1); m.p.=220-221° C.; IR (film) v$_{max}$ 2923, 2911, 1609, 1587, 1518, 1315, 1141 cm$^{-1}$; $^1$H NMR (300 MHz, CDCl$_3$) δ 6.84 (s, 1H), 6.57 (d, J=2.3 Hz, 1H), 6.54 (d, J=2.2 Hz, 1H), 6.36 (s, 1H), 6.30 (d, J 2.3 Hz, 1H), 6.28 (d, J=2.2 Hz, 1H), 3.89 (s, 3H), 3.83 (s, 3H), 3.82 (s, 3H), 3.78 (s, 3H), 3.77

(s, 3H), 3.70 (s, 3H), 3.10 (d, J=3.6 Hz, 2H); $^{13}$C NMR (75 MHz, CDCl$_3$) δ 159.1, 159.0, 156.2, 155.0, 147.7, 147.5, 146.3, 143.5, 133.4, 126.7, 125.2, 120.2, 115.1, 111.4, 102.9, 101.9, 96.4, 96.3, 56.1, 55.8, 55.6, 55.4, 55.3, 45.3, 37.4, 35.0; HRMS (FAB) calcd for C$_{27}$H$_{28}$O$_6$·[M$^+$] 448.1886. found 448.1896.

Cassigarol B Analog #1 (63)

Permethylated cassigarol B analog #1 (62, 15.0 mg, 0.033 mmol, 1.0 equiv) was dissolved in CH$_2$Cl$_2$ (1.0 mL), and the resultant solution was degassed by bubbling argon through it for 20 min. The solution was then cooled to −78° C. and treated with BBr$_3$ (0.40 mL, 1.0 M solution in CH$_2$Cl$_2$, 0.400 mmol, 12 equiv). The resultant red mixture was stirred for 1 h at −78° C., allowed to warm slowly to 25 OC over 1 h, and then stirred for an additional 2 h at 25° C. Upon completion, the reaction mixture was quenched with water (5 mL), poured into water (5 mL), and extracted with EtOAc (3×5 mL). The combined organic layers were then washed with water (5 mL) and brine (5 mL), dried (MgSO$_4$), and concentrated. The resultant crude brown oil was purified by preparative TLC (silica gel, CH$_2$Cl$_2$/MeOH, 9:1) to give cassigarol B analog #1 (63, 9.4 mg, 78%) as a clear oil. 63: R$_f$=0.11 (silica gel, CH$_2$Cl$_2$/MeOH, 9:1); IR (film) ν$_{max}$ 3377, 2914, 1592, 1490, 1365 cm$^{-1}$; $^1$H NMR (400 MHz, acetone-d$_6$) δ 8.16 (s, 1H), 8.09 (s, 1H), 7.92 (s, 1H), 7.90 (s, 1H), 7.43 (s, 1H), 7.39 (s, 1H), 6.76 (s, 1H), 6.40 (d, J=2.0 Hz, 1H), 6.37 (d, J=2.4 Hz, 1H), 6.30 (s, 1H), 6.20 (d, J=2.0 Hz, 1H), 6.18 (d, J=2.0 Hz, 1H), 4.91 (s, 1H), 4.46 (t, J=3.6 Hz, 1H), 2.96 (d, J=2.8 Hz, 2H); $^{13}$C NMR (75 MHz, acetone-d$_6$) δ 156.6, 156.5, 154.0, 152.9, 148.8, 144.9, 143.8, 142.4, 134.1, 126.4, 123.1, 118.8, 118.0, 115.5, 105.0, 104.3, 100.4, 100.3, 45.6, 37.9, 35.8; LRMS (APCI+) calcd for C$_{21}$H$_{16}$O$_6$· [M+H$^+$] 365. found 365.

Permethylated Cassigarol B analog #2 (113)

To a solution of alcohol 61 (15.0 mg, 0.032 mmol, 1.0 equiv) in CH$_2$Cl$_2$ (2.0 mL) was added concentrated TFA (0.303 mL, 0.19 mmol, 12 equiv) at 0° C. to give a brown solution. After 10 minutes of stirring at 0° C., the solution was warmed slowly to 25° C. and stirred for an additional 3 h. Solid NaCNBH$_3$ (42.0 mg, 0.64 mmol, 20 equiv) was then added in a single portion and the reaction contents were stirred vigorously for 10 min. Upon completion, the reactions contents were quenched with saturated aqueous NaHCO$_3$ (5 mL), poured into water (5 mL), and extracted with EtOAc (3×5 mL). The combined organic layers were then washed with water (5 mL) and brine (5 mL), dried (MgSO$_4$), and concentrated. The resultant brown oil was purified by flash column chromatography (silica gel, EtOAc/hexanes, 1:1) to give 113 (12.6 mg, 83%) as a white crystalline solid. 113: R$_f$=0.43 (silica gel, EtOAc/hexanes, 1:1); m.p.=108-109° C.; IR (film) ν$_{max}$ 2941, 2825, 1597, 1508, 1321, 1196, 1143 cm$^{-1}$; $^1$H NMR (300 MHz, CDCl$_3$) δ 6.92 (s, 1H), 6.91 (s, 1H), 6.56 (app t, 2H), 6.29 (d, J=2.4 Hz, 1H), 6.21 (d, J=2.4 Hz, 1H), 5.09 (s, 1H), 4.14 (t, J=3.8 Hz, 1H), 3.86 (s, 3H), 3.85 (s, 3H), 3.82 (s, 3H), 3.81 (s, 3H), 3.78 (s, 3H), 2.95 (d, J=3.6 Hz, 2H); $^{13}$C NMR (75 MHz, CDCl$_3$) δ 159.5, 159.3, 158.1, 155.1, 147.3, 147.1, 143.7, 142.5, 136.6, 133.0, 124.8, 115.1, 109.9, 109.2, 104.8, 102.8, 96.3, 95.9, 56.2, 56.0, 55.6, 55.4, 55.3, 55.1, 45.6, 45.4, 31.2; HRMS (FAB) calcd for C$_{27}$H$_{28}$O$_6$· [M$^+$] 448.1886. found 448.1880.

Cassigarol 8 Analog #2 (89)

Permethylated cassigarol B analog #2 (113, 15.0 mg, 0.033 mmol, 1.0 equiv) was dissolved in CH$_2$Cl$_2$ (1.0 mL), and the resultant solution was degassed by bubbling argon through it for 20 min. The solution was then cooled to −78° C. and treated with BBr$_3$ (0.40 mL, 1.0 M solution in CH$_2$Cl$_2$, 0.400 mmol, 12 equiv).

The resultant red mixture was stirred for 1 h at −78° C., allowed to warm slowly to 25° C. over 1 h, and then stirred for an additional 2 h at 25° C. Upon completion, the reaction mixture was quenched with water (5 mL), poured into water (5 mL), and extracted with EtOAc (3×5 mL). The combined organic layers were then washed with water (5 mL) and brine (5 mL), dried (MgSO$_4$), and concentrated. The resultant crude brown oil was purified by preparative TLC (silica gel, CH$_2$Cl$_2$/MeOH, 9:1) to give cassigarol B analog #1 (89, 9.8 mg, 81%) as a brown solid. [Note: this compound is highly sensitive to oxygen, so all operations must be performed under an argon atmosphere and conducted as quickly as possible]. 89: R$_f$=0.11 (silica gel, CH$_2$Cl$_2$/MeOH, 9:1); IR (film) ν$_{max}$ 2303, 2891, 2993, 1686, 1605, 1249, 1139 cm$^{-1}$; 1H NMR (300 MHz, acetone-d$_6$) δ 8.10 (s, 1H), 7.92 (s, 1H), 7.82 (s, 1H), 7.78 (s, 1H), 7.55 (s, 1H), 7.52 (s, 1H), 6.86 (s, 1H), 6.81 (s, 1H), 6.41 (d, J=1.8 Hz, 1H), 6.39 (d, J=2.7 Hz, 1H), 6.19 (d, J=1.0 Hz, 1H), 6.12 (d, J=2.1 Hz, 1H), 4.93 (s, 1H), 4.00 (t, J=3.6 Hz, 1H), 2.85 (d, J=3.6 Hz, 2H); $^{13}$C NMR (75 MHz, acetone-d$_6$) δ 159.8, 157.3, 165.7, 152.9, 145.0, 143.3, 142.9, 122.6, 118.8, 115.4, 113.5, 112.8, 107.1, 106.7, 104.9, 100.3, 96.7, 54.5, 45.5, 32.3; LRMS (APCI+) calcd for C$_{21}$H$_{16}$O$_6$·[M+H$^+$]365. found 365.

Figure S3. X-ray crystal structures of 111 and 113.

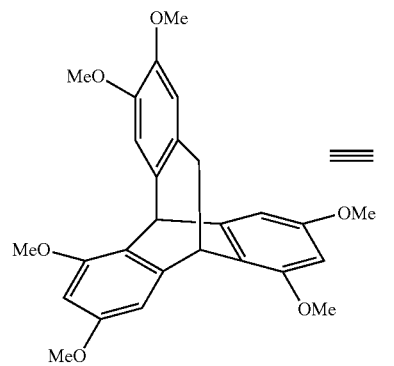

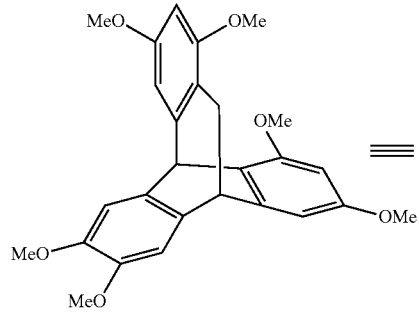

Enol Ether 115

Palladium (II) chloride bis-benzonitrile (0.041 g, 0.107 mmol, 1.0 equiv) and CuCl$_2$ (0.014 g, 0.107 mmol, 1.0 equiv) were added sequentially in single portions to a solution of alcohol 11 (0.050 g, 0.107 mmol, 1.0 equiv) in DMF (5 mL) at 25° C. The reaction solution was then warmed to 50° C. and stirred for 1 h. Upon completion, the reaction contents were concentrated directly to give a crude oil that was purified by flash column chromatography (silica gel, EtOAc/hexanes, 1:1) to afford a mixture of regioisomers 115 (0.037 g, 75%) and 39 (0.011 g, 22%) as white solids. [Note: due to the instability of 39, it was not characterized but rather utilized immediately in subsequent chemistry]. 115: $R_f$=0.55 (silica gel, EtOAc/hexanes, 1:1); IR (film) $v_{max}$ 2905, 2790, 1601, 1512, 1161, 851 cm$^{-1}$; $^1$H NMR (300 MHz, CDCl$_3$) δ 7.67 (d, J=9.0 Hz, 2H), 6.87 (d, J=9.0 Hz, 2H), 6.62 (s, 1H), 6.49 (app d, J=1.8 Hz, 2H), 6.36 (d, J=2.1 Hz, 1H), 6.31 (app d, J=2.1 Hz, 2H), 6.22 (s, 1H), 3.84 (s, 3H), 3.82 (s, 3H), 3.79 (s, 3H), 3.68 (s, 6H); $^{13}$C NMR (75 MHz, CDCl$_3$) δ 160.6, 160.4, 160.2, 156.2, 151.9, 143.5, 133.1, 127.3, 126.6, 113.6, 109.8, 105.2, 100.5, 99.4, 96.7, 73.4, 55.5, 55.4, 55.3, 55.1; HRMS (FAB) calcd for $C_{26}H_{26}O_6$+ [M$^+$] 434.1729. found 434.1715.

Nazarov Cyclisation Product 43

Pd(OAc)$_2$ (0.048 g, 0.0214 mmol, 0.20 equiv) and Cu(OAc)$_2$ (4.0 mg, 0.0214 mmol, 0.20 equiv) were added sequentially in single portions to a suspension of alcohol 11 (0.050 g, 0.107 mmol, 1.0 equiv) in 2-propanol (5 mL) at 25 SC. The reaction flask was then purged of air, kept under an O2 atmosphere, and warmed to 60° C. and stirred vigorously for 5 h or until palladium black was observed on the walls of the flask. At this time (when 39 had been formed cleanly in situ), the reaction contents were cooled to 25° C. and concentrated HCl (5 mL) was added dropwise. The resultant black solution was stirred for 16 h at 25° C. Upon completion, the reaction mixture was quenched by the addition of saturated aqueous NaHCO$_3$ (15 mL), poured into water (10 mL), and extracted with EtOAc (3×10 mL). The combined organic layers were then washed with water (15 mL) and brine (15 mL), dried (MgSO$_4$), and concentrated. The resultant black residue was purified by flash column chromatography (silica gel, EtOAc/hexanes, 1:1) to afford 43 (0.033 g, 72%) as a purple solid. [Note: this compound is an extremely effective chromophore, and even trace amounts of it can turn any solution deep red]. Alternatively, Nazarov cyclization product 43 could be prepared by the dropwise addition of concentrated HCl (1 mL) to a solution of 115 and 39 (3.3/1, 0.050 g, 0.115 mmol) in MeOH (5 mL) at 25° C. After 15 min of stirring, the solution turned purple; the reaction contents were stirred for a total of 16 h at 25° C. Upon completion, the reaction mixture was quenched by the addition of saturated aqueous NaHCO$_3$ (15 mL), poured into water (10 mL), and extracted with EtOAc (3×10 mL). The combined organic layers were then washed with water (15 mL) and brine (15 mL), dried (MgSO$_4$), and concentrated. The resultant black residue was purified by flash column chromatography (silica gel, EtOAc/hexanes, 1:1) to afford unreacted 115 (34.8 mg, 93% recovery) alongside 43 (11.9 mg, 90% yield based on initial amount of 39). 43: $R_f$=0.52 (silica gel, EtOAc/hexanes, 1:1); IR (film) $v_{max}$ 2932, 2834, 1704, 1605, 1455, 1308, 1156 cm$^{-1}$; $^1$H NMR (300 MHz, CDCl$_3$) δ 7.12 (d, J 8.4 Hz, 2H), 6.86 (d, J=1.8 Hz, 1H), 6.74 (d, J=8.7 Hz, 2H), 6.49 (app d, J=2.1 Hz, 2H), 6.43 (app d, J=2.1 Hz, 2H), 3.86 (s, 3H), 3.76 (s, 3H), 3.70 (s, 6H), 3.60 (s, 3H); $^{13}$C NMR (75 MHz, CDCl$_3$) δ 196.6, 162.5, 160.2, 158.7, 156.6, 154.7, 137.0, 134.1, 131.0, 130.6, 123.6, 122.7, 113.4, 106.6, 104.1, 102.8, 101.0, 55.9, 55.8, 55.3, 55.2; HRMS (FAB) calcd for $C_{26}H_{24}O_6$+ [M$^+$] 432.1573. found 432.1571. It is significant to note that 43 has previously been reported in the literature by Pan and co-workers [35]; however, their published carbon data did not fully match at two signals (108.0 versus our observed value of 106.6 and 114.2 versus our observed value of 113.4) and they are missing another signal entirely (our observed value of 122.7). As such, 43 was prepared via an alternate method from the previously confirmed permethylated paucifloral F (56'). To a solution of 56' (0.010 g, 0.023 mmol, 1.0 equiv) in THF (2 mL) at −78° C. was added NaHMDS (1.07 mL, 1.0 M in THF, 1.07 mmol, 3.0 equiv) and the resulting yellow solution was stirred at −78° C. for 30 min. Next, TMSCl (4.4 μL, 0.035 mmol, 1.5 equiv) was added dropwise, the solution was warmed slowly to 25° C., and was then stirred for an additional 1 h at 25° C. Upon completion, the reaction mixture was quenched with saturated aqueous NaHCO$_3$ (10 mL), poured into water (5 mL), and extracted with EtOAc (3×15 mL). The combined organic layers were then washed with water (5 mL) and brine (5 mL), dried (MgSO$_4$), and concentrated to afford the desired silyl enol ether intermediate. Pressing forward without any additional purification, this material was dissolved immediately in MeCN (2 mL) at 25° C. and then treated with Pd(OAc)$_2$ (5.6 mg, 0.0253 mmol, 1.1 equiv). The resulting dark solution was stirred for 12 h at 25° C. Upon completion, the reaction contents were concentrated directly and the resultant oily brown residue purified by flash column chromatography (silica gel, EtOAc/hexanes, 1:1) to afford 43 (5.0 mg, 48%), material that matched that obtained via the previously described Nazarov cyclization in all respects.

Natural Product Analog 121

Nazarov cyclization product 43 (15.0 mg, 0.0347 mmol, 1.0 equiv) was dissolved in CH$_2$Cl$_2$ (1.0 mL) and treated with BBr$_3$ (0.40 mL, 1.0 M solution in CH$_2$Cl$_2$, 0.40 mmol, 12 equiv) at −78° C. The resultant red mixture was stirred for 1 h at −78° C., allowed to warm slowly to 25 OC over 1 h, and then stirred for an additional 2 h at 25° C. Upon completion, the reaction mixture was quenched with water (5 mL), poured into water (5 mL), and extracted with EtOAc (3×5 mL). The combined organic layers were then washed with water (5 mL) and brine (5 mL), dried (MgSO$_4$), and concentrated. The resultant brown crude oil was purified by preparative TLC (silica gel, CH$_2$Cl$_2$/MeOH, 9:1) to give phenol 121 (12.4 mg, 83%) as a purple solid. 121: $R_f$=0.08 (silica gel, CH$_2$Cl$_2$/MeOH, 9:1); IR (film) $v_{max}$ 3190, 2954, 2923, 1686, 1605, 1437, 1201, 1152 cm$^{-1}$; $^1$H NMR (400 MHz, acetone-d) δ 7.08 (d, J=9.0 Hz, 2H), 6.68 (d, J=8.4 Hz, 2H), 6.62 (d, J=2.0 Hz, 1H), 6.39 (d, J=2.4 Hz, 2H), 6.36 (t, J=2.4 Hz, 1H), 6.34 (d, J=2.0 Hz, 1H); $^{13}$C NMR (75 MHz, acetone-d$_6$) δ 197.8, 161.7, 160.50, 160.47, 158.3, 158.2, 154.1, 136.1, 132.5, 130.9, 124.5, 120.4, 116.2, 109.6, 107.8, 106.5, 104.5; LRMS (APCI+) calcd for $C_{21}H_{14}O_6$+ [M+H$^+$] 363. found 363.

Synthesis of Nazarov Cyclisation Product 122

This compound was synthesized from intermediate 37' exactly as described above for 43. Intermediates S13 and S14 were prepared in exactly the same manner as well.

Scheme S7. Extension of the Nazarov cyclization process to an additional substrate.

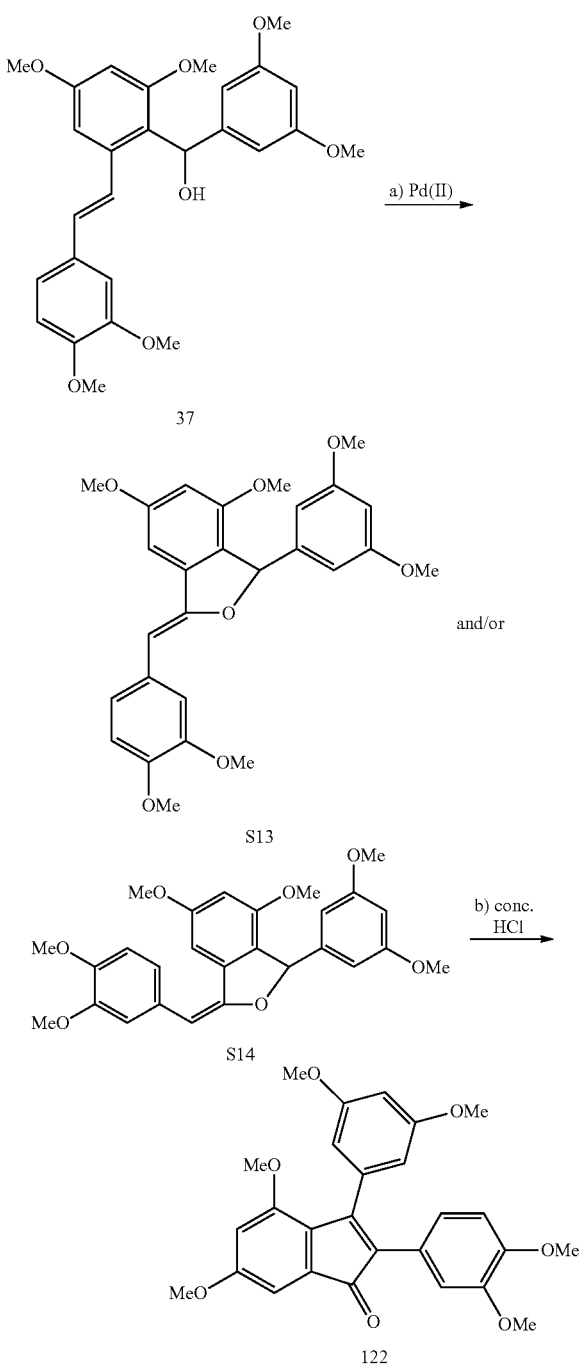

S13: $R_f$=0.40 (silica gel, EtOAc/hexanes, 1:1); IR (film) $v_{max}$ 2999, 2952, 2933, 1594, 1515, 1458, 1423, 1271, 1201, 1150 cm$^{-1}$; $^1$H NMR (400 MHz, CDCl$_3$) δ 7.32 (dd, J=7.5, 2.0 Hz, 1H), 7.21 (d, J=2.0 Hz, 1H), 6.84 (d, J=7.8 Hz, 1H), 6.63 (s, 1H), 6.48 (d, J=2.2 Hz, 2H), 6.37 (d, J=2.0 Hz, 1H), 6.32 (d, J=2.2 Hz, 1H), 6.31 (app t, J=2.2 Hz, 1H), 6.23 (s, 1H), 3.92 (s, 3H), 3.89 (s, 3H), 3.84 (s, 3H), 3.79 (s, 3H), 3.68 (s, 6H); $^{13}$C NMR (75 MHz, CDCl$_3$) δ 160.6, 160.4, 156.2, 151.8, 149.7, 148.6, 143.3, 133.0, 127.6, 118.2, 110.7, 109.9, 108.2, 105.2, 100.4, 99.8, 99.3, 96.7, 73.4, 55.9, 55.8, 55.5, 55.4, 55.1; HRMS (FAB) calcd for C$_{26}$H$_{25}$O$_7$$^+$ [M+H$^+$] 464.1835. found 464.1850.

S14: [Note: This compound is not stable and must be reacted immediately]. $R_f$=0.40 (silica gel, EtOAc/hexanes, 1:1); $^1$H NMR (400 MHz, CDCl$_3$) δ 7.41 (d, J=1.2 Hz, 1H), 7.28 (d, J=2.0 Hz, 1H), 6.83 (d, J=8.5 Hz, 1H), 6.63 (d, J=2.0 Hz, 1H), 6.54 (d, J=2.0 Hz, 2H), 6.48 (s, 1H), 6.39 (t, J=2.0 Hz, 1H), 6.36 (d, J=2.0 Hz, 1H), 5.86 (s, 1H), 3.88 (s, 3H), 3.87 (s, 3H), 3.83 (s, 3H), 3.74 (s, 6H), 3.72 (s, 3H).

Nasarov Product 122

$R_f$=0.40 (silica gel, EtOAc/hexanes, 1:1); IR (film) $v_{max}$ 2993, 2955, 2929, 1701, 1587, 1511, 1461, 1416, 1302, 1252 cm$^{-1}$; $^1$H NMR (300 MHz, CDCl$_3$) δ 6.92 (dd, J=8.4, 2.0 Hz, 1H), 6.86 (d, J=2.0 Hz, 1H), 6.67 (d, J=8.4 Hz, 1H), 6.66 (d, J=2.0 Hz, 1H), 6.51 (d, J=2.0 Hz, 2H), 6.43 (app d, J=1.0 Hz, 1H), 3.86 (s, 3H), 3.84 (s, 3H), 3.71 (s, 6H), 3.61 (s, 3H), 3.59 (s, 3H); $^{13}$C NMR (75 MHz, CDCl$_3$) δ 196.5, 162.6, 160.4, 156.7, 154.7, 148.2, 148.0, 137.3, 134.0, 130.3, 123.8, 122.6, 112.7, 110.6, 106.4, 104.0, 102.8, 100.8, 55.9, 55.7 (2C), 55.4 (3C); HRMS (FAB) calcd for C$_{26}$H$_{25}$O$_7$$^+$ [M+H$^+$] 463.1757. found 463.1746.

REFERENCES

[1] a) M. Jang, L. Cai, G. O. Udeani, K. V. Slowing, C. F. Thomas, C. W. W. Beecher, H. H. S. Fong, N. R. Farnsworth, A. D. Kinghorn, R. G. Mehta, R. C. Moon, J. M. Pezzuto, Science 1997, 275, 218-220; b) K. T. Howitz, K. J. Bitterman, H. Y. Cohen, D. W. Lamming, S. Lavu, J. G. Wood, R. E. Zipkin, P. Chung, A. Kisielewski, L.-L. Zhang, B. Scherer, D. A. Sinclair, Nature 2003, 425, 191-196; c) L. M. Szewczuk, L. Forti, L. A. Stivala, T. M. Penning, J. Biol. Chem. 2004, 21, 22727-22737; d) J. A. Baur, K. J. Pearson, N. L. Price, H. A. Jamieson, C. Lerin, A. Kalra, V. V. Prabhu, J. S. Allard, G. Lopez-Lluch, K. Lewis, P. J. Pistell, S. Poosala, K. G. Becker, O. Boss, D. Gwinn, M. Wang, S. Ramswamy, K. W. Fishbein, R. G. Spencer, E. G. Lakatta, D. Le Couteur, R. J. Shaw, P. Navas, P. Puigserver, D. K. Ingram, R. de Cabo, D. A. Sinclair, Nature 2006, 444, 337-342.

[2] G. J. Soleas, E. P. Diamandis, D. M. Goldberg, Clin. Biochemistry 1997, 30, 91-113.

(3) a) Y. Oshima, Y. Ueno, K. Hisamachi, M. Takeshita, Tetrahedron 1993, 49, 5801-5804; b) Y. Oshima, Y. Ueno, Phytochemistry 1993, 33, 179-182; c) M. Niwa, J. Ito, K. Terashima, T. Koizumi, Y. Takaya, K.-X. Yan, Heterocycles 2000, 53, 1475-1478; d) J. Ito, T. Tanaka, M. Iinuma, K. Nakaya, Y. Takahashi, R. Sawa, J. Murata, D. Darnaedi, J. Nat. Prod. 2004, 67, 932-937; e) H.-F. Luo, L.-P. Zhang, C.-Q. Hu, Tetrahedron 2001, 57, 4849-4854; f) M. A. Khan, S. G. Nabi, S. Prakash, A. Zaman, Phytochemistry 1986, 25, 1945-1948; g) H. A. Guebailia, K. Chira, T. Richard, T. Mabrouk, A. Furiga, X. Vitrac, J.-P. Monti, J.-C. Delaunay, J.-M. Merillon, J. Agric. Food Chem. 2006, 54, 9559-9564; h) T. Tanaka, T. Ito, K. Nakaya, M. Iinuma, S. Riswan, Phytochemistry 2000, 54, 63-69; i) Y. Takaya, K.-X. Yan, K. Terashima, J. Ito, M. Niwa, Tetrahedron 2002, 58, 7259-7265; j) B. Supudompol, K. Likhitwitayawuid, P. J. Houghton, Phytochemistry 2004, 65, 2589-2594; k) N. S. Aminah, S. A. Achmad, N. Aimi, E. L. Ghisalberti, E. H. Hakim, M. Kitajima, Y. M. Syah, H. Takayama, Filoterapia 2002, 73, 501-507.

[4] a) M. Ohyama, T. Tanaka, T. Ito, M. Iinuma, K. F. Bastow, K.-H. Lee, Bioorg. Med. Chem. Lett. 1999, 9, 3057-3060; b) K. Ohguchi, T. Tanaka, T. Ito, M. Iinuma, K. Matsumoto, Y. Akao, Y. Nozawa, Biosci. Biotechnol. Biochem. 2003, 67, 1587-1589; c) K. Ohguchi, Y. Akao, K. Matsumoto, T. Tanaka, T. Ito, M. Iinuma, Y. Nozawa, Biosci. Biotechnol. Biochem. 2005, 69, 353-356; d) T. Ito, Y. Akao, H. Yi, K.

Ohguchi, K. Matsumoto, T. Tanaka, M. Iinuma, Y. Nozawa, Carcinogenesis 2003, 24, 1489-1497.
[5] M. A. Fischbach, J. Clardy, Nature: Chem. Biol. 2007, 3, 353-355.
[6] J. M. Aguirre, E. N. Alesso, G. Y. M. Iglesias, J. Chem. Soc., Perkin Trans 1 1999, 1353-1358.
[7] X.-C. Li, D. Ferreira, Tetrahedron 2003, 59, 1501-1507.
[8] Y. Takaya, K. Terashima, J. Ito, Y.-H. He, M. Takeoka, N. Yamaguchi, M. Niwa, Tetrahedron 2005, 61, 10285-10290.
[9] P. Langcake, R. J. Pryce, J. Chem. Soc., Chem. Commun. 1977, 208-210.
[10] M. Sako, H. Hosokawa, T. Ito, M. Iinuma, J. Org. Chem. 2004, 69, 2598-2600.
[11] W. Li, H. Li, Z. Hou, Angew. Chem. 2006, 118, 7771-7773; Angew. Chem. Int. Ed. 2006, 45, 7609-7611.
[12] L. Botella, C. Nájera, Tetrahedron 2004, 60, 5563-5570.
[13] P. S. Baran, N. Z. Burns, J. Am. Chem. Soc. 2006, 128, 3908-3909.
[14] R. J. K. Taylor, Chem. Comm. 1999, 217-227.
[15] C. Y. Meyers, A. M. Malte, W. S. Matthews, J. Am. Chem. Soc. 1969, 91, 7510-7512; T. Tanaka, M. Iinuma, H. Murata, Phytochemistry 1998, 48, 1045-1049.
[16] Y. Takaya, K.-X. Yan, K. Terashima, Y.-H. He, M. Niwa, Tetrahedron 2002, 58, 9265-9271.
[17] S. A. Adesanya, R. Nia, M.-T. Martin, N. Boukamcha, A. Montagnac, M. Pals, J. Nat. Prod. 1999, 62, 1694-1695.
[18] F. Effenberger, Angew. Chem. 2002, 114, 1775-1776; Angew. Chem. Int. Ed. 2002, 41, 1699-1700.
[19] T. Tanaka, T. Ito, K. Nakaya, M. Iinuma, Y. Takahashi, H. Naganawa, S. Riswan, Heterocycles 2001, 55, 729-740.
[20] a) M. Harmata, S. Wacharasindhu, Org. Lett. 2005, 7, 2563-2565; b) M. Miesch, A. Cotté, M. Frank-Neumann, Tetrahedron Lett. 1993, 34, 8085-8086.
[21] J. Ito, T. Tanaka, M. Iinuma, K. Nakaya, Y. Takahashi, R. Sawa, J. Murata, D. Darnaedi, J. Nat. Prod. 2004, 67, 932-937.
[22] Y. Takaya, K.-X. Yan, K. Terashima, J. Ito, M. Niwa, Tetrahedron 2002, 58, 7259-7265.
[23] S. A. Adesanya, R. Nia, M.-T. Martin, N. Boukamcha, A. Montagnac, M. Pals, J. Nat. Prod. 1999, 62, 1694-1695.
[24] M. A. Khan, S. G. Nabi, S. Prakash, A. Zaman, Phytochemistry 1986, 25, 1945-1948.
[25] a) A. J. Frontier, C. Collison, Tetrahedron 2005, 61, 7577-7606; b) D. J. Kerr, C. Metje, B. L. Flynn, Chem. Comm. 2003, 1380-1381.
[26] K. Baba, K. Maeda, Y. Tabata, M. Doi, M. Kozawa, Chem. Pharm. Bull. 1988, 36, 2977-2983.
[27] Siddiqui, Z. S.; Rahman, M.; Khan, M. A.; Lavaud, C.; Massiot, G.; Nuzillard, J. M.; Connolly, J. D.; Rycroft, D. S. Tetrahedron 1993, 49, 10393-10396.
[28] Vetter, S. Syn. Comm. 1998, 28, 3219-3223.
[29] Rosenfeld, D. C.; Shekhar, S.; Takemiya, A.; Utsunomiya, M.; Hartwig, J. F. Org. Lett. 2006, 8, 4179-4182.
[30] a) Luo, H.-F.; Zhang, L.-P.; Hu, C.-Q. Tetrahedron 2001, 57, 4849-4854 b) Zhu, J.; Zhong, C.; Lu, H.-F.; Li, G.-Y.; Sun, X. Synlett 2008, 458-462.
[31] Zimmerman, H. E. J. Am. Chem. Soc. 1956, 78, 1168-1173.
[32] Yang, G.; Zhou, J.; Li, Y.; Hu, C. Planta Medica 2005, 71, 569-571.
[33] Nicolaou, K. C.; He, Y.; Vourloumis, D.; Vallberg, H.; Roschanger, F.; Sarabia, F.; Ninkovic, S.; Yang, Z.; Trujillo, J. I. J. Am. Chem. Soc. 1997, 119, 7960-7973.
[34] Tanaka, T.; Ito, T.; Nakaya, K; Iinuma, M.; Takahashi, Y.; Naganawa, H.; Riswan, S. Heterocycles 2001, 55, 729-740.
[35] Chen, B.; Xie, X.; Lu, J.; Wang, Q.; Zhang, J.; Tang S.; She, X.; Pan, X. Synlett 2006, 259-262.

What is claimed is:

1. A solid composition, free of plant extract, comprising a solid compound having the structure:

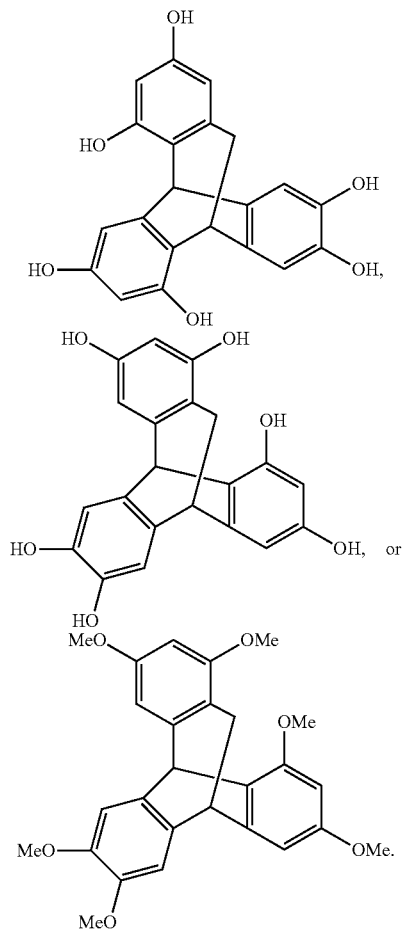

2. A pharmaceutical composition, free of plant extract, comprising a pharmaceutically acceptable carrier and a solid compound having the structure:

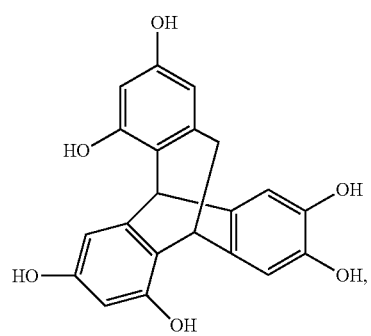

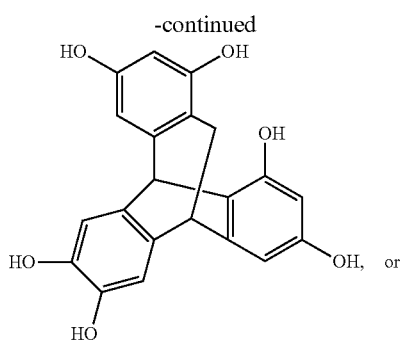

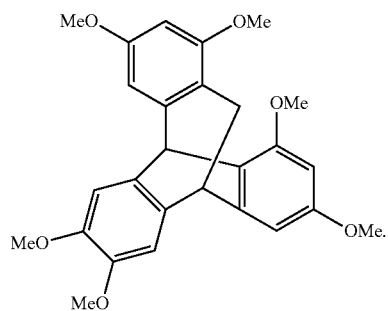 [SMILES: COc1cc(OC)c2c(c1)C1Cc3c(OC)cc(OC)cc3C2c2cc(OC)c(OC)cc21]

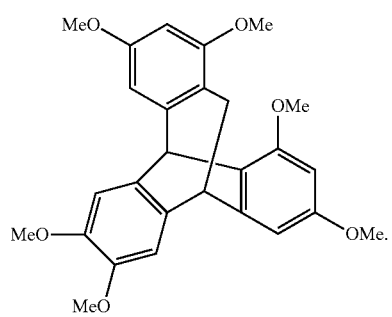

6. The pharmaceutical composition of claim 2, wherein the compound has the structure:

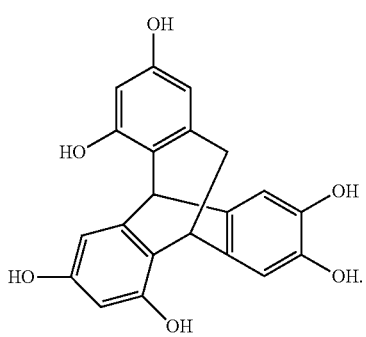 [SMILES: Oc1cc(O)c2c(c1)CC1c3cc(O)c(O)cc3C2c2cc(O)cc(O)c21]

3. The solid composition of claim 1, wherein the compound has the structure:

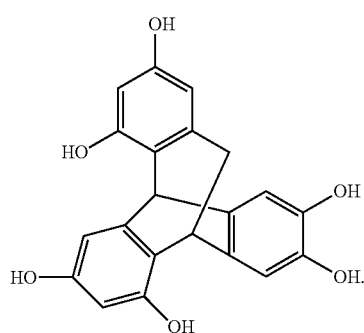

7. The pharmaceutical composition of claim 2, wherein the compound has the structure:

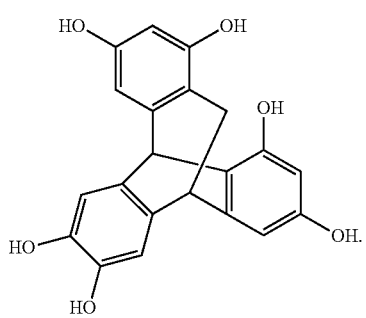 [SMILES: Oc1cc(O)c2c(c1)C1Cc3c(O)cc(O)cc3C2c2cc(O)c(O)cc21]

4. The solid composition of claim 1, wherein the compound has the structure:

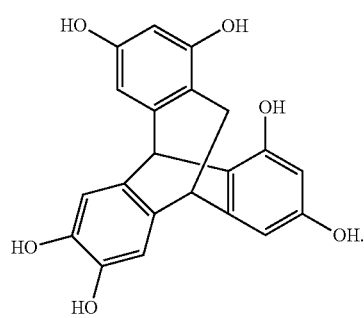

8. The pharmaceutical composition of claim 2, wherein the compound has the structure:

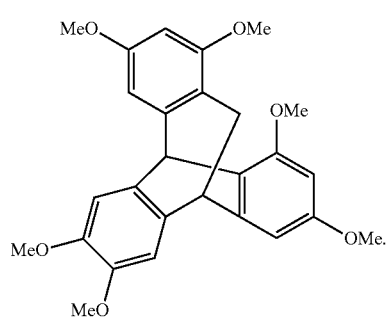 [SMILES: COc1cc(OC)c2c(c1)C1Cc3c(OC)cc(OC)cc3C2c2cc(OC)c(OC)cc21]

5. The solid composition of claim 1, wherein the compound has the structure:

* * * * *